United States Patent
Jensen et al.

(10) Patent No.: US 10,024,854 B2
(45) Date of Patent: Jul. 17, 2018

(54) METHOD FOR DETECTING AND PURIFYING PANCREATIC BETA CELLS

(71) Applicants: The Cleveland Clinic Foundation, Cleveland, OH (US); The Regent of the University of Colorado, A Body Corporate, Denver, CO (US)

(72) Inventors: Jan Jensen, Shaker Heights, OH (US); John Hutton, Aurora, CO (US); Xiaoling Qu, Beachwood, OH (US); Howard Davidson, Denver, CO (US)

(73) Assignees: THE CLEVELAND CLINIC FOUNDATION, Cleveland, OH (US); THE REGENT OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 15/457,973

(22) Filed: Mar. 13, 2017

(65) Prior Publication Data

US 2017/0254807 A1 Sep. 7, 2017

Related U.S. Application Data

(63) Continuation of application No. 14/579,578, filed on Dec. 22, 2014, now abandoned, which is a continuation of application No. 13/128,181, filed as application No. PCT/US2009/063417 on Nov. 5, 2009, now abandoned.

(60) Provisional application No. 61/198,763, filed on Nov. 7, 2008.

(51) Int. Cl.
| | |
|---|---|
| *C07K 14/705* | (2006.01) |
| *G01N 33/569* | (2006.01) |
| *C07K 16/28* | (2006.01) |
| *G01N 33/68* | (2006.01) |
| *C12N 5/071* | (2010.01) |
| *G01N 33/50* | (2006.01) |

(52) U.S. Cl.
CPC ..... *G01N 33/56966* (2013.01); *C07K 14/705* (2013.01); *C07K 14/70503* (2013.01); *C07K 16/28* (2013.01); *C07K 16/2803* (2013.01); *C12N 5/0676* (2013.01); *G01N 33/507* (2013.01); *G01N 33/5032* (2013.01); *G01N 33/6893* (2013.01); *C07K 2319/30* (2013.01); *G01N 2333/705* (2013.01); *G01N 2800/042* (2013.01)

(58) Field of Classification Search
CPC ........ G01N 33/56966; G01N 33/5032; G01N 33/507; G01N 33/6893; G01N 2333/705; G01N 2800/042; C07K 14/705; C07K 14/70503; C07K 16/28; C07K 16/2803; C07K 2319/30; C12N 5/0676
See application file for complete search history.

(56) References Cited

U.S. PATENT DOCUMENTS

| | | | | |
|---|---|---|---|---|
| 8,415,455 | B2* | 4/2013 | Levine | C07K 14/47 530/350 |
| 9,107,862 | B2* | 8/2015 | Toporik | C07K 14/47 |
| 2006/0246442 | A1 | 11/2006 | Seve et al. | |
| 2007/0105191 | A1 | 5/2007 | Desnoyers et al. | |
| 2007/0141566 | A1* | 6/2007 | Rupp | C07K 14/47 435/6.11 |
| 2009/0202428 | A1 | 8/2009 | Harris et al. | |
| 2015/0118158 | A1 | 4/2015 | Jensen et al. | |

FOREIGN PATENT DOCUMENTS

| | | |
|---|---|---|
| WO | WO 99/14328 | 3/1999 |
| WO | WO 2004/046355 A2 | 6/2004 |
| WO | WO 2007/005283 A2 | 1/2007 |
| WO | WO 2009/101181 A2 | 8/2009 |

OTHER PUBLICATIONS

Clark, H.F., et al., "The Secreted Protein Discovery Initiative (SPDI), A Large-Scale Effort to Identify Novel Human Secreted and Transmembrane Proteins: A Bioinformatics Assessment," *Genome Research*, 13:2265-2270 (2003).
Database UniProt, XP-002571543 (Dec. 4, 2007), Accession No. A8MVW5; Q6UXI0, "HECA2_HUMAN", [online], [retrieved Apr. 3, 2010], retrieved from internet <URL http://www.uniprot.org/uniprot/A8MVW5.txt?version=12.
Database UniProt, XP-002571545 (Jul. 5, 2005), Accession No. Q4VAH7, "HECA2_MOUSE", [online], [retrieved Apr. 3, 2010], retrieved from internet <URL http://www.uniprot.org/jobs/KR1C.txt.
Faivre-Sarraih, C., et al., "*Drosophila* Contactin, A Homolog of Vertebrate Contactin, Is Required for Septate Junction Organization and Paracellular Barrier Function," *Development*, 131(20): 4931-4942 (2004).
Flamez, D., et al., "A Platform for the Identification and Validation of Beta Cell Specific Membrane Biomarkers,"*Diabetologia*, 51 [Suppl. 1]: S333 (2008).
Hoffman, B.G., et al.,"Identification of Transcripts With Enriched Expression in the Developing and Adult Pancreas," *Genome Biology*, 9(6): R99.1-R99.19 (2008).

(Continued)

*Primary Examiner* — Gailene Gabel
(74) *Attorney, Agent, or Firm* — Hamilton, Brook, Smith & Reynolds, P.C.

(57) ABSTRACT

The invention is based, in part, on the discovery that a polypeptide, referred to herein as Betacam, is selectively expressed on the surface of pancreatic islet cells. Thus, in one aspect, the invention is directed to compositions comprising Betacam or that can be used to detect Betacam. In another aspect, the invention provides methods of detecting (e.g., non-invasively) pancreatic beta cells from a mammalian cell source. Another aspect of the invention is directed to cellular purification of pancreatic beta cells from a heterogeneous cell source of multiple kinds. In another aspect, the invention provides methods of identifying agents that modulate activity of Betacam. In yet another aspect, the invention provides for improved treatment and diagnosis of diabetes.

16 Claims, 86 Drawing Sheets

(56) References Cited

OTHER PUBLICATIONS

Moh, C.M., et al., "Cloning and Charcterization of HepaCAM, A Novel Ig-Like Cell Adhesion Molecule Suppressed in Human Hepatocellular Carcinoma," *Journal of Hepatology* 42: 833-841 (2005).

NCIB (cDNA), Accession No. AI987662, "um05b04.xl Sugano Mouse Kidney mkia Mus musculus cDNA clone Image:2182159 3-, mRNA sequence", [online], Sep. 2, 1999, [retrieved on Nov. 21, 2011]. Retrieved from the internet <URL:http://www.ncib.nlm.nih.gov/nucest/AI987662.

NCIB (mRNA), Accession No. NM_001039372, "*Homo sapiens* HEPACAM family member 2 (HEPACAM2), transcript variant 1, mRNA", [online],Jul. 20, 2008, [retrieved on Nov. 6, 2008]. Retrieved from the internet <URL:http://www.ncib.nlm.nih.gov/entrez/viewer.fcgi?val=NM_001039372.1.

Saudek, F., et al., "Imaging the Beta-Cell Mass: Why and How," *The Review of Diabetic Studies*, 5(1): 6-12 (2008).

Notification of Transmittal of the International Search Report and the Written Opinion of the International Searching Authority for PCT/US2009/063417, "Method for Detecting and Purifying Pancreatic Beta Cells", dated Mar. 26, 2010.

Notification Concerning Transmittal of International Preliminary Report on Patentability for PCT/US2009/063417, "Method for Detecting and Purifying Pancreatic Beta Cells", dated May 19, 2011.

Non-Final Office Action for U.S. Appl. No. 13/128,181, "Method for Detecting and Purifying Pancreatic Beta Cells", dated Jun. 20, 2014.

Non-Final Office Action for U.S. Appl. No. 13/128,181, "Method for Detecting and Purifying Pancreatic Beta Cells", dated Nov. 14, 2013.

Non-Final Office Action for U.S. Appl. No. 14/579,578, "Method for Detecting and Purifying Pancreatic Beta Cells", dated Sep. 14, 2016.

* cited by examiner

FIG. 1

Report for Gene ID 253012

| CCDS | Status | Species | Chrom. | Gene | NCBI Builds | Links |
|---|---|---|---|---|---|---|
| 5629.1 | Public | *Homo sapiens* | 7 | LOC253012 | 35.1 - 36.2 | H G C |

Sequence IDs included in CCDS 5629.1

| Original | Current | Source | Nucleotide ID | Protein ID | Status in CCDS | Seq. Status | Links |
|---|---|---|---|---|---|---|---|
| | ✓ | EBI,WTSI | ENST00000341723 | ENSP00000340532 | Accepted | alive | N P N P |
| | ✓ | NCBI | NM_198151.1 | NP_937794.1 | Accepted | alive | N P N P |

Chromosomal Locations for CCDS 5629.1
On '-' strand of Chromosome 7 (NC_000007.12)
Genome Browser links: N U E

| Chromosome | Start | Stop | Links |
|---|---|---|---|
| 7 | 92656516 | 92656519 | N N U E |
| 7 | 92659503 | 92659612 | N N U E |
| 7 | 92663077 | 92663150 | N N U E |
| 7 | 92664490 | 92664527 | N N U E |
| 7 | 92664622 | 92664646 | N N U E |
| 7 | 92664734 | 92664859 | N N U E |
| 7 | 92675829 | 92676125 | N N U E |
| 7 | 92682650 | 92682934 | N N U E |
| 7 | 92686350 | 92686743 | N N U E |

CCDS Sequence Data

Blue highlighting indicates alternate exons.

FIG. 2

Red highlighting indicates amino acids encoded across a splice junction.

Nucleotide Sequence (1353 nt):
ATGTGGCTCAAGGTCTTCACAACTTTCCTTTCCTTGCAACAGGTGCTTGCTCGGGGCTGAAGGTGACAG
TGCCATCAGCACACTGTCCAATGCCTGCAGTTCAGGAGGTCAGAGCCTTCCACTACCCGTCCACTATGCCTTCCACAC
TCCAGCATCAGACATCCAGAATCCATTTGAGAGACCAACACAAGTTCCCCAAATACTTACTGGC
TCTGTGAATAAGTCTGTGTTCCTGACTTGGACTTCCCTGATGAAGGCAATTACATCGTGAAGGTCAACATTCAGGAAA
CTCTGCTTATCAACCCACTGACTTCCCTGATGAAGGCAATTACATCGTGAAGGTCAACATTCAGGAAA
TGGAACTCTATCTGCCAGTCAGAAGATACAAGTCACGGTTGATGATCCTGTCACAAAGCCAGTGGTCAG
ATTCATCCTCCCCTCGGGGCTGTGGAGTATGTGGGAACATGACCCTGACATGCCATGTGGAAGGGCA
CTCGGCTAGCTTACCAATGGCTAAAAAATGGGAGAGAGACCTGTCCACACCAGCTCCACCACTACTCCTTTCTCC
CCAAAACAATACCCTTCATATTGTCCAGTAACCAAGGAAGACATTGGAATTACAGCTGCCTGGTGAGG
AACCCTGTCAGTGAAATGATATCATTATGCCATCATATATTGACCTTGTTGACCTTTATGGACTTCAAG
TGAATTCTGATAAAGGGCTAAATCCCCCAACACCTGGAAGTGTTTACTCCTGGATTAGGAGGACTGACAATCTACATATATCAC
TTGTTCTGCTGATTCTCATCCCCTCGCTTAGAAGTTGCATCTGAAAAAGTAGCCCAAGATGAAACTCAT
ATTAAGCATGGGCCTCGCTTAGAAGTTGCATCTGAAAAAGTAGCCCAAGATGAAACTCAT
GTGCTTACAACACATAACCGGCAGAGAAATCATTGTCACCTTTAGCAAGTATAACTGGAATATCACTATTTTG
GGAGAAGCTTGCACAGAAGTTGCACAGAAGAAATCATTGTCACCTTTAGCAAGTATAACTGGAATATCACTATTTTG
ATTATATCCATGTGTCTTCTCTTCCTATGCAAAATATCAACCTACAAGTTATAAACAGAAACTAG
AAGGCAGGCCAGAACAGAATACAGGAAAGCTCAAACATTTTCAGCCATGAAGCTCTGGATGACTTT
CGGAATATATGCTTGATTGTGTATCGGGGCAAGATTTGCAGAATTTGCTTTTCCAGATGAAGTGTTCCAAGAGTCTGTTCCA
GCCTCTGATTGTGTATCGGGGCAAGATTTGCACGGTAGAAGTGAAGTGTTCCAAGAGTCTGTTCCA
AGCAGCAAGACCATCCAGAGTGA

Translation (450 aa):
MWLKVFTTFLSFATGACSGLKVTVPSHTVHGVRGQALYLPVHYGFHTPASDIQIIWLFERPHTMPKYLLG
SVNKSVVPDLEYQHKFTMPPNASLLINPLQFPDEGNYIVKVNIQGNGTLSASQKIQVTVDDPVTKPVVQ
IHPPSGAVEYVGNMLTCHVEGGTRLAYQWLKNGRPVHTSSTYSFSPQNNTLHIAPVTKEDIGNYSCLVR
NPVSEMESDIMPIIYYGPYGLQVNSDKGLKVGEVFTVDLGEAILFDCSADSHPPNTYSWIRRTDNTTYI
IKHGPRLEVASEKVAQKTMDYVCCAYNNITGRQDETHFTVIITSVGLEKLAQKGKSLSPLASITGISLFL
IISMCLLFLWKKYQPYKVIKQKLEGRPETEYRKAQTFSGHEDALDDFGIYEFVAFPDVSGVSRIPSRSVP
ASDCVSGQDLHSTVYEVIQHIPAQQDHPE

FIG. 3

```
LOCUS       NP_001034461     462 aa     linear    PRI  26-JUN-2007
DEFINITION  hypothetical protein LOC253012 isoform 1 [Homo sapiens].
ACCESSION   NP_001034461
VERSION     NP_001034461.1  GI:86439957
DBSOURCE    REFSEQ: accession NM_001039372.1
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
REFERENCE   1  (residues 1 to 462)
  AUTHORS   Clark,H.F., Gurney,A.L., Abaya,E., Baker,K., Baldwin,D., Brush,J.,
            Chen,J., Chow,B., Chui,C., Crowley,C., Currell,B., Deuel,B.,
            Dowd,P., Eaton,D., Foster,J., Grimaldi,C., Gu,Q., Hass,P.E.,
            Heldens,S., Huang,A., Kim,H.S., Klimowski,L., Jin,Y., Johnson,S.,
            Lee,J., Lewis,L., Liao,D., Mark,M., Robbie,E., Sanchez,C.,
            Schoenfeld,J., Seshagiri,S., Simmons,L., Singh,J., Smith,V.,
            Stinson,J., Vagts,A., Vandlen,R., Watanabe,C., Wieand,D., Woods,K.,
            Xie,M.H., Yansura,D., Yi,S., Yu,G., Yuan,J., Zhang,M., Zhang,Z.,
            Goddard,A., Wood,W.I., Godowski,P. and Gray,A.
  TITLE     The secreted protein discovery initiative (SPDI), a large-scale
            effort to identify novel human secreted and transmembrane proteins:
            a bioinformatics assessment
  JOURNAL   Genome Res. 13 (10), 2265-2270 (2003)
  PUBMED    12975309
  REMARK    Erratum:[Genome Res. 2003 Dec;13(12):2759]
```

PRIOR ART

FIG. 5

```
COMMENT     PREDICTED REFSEQ: The mRNA record is supported by experimental
            evidence; however, the coding sequence is predicted. The reference
            sequence was derived from AK096002.1.
FEATURES            Location/Qualifiers
     source          1..462
                     /organism="Homo sapiens"
                     /db_xref="taxon:9606"
                     /chromosome="7"
                     /map="7q21.3"
     Protein         1..462
                     /product="hypothetical protein LOC253012 isoform 1"
                     /calculated_mol_wt=51276
     Region          34..124
                     /region_name="V-set"
                     /note="Immunoglobulin V-set domain. This domain is found
                     in antibodies as well as neural protein P0 and CTL4
                     amongst others; pfam07686"
                     /db_xref="CDD:87333"
     Region          155..231
                     /region_name="IGcam"
                     /note="Immunoglobulin domain cell adhesion molecule (cam)
                     subfamily; members are components of neural cell adhesion
                     molecules (N-CAM L1), Fasciclin II and the insect immune
                     protein Hemolin; cd00931"
                     /db_xref="CDD:28983"
```

PRIOR ART

FIG. 5 cont.

```
     Site            order(157,159,161)
                     /site_type="other"
                     /note="FGF/FGF-Receptor Interaction"
                     /db_xref="CDD:28983"
     CDS             1..462
                     /gene="LOC253012"
                     /coded_by="NM_001039372.1:24..1412"
                     /GO_component="integral to membrane"
                     /note="isoform 1 is encoded by transcript variant 1"
                     /db_xref="GeneID:253012"
ORIGIN
    1 mgqdafmepf gdtlgvfqck iylllfgacs glkvtvpsht vhgvrgqaly lpvhygfhtp
   61 asdiqiiwlf erphtmpkyl lgsvnksvvp dleyqhkftm mppnasllin plqfpdegny
  121 ivkvniggng tlsasqkiqv tvddpvtkpv vqihppsgav eyvgnmtltc hveggtrlay
  181 qwlkngrpvh tsstysfspq nntlhiapvt kedignyscl vrnpvsemes diimpiiyyg
  241 pyglqvnsdk glkvgevftv dlgeailfdc sadshppnty swirrtdntt yiikhgprle
  301 vasekvaqkt mdyvccaynn itgrqdethf tviitsvgle klaqkgksls plasitgisl
  361 fliismcllf lwkkyqpykv ikqklegrpe teyrkaqtfs ghedalddfg iyefvafpdv
  421 sgvsripsrs vpasdcvsgq dlhstvyevi qhipaqgqdh p
```

PRIOR ART

FIG. 5 cont.

| | |
|---|---|
| LOCUS | NP_937794 450 aa linear PRI 17-NOV-2006 |
| DEFINITION | hypothetical protein LOC253012 isoform 2 [Homo sapiens]. |
| ACCESSION | NP_937794 XP_173199 XP_353642 |
| VERSION | NP_937794.1 GI:37700249 |
| DBSOURCE | REFSEQ: accession NM_198151.1 |
| KEYWORDS | . |
| SOURCE | Homo sapiens (human) |
|   ORGANISM | Homo sapiens |
| | Eukaryota; Metazoa; Chordata; Craniata; Vertebrata; Euteleostomi; |
| | Mammalia; Eutheria; Euarchontoglires; Primates; Haplorrhini; |
| | Catarrhini; Hominidae; Homo. |
| REFERENCE | 1 (residues 1 to 450) |
|   AUTHORS | Clark,H.F., Gurney,A.L., Abaya,E., Baker,K., Baldwin,D., Brush,J., |
| | Chen,J., Chow,B., Chui,C., Crowley,C., Currell,B., Deuel,B., |
| | Dowd,P., Eaton,D., Foster,J., Grimaldi,C., Gu,Q., Hass,P.E., |
| | Heldens,S., Huang,A., Kim,H.S., Klimowski,L., Jin,Y., Johnson,S., |
| | Lee,J., Lewis,L., Liao,D., Mark,M., Robbie,E., Sanchez,C., |
| | Schoenfeld,J., Seshagiri,S., Simmons,L., Singh,J., Smith,V., |
| | Stinson,J., Vagts,A., Vandlen,R., Watanabe,C., Wieand,D., Woods,K., |
| | Xie,M.H., Yansura,D., Yi,S., Yu,G., Yuan,J., Zhang,M., Zhang,Z., |
| | Goddard,A., Wood,W.I., Godowski,P. and Gray,A. |
|   TITLE | The secreted protein discovery initiative (SPDI), a large-scale |
| | effort to identify novel human secreted and transmembrane proteins: |
| | a bioinformatics assessment |
|   JOURNAL | Genome Res. 13 (10), 2265-2270 (2003) |
|   PUBMED | 12975309 |
|   REMARK | Erratum:[Genome Res. 2003 Dec;13(12):2759] |

PRIOR ART

FIG. 6

```
COMMENT     PREDICTED REFSEQ: The mRNA record is supported by experimental
            evidence; however, the coding sequence is predicted. The reference
            sequence was derived from AY358345.1.
            On or before Dec 17, 2003 this sequence version replaced
            gi:27479200, gi:37539102.
FEATURES             Location/Qualifiers
     source          1..450
                     /organism="Homo sapiens"
                     /db_xref="taxon:9606"
                     /chromosome="7"
                     /map="7q21.3"
     Protein         1..450
                     /product="hypothetical protein LOC253012 isoform 2"
                     /calculated_mol_wt=49983
     CDS             1..450
                     /gene="LOC253012"
                     /coded_by="NM_198151.1:64..1416"
                     /GO_component="integral to membrane"
                     /note="isoform 2 is encoded by transcript variant 2"
                     /db_xref="CCDS:CCDS5629.1"
                     /db_xref="GeneID:253012"
                     /db_xref="HPRD:14138"
ORIGIN
        1 mwlkvfttfl sfatgacsgl kvtvpshtvh gvrgqalylp vhygfhtpas diqiiwlfer
       61 phtmpkyllg svnksvvpdl eyqhkftmmp ihppsgavey vgnmtltchv eggtrlayqw
      121 sasqkiqvtv ddpvtkpvvq ihppsgavey vgnmtltchv eggtrlayqw lkngrpvhts
      181 stysfspqnn tlhiapvtke dignysclvr npvsemesdi irrtdnttyi ikhgprleva
      241 kvgevftvdl geailfdcsa dshppntysw irrtdnttyi ikhgprleva sekvaqktmd
      301 yvccaynnit grqdethftv iitsvglekl aqkgkslspl asitgislfl iismcllflw
      361 kkyqpykvik qklegrpete yrkaqtfsgh edalddfgiy efvafpdvsg vsripsrsvp
      421 asdcvsggdl hstvyeviqh ipaqqqdhpe
//
```

FIG. 6 cont.
PRIOR ART

SIGNAL PEPTIDE DETECTION IN MOUSE BETACAM

Most likely cleavage site between pos. 31 and 32: CLG-LK

SIGNAL PEPTIDE DETECTION IN HUMAN BETACAM ISOFORM 1

```
         >Sequence          length = 70
# Measure  Position  Value  Cutoff  signal peptide?
  max. C     32      0.265   0.32      NO
  max. Y     32      0.398   0.33      YES
  max. S     30      0.865   0.87      NO
  mean S    1-31     0.425   0.48      NO
     D      1-31     0.411   0.43      NO
# Most likely cleavage site between pos. 31 and 32: CSG-LK
```

| Affymetrix expression analysis | | |
|---|---|---|
| Tissue | norm. value | call |
| Adult Islets (wt/wt), 9 week | 5813.0 | P |
| Adult islets (Ob/Ob), Diabetic, 9wk | 8105.6 | P |
| Adult islets (Ob/Ob), Diabetic, 14wk | 8689.1 | P |
| FACS islet cells (Phogrin EGFP+, E15.5) | 2916.6 | P |
| FACS islet cells (Phogrin EGFP+, E18.5) | 3557.3 | P |
| FACS islet cells (Phogrin EGFP+, P24) | 7642.4 | P |
| FACS islet cells (Phogrin EGFP+, P25) | 5680.5 | P |
| αTC | 637.3 | P |
| βTC | 9048.8 | P |
| Emb. Pancreas E12.5 | 149.0 | P |
| Emb. Pancreas E13.5 | 336.0 | P |
| Emb. Pancreas E14.5 | 578.0 | P |
| Emb. Pancreas E15.5 | 643.0 | P |
| Emb. Pancreas E16.5 | 439.0 | P |
| Emb. Pancreas E17.5 | 335.0 | P |
| Emb. Pancreas E18.5 | 510.0 | P |
| E18.5 Ngn KO | 23.0 | A |
| E18.5 Ngn3 WT | 334.1 | P |

FIG. 16

DATA from ACEVIEW

Homo sapiens complex locus LOC253012, encoding hypothetical protein LOC253012
Expression and GenBank cDNA support ↑
Tissues where expression was observed (from 61 cDNA clones)
Origin of the cDNAs, as reported in GenBank/dbEST (tissue, stage, pathological or normal) shows that the gene is expressed in pancreas (seen 18 times), purified pancreatic islet (15), kidney (10), stomach (10), ascites (9), colon (6), liver and spleen (6), small intestine (5), 2 pooled tumors (clear cell type) (2), islets of langerhans (2), pooled colon, kidney, stomach (2), testis (2), blood (once), colon, kidney, stomach, adult, whole pooled (once), insulinoma (once), lung (once), lung carcinoma (once), pancreatic islet (once), pituitary (once).

FIG. 18A
FIG. 18B
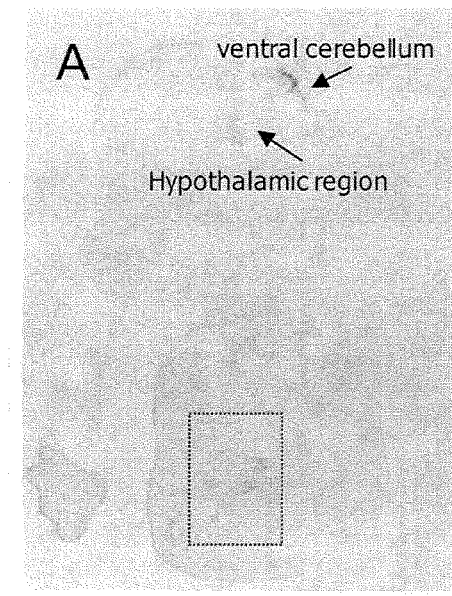
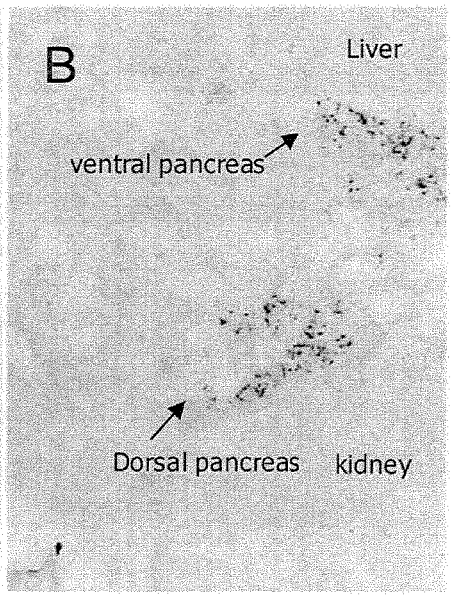
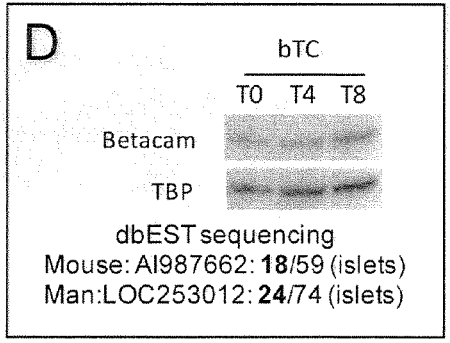
FIG. 18C
FIG. 18D

FIG. 30 pIRES2-EGFP Vector Information

PT3267-5
Catalog #6029-1

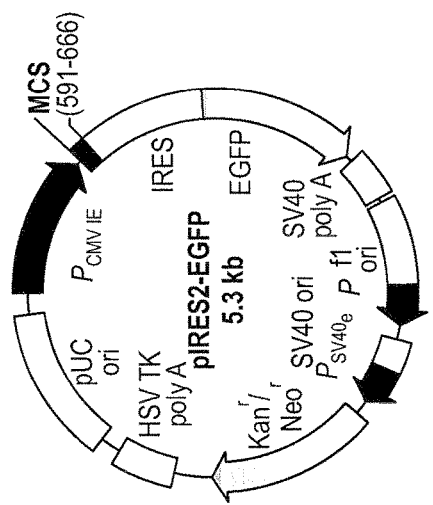

```
591         601         611         621         631         641         651         661
GCTAGCGCTACCGGACTCAGATCTCGAGCTCAAGCTTCGAATTCTGCAGTCGACGGTACCGCGGGCCCGCGGATCC...IRES
Nhe I  Eco47 III     Bgl II  Xho I     Hind III   EcoR I  Pst I  Sal I    Kpn I     Apa I     BamH I
                                Sac I                     Acc I    Asp718 I   Bsp120 I
                                Ecl136 II                                 Sac II   Xma I
                                                                                   Sma I
```

Restriction Map and Multiple Cloning Site (MCS) of pIRES2-EGFP Vector. Unique restriction sites are in bold. Note that the *Eco47 III* site has not been confirmed in the final construct.

Description:
pIRES2-EGFP contains the internal ribosome entry site (IRES; 1,2) of the encephalomyocarditis virus (ECMV) between the MCS and the enhanced green fluorescent protein (EGFP) coding region. This permits both the gene of interest (cloned into the MCS) and the EGFP gene to be translated from a single bicistronic mRNA. pIRES2-EGFP is designed for the efficient selection (by flow cytometry or other methods) of transiently transfected mammalian cells expressing EGFP and the protein of interest. This vector can also be used to express EGFP alone or to obtain stably transfected cell lines without time-consuming drug and clonal selection.

FIG. 44

PLASMID FEATURES
• hIgG1-Fc (human): The Fc region comprises the CH2 and CH3 domains of the IgG heavy chain and the hinge region. The hinge serves as a flexible spacer between the two parts of the Fc-fusion protein, allowing each part of the molecule to function independently. Human IgG1 dispays high ADCC and CDC, and is the most suitable for therapeutic use against pathogens and cancer cells.
• hEF1-HTLV prom is a composite promoter comprising the Elongation Factor-Iα (EF-Iα) core promoter[1] and the R segment and part of the U5 sequence (R -U5'[1]) of the Human T-Cell Leukemia Virus (HTLV) Type 1 Long Terminal Repeat[2]. The EF-1α promoter exhibits a strong activity and yields long lasting expression of a transgene *in vivo*. The R-U5' has been coupled to the EF-Iα core promoter to enhance stability of RNA.
• IL2 ss: The IL2 signal sequence contains 21 amino acids and share common characteristics with signal peptides of other secretory proteins. The intracellular cleavage of the IL2 signal peptide occurs after Ser20 and leads to the secretion of the antigenic protein.
• MCS: The multiple cloning site contains several restriction sites that are compatible with many other enzymes, thus facilitating cloning.
• SV40 pAn: the Simian Virus 40 late polyadenylation signal enables efficient cleavage and polyadenylation reactions resulting in high levels of steady-slate mRNA[3].
• ori: a minimal *E. coli* origin of replication to limit vector size, but with the same activity as the longer Ori.
• CMV enh / hFerL prom: This composite promoter combines the human cytomegalovirus immediate-early gene 1 enhancer and the core promoter of the human ferritin light chain gene. This ubiquitous promoter drives the expression of the Zeocin™ resistance gene in mammalian cells.
• EM2KC is a bacterial promoter that enables the constitutive expression of the antibiotic resistance gene in *E. coli*. EM2KC is located within an intron and is spliced out in mammalian cells.
• Zeo: Resistance to Zeocin™ is conferred by the *Sh ble* gene from *Streptoalloteichus hindustanus*. The same resistance gene confers selection in both mammalian cells and *E. coli*.
• BGlo pAn: The human beta-globin 3' UTR and polyadenylation sequence allows efficient arrest of the transgene transcription[4].

1. Kim DW *et al*. 1990. Use of the human elongation factor 1 alpha promoter as a versatile and efficient expression system. 91(2):217-23.
2. Takebe Y. *et al*. 1988. SR alpha promoter: an efficient and versatile mammalian cDNA expression system composed of the simian virus 40 early promoter and the R-U5 segment of human T-cell leukemia virus type 1 long terminal repeat. Mol Cell Biol 8(1):466-72.
3. Carswell S. & Alwine JC. 1989. Efficiency of utilization of the simian virus 40 late polyadenylation site: effects of upstream sequences. Mol Cell Biol. 9(10)4248-58.
4. Yu J. & Russell JE. 2001. Structural and functional analysis of an mRNP complex that mediates the high stability of human beta globin mRNA. Mol Cell Bio1 21(17):5879-88.

FIG. 46 cont.

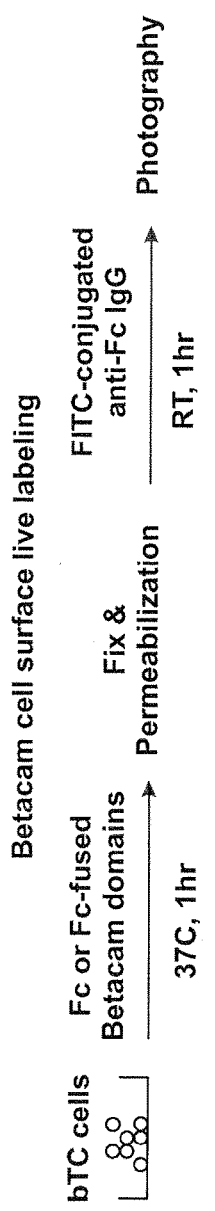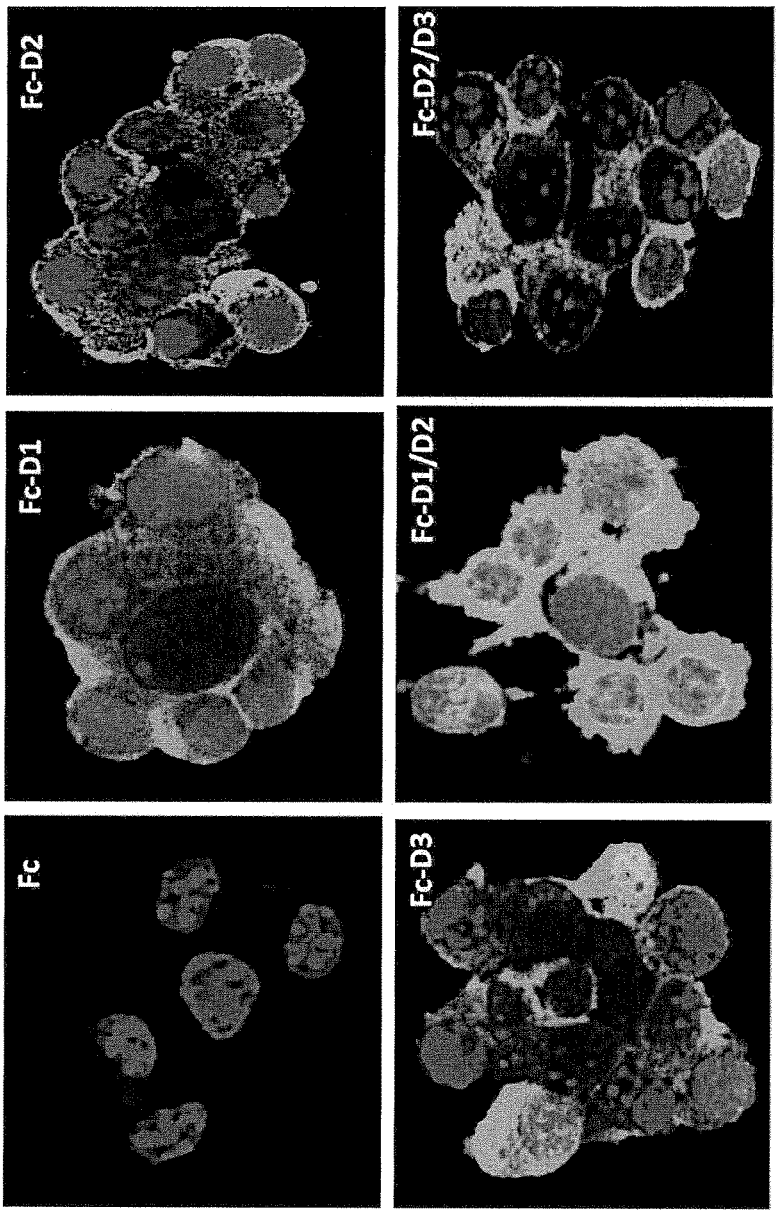
FIG. 56

**BetacamV5His Transfected Att-20 Cells
Clone 12E**
Clone 12E 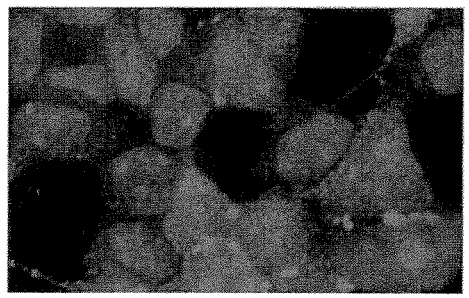  wt cells 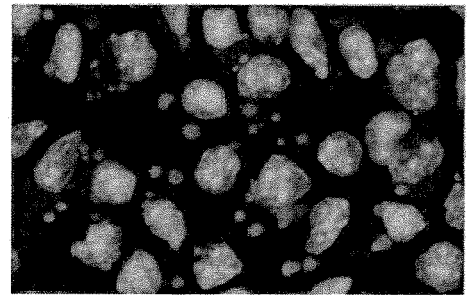
1° mouse anti-V5
2° Goat anti Mouse Cy3
FIG. 77
Immunohistochemistry of Stably transfected Att-20-BetacamV5
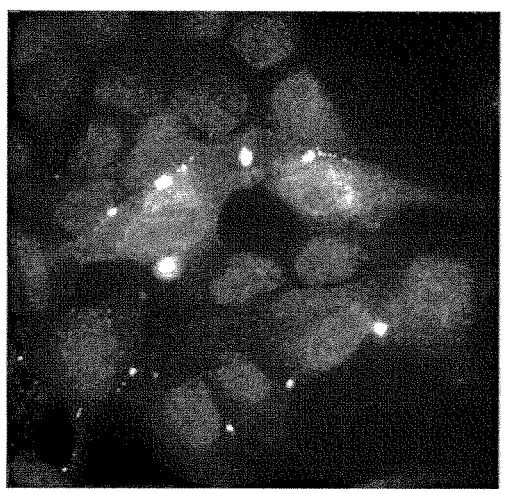 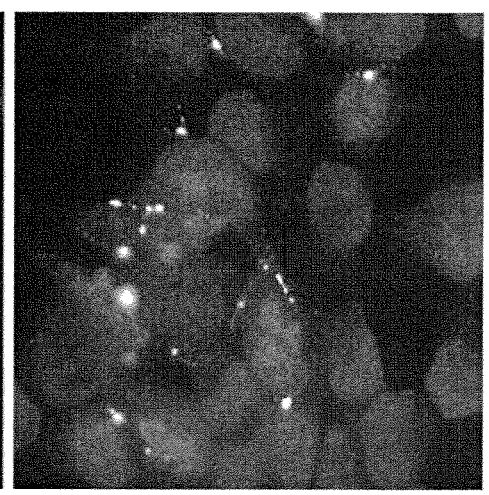
clone 12E Att-20-BetacamV5
FIG. 78

```
GGGCTGAAGGTGACAGTGCCATCACACACTGTCCATGGGCGTCAGAGGTCAGGCCCTCTACCGTCCACTATGGCTTCCACACTCCAGCATCCAGACATCCAGATCA
TATGGCTATTTGAGAGACCCCACACCAATGCCCAAATACTTGGGCTCTGTGAATAAGTCTGTGGTTCCTGACTTGAATACCAACACAAGTTCACCATGATGCCACC
CAATGCATCTCTGCTTATCAACCCACTGCAGTTCCCTGATGAAGGCAATTACATCGTGAAGGTCAACATTCAGGGAACTCTATCTGCCAGTCAGAAGATACAA
GTCACGGTTGATGATCCTGTCACAAAGGCCAGTGGTGCAGATTCATCCTCCCCTGGGCTGTGAGTATGTGGGAACATGACCTGACATGCCATGCCTTCATATTGCTCCAGTAACCAAGGA
CTCGGCTAGCTTACCAATGGCTAAAATGGGAACCAGTCTGTCCACACCAGCCTGTCCACTACTCCCTTCATTTCTCTCCCCAAAACAATACCCTTCATATTGCTCATATTCCTCCAGTAACCAAGGA
AGACATTGGGAATTACAGCTGCCTGGTGAGGAACCCTGTCAGTGAAATGGAAATCATTATGCCCATTGATATATTATGGACCTTATGACTTCAAGTGAATTCT
GATAAAGGGCTAAAATACTAACATATATCATTAAGCATGGGCCTCGCTTGTTGACCTTGGAGAGGCCATCCTATTTGATTGTTCTGCTGATTCTCATCCCCCAACACCTACTCCTGATTAGGA
GGACTGACAATACTACATATATCATTAAGCATGGGCCTCGCTTGTTGACCTTGGAGAGGCCATCCTATTTGATTGTTCTGCTGATTCTCATCCCCCAACACCTACTCCTGATTAGGA
AACCGGCAGGCAAGATGAAACTCATTCACAGTTATCATCACTTCCACAGTTATCATCACTTCCGTAGGACTGGACTGGACTGTGCACAGAAGGAAAGGAAAATCATTGTCA
```

FIG. 82

Amino acid sequence of pGEX-4T3-Betacam33-80.

Highlighted in yellow is GST and in green is Betacam.

METHOD FOR DETECTING AND PURIFYING PANCREATIC BETA CELLS

RELATED APPLICATIONS

This application is a continuation of U.S. application Ser. No. 14/579,578 filed on Dec. 22, 2014, which is a continuation of U.S. application Ser. No. 13/128,181 filed on Nov. 5, 2009 which is the U.S. National Stage of International Application No. PCT/US2009/063417, filed Nov. 5, 2009, which designates the U.S., published in English, and claims the benefit of U.S. Provisional Application No. 61/198,763, filed Nov. 7, 2008. The entire teachings of the above applications are incorporated herein by reference.

GOVERNMENT SUPPORT

This invention was made with government support under Grant Numbers P30 DK057516 and U19 DK061248 awarded by the National Institutes of Health. The government has certain rights in the invention.

INCORPORATION BY REFERENCE OF MATERIAL ON COMPACT DISK

This application incorporates by reference the Sequence Listing contained in the following ASCII text file being submitted concurrently herewith:

File name: 37861039004SEQLIST.txt; created 03/13/17, 133 KB in size.

BACKGROUND OF THE INVENTION

Diabetes is a devastating disease that is caused by either the complete destruction of the pancreatic beta-cell (type I, or juvenile diabetes) or the deterioration of the function of such cells (Type II, or adult diabetes). Many people suffer from the diseases, with an estimated number in this country of app. 17.5 million diagnosed. As a percentage of the total population, this figure is rising. Associated health costs as outlined by the American Diabetes Association are estimated at $174 billion, of which one third is accredited to a loss of national productivity. The average cost for health care expenses for a diabetic person is 2.3 fold higher than in absence of diabetes, and is currently set at $11,744/year.

Temporal curing of diabetes has been achieved. Presently, a sparse supply of organ donor cadaveric human islets can be used to transplant a limited number of type I diabetic patients. Such recipients become insulin-independent, for periods now up to several years.

The etiology of the disease is related to the role of the pancreatic insulin-producing cell, the beta cell. The normal function of the pancreatic beta cell is to control blood glucose homeostasis, and in absence of such regulation several detrimental effects are observed in patients with the disease, even in the presence of intensive treatment. Such long-term complications affect the function of the kidneys (nephropathy), eye degeneration (retinopathy), loss of extremities by amputation (vascular complications) and diabetes is furthermore associated with increased cardiovascular risk, and results in a shortened lifespan.

In both type I and type II diabetes, focus is on the life and function of the pancreatic beta cell. This cell type is unique in multiple aspects, the most important being that it is the only cell type in the body capable of producing insulin. Consequently, a loss of such cells leads to insulin dependence. Type I or type II diabetes is diagnosed at a point where the function of such cells have decreased to a level not meeting initial demand for appropriate blood glucose lowering following a meal. It is generally believed, however, that if one could assess beta cell mass, and function prior to diagnosis, intervention strategies may be applied to circumvent the further demise of the failing cell population. For type I diabetes, current focus is on identifying the presence of circulating anti-islet auto-antigens, as such may help identify those children that are at-risk, or are overtly pre-diabetic due to an ongoing immune destruction. For type II diabetes, current focus is on establishing clinical testing, such as the use of oral glucose tolerance testing (OGTT), now suggested as a standard evaluation of males approaching 50 years of age. The result of an OGTT can help identify individuals that are at the pre-diabetic point, and interventions can be performed, mostly including counseling related to the benefits of lifestyle changes involving increased exercise, caloric intake, and balancing diets. In both cases, non-invasive imaging of the beta cell mass, if aided by reagents capable of marking the cell population, could substantially improve the diagnostic toolbox.

Presently, there is no method by which beta cell mass can be assessed in a non-biased manner non-invasively in human subjects. Accurate measurement of beta cell mass in pancreas is dependent on biopsy analysis followed by histological assessment of beta cell numbers and morphometric counting; in most cases obtained post-mortem through autopsy material. The amount of donor material reflecting on progressive disease development is therefore significantly limited, and kinetic studies on disease progression in an individual are impossible using this technology. Another important aspect related to a growing need for beta cell mass assessment is following islet transplantation. Although only performed in few individuals, this technology is becoming more widespread. It is carried out by isolating an islet-enriched cellular fraction from a human donor post-mortem, which is subsequently transplanted through portal vein injection into a HLA-matched type I diabetic recipient. Following transplantation, there is generally no means to assess the viability and health of the grafted islet cells, as these are inaccessible in the recipient's liver vascular system. A general assessment of graft function is determined by measurements of insulin-dependency, gradually lowering injected insulin as cells in the graft become capable of providing insulin. Often, multiple transplants are required, empirically defined based on outcome. There is no unbiased assessment of the actual viable islet cell mass that engrafts within the liver, and it cannot be followed. It should be mentioned that given the local production of insulin by such grafted islets, a local adipogenic effect occurs within the liver, and such changes may be measured non-invasively by MRI. However, in the best case, this only provides a read out of grafting efficiency; it is not able to accurately measure numbers/mass of viable grafted islet cells.

Thus, a need exists for methods of assessing beta cell mass and/or activity non-invasively.

SUMMARY OF THE INVENTION

The invention is based, in part, on the discovery that a polypeptide, referred to herein as Betacam, is selectively expressed on the surface of pancreatic islet cells. Thus, in one aspect, the invention is directed to compositions comprising Betacam or that can be used to detect Betacam. In another aspect, the invention provides methods of detecting (e.g., non-invasively) pancreatic beta cells from a mammalian cell source. Another aspect of the invention is directed to cellular purification of pancreatic beta cells from a heterogeneous cell source of multiple kinds. In another aspect, the invention provides methods of identifying agents that modulate activity of Betacam. In yet another aspect, the invention provides for improved treatment and diagnosis of diabetes.

Accordingly, in particular aspects, the invention is directed to an isolated nucleic acid that encodes an amino acid sequence of Betcam wherein the amino acid sequence comprises, consists essentially of, or consists of amino acids 31 through 462 of SEQ ID NO: 1, amino acids 19 through 450 of SEQ ID NO:2 or amino acids 30 through 463 of SEQ ID NO: 3. In other aspects the invention is directed to an isolated nucleic acid that encodes an amino acid sequence of an extracellular domain of Betacam, wherein the amino acid sequence comprises, consists essentially of, or consists of SEQ ID NO: 14, SEQ ID NO: 15, an amino acid sequence that has at least 50% identity to SEQ ID NO: 14 or an amino acid sequence that has at least 50% identity to SEQ ID NO: 15. In a particular aspect, the invention is directed to an isolated nucleic acid comprising, consisting essentially of, or consisting of SEQ ID NO: 26.

In another aspect, the invention is directed to an isolated polypeptide that comprises, consists essentially of, or consists of amino acids 31 through 462 of SEQ ID NO: 1, amino acids 19 through 450 of SEQ ID NO:2 or amino acids 30 through 463 of SEQ ID NO: 3. In another aspect, the invention is directed to an isolated polypeptide that comprises, consists essentially of, or consists of SEQ ID NO: 14, SEQ ID NO: 15, an amino acid sequence that has at least 50% identity to SEQ ID NO: 14 or an amino acid sequence that has at least 50% identity to SEQ ID NO: 15.

Also included in the invention are antibodies that have binding specificity for the Betacam polypeptide.

Another aspect of the invention is directed to a method of detecting beta cells in a mixture of pancreatic cells comprising detecting the presence of a polypeptide on the surface of the cells, wherein the polypeptide comprises SEQ ID NO: 14, SEQ ID NO: 15, an amino acid sequence that has at least 50% identity to SEQ ID NO: 14 or an amino acid sequence that has at least 50% identity to SEQ ID NO: 15, and detection of expression of the polypeptide on the surface of the cells indicates that the cells are pancreatic beta cells. The method can further comprise isolating the pancreatic beta cells from the mixture of cells.

Another aspect of the invention is directed to a method of detecting pancreatic beta cells in an individual in need thereof, comprising administering to the individual an agent that detects the presence of a polypeptide on the surface of the pancreatic beta cells, wherein the polypeptide comprises SEQ ID NO: 14, SEQ ID NO: 15, an amino acid sequence that has at least 50% identity to SEQ ID NO: 14 or an amino acid sequence that has at least 50% identity to SEQ ID NO: 15. This method can be used, for example, to determine whether an individual is at risk of developing diabetes, or to assess the beta cells of an individual that has diabetes (e.g., to determine the appropriate treatment needed for a diabetic patient or to assess the efficacy of a diabetic patient's existing treatment). In one embodiment, the individual has Type I diabetes, and in another embodiment, the individual has Type II diabetes. In yet another embodiment, the individual has had an islet cell transplantation.

In another aspect, the invention is directed to a method of isolating pancreatic beta cells from a mixture of pancreatic cells comprising contacting the mixture with a reagent that specifically binds to a polypeptide present on the surface of pancreatic beta cells, wherein the polypeptide comprises SEQ ID NO: 14, SEQ ID NO: 15, an amino acid sequence that has at least 50% identity to SEQ ID NO: 14 or an amino acid sequence that has at least 50% identity to SEQ ID NO: 15, thereby producing a combination. The combination is maintained under conditions in which the reagent binds to the polypeptide present on the surface of the pancreatic beta cells, thereby producing a complex of pancreatic beta cells bound to the reagent; and the complex is separated from the combination, thereby isolating pancreatic beta cells from the mixture of pancreatic cells.

In yet another aspect, the invention is a method of identifying an agent that modulates (e.g., inhibits; enhances) the biological activity of betacam comprising contacting a composition comprising a polypeptide, wherein the polypeptide has an amino acid sequence comprising SEQ ID NO: 14, SEQ ID NO: 15, an amino acid sequence that has at least 50% identity to SEQ ID NO: 14 or an amino acid sequence that has at least 50% identity to SEQ ID NO: 15 with an agent to be assessed. The biological activity of the polypeptide in the presence of the agent is measured and compared to a suitable control, wherein if the polypeptide modulates the activity of the polypeptide in the presence of the agent compared to the control, then the agent modulates the biological activity of betacam. In a particular embodiment, the composition is one or more pancreatic beta cells.

BRIEF DESCRIPTION OF THE DRAWINGS

FIG. 1 is a copy of the .html output page from NCBI Unigene number Mm.206911, for the mouse gene locus AI987662.

FIG. 2 is the output page for human CCDS locus 253012, listing the exon/intron structure of the human gene, isoform 2.

FIG. 3 shows the nucleotide sequence (SEQ ID NO: 25) and amino acid (450 amino acids) sequence (SEQ ID NO: 2) of human Betacam, isoform 2.

FIG. 5 is the html output page for human LOC253012, isoform 1 (SEQ ID NO: 1).

FIG. 6 is the html output page for human LOC253012, isoform 2 (SEQ ID NO: 2).

FIG. 16 is an extraction of GeneChip expression data for mouse Betacam. Expression levels are based on the Affymetrix MOE430v2 platform, similarly normalized (MAS5.0) and similarly scaled (500) expression data. Data are shown for Adult islets, isolated Phogrin-EGFP cells, corresponding to pancreatic beta cells, insulinoma (bTC), glucagonoma (aTC), embryonic pancreas and late stage embryonic pancreas obtained from an endocrine-cell devoid organ: Ngn3 KO. Supportive data based on EST-expression is shown below: ACEView, lists that the human gene, LOC253012 has been sequenced a total of 15 times from purified pancreatic islets.

FIG. 18A is derived from Genepaint. This is a freely available data resource based in in situ hybridization. Betacam is expressed at E14.5 in the CNS ventral cerebellum, and hypothalamic region. Outside the brain, expression is detected in both dorsal and ventral pancreas, but not elsewhere. FIG. 18B is a magnified view of FIG. 18A. The speckled expression patterns correspond to developing endocrine cells in the organ. FIG. 18C is an in situ hybridization. Expression is detected in the non-exocrine regions of the E18.5 mouse pancreas. FIG. 18D is a multiplex RT-PCR low cycle validation of Betacam expression using gene-specific primers. The gene is expressed in bTC cells. TBP is included as internal control. dbEST sequencing from NCBI Unigene lists that 18 and 24 instances of Betacam sequencing has been obtained from islets in mouse, and man, respectively.

FIG. 30 is an extraction view of the Betacam alignment sequence (cf (SEQ ID NO: 39), mm (SEQ ID NO: 40), m (SEQ ID NO: 41), hs (SEQ ID NO: 42), pt (SEQ ID NO: 43) and consensus (SEQ ID NO: 44)) in which the docking residues are highlighted.

FIG. 44 is a graphical presentation of the cloning vector pIRES2-EGFP (SEQ ID NO: 48).

FIG. 56 shows cell surface live labeling of pancreatic insulinoma cells (bTC) with Fc-Betacam versions as outlined on the figure. The experimental conditions are shown at the top.

FIG. 77 shows immunofluorescence analysis of stably expressing Att20 cells, clone 12E, imaged for expression of V5-tagged Betacam fusion protein. Control cells are shown to the right.

FIG. 78 shows confocal immunofluorescence analysis of stably expressing Att20 cells, clone 12E, imaged for expression of V5-tagged Betacam fusion protein.

FIG. 82 shows an example of a nucleotide sequence (SEQ ID NO: 26) that encodes an extracellular domain of Betacam.

FIG. 83 shows the amino acid sequence (SEQ ID NO: 27) of PGEX-4T3-Betacam 33-80.

DETAILED DESCRIPTION OF THE INVENTION

The invention is based, in part, on the discovery that a polypeptide, referred to herein as Betacam, is selectively expressed on the surface of pancreatic islet cells. Specifically, as shown herein, expression of Betacam occurred in both normal and obese mouse pancreatic islet cells and was observed throughout the course of mouse pancreatic development. Expression of Betacam in human islets was validated through EST-sequencing, and the Betacam mRNA was detected 15 times through random sequencing of human islet cDNA.

Figure 1:
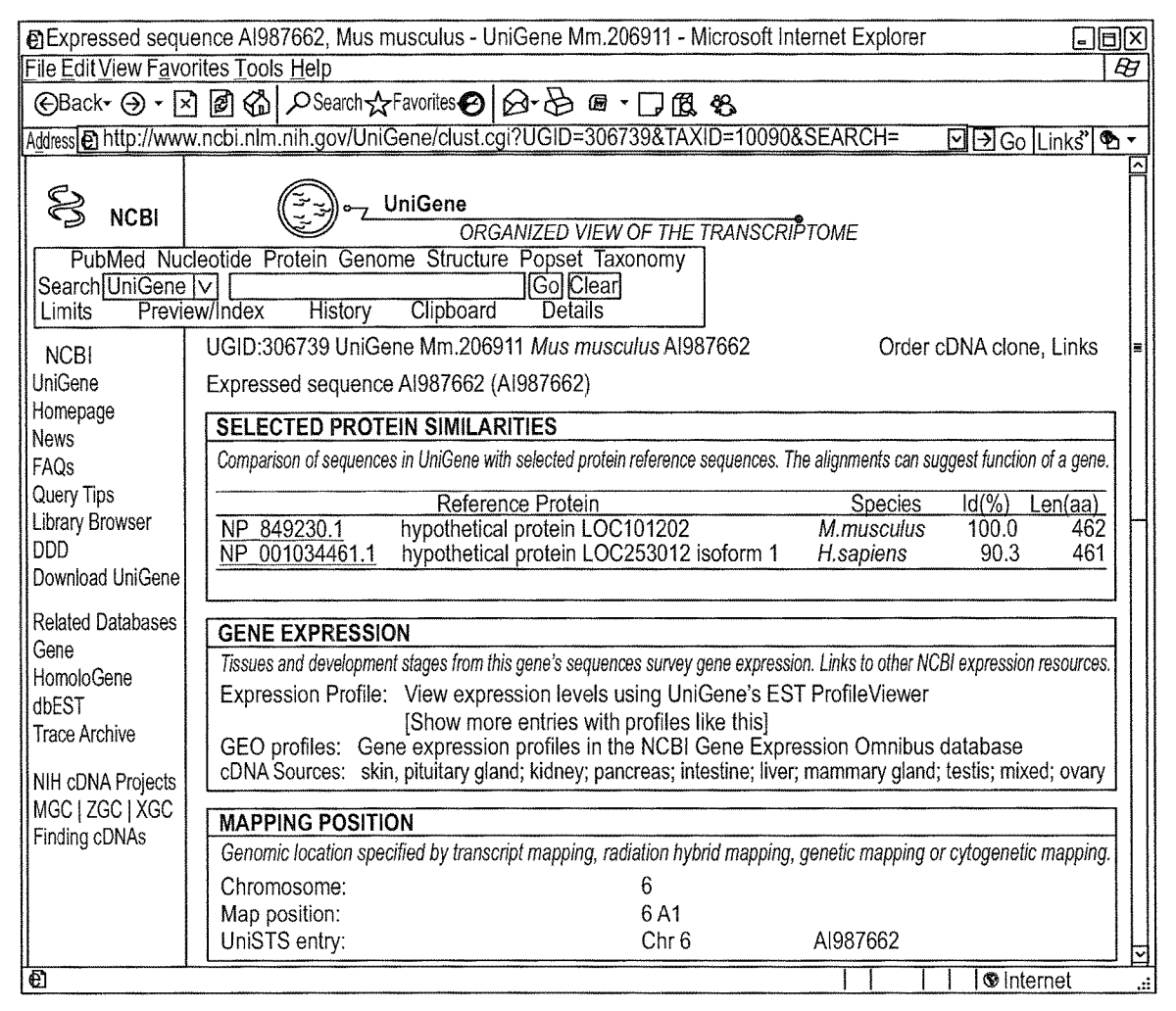
Figure 4:
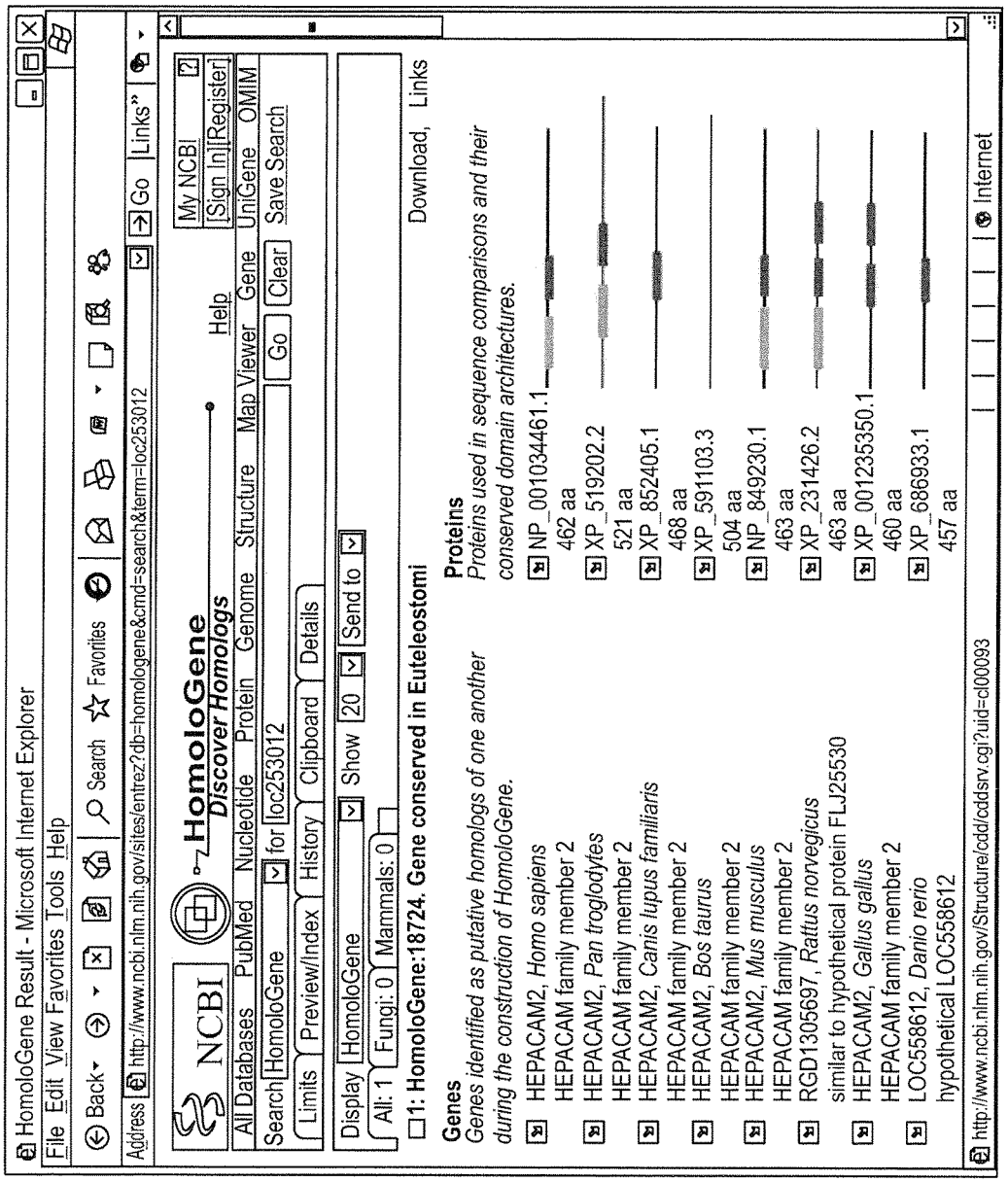
FIG. 4 is a copy of the .html output page from NCBI HomoloGene 18724, for the human locus LOC253012. The listed genes are the closest homologues (i.e. orthologues) in multiple species.

The inventors named the gene locus in mouse, corresponding to Unigene Mm.206911, FIG. 1, Betacam. The encoded protein was henceforth named Betacam. Its NCBI gene ID is 101202. The current name of the gene as used by NCBI is "expressed sequence AI987662" (FIG. 1). The inventors name the gene locus LOC253012 in humans, its GeneID: 253012 (FIG. 2 and FIG. 3), and its corresponding to UniGene Hs.443169, Betacam as well. The inventors name the protein encoded by the human GeneID 253012 Betacam. These Betacam genes are part of a homologous gene group, conserved during evolution, and NCBI refers to this group as HomoloGene 18724 (FIG. 4). This group was recently named HEPACAM2 based on its weak similarity to the HEPACAM orthologous group. Betacam is a conserved gene between vertebrate species to the extent that it represents a single orthologous group. The closest immediate neighbor is represented by Homologene group 17652, HEPACAM, which displays <40% amino acid identity to the Betacam group.

The naming selected is one of convenience; none of the above genes/proteins are named based on previous knowledge of function, or expression in the liver. The arbitrary selection of gene/protein name Betacam is based on information provided within, where the inventors show that the protein is a member of a cell adhesion family group (-cam extension), and selectively expressed in pancreatic beta cells (beta-). It is believed that no other existing and described cell surface marker is known with a similar specificity of expression, as that displayed by the Betacam-encoded protein Betacam.

Betacam in humans exists in two alternative forms, isoform 1 (FIG. 5), and isoform 2 (FIG. 6). The difference between these forms lies in alternative exon-1 usage, explained by differential promoter usage. The predicted sequence of either form of the encoded proteins differs in the amino terminal sequence. Translation of isoform 1 gives a protein of 462 amino acids [SEQ ID NO: 1], translation of isoform 2 gives a protein of 450 amino acids [SEQ ID NO: 2].

Figure 19:
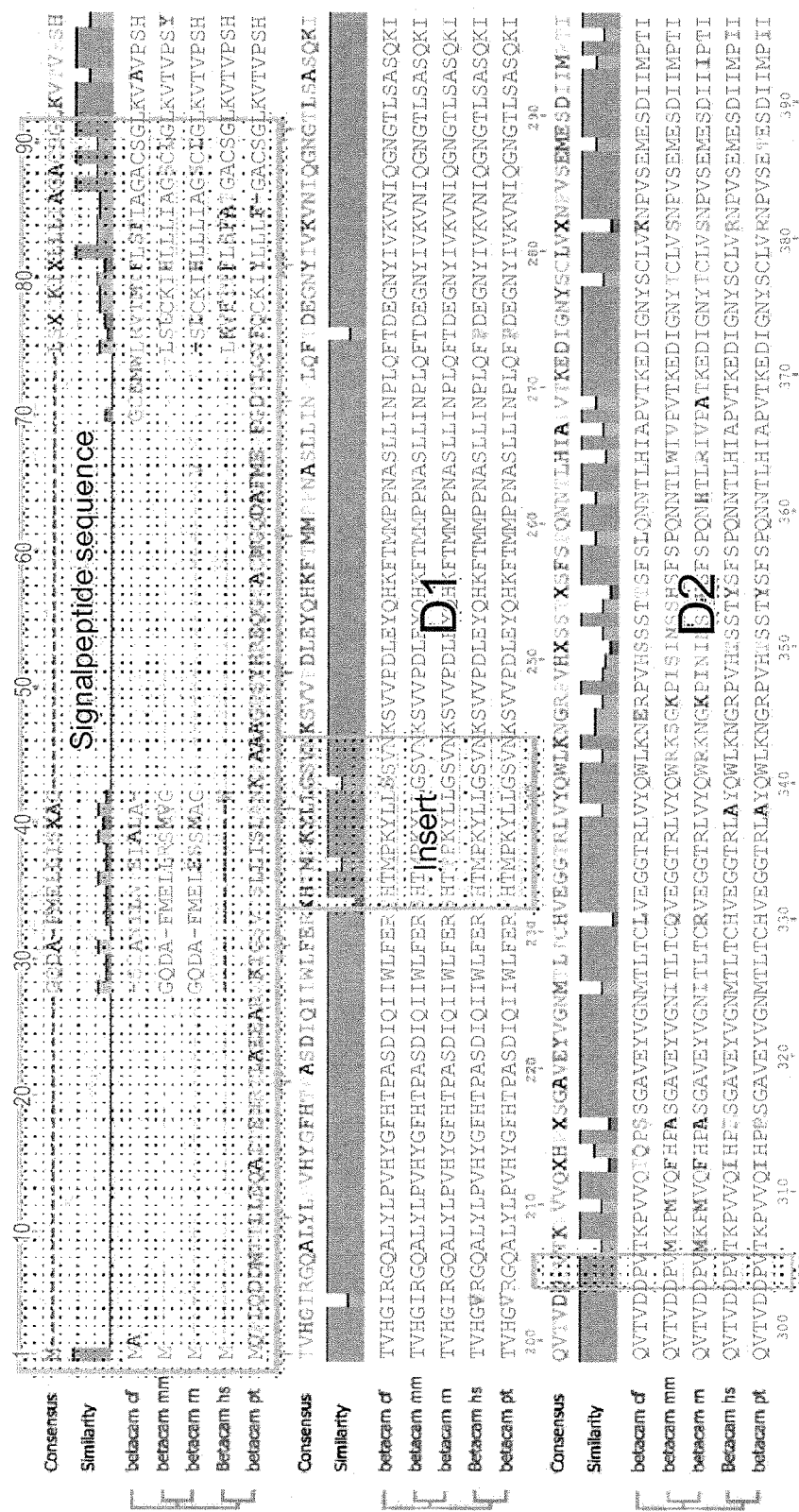
FIG. 19 is a multiple alignment of Betacam proteins in 5 selected species (cf (SEQ ID NO: 33), mm (SEQ ID NO: 34), m (SEQ ID NO: 35), hs (SEQ ID NO: 36), pt (SEQ ID NO: 37) and consensus (SEQ ID NO: 38)). Nomenclature assigned on the alignment for signal peptide, D1, D2, D3, TM domain, cytoplasmic domain. Proline 146 links D1-D2, Tyrosine 239 links D2-D3, the terminal end of D3 is highlighted by isoleucine 335. The "insert" sequence in D1 is a 13 amino acid stretch that is not present in NCAM, against which the protein structural fold-comparisons are done in the following.
Figure 19:
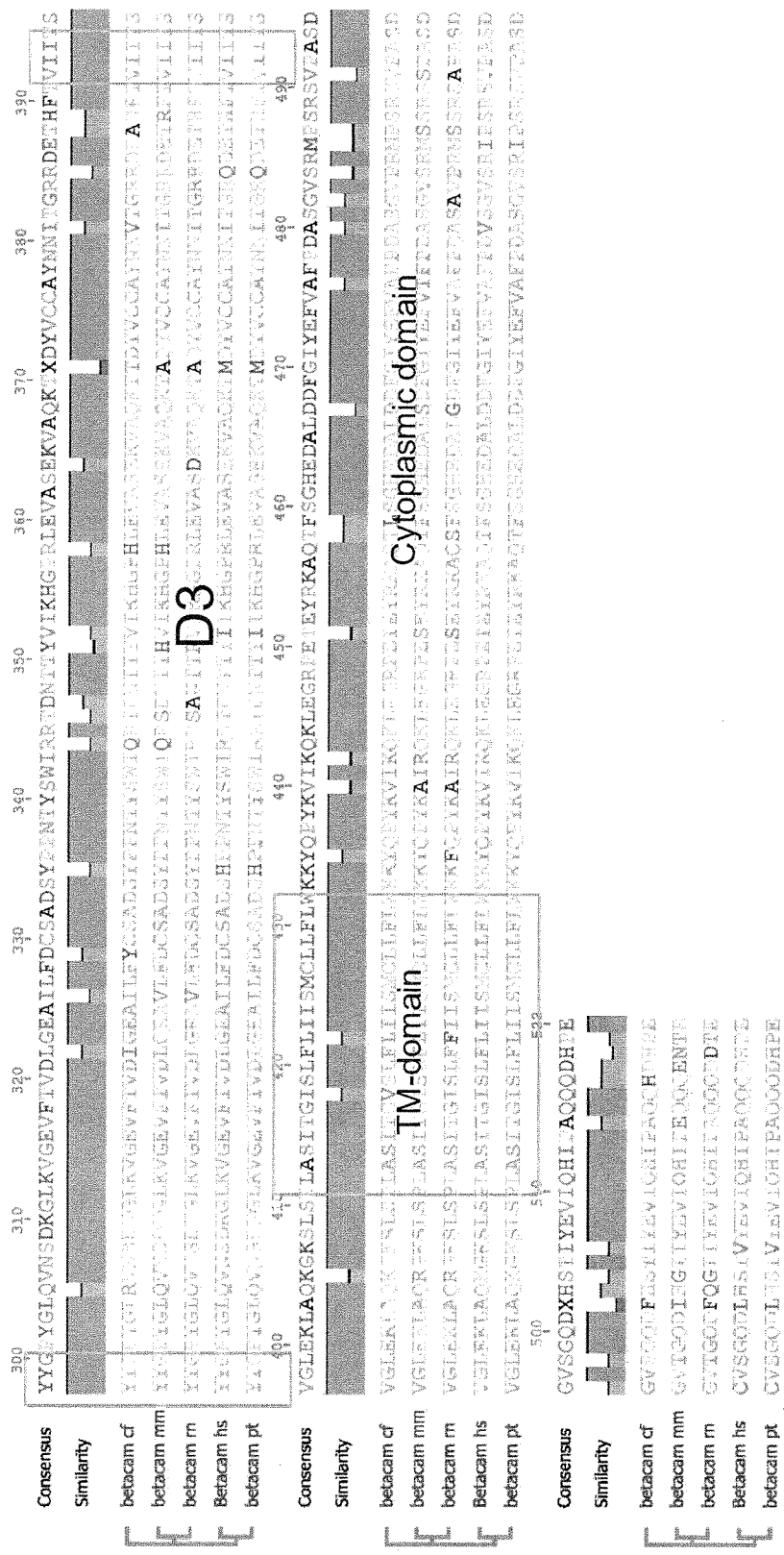

Accordingly, particular aspects of the invention are directed to a composition (e.g., a cell adhesion modulating agent; pharmaceutical compositions) that comprises a select amino-acid sequence derived from proteins encoded by the group HomoloGene:18724, as shown in FIG. 2, or other species orthologues to HomoloGene group 18724, which comprise >50% amino acid identity over the extracellular domain, as shown in FIG. 19. In another aspect the composition comprises select amino acids in the extracellular, but not trans-membrane, or intracellular, portion of such proteins, examples of which are shown in SEQ ID NO: 14 and SEQ ID NO: 15. In yet another aspect, the invention is directed to a composition comprising amino acids derived from the D1-D2-D3 region of a Betacam protein, not less than 6 amino acids longs, and no longer than 330 amino acids. In a particular embodiment, the composition comprises an N-terminal acetyl group. Other aspects of the invention are directed to a variety of uses of Betacam.

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, Methods of Enzymology, Vol. 194, Guthrie et al., eds., Cold Spring Harbor Laboratory Press (1990); Molecular Cloning: A Laboratory Manual, second edition (Sambrook et al., 1989) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2001); PCR: The Polymerase Chain Reaction, (Mullis et al., eds., 1994); Harlow and Lane (1988) Antibodies, A Laboratory Manual, Cold Spring Harbor Publications, New York; Harlow and Lane (1999) Using Antibodies: A Laboratory Manual Cold Spring Harbor Laboratory Press, Cold Spring Harbor, N.Y. (jointly referred to herein as "Harlow and Lane"), Beaucage et al. eds., Current Protocols in Nucleic Acid Chemistry John Wiley & Sons, Inc., New York, 2000).

In accordance with the present invention, an isolated polynucleotide (also referred to as an isolated nucleic acid) is a nucleic acid molecule that has been removed from its natural milieu (e.g., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. The polynucleotides useful in the present invention are typically a portion of a gene (sense or non-sense strand) of the present invention that is suitable for use as a hybridization probe or PCR primer for the identification of a full-length gene (or portion thereof) in a given sample, or that is suitable for encoding a Betacam protein or fragment thereof. An isolated nucleic acid molecule can include a gene or a portion of a gene (e.g., the regulatory region or promoter), for example, to produce a reporter construct or a recombinant protein. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In one embodiment, an isolated nucleic acid molecule of the present invention is produced using recombinant DNA technology (e.g., polymerase chain reaction (PCR) amplification, cloning) or chemical synthesis.

Another aspect of the invention are orthologous nucleic acids (e.g., orthologous gene). Orthologous nucleic acids (e.g., genes) are sequences or genes in different organisms that are direct evolutionary counterparts; that is, they are related by descent from a common ancestor. Orthologous nucleic acids normally have the same cellular function. Select members of the orthologous group of Betacam nucleic acids are displayed in FIG. 8. Through the animal kingdom, it is expected to most, if not all, species contain a member of the orthologous nucleic acid group for Betacam. Such nucleic acid members are in this invention considered as being part of the orthologous nucleic acid group of Betacam.

The minimum size of a nucleic acid molecule or polynucleotide of the present invention is a size sufficient to encode a protein having a desired biological activity, such as sufficient to form a probe or oligonucleotide primer that is capable of forming a stable hybrid with the complementary sequence of a nucleic acid molecule encoding the full length (e.g., natural) protein (e.g., under moderate, high or very high stringency conditions) or a biologically active fragment thereof, or to otherwise be used as a target or agent in an assay or in any therapeutic method discussed herein. If the polynucleotide is an oligonucleotide probe or primer, the size of the polynucleotide can be dependent on nucleic acid composition and percent homology or identity between the nucleic acid molecule and a complementary sequence as well as upon hybridization conditions per se (e.g., temperature, salt concentration, and formamide concentration). The minimum size of a polynucleotide that is used as an oligonucleotide probe or primer is at least about 5 nucleotides in length, and preferably ranges from about 5 to about 50 or about 500 nucleotides or greater (1000, 2000, etc.), including any length in between, in whole number increments (i.e., 5, 6, 7, 8, 9, 10, . . . 33, 34, . . . 256, 257, . . . 500 . . . 1000 . . . ), and more preferably from about 10 to about 40 nucleotides, and most preferably from about 15 to about 40 nucleotides in length. In one aspect, the oligonucleotide primer or probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a protein-encoding sequence or a nucleic acid sequence encoding a full-length protein. According to the present invention, an oligonucleotide probe (or simply, probe) is a nucleic acid molecule which most typically ranges in size from about 8 nucleotides to several hundred nucleotides in length. PCR primers are also nucleic acid sequences, although PCR primers are typically oligonucleotides of fairly short length that are used in polymerase chain reactions. PCR primers and hybridization probes can readily be developed and produced by those of skill in the art, using sequence information from the target sequence. (See, for example, Sambrook et al., supra or "Molecular Biotechnology," Second Edition, by Glick and Pasternak, ASM Press, Washington D.C., 1998, pp. 555-590). Knowing the nucleic acid sequences of certain nucleic acid molecules of the present invention allows one skilled in the art to, for example, (a) make copies of those nucleic acid molecules and/or (b) obtain nucleic acid molecules including at least a portion of such nucleic acid molecules (e.g., nucleic acid molecules including full-length genes, full-length coding regions, regulatory control sequences, truncated coding regions). Such nucleic acid molecules can be obtained in a variety of ways including traditional cloning techniques using oligonucleotide probes to screen appropriate libraries or DNA and PCR amplification of appropriate libraries or DNA using oligonucleotide primers. Preferred libraries to screen or from which to amplify nucleic acid molecule include mammalian genomic DNA libraries. Techniques to clone and amplify genes are disclosed, for example, in Sambrook et al., ibid.

In particular aspects, the invention is directed to an isolated nucleic acid that encodes an amino acid sequence of Betcam wherein the amino acid sequence comprises, consists essentially of, or consists of amino acids 31 through 462 of SEQ ID NO: 1, amino acids 19 through 450 of SEQ ID NO: 2 or amino acids 30 through 463 of SEQ ID NO: 3. In other aspects the invention is directed to an isolated nucleic acid that encodes an amino acid sequence of an extracellular domain of Betacam, wherein the amino acid sequence comprises, consists essentially of, or consists of SEQ ID NO: 14, SEQ ID NO: 15, an amino acid sequence that has at least 50% identity to SEQ ID NO: 14 or an amino acid sequence that has at least 50% identity to SEQ ID NO: 15. In a particular aspect, the invention is directed to an isolated nucleic acid comprising, consisting essentially of, or consisting of SEQ ID NO: 26.

Other aspects of the invention are directed to RNA molecules such as antisnese and interfering RNA molecules specific for Betacam. As used herein, an anti-sense nucleic acid molecule is defined as an isolated nucleic acid molecule that reduces expression of a protein by hybridizing under high stringency conditions to a gene encoding the protein. Such a nucleic acid molecule is sufficiently similar to the gene encoding the protein that the molecule is capable of hybridizing under high stringency conditions to the coding or complementary strand of the gene or RNA encoding the natural protein. RNA interference (RNAi) is a process whereby double stranded RNA, and in mammalian systems, short interfering RNA (siRNA), is used to inhibit or silence expression of complementary genes. In the target cell, siRNA are unwound and associate with an RNA induced silencing complex (RISC), which is then guided to the mRNA sequences that are complementary to the siRNA, whereby the RISC cleaves the mRNA.

A recombinant nucleic acid molecule is a molecule that can include at least one of any nucleic acid sequence encoding a Betacam protein or other protein described herein. In one embodiment, a recombinant nucleic acid molecule is operatively linked to at least one expression control sequence capable of effectively regulating expression of the nucleic acid molecule(s) in a host cell. Preferably, a recombinant nucleic acid molecule is produced using recombinant DNA technology (e.g., polymerase chain reaction (PCR) amplification, cloning).

A recombinant nucleic acid molecule includes a recombinant vector, which is any nucleic acid sequence, typically a heterologous sequence, which is operatively linked to the isolated nucleic acid molecule encoding a protein (e.g., Betacam), which is capable of enabling recombinant production of the protein, or which is capable of delivering the nucleic acid molecule into a host cell in vitro, ex vivo or in vivo, according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules. Recombinant vectors are preferably used in the expression of nucleic acid molecules, and can also be referred to as expression vectors. Preferred recombinant vectors are capable of being expressed in a transfected host cell, and particularly, in a transfected mammalian host cell in vivo.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. The phrase "operatively linked" refers to linking a nucleic acid molecule to an expression control sequence in a manner such that the molecule is expressed when transfected (i.e., transformed, transduced or transfected) into a host cell. Transcription control sequences are sequences that control the initiation, elongation, and termination of transcription. Particularly important transcription control sequences are those that control transcription initiation, such as promoter, enhancer, operator and repressor sequences. Suitable transcription control sequences include any transcription control sequence that can function in a host cell according to the present invention. A variety of suitable transcription control sequences are known to those skilled in the art. Particularly preferred transcription control sequences include inducible promoters, cell-specific promoters, tissue specific promoters (e.g., insulin or Pdx1 promoters) and enhancers. Transcription control sequences of the present invention can also include naturally occurring transcription control sequences naturally associated with the protein to be expressed prior to isolation. In one embodiment, a transcription control sequence includes an inducible promoter.

One type of recombinant vector useful in a recombinant nucleic acid molecule of the present invention is a recombinant viral vector. Such a vector includes a recombinant nucleic acid sequence encoding a Betacam protein of the present invention that is packaged in a viral coat that can be expressed in a host cell in an animal or ex vivo after administration. A number of recombinant viral vectors can be used, including, but not limited to, those based on alphaviruses, poxviruses, adenoviruses, herpesviruses, lentiviruses, adeno-associated viruses and retroviruses. Viral vectors suitable for gene delivery are well known in the art and can be selected by the skilled artisan for use in the present invention. A detailed discussion of current viral vectors is provided in "Molecular Biotechnology," Second Edition, by Glick and Pasternak, ASM Press, Washington D.C., 1998, pp. 555-590, the entirety of which is incorporated herein by reference. Suitable host cells to transfect with a recombinant nucleic acid molecule according to the present invention include any microbial, insect, or animal cell that can be transfected. Host cells can be either untransfected cells or cells that are already transfected with at least one nucleic acid molecule.

According to the present invention, the term "transfection" is used to refer to any method by which an exogenous nucleic acid molecule (i.e., a recombinant nucleic acid molecule) can be inserted into the cell. The term "transformation" can be used interchangeably with the term "transfection" when such term is used to refer to the introduction of nucleic acid molecules into microbial cells, such as bacteria and yeast. In microbial systems, the term "transformation" is used to describe an inherited change due to the acquisition of exogenous nucleic acids by the microorganism and is essentially synonymous with the term "transfection". However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass both transfection of animal cells and transformation of microbial cells, to the extent that the terms pertain to the introduction of exogenous nucleic acids into a cell. Therefore, transfection techniques include, but are not limited to, transformation, electroporation, microinjection, lipofection, adsorption, infection and protoplast fusion.

As used herein, reference to an isolated protein, also referred to herein an isolated polypeptide, in the present invention, including a Betacam protein, is a protein that has been removed from its natural milieu (i.e., that has been subject to human manipulation), and includes full-length proteins, fusion or chimeric proteins, or any fragment or homologue of such a protein. Such a protein can include, but is not limited to, purified proteins, partially purified proteins, recombinantly produced proteins, synthetically produced proteins, membrane-bound proteins, proteins complexed with lipids, soluble proteins and isolated proteins associated with other proteins. As such, "isolated" does not reflect the extent to which the protein has been purified. Preferably, an isolated protein of the present invention is produced recombinantly. In addition, and again by way of example, a "human Betacam protein" or a protein "derived from" a human Betacam protein refers to a Betacam protein (generally including a homologue of a naturally occurring Betacam protein) from a human (*Homo sapiens*) or to a Betacam protein that has been otherwise produced from the knowledge of the structure (e.g., sequence) and perhaps the function of a naturally occurring Betacam protein from *Homo sapiens*. In other words, a human Betacam protein includes any Betacam protein that has substantially similar structure and function of a naturally occurring Betacam protein from *Homo sapiens* or that is a biologically active (i.e., has biological activity) homologue of a naturally occurring Betacam protein from *Homo sapiens* as described in detail herein. As such, a Betacam protein can include purified, partially purified, recombinant and synthetic proteins. Another aspect of the invention is directed to modified or mutated Betacam polypeptides. According to the present invention, the terms "modified", "modification", "mutated" and "mutation" can be used interchangeably, particularly with regard to the modifications/mutations to the amino acid sequence of protein (or nucleic acid sequences) described herein.

In particular aspects, the invention is directed to an isolated polypeptide that comprises, consists essentially of, or consists of amino acids 31 through 462 of SEQ ID NO: 1, amino acids 19 through 450 of SEQ ID NO: 2 or amino acids 30 through 463 of SEQ ID NO: 3. In another aspect, the invention is directed to an isolated polypeptide that comprises, consists essentially of, or consists of SEQ ID NO: 14, SEQ ID NO: 15, an amino acid sequence that has at least 50% identity to SEQ ID NO: 14 or an amino acid sequence that has at least 50% identity to SEQ ID NO: 15.

Fusion proteins and chimeric proteins are also encompassed by the invention. A fusion protein is a protein produced by linking (typically recombinantly, although chemical and other types of linkage are encompassed by the invention) of a protein or peptide of the invention (e.g., Betacam or a variant or fragment thereof) to a fusion partner (fusion segment). Suitable fusion partners for use with the present invention include, but are not limited to, fusion partners that can: enhance a protein's stability; enhance or permit secretion of a protein from the host cell; provide other biological activity; and/or assist purification of a protein from a host cell (e.g., by affinity chromatography or affinity pull-down). A suitable fusion partner can be a protein or domain or fragment thereof of any size that has the desired function (e.g., imparts increased stability, solubility, action or activity; provides other activity; and/or simplifies purification of a protein). Fusion partners can be joined to amino and/or carboxyl termini of the protein of interest (e.g., Betacam), and can be susceptible to cleavage in order to enable straight-forward recovery of the expressed exogenous protein. A chimeric protein is similar to a fusion protein, and the terms may be used interchangeably, except that in the case of the chimeric protein, the fusion partner is most typically a second protein of interest (or a fragment thereof), such as a second protein with a desired biological activity. Accordingly, a chimeric protein may have the activity of each/both of the protein/peptide components, or a new activity resulting from the combination of protein domains.

In one preferred embodiment, proteins (including peptides and homologues) are produced using in vitro translation systems, such as systems based on reticulocyte lysate, wheat germ, yeast and bacteria. The systems preferably correctly post-translationally process the protein, e.g., by proteolysis and/or glycosylation. Products of in vitro translation systems are most typically used in the methods of the invention, although the invention is not limited to such products. As used herein, the term "homologue" or "variant" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in 1, 2, 3, 4, 5, 6, 7, 8, 9, 10, or a few more 30 amino acid side chains; changes 1, 2, 3, 4, 5, 6, 7, 8, 9, 10, or a few more amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, or substantially similar properties as compared to the naturally occurring protein or peptide. A homologue can include an agonist of a protein or an antagonist of a protein. Homologues can be the result of natural allelic variation or genetic polymorphism, or any natural mutation. A naturally occurring allelic variant or genetic polymorphism of a nucleic acid encoding a protein is a gene that occurs at essentially the same locus (or loci) in the genome as the gene which encodes such protein, but which, due to natural variations, has a similar but not identical sequence. Allelic variants typically encode proteins having similar activity to that of the protein encoded by the gene to which they are being compared. A single nucleotide polymorphism (SNP) is a DNA sequence variation occurring when a single nucleotide in the genome differs between members of a species, or between paired chromosomes in an individual. Due to variations between human populations, a SNP allele that is common in one geographical or ethnic group may be much rarer in another. In addition, variations in the DNA sequences of humans can affect how humans develop diseases and respond to pathogens, chemicals, drugs, vaccines, and other agents.

One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

According to the present invention, an isolated protein, including a biologically active homologue or fragment thereof, has at least one characteristic of biological activity of activity the wild-type, or naturally occurring reference protein (which can vary depending on whether the homologue or fragment is an agonist or antagonist of the protein, or whether an agonist or antagonist mimetic of the protein is described). In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions).

The biological activity of a Betacam protein of the invention includes homotypic cell adhesion between Betacam-expressing cells, including pancreatic beta cells. More particularly, a biological activity of Betacam according to the invention includes the homotypic association of a Betacam protein expressed on one Betacam-expressing cell to another Betacam protein expressed on a neighboring cell. This includes β cells of the islet. Such biological activities of Betacam useful in the present invention include the generation and use of molecular components designed to bind to, activate, or inhibit, or otherwise modulate the function of Betacam. Modifications, activities or interactions which result in a decrease in protein expression or a decrease in the activity of the protein (complete or partial), can be referred to as inactivation, down-regulation, inhibition, reduced action, or decreased action or activity of a protein. Similarly, modifications, activities or interactions that result in an increase in protein expression or an increase in the activity of the protein, can be referred to as amplification, overproduction, activation, enhancement, up-regulation or increased action of a protein. The biological activity of a protein according to the invention, and particularly a Betacam protein, can be measured or evaluated using any assay for the biological activity of the protein as known in the art. Such assays can include, but are not limited to, binding assays (including a variety of immunological assays), assays to determine internalization or localization of the protein and/or associated proteins, and/or assays for determining downstream cellular events that result from the activity of the protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI30 BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using, for example, the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

As used herein, reference to an "agonist" of a given protein refers to any compound that is characterized by the ability to agonize (e.g., stimulate, induce, increase, enhance, or mimic) the biological activity of the naturally occurring protein, and includes any homologue, binding protein (e.g., an antibody), agent that interacts with a protein or receptor bound by the protein, or any suitable product of drug/compound/peptide design or selection which is characterized by its ability to agonize (e.g., stimulate, induce, increase, enhance) the biological activity of the naturally occurring protein in a manner similar to the natural agonist, which is the reference protein.

Similarly, reference to an "antagonist" refers to any compound which inhibits (e.g., antagonizes, reduces, decreases, blocks, reverses, or alters) the effect of a given agonist of a protein (including the protein itself) as described above. More particularly, an antagonist is capable of acting in a manner relative to the activity of the protein, such that the biological activity of the natural agonist or reference protein, is decreased in a manner that is antagonistic (e.g., against, a reversal of, contrary to) to the natural action of the protein. Such antagonists can include, but are not limited to, a protein, peptide, or nucleic acid (including ribozymes, RNAi, aptamers, and antisense), antibodies and antigen binding fragments thereof, or product of drug/compound/peptide design or selection that provides the antagonistic effect. Homologues of a given protein such as Betacam, including peptide and non-peptide agonists and antagonists (analogs), can be products of drug design or selection and can be produced using various methods known in the art. Such homologues can be referred to as mimetics. Various methods of drug design, useful to design or select mimetics or other therapeutic compounds useful in the present invention are disclosed in Maulik et al., 1997, Molecular Biotechnology: Therapeutic Applications and Strategies, Wiley-Liss, Inc., which is incorporated herein by reference in its entirety.

An isolated protein useful as an antagonist or agonist according to the present invention can be isolated from its natural source, produced recombinantly or produced synthetically.

As used herein, a mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art. A mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi). Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Also included in the present invention are antibodies and antigen binding fragments thereof that selectively bind to all or a portion (e.g., biologically active portion) Betacam, as well as the use of such antibodies and antigen binding fragments thereof in any of the methods described herein. Antibodies that selectively bind to a protein can be produced using the structural information available for the protein (e.g., the amino acid sequence of at least a portion of the protein). As used herein, the term "selectively binds to" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art, including, but not limited to: Western blot, immunoblot, enzyme-linked immunosorbant assay (ELISA), radioimmunoassay (MA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

According to the present invention, an "epitope" of a given protein or peptide or other molecule is generally defined, with regard to antibodies, as a part of or site on a larger molecule to which an antibody or antigen-binding fragment thereof will bind, and against which an antibody will be produced. The term epitope can be used interchangeably with the term "antigenic determinant", "antibody binding site", or "conserved binding surface" of a given protein or antigen. More specifically, an epitope can be defined by both the amino acid residues involved in antibody binding and also by their conformation in three dimensional space (e.g., a conformational epitope or the conserved binding surface). An epitope can be included in peptides as small as about 4-6 amino acid residues, or can be included in larger segments of a protein, and need not be comprised of contiguous amino acid residues when referring to a three dimensional structure of an epitope, particularly with regard to an antibody-binding epitope. Antibody-binding epitopes are frequently conformational epitopes rather than a sequential epitope (i.e., linear epitope), or in other words, an epitope defined by amino acid residues arrayed in three dimensions on the surface of a protein or polypeptide to which an antibody binds. As mentioned above, the conformational epitope is not comprised of a contiguous sequence of amino acid residues, but instead, the residues are perhaps widely separated in the primary protein sequence, and are brought together to form a binding surface by the way the protein folds in its native conformation in three dimensions. Accordingly, the present invention includes proteins or peptides comprising, consisting essentially of, or consisting of Betacam epitopes, as well as antibodies, antigen-binding fragments, or other binding partners (binding peptides) that bind to any epitope of a Betacam protein. An "isoepitope", according to the invention, is an epitope that exists in variant forms or isoforms (naturally or by synthetic design), such as an epitope containing a polymorphic variant amino acid position. One of skill in the art can identify and/or assemble conformational epitopes and/or sequential epitopes using known techniques, including mutational analysis (e.g., site-directed mutagenesis); protection from proteolytic degradation (protein footprinting); mimotope analysis using, e.g., synthetic peptides and pepscan, BIACORE or ELISA; antibody competition mapping; combinatorial peptide library screening; matrix-assisted laser desorption/ionization time-of-flight (MALDI-TOF) mass spectrometry; or three-dimensional modeling. For example, one can use molecular replacement or other techniques and the known three-dimensional structure of a related protein to model the three-dimensional structure of Betacam and predict the conformational epitope of antibody binding to this structure. Indeed, one can use one or any combination of such techniques to define the antibody binding epitope.

Antibodies useful in the present invention can include polyclonal and monoclonal antibodies, divalent and monovalent antibodies, bi- or multi-specific antibodies, serum containing such antibodies, antibodies that have been purified to varying degrees, and any functional equivalents of whole antibodies. Isolated antibodies of the present invention can include serum containing such antibodies, or antibodies that have been purified to varying degrees. Alternatively, functional equivalents of whole antibodies, such as antigen binding fragments in which one or more antibody domains are truncated or absent (e.g., Fv, Fab, Fab', or F(ab)2 fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Genetically engineered antibodies include those produced by standard recombinant DNA techniques involving the manipulation and re-expression of DNA encoding antibody variable and/or constant regions. Particular examples include, chimeric antibodies, where the VH and/or VL domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617. Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (Nature 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

In particular aspects, the invention is directed to an antibody that has binding specificity (e.g., epitopic specificity) for the Betacam polypeptide. In one embodiment, the invention is directed to an antibody that has binding specificity for a polypeptide that comprises, consists essentially of, or consists of amino acids 31 through 462 of SEQ ID NO: 1, amino acids 19 through 450 of SEQ ID NO: 2 or amino acids 30 through 463 of SEQ ID NO: 3. In another embodiment, the antibody has binding specificity for amino acids 31 through 462 of SEQ ID NO: 1, amino acids 19 through 450 of SEQ ID NO: 2 or amino acids 30 through 463 of SEQ ID NO: 3. In another embodiment, the antibody has binding specificity for a polypeptide that comprises, consists essentially of, consists of SEQ ID NO: 14, SEQ ID NO: 15, an amino acid sequence that has at least 50% identity to SEQ ID NO: 14 or an amino acid sequence that has at least 50% identity to SEQ ID NO: 15. In yet another embodiment, the antibody has binding specificity for SEQ ID NO: 14, SEQ ID NO: 15, an amino acid sequence that has at least 50% identity to SEQ ID NO: 14 or an amino acid sequence that has at least 50% identity to SEQ ID NO: 15.

Betacam proteins, homologues (including altered peptides), fragments, peptides, peptide and non-peptide mimetics, and antibodies and antigen-binding fragments thereof can be included in compositions and formulations. Such compositions, or formulations, can include a pharmaceutically acceptable carrier, which includes pharmaceutically acceptable excipients and/or delivery vehicles. As used herein, a pharmaceutically acceptable carrier refers to any substance suitable for delivering a composition, formulation or vaccine useful in the method of the present invention to a suitable in vivo or ex vivo site. Preferred pharmaceutically acceptable carriers are capable of maintaining the agent to be delivered (e.g., Betacam proteins, homologues (including altered peptides), fragments, peptides, peptide and non-peptide mimetics, and antibodies and antigen-binding fragments thereof) in a form that, upon arrival of the agent to a target cell or target site, the agent is capable of acting at that cell or site (e.g. capable of inducing an immune response). Suitable excipients of the present invention include excipients or formularies that transport or help transport, but do not specifically target an agent to a site (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized. One type of pharmaceutically acceptable carrier includes a controlled release formulation that is capable of slowly releasing a composition of the present invention into an animal. As used herein, a controlled release formulation comprises an agent useful in the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Suitable delivery vehicles also include, but are not limited to liposomes, viral vectors or other delivery vehicles, including ribozymes. Natural lipid-containing delivery vehicles include cells and cellular membranes. Artificial lipid-containing delivery vehicles include liposomes and micelles. A delivery vehicle of the present invention can be modified to target to a particular site in a patient, thereby targeting and making use of an agent at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type.

The invention also extends to PET-tracer (positron emission tomography) methodology, related to the formulation of compounds derived from the Betacam sequence, which are traceable using PET methodology. A biomolecule that serves as a marker for some function can be labeled with an isotope that emits positrons—subatomic particles akin to positively charged electrons—such as 11C, 13N, and 15O, as well as 18F, which often replaces 1H. Upon tracer administration, emitted positrons interact with electrons from atoms in nearby tissues, usually within 1 mm. The collisions result in annihilation events that each simultaneously liberate two gamma rays at 180°. A scintillator (bismuth germanate is standard) and photomultipliers in the tomograph encircling the subject detect this energy pattern and extrapolate the approximate origin of the energy. About 500,000 annihilation events constitute a single slice or scan of body tissues. Scans allow visualization of the internal locations of the tracers, designed for measuring general body functions (e.g., glucose metabolism or blood flow in an organ) or highly specific functions (e.g., occupancy of a subtype of brain dopamine receptor). The intensity of emitted gamma radiation is proportional to the tracer concentration. Anatomical considerations and correlation of the range of radiation densities with colors of the spectrum provide quantitative and/or color representations of the magnitude of a physiological function. In humans, typical tissue resolution with PET is 4-7 mm—the width of a pencil. The potential for development of a PET system was realized in the 1950s, when interest in positron-emitting isotopes emerged. Invention of the PET scanner in the early 1970s is credited to Michael E. Phelps.

PET tracers can be divided into three broad categories based on what they measure. The first type of tracer provides general metabolic data, such as glucose uptake and protein synthesis, via labeled biomolecules (e.g., 11C-deoxyglucose and 11C-methionine, respectively) that leave the bloodstream and enter cells. The second type provides estimates for grosser physiological parameters, such as blood flow (e.g., 15O-H2O or 11CO2), and essentially remains in the bloodstream over the effective study duration. The third tracer type delineates and quantifies highly specific molecular targets, such as cellular receptors and transporters, for which tracers are either endogenous ligands or drugs (e.g., 11C-raclopride for the DA2 dopamine receptor). The high specific activity and sensitivity of PET tracers make them well suited for studying molecular targets present to low nanomolar concentrations. The design or selection of the optimal PET tracer integrates knowledge of cellular physiology and biochemistry, advances in radio- and synthetic chemistry, tracer pharmacology and kinetics, and refinements in cyclotron and PET technologies. Successful PET imaging requires consideration of the innate properties of both radioisotope and tracer molecule, and the route of tracer administration. Radioisotope selection criteria must include the ability to incorporate the isotope into the molecule of interest and the appropriateness of its radioactive half-life for the study design. Half-lives of positron emitters range from 20 min (11C) to 110 min (18F). All steps, from cyclotron generation to subject administration, must occur within the useful lifespan of the label—approximately 3 half-lives—to maximize the signal-to-noise ratio. Ideally, PET tracers have properties that accurately reflect what they are meant to measure and minimize radiolabeling effects on the parent molecule. Such properties include high target-site selectivity, specificity, sensitivity, minimal metabolism, and the attainment of equilibrium in the body during the study. Inherent in tracer design is consideration of the tracer administration route. Intravenous tracers, by virtue of their rapid delivery, systemic distribution, and bypassing of gastrointestinal metabolism, are ideal and are most common. Inhalation, the second most prevalent administration route, suffers from complications related to swallowing, dispersal, physicochemical interactions between drug and vehicle, and patient-related issues. Ingested tracers are characterized by slower absorption, systemic distribution, and a greater chance of metabolites forming, making them much less attractive.

PET methodologies for detecting cells in-vivo: cancer. Early diagnosis and treatment of cancer are often crucial to a good prognosis. PET allows the detection of cancerous cells before tumors even form and can sometimes obviate the need for biopsies. PET's ability to detect tumors, determine malignancy and cancer progression, and ascertain cancer metastases stems from its capacity to assess the relatively higher energy needs of actively growing cancer cells. In particular for the present invention, the use of PET technology for detecting beta cells, is not dissimilar to that use of the PET technology of detecting cancerous cells. Glucose is in higher demand as an energy source by rapidly dividing cancer cells than by normal cells. Using a 11C- or 18F-labeled 2-deoxyglucose tracer (a non-metabolized glucose analogue), PET can detect cancer and establish a baseline tumor growth rate (the glucose utilization rate) in a patient. It can also assess antitumor activity during and after therapy. Successful therapy depends on eliminating tumor growth (metabolism), which is determined by decreased glucose uptake by tumor cells. Radiolabeled amino acids can be used in a similar way to deoxyglucose. Other indices of tumor growth, such as the extent and rate of tumor perfusion, and their projected decreases with treatment, can also be determined.

Cardiovascular Disease. PET has proved useful in the study and quantification of various aspects of heart and blood vessel function. As with cancer, clinical studies show an important role for PET in diagnosing patients, describing disease, and developing treatment strategies. PET has been applied in two major areas: assessment of coronary artery disease and impaired blood flow, and determination of the viability of heart tissue for revascularization. The latter helps physicians decide whether bypass surgery or heart transplant is a more viable option for a patient. Tracers that assess blood flow include 15O—H2O, 11CO2, and 13NH3, help establish the extent and progression of arterial blockage as well as the efficacy of drug therapy or surgery. They also are used to monitor the recovery and maintenance of a blockage-free state.

Central Nervous System. Conditions. PET can be used to diagnose functional brain disorders, such as Alzheimer's and Parkinson's diseases, childhood seizures, brain development disorders, and brain tumors. Cause and effect can also be investigated. In memory loss, PET can ascertain whether the loss is due to decreased blood flow, depression, or a molecular depletion, as in Alzheimer's disease. In addition, the appropriateness of therapies or interventions for these disorders can be monitored. PET even maps brain regions involved in specific activities, such as laughing, hearing, memory, and emotions, a useful function for planning neurosurgical procedures. PET also can measure the effects of drugs on region-specific brain functions. For a given drug, the capacity and occupancy of brain receptor molecules—the sites of action of antipsychotic drugs—and transporter molecules—associated with drug addiction and drugs of intervention—can be assessed. Tracers that bind to these molecules generate regional maps of receptors and transporters, estimate their occupancy by drugs of interest, and correlate drug occupancy with degrees of clinical efficacy. Examples of PET Radiocompounds include:

15O-oxygen Oxygen metabolism
15O-carbon monoxide Blood volume
15O-carbon dioxide Blood flow
13N-ammonia Blood flow
18F-fluorodeoxyglucose Glucose metabolism
18F-fluoromisonidazole Hypoxic cell tracer
11C-SCH23390 Dopamine DI receptor
11C-flumazenil Benzodiazepine receptor Particular aspects of the invention relate to a specific homologous gene group, referred to as the Betacam group of genes. Aspects of the present invention also include a variety of methods that make use of the identification of Betacam as a novel cell surface determinant of pancreatic beta cells.

A current focus on developing methods to measure beta cells in vitro and/or in vivo is highly prioritized by the juvenile diabetes foundation, as well as the NIH through particular funding mechanisms. However, such reagents and/or methods would not be limited to screening of pre-onset diabetes development in otherwise healthy subjects. The application extends to tracking pancreatic insulin cells in multiple scenarios, ranging from applications related to increasing the success of islet cell transplantation, the generation of novel beta cells from non-islet sources, and the purification of pancreatic beta cells from heterogeneous cell populations of various kinds. Such considerations relate to finding cell surface determinants present on normal beta cells, simultaneously absent from most other cells, as this criterion of specificity is an absolute requirement for further successful development of both such a reagent type, and the methodology related to its application.

Some considerations as to the importance and significance of succeeding in the above ventures are as follows. Diabetes is presently incurable, and islet transplantation is only offered to very few individuals. Yet, envisioning the cure is simple: replenishment of the lost cell pool of insulin-producing cells (type I diabetes, juvenile form), or restoration of insulin producing cells in late-onset diabetes (type II diabetes), as their function has deteriorated to a level leading to incomplete control of glycaemia. The availability of a universal cell replacement source for insulin-producing cells would have significant impact on total people suffering from the disease, and lowering of health-care associated expenses. Likewise, if early diagnosis of pre-clinical symptoms of diabetes could be achieved, it would be expected that total numbers of patients would be reduced given early intervention.

One aspect of the invention is directed to a method of detecting beta cells in a mixture of pancreatic cells comprising detecting the presence of a polypeptide on the surface of the cells, wherein the polypeptide comprises SEQ ID NO: 14, SEQ ID NO: 15, an amino acid sequence that has at least 50% identity to SEQ ID NO: 14 or an amino acid sequence that has at least 50% identity to SEQ ID NO: 15, and detection of expression of the polypeptide on the surface of the cells indicates that the cells are pancreatic beta cells. The method can further comprise isolating the pancreatic beta cells from the mixture of cells.

The mixture of pancreatic cells can be present in a variety of milieus. In one embodiment, the mixture of pancreatic cells are present in a biological sample. Examples of biological samples include pancreatic tissue (e.g., pancreatic donor tissue from, e.g., from a cadaver).

As will be appreciated by one of skill in the art, the Betacam polypeptide present on the surface of the beta cells can detected using a variety of reagents, and in particular labeled or tagged reagents, and methods for detecting such reagents. In one embodiment, an antibody that has binding affinity for the Betacam polypeptide is used. In another embodiment, since as shown herein homotypic interactions of Betacam/Betacam occur, a Betacam polypeptide can be used to detect the expression of Betacam on the surface of a pancreatic beta cell.

Particular aspects of the invention include the detection of pancreatic beta cells in pancreatic material obtained from a human cadaver. An application of the invention for this purpose could include contacting a labeled Betacam derived polypeptide, a Betacam reacting antibody, or a small engineered molecule (Betacam-derived reagent) designed to bind the Betacam protein surface, to a mixture of pancreatic beta cells (e.g., crude fractions of pancreatic cell suspensions, originating from donor pancreata).

It is known to those skilled in the art, that Betacam-derived molecules (i.e., nucleic acid, polypeptide) can be artificially labeled with multiple technologies, including fluorescent molecules, radioactive molecules (e.g., radioactive nucleotide), enzymatic components (e.g., enzymes), select Tag sequence, PET-tracers, NMR tracers, or a drug for use in the methods described herein. Following contacting the cells with the molecule defined by the invention, measurements of labeling can be performed to assess islet cell purity as a function of total cell content based on the labeling component selected.

Crude isolated fractions of human islet preparations are often used for transplantation purpose for alleviating diabetic symptoms for extended periods (>1 year) in recipient individuals based on the more recent technology of islet cell transplantation as defined by the now commonly known "Edmonton protocol". Enhancements of this particular protocol is envisioned as a particular application of the present invention. More specifically, an application of the invention would include tracking such islet cell preparations post-transplantation, as afforded by pre-contacting the islet cell preparation to a trackable Betacam-derived formulation, consequently labeling such and islet cell preparation. Considering that the trackable Betacam-derived reagent would facilitate non-invasive measurement of the transplanted cell population, methods for optimizing grafting methodology can be envisioned. Also, assessment of grafting, or transplantation, effectiveness, can be measured. This may be done very likely early following transplantation. Considering a certain stability of the Betacam-derived reagent, it may be possible to monitor the viability of the transplanted cells, which would be a benefit, as such measurements are not possible with existing technology.

Another aspect of the invention is directed to a method of detecting pancreatic beta cells in an individual in need thereof, comprising administering to the individual an agent that detects the presence of a polypeptide on the surface of the pancreatic beta cells, wherein the polypeptide comprises SEQ ID NO: 14, SEQ ID NO: 15, an amino acid sequence that has at least 50% identity to SEQ ID NO: 14 or an amino acid sequence that has at least 50% identity to SEQ ID NO: 15. This method can be used, for example, to determine whether an individual is at risk of developing diabetes, or to assess the beta cells of an individual that has diabetes (e.g., to determine the appropriate treatment needed for a diabetic patient or to assess the efficacy of a diabetic patient's existing treatment). In one embodiment, the individual has Type I diabetes, and in another embodiment, the individual has Type II diabetes. In yet another embodiment, the individual has had an islet cell transplantation.

Another particular embodiment would apply a Betacam-derived formulation as described above for injection intravenously into the bloodstream after which contact to a beta cell surface would occur. Upon binding of said molecule to the surface to beta cells, and the emittance of a signal based on a trackable moiety, beta cell mass may be measured in a patient separately from the parameters of glucose dependent insulin secretion assays, and separate from oral glucose tolerance tests, which reflects on basal islet cell functionality, but not total beta cell mass. As such, the invention may be used to develop non-invasive assays for detecting various degrees of beta-cell loss in a human individual, which are of relevance for prognosis of disease. During the progression of type I diabetes, prior to diagnosis of the disease, an ongoing autoimmune attack is known to gradually eliminate the beta cell population. Similarly, the detection of a progressive deterioration of the beta-cell mass, as it gradually is lost in type II pre-diabetic individuals, is of clinical relevance. Consequently, for either consideration, detecting an ongoing beta cell loss may be of significant value in guiding decisions of prediction, and prevention, of type I and type II diabetes, based on earlier intervention.

In yet another method, the invention includes the development of a reagent capable of purification of pancreatic beta cells from human pancreatic donor material. More particularly, a Betacam-derived polypeptide, a Betacam reacting antibody, or a small engineered molecule, would be contacted to crude fractions of pancreatic cell suspensions, originating from donor pancreata. If said Betacam-derived polypeptide; Betacam reacting antibody; or a small engineered molecule was previously conjugated or otherwise stably connected to a ligand, affinity-Tag moiety, or fusion protein domain which allows binding to a support material (e.g., plastic dish, plastic tube, sutures, membranes, ultra thin films, bioreactors, microparticles) or suitable matrix (e.g., polymeric matrix), cellular fractional enrichment either through centrifugal spinning, gravitational force, magnetic bead cell adhesion, flow-sorting or other fluid-pressure methodologies, enrichment of the Betacam-expressing cell population, including pancreatic beta cells could be achieved. Such enrichment would be expected to favorably improve on current transplantation clinical outcomes.

In a particular aspect, the invention is directed to a method of isolating pancreatic beta cells from a mixture of pancreatic cells comprising contacting the mixture with a reagent that specifically binds to a polypeptide present on the surface of pancreatic beta cells, wherein the polypeptide comprises SEQ ID NO: 14, SEQ ID NO: 15, an amino acid sequence that has at least 50% identity to SEQ ID NO: 14 or an amino acid sequence that has at least 50% identity to SEQ ID NO: 15, thereby producing a combination. The combination is maintained under conditions in which the reagent binds to the polypeptide present on the surface of the pancreatic beta cells, thereby producing a complex of pancreatic beta cells bound to the reagent; and the complex is separated from the combination, thereby isolating pancreatic beta cells from the mixture of pancreatic cells. The method can further comprise separating the pancreatic beta cells from the reagent.

In yet another method, the invention includes the development of technology leading to improved characterization of fraction enrichment of pancreatic beta cells from a heterogenous source of cells, including forward differentiated human embryonic stem cells. Current emphasis is presently on developing a universally available islet cell replacement cell resource, and particular efforts are directed on using human embryonic stem cells as a starting material. It is also known that such cells are pluripotent, and can adopt multiple cellular fates upon entering a differentiation process, which is controlled by an investigator. The promise of such cells is offset by the difficulties in specific directed differentiation method, which at present do not lead to a pure cell population of pancreatic beta cells. Other problems relate to the development of teratoma-type tumors upon transplantation to a live host. This particular problem is accredited to the co-transplantation of a limited set of undifferentiated, pluripotent, stem cells, existing along the more differentiated progeny. The consequence is detrimental, as such latent tumor forming capacity is posing a significant danger to a potential recipient. A solution to the problem would be to purify the insulin producing cell population to a level where such cells are not present. Therefore, in particular, one method of the invention would be to contact a Betacam-derived reagent to a forward-differentiated embryonic stem cell population, and purifying the insulin producing, Betacam expressing cells from contaminating non-endocrine cell types. Measures of purification capacity can be given in relative insulin expression per cell, or per DNA weight, as examples. Another measure of the purification can be given in the relative reduction of tumor forming capacity as events per million cells transplanted.

Accordingly, one, or more, embodiments of the invention relate to a method related to development of improved methods whereby the purification of pancreatic beta cells from any heterogenous source of cells can be achieved. It is known to those skilled in the arts that endocrine cells, including that of the pancreatic insulin-type, may possibly be derived from non embryonic stem cell sources. Regarding the emerging technologies of creating a universal cell source for diabetes treatment, these cover a wide area of investigative entries. Possible cell sources investigated as a means to this end includes in addition to human embryonic stem cells (hES), also hematopoietic stem cells (HSC), mesenchymal stem cell (MSC), multipotent adult progenitor cells (MPAC), pancreatic progenitor cells hPPCs), non-endocrine pancreatic epithelial cells (NEPECs), adult liver cells (Liver), adult GIP cells (K-cells), adult human duct cells (hDuct), adult human exocrine cells (hExocrine), genetically programmed transformed islet tumor cells, porcine embryonic pancreas (PEP), porcine islet cells (PIC), and ex-vivo expanded human islet cells. In all cases, the issue of initial clonal heterogeneity is a concern, and the end-point always defined by increasing the homogeneity of the end stage cell population. This invention relates to a method whereby purification of pancreatic beta cells from any such original heterogenous source of cells can be achieved.

Regarding the emerging technologies of creating a universal cell source for diabetes treatment, these cover a wide area of investigative entries, all having a similar end-point in common. The endpoint would be a glucose-responsive, insulin-producing cell, capable of being grafted into a human recipient. Possible cell sources investigated as a means to this end includes human embryonic stem cells (hES), hematopoietic stem cells (HSC), mesenchymal stem cell (MSC), multipotent adult progenitor cells (MPAC), pancreatic progenitor cells (PPCs), non-endocrine pancreatic epithelial cells (NEPECs), adult liver cells (Liver), adult GIP cells (K-cells), adult human duct cells (hDuct), adult human exocrine cells (hExocrine), genetically programmed transformed islet tumor cells, porcine embryonic pancreas (PEP), porcine islet cells (PIC), and ex-vivo expanded human islet cells. Other cell sources have been mentioned in literature, and the above list is not exhaustive, nor meant to be. For the remainder of the disclosure, all such cells are commonly referred to as a "progenitor cell source" (PCS), not requiring that such cells are defined as "progenitors" in the strict meaning of the word as employed by those skilled in the arts, but more generally applying the semantic use of "progenitor" as being a cell capable of change into another type, in this case pancreatic insulin-producing cells. Similarly, regarding the semantic use of "pancreatic beta cell" in this disclosure is not limited to the strict definition of a pancreatic beta cell by those skilled in the arts, but for the remainder of the disclosure encompasses any cell type capable of producing insulin, and secreting this hormonal product in response to extra-cellular glucose, which is hereby defined as the minimal set of requirements.

Another aspect of the invention is a method of identifying an agent that modulates (e.g., inhibits; enhances) the biological activity of betacam comprising contacting a composition comprising a polypeptide, wherein the polypeptide has an amino acid sequence comprising SEQ ID NO: 14, SEQ ID NO: 15, an amino acid sequence that has at least 50% identity to SEQ ID NO: 14 or an amino acid sequence that has at least 50% identity to SEQ ID NO: 15 with an agent to be assessed. The biological activity of the polypeptide in the presence of the agent is measured and compared to a suitable control, wherein if the polypeptide modulates the activity of the polypeptide in the presence of the agent compared to the control, then the agent modulates the biological activity of betacam. In a particular embodiment, the composition is one or more pancreatic beta cells. Any biological activity of betacam can be measured such as homotypic cell adhesion between betacam-expressing pancreatic beta cells. In addition, as will be appreciated by those of skill in the art, a variety of suitable controls are available for use in the method. In one embodiment, the control comprises pancreatic beta cells which have not been contacted with the agent to be assessed.

The following examples are provided for the purpose of illustration and are not intended to limit the scope of the present invention. Each publication or other reference disclosed below and elsewhere herein is incorporated herein by reference in its entirety.

EXAMPLE 1

Identification of Betacam as a Novel Cell Surface Molecule

In the following, a description of the amino acid sequence of the protein Betacam is provided. Homologous regions were easily detected for multiple species including human, pan troglodytes, *canis familiaris*, rat *rattus*, and *gallus gallus*, and several other species. Otherwise specified, the amino acid sequence numbering is in the following referring to that of mouse Betacam protein, isoform 1 [SEQ ID NO: 3], encoding a total of 463 amino acids.

In particular, the inventors named the gene locus in mouse, corresponding to Unigene Mm.206911, FIG. 1, Betacam. The encoded protein was henceforth named Betacam. Its NCBI gene ID is 101202. The current name of the gene as used by NCBI is "expressed sequence AI987662" (FIG. 1). The inventors name the gene locus LOC253012 in humans, its GeneID: 253012 (FIG. 2 and FIG. 3), and its corresponding to UniGene Hs.443169, Betacam as well. The inventors name the protein encoded by the human GeneID 253012 Betacam.

These above mentioned Betacam genes are part of a homologous gene group, conserved during evolution, and NCBI refers to this group as HomoloGene 18724 (FIG. 4). This group was recently named HEPACAM2 based on its weak similarity to the HEPACAM orthologous group. Betacam is a conserved gene between vertebrate species to the extent that it represents a single orthologous group. The closest immediate neighbor is represented by Homologene group 17652, HEPACAM, which displays <40% amino acid identity to the Betacam group.

The Betacam orthologous group contains multiple members in a large diversity of living species. The following sequence identities refer to individual members. SEQUENCE IDENTITY 1 [SEQ ID NO: 1] is human Betacam, isoform 1 (*Homo Sapiens*). [SEQ ID NO: 2] is human Betacam isoform 2 (*Homo Sapiens*). [SEQ ID NO: 3] is mouse Betacam isoform 1 (*Mus Musculus*). [SEQ ID NO: 4] is rat (rat *rattus*) Betacam. [SEQ ID NO: 5] is Bovine Betacam (*Bos Taurus*). [SEQ ID NO: 6] is dog Betacam (*Canis familiaris*). [SEQ ID NO: 7] is for Zebrafish Betacam (*Danio Rerio*). [SEQ ID NO: 8] is for horse Betacam (*Equus caballus*). [SEQ ID NO: 9] is for chicken Betacam (*gallus gallus*). [SEQ ID NO: 10] is for Chimpanzee Betacam (Pan troglodytes), [SEQ ID NO: 11] is for Macaque Monkey Betacam (*Macaca Mulatta*). [SEQ ID NO: 12] is for pufferfish Betacam (*Tetraodon nigriviridis*). [SEQ ID NO: 13] is for fruit fly (*Drosophila Melanogaster*) Lachesin.

The naming selected is one of convenience; none of the above genes/proteins are named based on previous knowledge of function, or expression in the liver. The arbitrary selection of gene/protein name Betacam is based on information provided within, where the inventors show that the protein is a member of a cell adhesion family group (-cam extension), and selectively expressed in pancreatic beta cells (beta-). The invention in particular is based on published knowledge that no other existing and described cell surface marker is known with a similar specificity of expression, as that displayed by the Betacam-encoded protein Betacam.

Betacam in humans exists in two alternative forms, isoform 1 (FIG. 5), and isoform 2 (FIG. 6). The difference between these forms lies in alternative exon-1 usage, explained by differential promoter usage. The predicted sequence of either form of the encoded proteins differs in the amino terminal sequence. Translation of isoform 1 gives a protein of 462 amino acids [SEQ ID NO: 1], translation of isoform 2 gives a protein of 450 amino acids [SEQ ID NO: 2].

Figure 7:
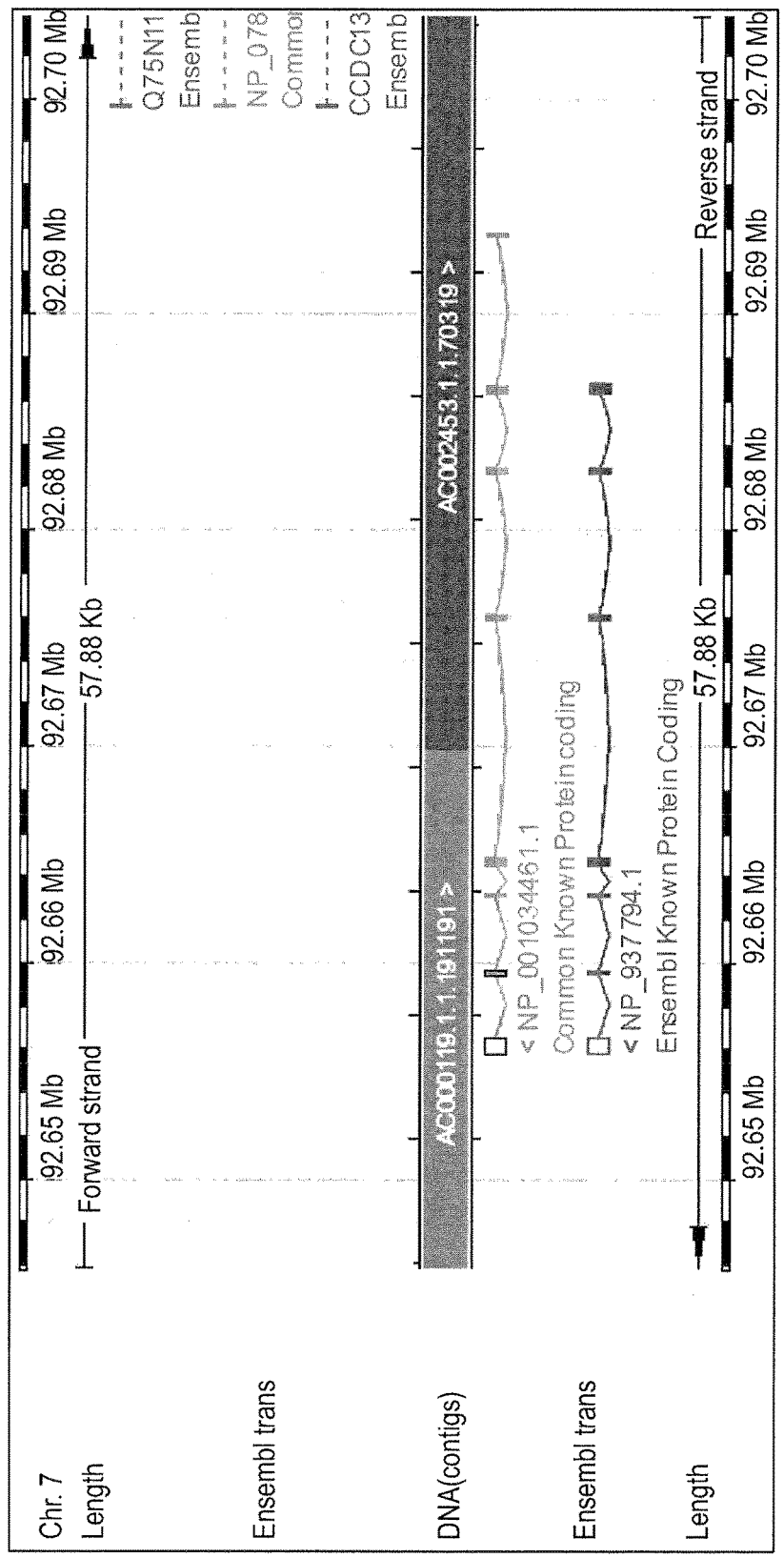
FIG. 7 is the output page from ENSEMBL, listing graphically the exon/intron structure of Betacam. It is encoded on the reverse strand of Chr. 7.

In humans, Betacam resides on Chromosome 7, and is encoded on the reverse strand. It consists of 9 exons. (FIG. 7). This image was created using the genome browser "Ensembl".

Figure 8:
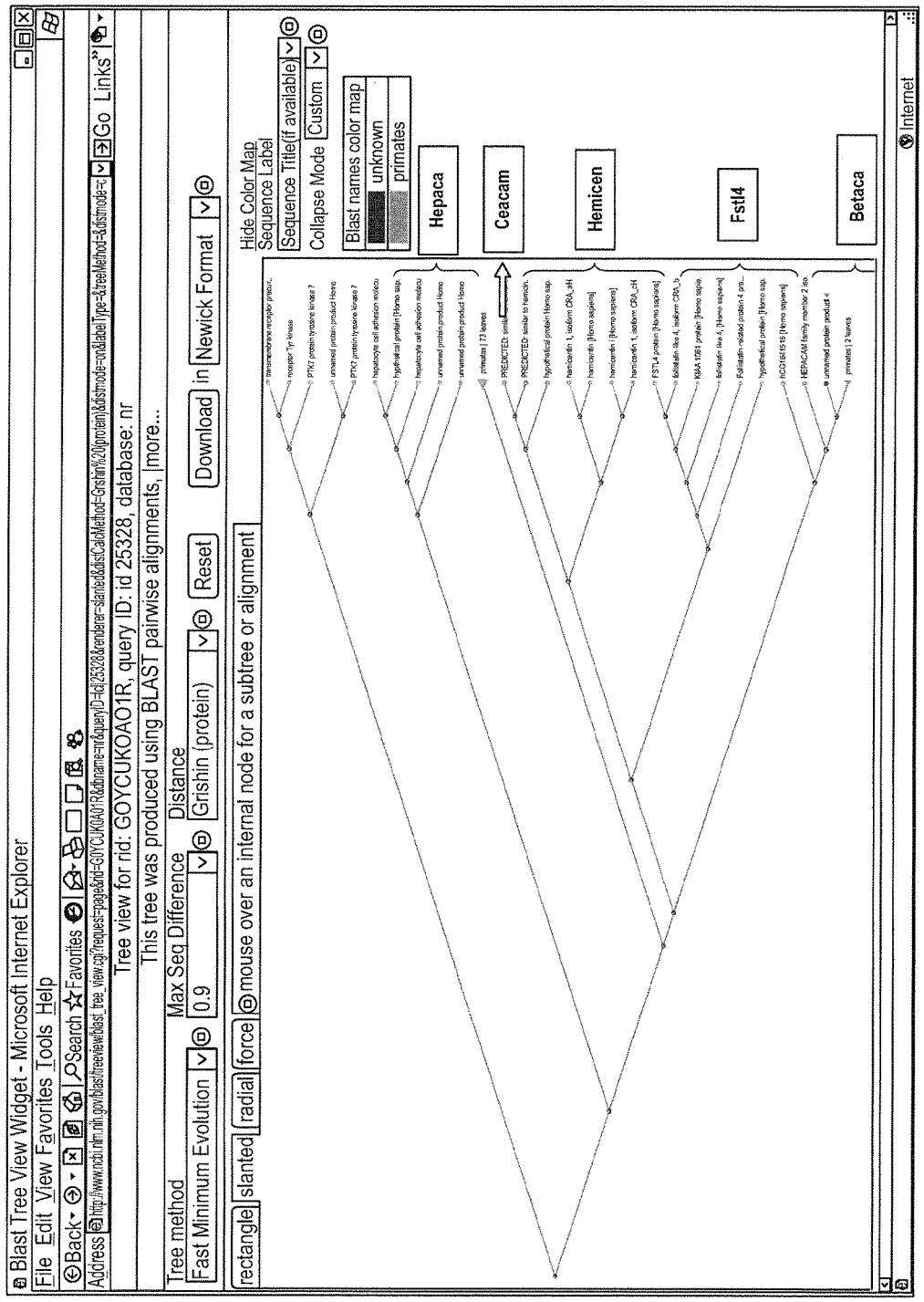
FIG. 8 is a tree-view of homologous proteins existing in the same species (*homo sapiens*). Node distances reflect phylogenetic divergence.

A protein-Blast analysis of human Betacam protein sequence, isoform 1 against known human protein sequences was performed. This was done in order to assess which other protein share similarity to Betacam within the same species. A tree view is shown in FIG. 8, in which the Betacam protein is shown at bottom. It was observed that the closest homologues to Betacam are Follistatin-like 4, hemicentin, the CEACAM group, and finally Hepacam. The phylogenetic distance to Hepacam argued that Betacam/Hepacam2 are functionally distinct proteins.

Figure 9:
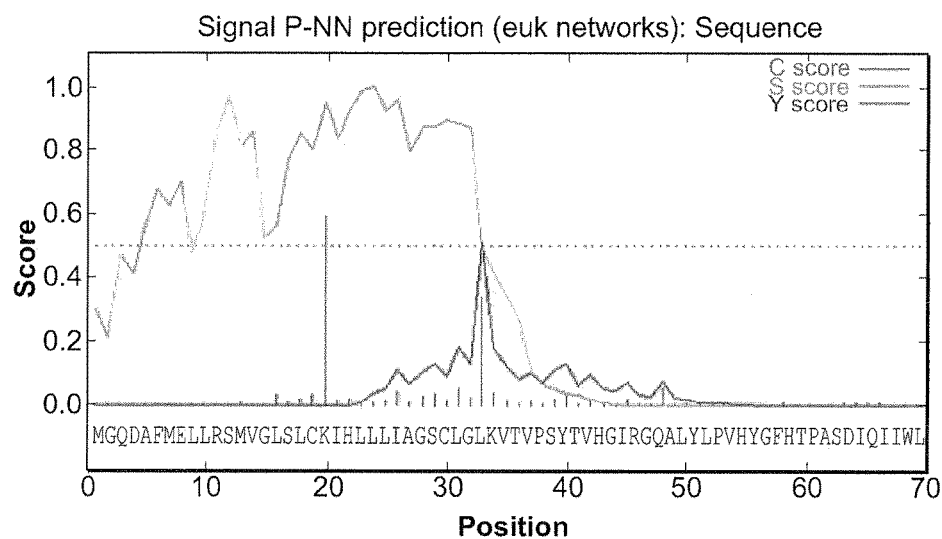
FIG. 9 is an evaluation of the presence of a signal peptide (SEQ ID NO: 28) in mouse Betacam. This is detected with high accuracy between positions 31-32.

As shown herein, mouse Betacam contained a clearly detectable signal peptide (FIG. 9). The confidence in predicting cleavage is 1.0. Cleavage will occur following amino acid Glycine 31. This occurs upon ER-docking, and the signal peptide recognition particle will facilitate docking of the nascent peptide chain emerging from a translating ribosome. Membrane-type components are known to contain signal peptides, in order to get routed to the membrane.

Figure 10:
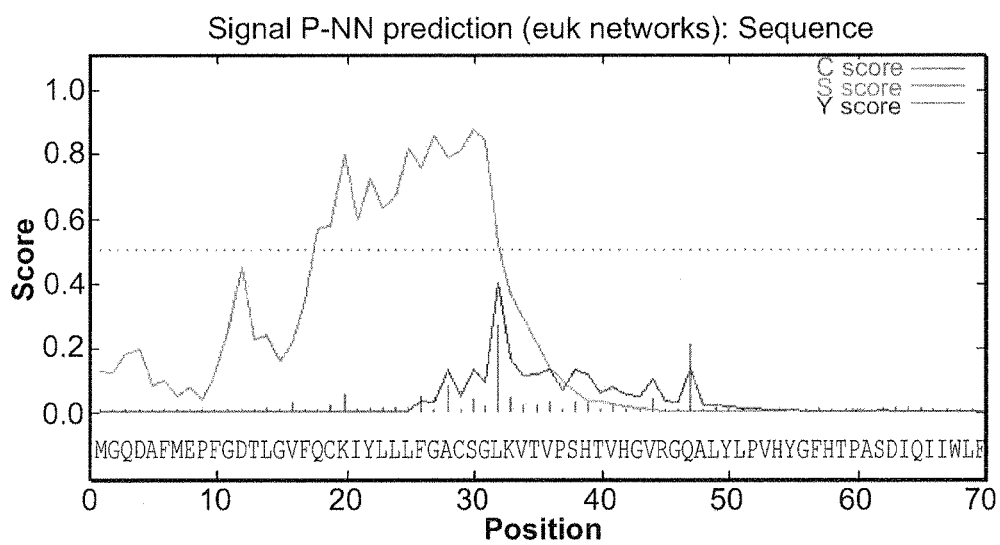
FIG. 10 is an evaluation of the presence of a signal peptide (SEQ ID NO: 29) in human Betacam isoform 1. This is detected with high accuracy between positions 31-32.

As also shown herein, human Betacam isoform 1 contains a clearly detectable signal peptide (FIG. 10). The confidence in predicting cleavage is 1.0. Cleavage will occur following amino acid Glycine 31.

Figure 11:
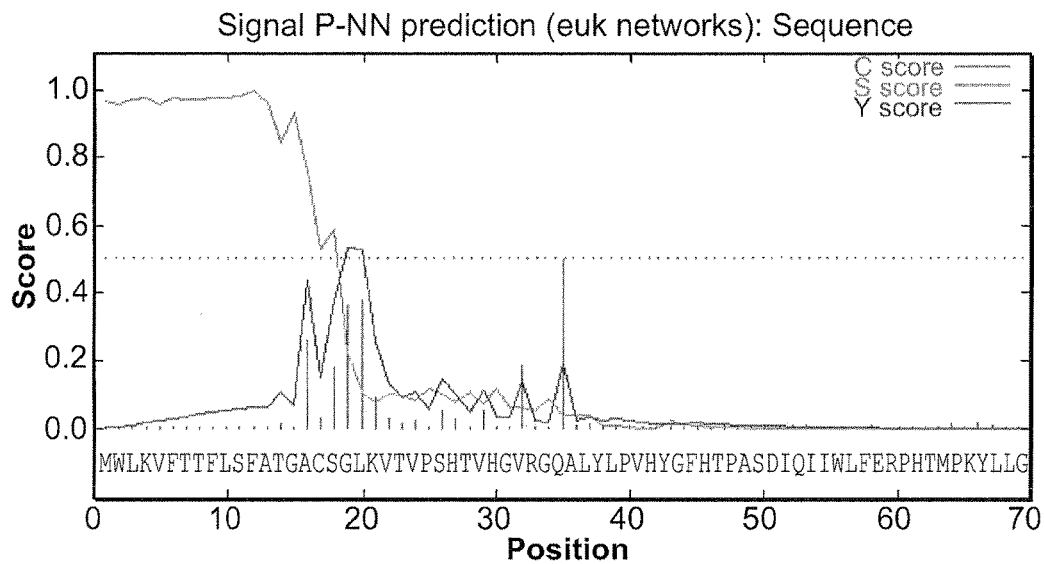
FIG. 11 is an evaluation of the presence of a signal peptide (SEQ ID NO: 30) in human Betacam isoform 2. This is detected with high accuracy between positions 18-19.

Also shown herein, Betacam isoform 2 contained a clearly detectable signal peptide (FIG. 11). The confidence in predicting cleavage is 1.0. Cleavage will occur following amino acid Glycine 19, which is identical to Glycine 31 in isoform 1. The resulting protein of isoform 1, and isoform 2 types are consequently identical following pre-peptide cleavage.

Figure 12:
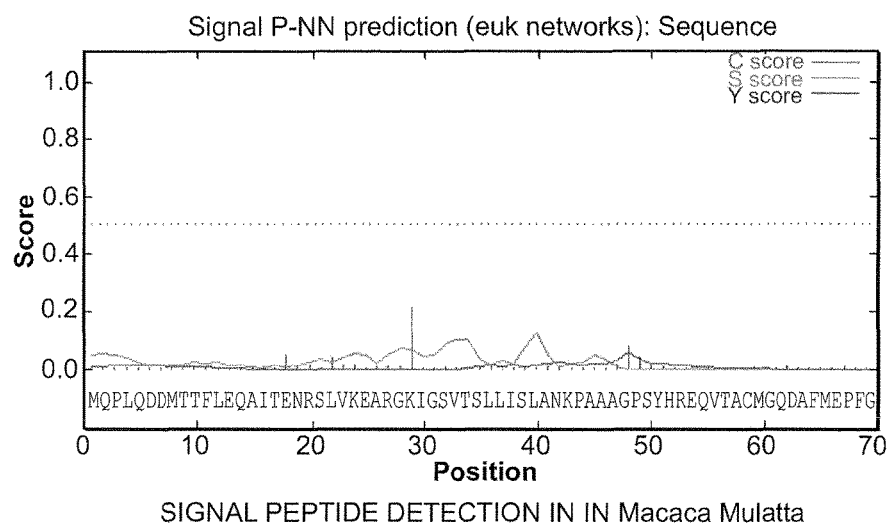
FIG. 12 is an evaluation of the presence of a signal peptide (SEQ ID NO: 31) in monkey Betacam, long form (SEQ ID: 10). No signal peptide is detected.
Figure 13:
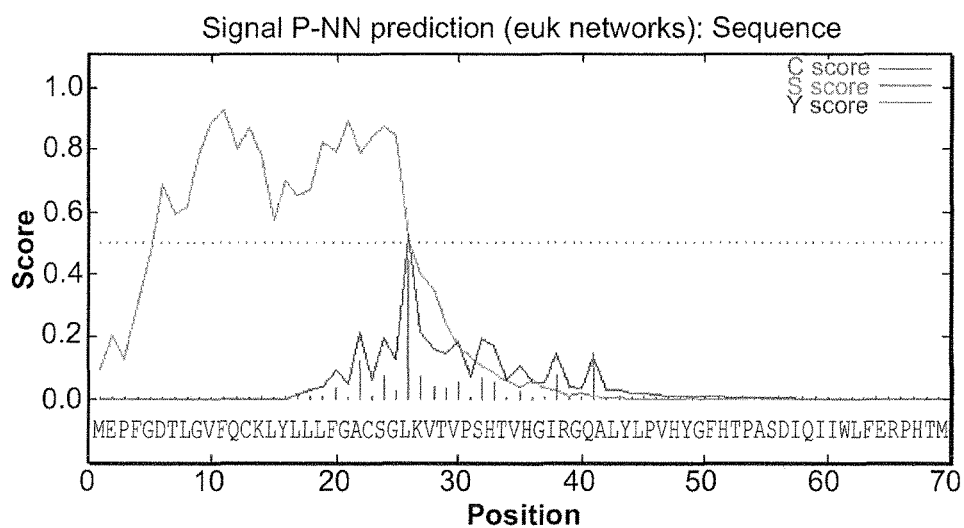
FIG. 13 is an evaluation of the presence of a signal peptide (SEQ ID NO: 32) in monkey Betacam, short form (SEQ ID: 11). This is detected with high accuracy between positions 25-26.

Also shown herein is that the long form of Betacam from *macacca mulatta* [SEQ ID NO: 11], does not contain a signal peptide (FIG. 12), and the short form of Betacam from *Macacca Mulatta* does contain a signal peptide (FIG. 13).

Figure 14:
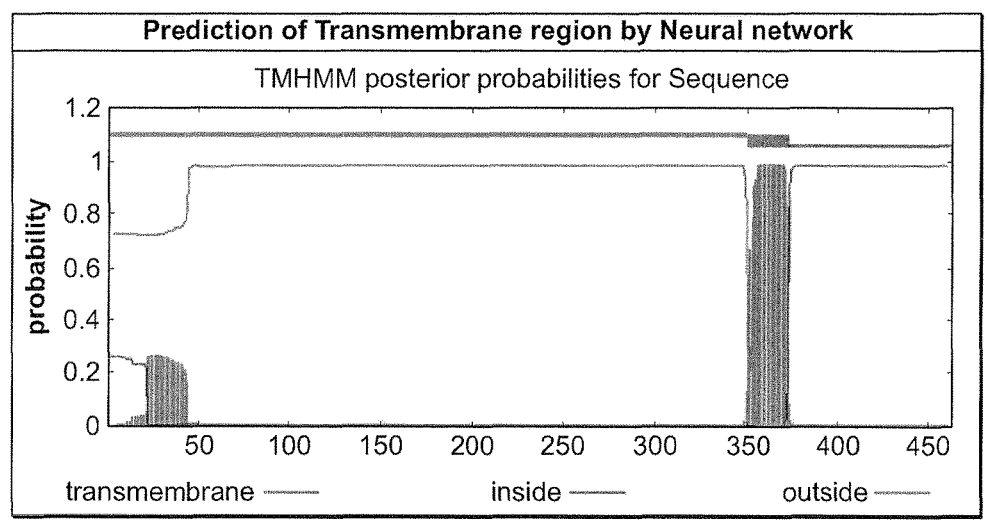
FIG. 14 is the detection of transmembrane (TM) regions in mouse Betacam. A single TM domain is detected between pos. 352-pos. 373.

Also shown herein is that Betacam contains a clearly detectable trans-membrane region, between amino acids proline 352 to tryptophan 373 (FIG. 14). Consequently, the protein encoded by Betacam is a single-pass trans-membrane spanning polypeptide, of from about amino acid leucine 32 to about serine 350 are extracellular in human Betacam, isoform 1 (SEQ ID NO: 1). Particular aspects of the invention relate to this extracellular portion of Betacam. The extracellular domain of Mouse Betacam is shown in SEQ ID NO: 14. The extracellular domain of Human Betacam is shown in SEQ ID NO: 15.

Figure 15:
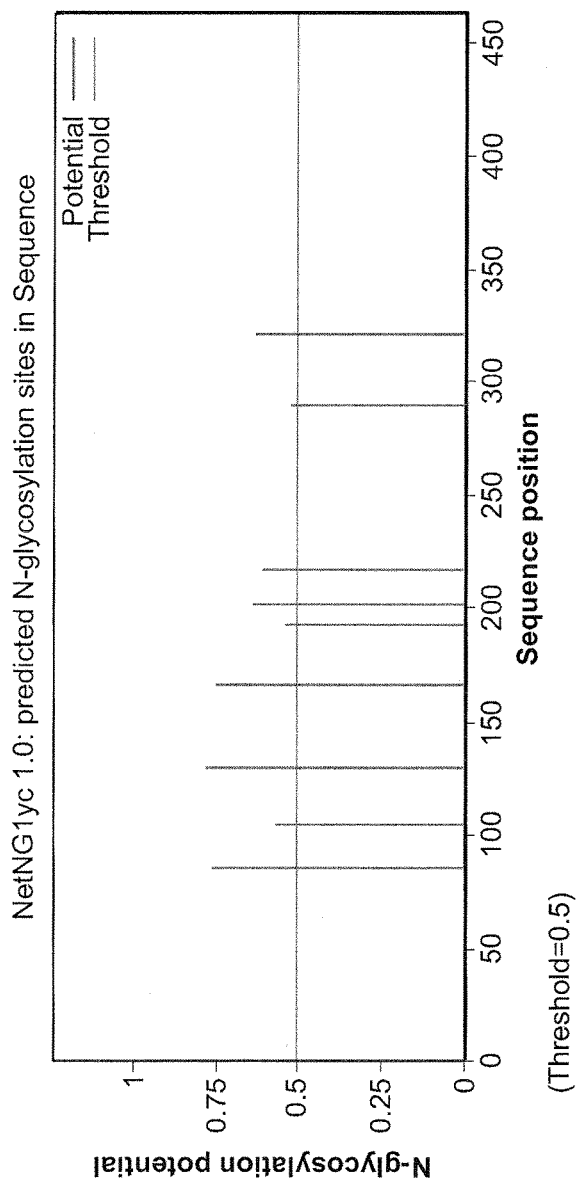
FIG. 15 is a graphical view of the presence and number of neural network predicted N-linked glycosylation residues in Betacam.

Referring now to the invention in more detail, the inventors show that Betacam contains a series of high-probability N-linked glycosylation asparagines residues. A prediction analysis was carried out using the Net-N-glyc neural-network based prediction server a Center for Biological Sequence analysis. The consensus sequence is Asn-X-Ser/Thr, and such sequences are detected at 9 positions in the extracellular domain of Betacam (FIG. 15).

EXAMPLE 2

Expression of Betacam on Pancreatic Insulin-Producing Beta Cells

Initial assessment of expression of Betacam using genomics-type data was performed (FIG. 16). Genomics data were either publicly available, or produced for the purpose of finding novel genes displaying beta-cell expression. To obtain data on expression, RNA was isolated for select tissues, or cell types. The resulting RNA was subjected to cDNA conversion, whereafter hybridization to select commercial genomics expression DNA-chips were performed. Such chips included types of Affymetrix, and Illumina commercial-type platforms. Expression data were normalized in software packages suitable for the need, including the GeneSpring analysis program and the Partek analysis program. Normalization of DNA chip scans were performed using the MAS5.0 algorithm for Affymetrix-type datasets, whereas Illumina type data sets were normalized using "average" normalization within the vendor-supplied program "BeadStudio". Affymetrix scan data were all normalized to the arbitrary value of 500.

Oligonucleotide microarray experiments were performed on pancreatic-related samples using human U133 and mouse MOE430 Affymetrics chips that cover virtually the entire genome. Data was obtained from isolated islets from normal mice, diabetic models (NOD and ob/ob) and mice with deficiencies in the Ngn 3 as well as from mouse pancreatic tumor cell lines (aTC1-6 glucagonoma, βTC3 and Min6 insulinomas, and mPAC ductal tumor line). The data was analyzed to highlight transcripts that display islet cell-type-specific expression, and their segregation between pancreatic α- and β-cells.

Specifically, the advent of gene microarrays covering almost the complete spectrum of encoded mouse mRNAs (transcriptome) enabled the identification of the subsets of genes that are expressed in pancreatic islets. A number of published studies have documented genes that are expressed in pancreatic islet tissue, specific islet cell types and islet-derived cell lines (Shalev, 2002). In addition, studies have reported on the responses of islets to physiological and pathophysiological manipulation such as stimulation with glucose or inflammatory cytokines in vitro, and from mice carrying mutant genes that affect pancreatic function or development. The inventors performed more than 50 microarray experiments using both human U133 and mouse MOE430 oligonucleotide chips that report on virtually all transcripts from each species. This includes data from normal mice, diabetic models (NOD and ob/ob) and mice with deficiencies in Ngn3. Ngn3 null pancreas is completely devoid of pancreatic endocrine cells, and thus analysis at different gestational time points allowed the identification of transcripts that are highly expressed in the endocrine cells relative to exocrine and ductal tissue throughout development.

Further evaluation of tissue-specificity in-silico was made through queries against a larger series non-pancreatic type. Specifically, data were compared to array data obtained from a large non-pancreatic tissue pool of 45 tissue types (Novartis dataset and Unigene expression profiles). In addition, analysis of mouse pancreatic tumor cell lines (αTC1-6 glucagonoma, βTC3 and Min6 insulinomas, and mPAC ductal tumor line) further allowed the generation of predictive scores for select transcripts likely to display islet cell-type-specific expression, and their segregation between pancreatic α- and β-cells. These cell lines express genes related to the tumor cell phenotype and thus analyses were also performed on isolated pancreatic β-cell from a transgenic mouse expressing the autoantigen Phogrin linked to EGFP under the rat insulin 2 promoter. This resource was created by the inventors. The Table lists some of the genes for which transcripts were defined by ANOVA analysis, firstly as being differentially expressed in Ngn3 wild-type and knock-out mice at any embryological age (pancreatic endocrine and precursors) and secondly as being present in adult mouse islets. The list was then stratified on the basis of the relative expression in αTC and βTC cell lines. These approaches successfully predicted the islet cell specificity of the majority of the known transcriptional regulatory components involved in islet development, such as Ipf1, Arx, Pax4, Pax6, Brn4, NeuroD and known cell type specificity of several α- and β cell genes. Known neuroendocrine transcripts such as PTPRN (IA-2), prohormone convertases (Pcsk1, Pcsk2, Cpe) and the granins (Chga, Chgb Scg2, Sgne1) were in a pool of common αTC and βTC transcripts.

Genes associated with other islet endocrine cells were, as predicted, not expressed in either (Ppy, Pyy, and ghrelin).

Referring now to the invention in more detail, the inventors describe in the following the discovery process of the Betacam gene. As an initial guide to the identification of pancreatic endocrine cell transcripts, E18.5 embryonic Ngn3 null pancreas was compared to WT littermate. This identified app. 180 individual transcripts that were absent in the endocrine-deficient pancreas, most of which correspond to known genes (the Table).

A limited number of transcript hits were previously uncharacterized, and further scrutinized by various prediction methods, results of which applying to AI987662/Betacam are shown in Example 1. Through this process, one particular gene, known as mouse gene AI987662 was discovered, which forms the basis of the particular aspects of the invention. Within the stratification method described in the Table, gene locus was observed within the pool of transcripts belonging to those >5-fold enriched in bTC cells versus aTC cells.

TABLE

Gene transcripts that were depleted in the Ngn3 ko pancreas at e12.5, e15.5 or 18.5 were examined for expression in the endocrine cell lines αTC and βTC and adult islets. Components of islet endocrine cells are underlined; known autoantigens are highlighted in bold type.

| >5-fold enriched in αTC | >5-fold enriched in βTC | Not enriched in αTC or βTC | Not expressed in αTC or βTC |
|---|---|---|---|
| 1110005D19Rik | 1100001E04Rik | 7-Sep 9030612M13Rik | 1810044E12Rik |
| 1700040L02Rik | 1110035L05Rik | 9830160H19Rik | 2310010l16Rik |
| 2310014L03Rik | 1700041C02Rik | A430107J06Rik Abcc8 | 2310067E08Rik |
| 2810431N21Rik | 1810018P12Rik | Aco1 Actr3 ank Aplp1 | 4731413G05Rik |
| 2900052J15Rik | 2010011l20Rik | Atp1a1 AW011752 | 5133401E04Rik |
| 6430527G18Rik | 2310007H09Rik | AW011752 Banf1 | 5730453H04Rik |
| 6430527G18Rik | 2610016M12Rik | BC016198 BC042620 | 5930418K15Rik |
| 7420452D20Rik | 2700049B16Rik | BC061928 C130083N04Rik | 6430401D08 6720464l07Rik |
| 9430022M17Rik | 2900001G08Rik | C230068E13 | 8430421H08Rik |
| 9430023B20 | 3100002J23Rik | C820002P14Rik Calm1 | 9030425P06Rik AA589382 |
| 9530058B02Rik | 3110018A08Rik | Capza2 Ccnb1 Ccnh Ccni | Ace2 Acvr2 Apoa1 Arfgef1 |
| A630013F22Rik Apoa2 <u>Arx</u> | 3110050F08Rik | Cda08-pending Cdc5l | Asah2 B230312l18Rik |
| B230206N24Rik | 5830437M04Rik | Cdkn2d Cgef2-pending | BC027756 BC054438 Braf |
| B230309E09Rik | 5930418K15Rik | Chga <u>Chgb</u> Chic1 Clcn3 | C030034l22Rik |
| B430319H24Rik Btg2 | 9330186A19Rik | Cotl1 <u>Cpe</u> Csnk1d | C130047D21Rik |
| Cald1 Car2 CGI-141-pending Copg2as2 | 9830147J24Rik | D16lum22e D7Ertd743e | C130099L13Rik C1qb C3 |
| D6Ertd253e Ednra Eno2 | A530058N18Rik | D9Wsu20e Ddx9 Donson | C430010P07Rik Cdw92 |
| Epb7.2 FBp2 Fev-pending | A930001M12Rik | Dscr2 Emb Emb Foxa2 | Ceacam2 Cfh Cpne3 Ctss |
| Foxf2 Galnt7 <u>Gcg</u> Gfra1 | A930009L07Rik Adcy7 | Gna11 Gng5 H2-D1 | Dnajc13 E130113K08Rik |
| Glcci1 Gpr30 Gstt2 <u>Hes1</u> | Adra2a Al173274 Al315068 | Hdac2 Hmgcr Hmgn3 | Ecm1 Enah Fabp1 Fabp4 |
| Hs3st1 Ier3 Irx2 Itih2 Kap | AI987662 Ang Asc-pending | Hmgn3 Hnrpab Hnrpu | Fbxl12 Fcgr2b Fgl2 Flt1 |
| LOC224093 Mttp Pde3a | Atp2a3 AW125421 | Hspa5 Ierep04-pending <u>Isl1</u> | <u>Foxa3</u> <u>Frzb</u> Gbp2 Gca |
| Pde3a <u>Pou3f4</u> Rbp4 Rgs4 | B630019K06Rik | Khdrbs3 Kif11 Kif5b | <u>Ghrl</u> H2-Ab1 Hba-a1 |
| Sbsn-pending Sdc4 Sdc4 | B930068K11Rik BCO26600 | LOC218490 LOC226144 | Homez Hpvc2 ll6ra <u>Insrr</u> |
| Slc38a1 Soat1 Spp1 Tfpi | BC052055 Bicc1 Bok Cat | LOC231887 LOC240396 | Jarid1c Klf9 LOC214424 |
| Tle6 Trf Ttr | Cav2 Cd44 Crip Crp | Map3k7 Matr3 Matr3 | L0C56628 Lyzs Lyzs Lyzs |
| 4930459B04Rik Ttyh1 | D930029E11Rik Dach2 Dcx | MGC65558 MGC6694 | Mapk14 MGC25863 Mglap |
| Ttyh1 <u>Vegfc</u> Vldlr Zdhhc14 Zfp52. | Dpep1 Dpp4 Dscr1l1 Ebf3 | Mrps16 Mtch2-pending | Mta3 Narg2 Ndel1 Nedd9 |
| | Eif2s3y Elovl2 F13a | Ndr3 <u>Neurod1</u> <u>Nkx2-2</u> | Nov Pah Pkhd1 Ppy <u>Pyy</u> |
| | Frabin-pending G6pc-rs | Np95 Paxip1 <u>Pcsk1n</u> | Rbp7 Ret Rgpr-pending |
| | Gch Gck <u>Gipr</u> <u>Glp1r</u> | Pcsk2 Pctk1 Pfdn1 Pitpnb | S100a6 S100a8 Scp2 |
| | Gna13 Gpr27 H2-D1 | Prnp <u>Psk1-pending</u> Psmb3 | Siat8c <u>Sst</u> Sycp3 Tacstd1 |
| | Hlxb9 Hpca Hspa12a-pending Iapp Ins1 Ins2 | Ptprn Pttg1 Rab6 Rad21 | Timp3 Tm4sf3 Tnfrsf11b |
| | <u>Insm1</u> <u>Ipf1</u> Iqgap1 Krt2-8 | Ramp2 Ranbp1 Rbpms | Tor3a Tpra40-pending |
| | Lgals2 Lhx2 Lmwdsp20-pending LOC194126 | Rcn2 Refbp2 Resp18 | Trim44 Tsll2-pending |
| | LOC215866 LOC328644 | Risc-pending Rnpc2 <u>Scg2</u> | Usp15 Usp47 Utx <u>Vcam1</u> |
| | Maob Mbc2 MGC47419 | Sdfr1 Sfrs3 <u>Sgne1</u> Smc4l1 | Waspip Zfp219 Zfp36l1 |
| | Myo7b Necab2-pending | Spi1-1 Sqle Ssb <u>Syt13</u> | Zfp40 Zfpn1a2. |
| | Nmi <u>Nnat</u> <u>Npy</u>Nudt7 | <u>Syt7</u> <u>Syt7</u> Tmpo Tomm20-pending Txnrd1 Ube1c | |
| | Papss2 Papss2 <u>Pclo</u> | Ubl3 Ubqln2 Vdu1-pending | |
| | Ppp1r1a Prcad-pending | Wwp4-pending Xlr3a | |
| | Prkcb Pvrl3 <u>Ramp1</u> Rasd1 | Ywhab Ywhaz Yy1 | |
| | Rasgrf1 Sepp1 Slc12a7 | Zfp364. | |
| | <u>Slc2a2</u> Slitl2 Stx3 Svil | | |
| | Sytl4 Tec Tnnt1 Ubap1 | | |
| | <u>Wbscr14.</u> | | |

Using the additionally available genomics datasets, it was found that expression of Betacam occurred in both normal, and obese mouse pancreatic islet cells (FIG. 16). Expression of Betacam was observed in Flow-cytometry sorted (FACS) mouse pancreatic β-cells, as defined by phogrin-EGFP expressing cells at embryonic day E18.5, corresponding to a time when pancreatic beta cells are recently formed. Phogrin is selectively expressed by the pancreatic beta cell, and not other pancreatic endocrine cells. Expression of Betacam was observed in Flow-cytometry sorted (FACS) mouse pancreatic β-cells, as defined by phogrin-EGFP expressing cells at postnatal day 24 and 25, corresponding to weaning age, a time when the pancreatic β-cells are mature. Expression of Betacam was observed in pancreatic glucagonoma cells (αTC) at low levels, and much increased in pancreatic insulinoma cells (βTC), indicating beta-cell enrichment.

Expression of Betacam was observed throughout the course of mouse pancreatic development, increasing at E13.5-E14.5, which is known as the secondary transition, and is the time when pancreatic beta cells start to form. Expression of Betacam was lost in mouse pancreas of Ngn3 null genotype, but present in WT littermates. Expression of Betacam in human islets was validated through EST-sequencing, and the Betacam mRNA was detected 15 times through random sequencing of human islet cDNA.

Figure 17:
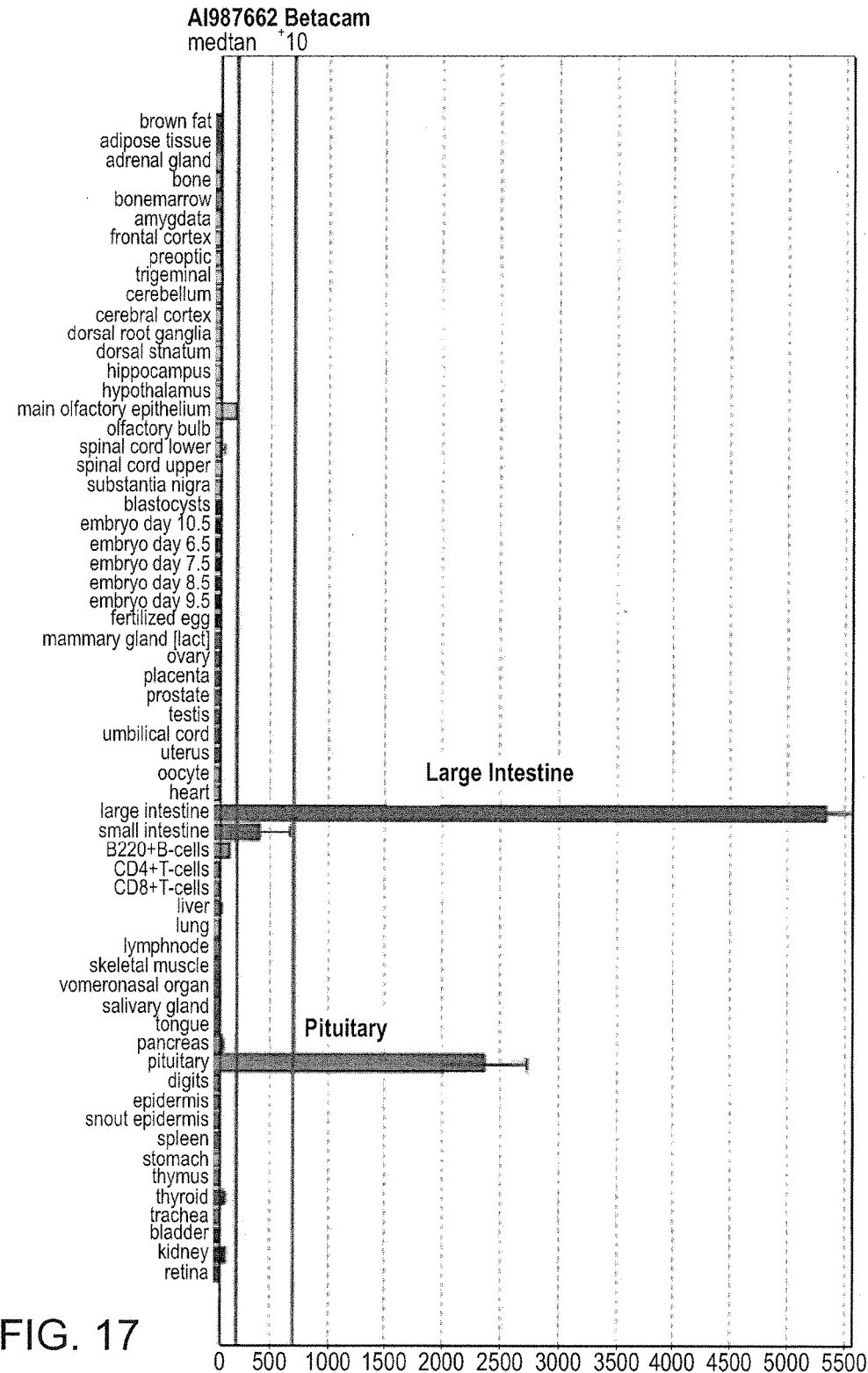
FIG. 17 is an expression analysis graph of mouse Betacam. This is based on the Novartis SymAtlas datasets providing a wide-tissue batch expression analysis. The gene is generally absent from most tissues, except for Large, and Small intestine, and pituitary. Islets are not present in this set.

It was also found that Betacam is expressed in the pituitary, small intestine and large intestine, but not elsewhere as judged from a genomics screen of multiple tissues (FIG. 17).

It was also found that expression of Betacam as performed by GenePaint, is observed in developing pancreas at E14.5, with a centrally regionalized expression pattern corresponding to that of developing endocrine cells (FIG. 18A). Outside the pancreas, expression is noted in limited regions of the developing brain (FIG. 18B). In situ hybridization was performed and revealed expression of Betacam in developing E18.5 pancreas, corresponding to endocrine cells (FIG.18C). Radioactive labeling and RT-PCR analysis was performed and revealed expression of Betacam in pancreatic insulinoma cells (βTC). EST sequencing confirms the presence of Betacam mRNA in cDNA libraries from both mouse and man (FIG.18D).

EXAMPLE 3

Structural Prediction Analysis of the Folding Conformation of the Extra-Cellular Region of Betacam The data on the predicted structural fold of the Betacam extracellular portion was based on a method known as "threading", and provides to those skilled in the art, a confidence level basis for understanding an unknown 3-dimensional fold, as judged through comparisons to other similarly folding proteins. The resource that was applied to obtain these results is known as "Phyre", provide by the imperial College, U. K. Uploading the amino acid sequence for mouse Betacam, the Phyre resource first performed a Psi-blast homology detection algorithm analysis using sequence identities for proteins for which a 3-dimensional structure has been solved, and is publicly available. Hits passing a minimal threshold were used for a "threading analysis" in which the novel protein sequence, in this case that of Betacam, was threaded through the fold libraries represented by the Psi-blast hit table. 3-dimensional "fits" were evaluated based on energy considerations, and if the unknown sequence is capable of adopting a fold structure similar to that of one, or more, of the library folds. The results were presented such that a 3D coordinate set for the unknown protein sequence, congruent to the library hit, was downloaded. A score, relating to the confidence of the particular prediction analysis was obtained. A detailed description of phyre is found within "Exploring the extremes of sequence/structure space with ensemble fold recognition in the program Phyre. By Bennett-Lovsey RM, Herbert AD, Sternberg MJE, Kelley LA. Proteins: Structure, Function Bioinformatics, vol 70(3)611-625 (2008)."

Based on results of above, it was found that the extracellular domain consists of 3 Ig-type domains. Based on 3-dimensional modeling to distant relatives using the Phyre threading service, the structural fold of 95% of the extracellular domain, ranging from amino acid leu32 to Isoleucine 306 was predicted, and was fitted to the NCAM 3-dimensional fold, represented by the structure known in the Brookhaven protein data bank as structure c1qz1A.pdb.

Based on above results, a homotypic interaction method for Betacam/Betacam protein dimers was predicted. The homotypic interaction basis allows for the specific design of Betacam-derived single-molecules that are capable of interfering with Betacam/Betacam interactions, or binding to Betacam proteins localized on the beta cell surface.

FIG. 19 is a multi-alignment of Betacam protein sequences from 5 selected vertebrate species upon which a domain-assignment was provided. 3 Ig-type domains were detected, and named D1, D2, D3, where D1 represents the domain located most N-terminally, D2 is between D1 and D3, and D3 occupies a position C-terminally, closest to the membrane. For convenience, the amino acid numbering for the structural analyses were provided based on cleavage of the signal peptide. Consequently, this trimmed off the first 32 amino terminal residues, and amino acid 1 (leucine) corresponds to amino acid 33 (leucine) when the signal peptide is present. Amino acid residues located at the junction between these domains are as follows: Pro114 is the bridging residue between D1 and D2, Tyrosine 207 and Tyrosine 208 bridge between D2 and D3 and Isoleucine 303 is the most C-terminally located residue in the fold prediction analysis. The sequence $^{304}$TSVGLEKLAQRGKSLS319 (SEQ ID NO: 51) corresponds to the remaining extracellular sequence, which is not modeled and predicted to behave as a linker between D3 and the transmembrane domain. A series of amino acids are present in Betacam, from Arginine 41 to Asparagine 54, which are not present in NCAM, and cannot be modeled. his 12 amino acid stretch ($^{42}$SHTMPKYL-LGSV$^{53}$ (SEQ ID NO: 52)) is referred to as the "D1 loop".

Figure 20:
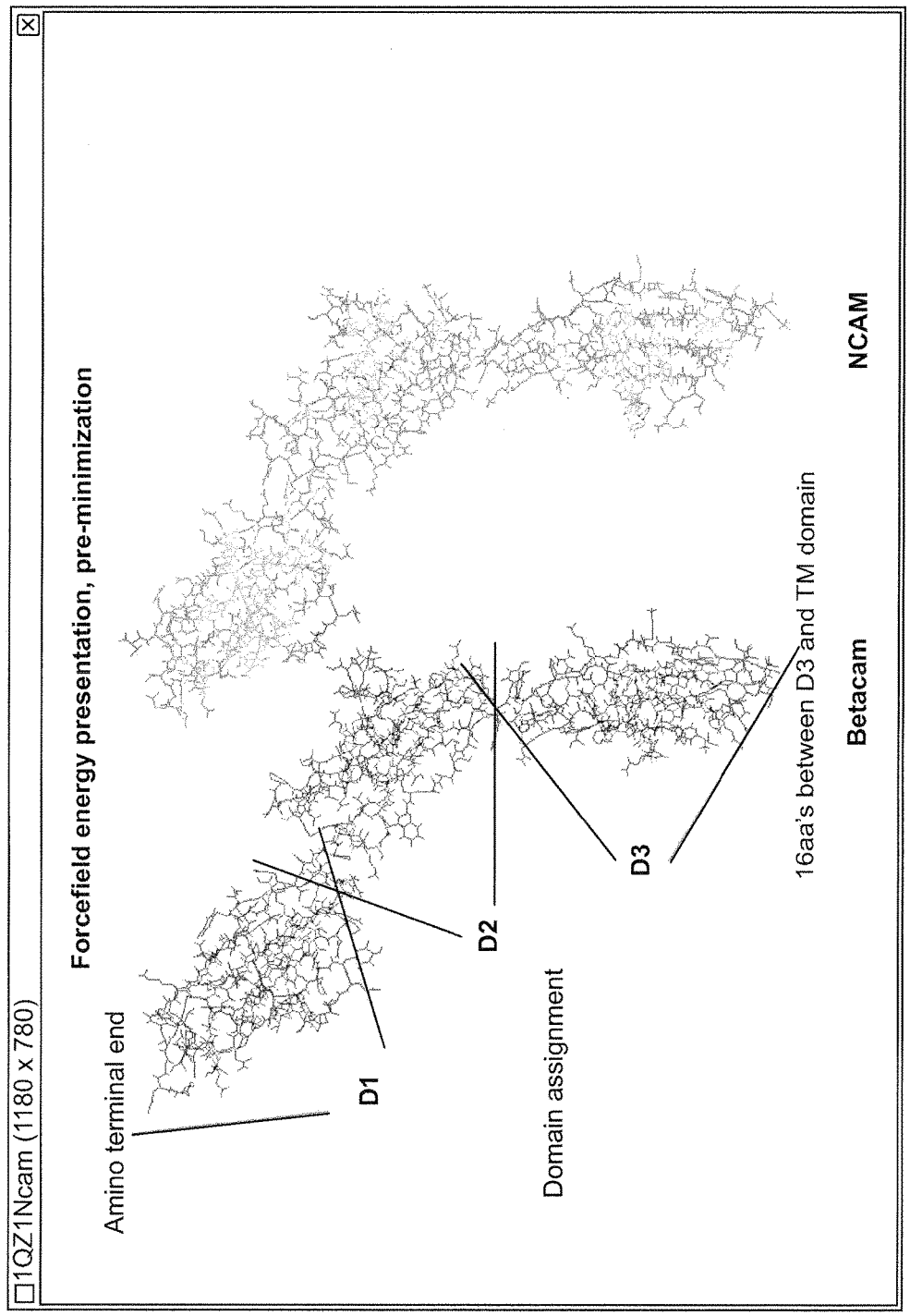
FIG. 20 is a structural view of Betacam (left), threaded onto the NCAM fold (right), forcefield energy is shown. This was done using the Phyre threading serving, using the 3D coordinates of NCAM. D1, D2, D3 depicted on the figure. Green color denotes low energy (stable), blue to orange to red indicates conflicts. Figure created by the DeepView program.

FIG. 20 is structural view of Betacam (left) compared to NCAM (right), force field view. No minimization occurred, and the conformation of Betacam was not stable. The image was created by the DeepView program, which is a freely available program for structural analysis of proteins, using pdb-coordinate sets. Information on the Deepview program, also known as the Swisspdb Viewer.

Figure 21:
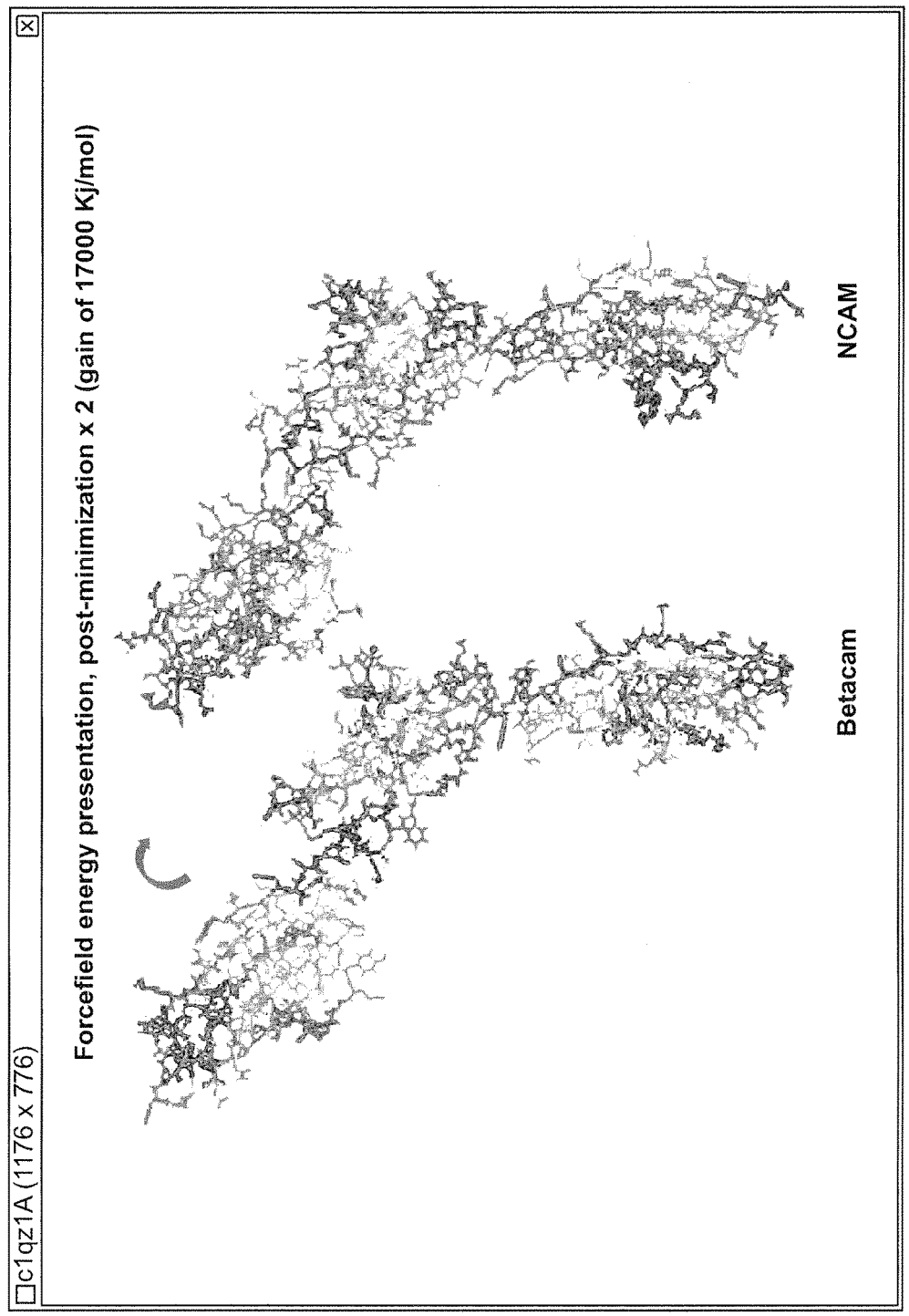
FIG. 21 is a structural view of Betacam (left), threaded onto the NCAM fold (right), forcefield energy is shown. The Betacam molecule has been energy-minimized in Deep-View, by adjusting side chain position, and 2× overall molecule energy minimization. The end result is a molecule in stable conformation. The numbering of the amino acid residues follow the sequential numbering of the cleaved form of Betacam. SEQ ID NO: 14 lists the amino acid sequence of the extracellular sequence of mouse Betacam, SEQ ID NO:15 lists the amino acid sequence of the extracellular sequence of human Betacam.

FIG. 21 is structural view of Betacam (left) following energy minimization. A significant gain in energy was attained, the molecule was more stable, and side chains were in a more favorable conformation. The structure stability approaches that of NCAM (right)

Figure 22:
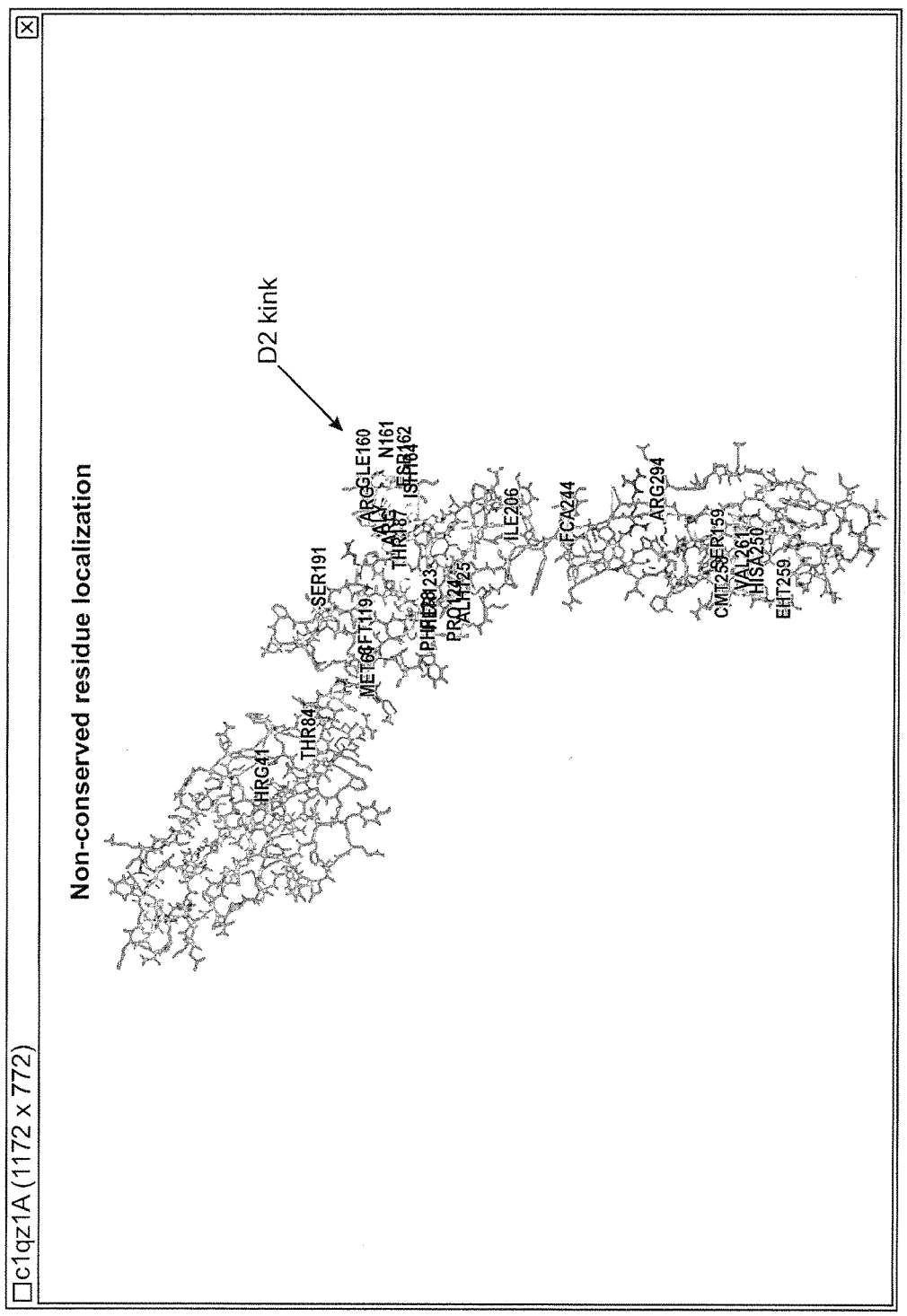
FIG. 22 is a structural view of Betacam in which non-conserved residues are labeled. A given region in D2, here named the "D2-kink" is the predominant region at which Betacam is not conserved. D1 is highly conserved in evolution. A region of D3 is also containing variation.

FIG. 22 is structural view of Betacam (left) following energy minimization, where labeling of amino acids displaying incomplete conservation during evolution has been provided. Residues in D1 were generally conserved. A patch of residues, on the kink-region of D2 "D2-kink", are diverging during evolution. This area of the molecule was expected to be solvent accessible, and unlikely to be involved in protein/protein interactions, as such interactions would require a stronger evolutionary fixation. A region/patch of amino acids in D3 is non-conserved.

Figure 23:
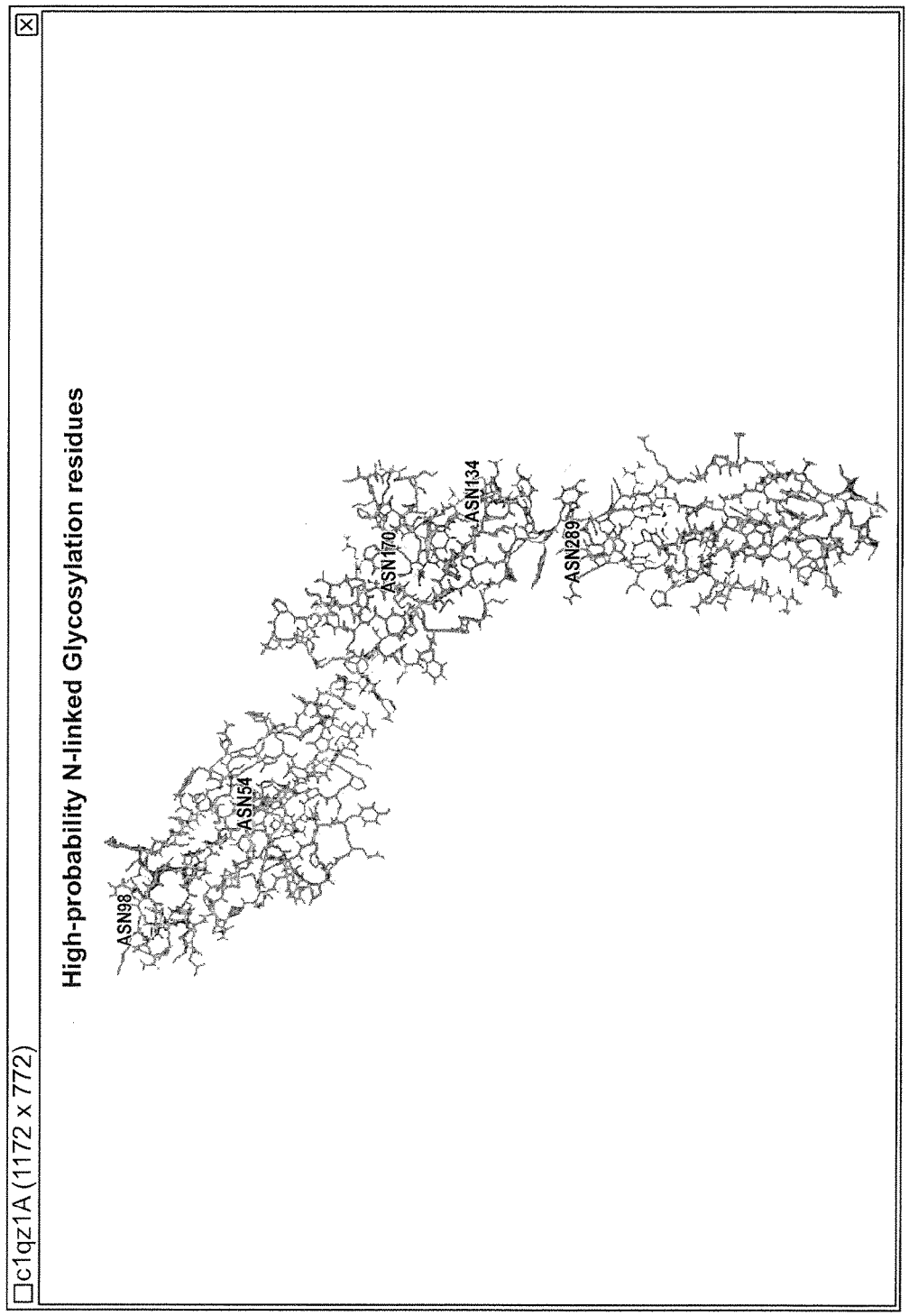
FIG. 23 is a structural view of Betacam in which residues highly likely to be glycosylated through N-linked glycosylation are labeled. Such Asparagine-residues are localized throughout the molecule.

FIG. 23 shows the position of highly probably N-linked glycosylation sites on the Betacam molecule as predicted using the Net-N-Glyc server. Such sites were found within the regions corresponding to D1, D2 and D3.

Figure 24:
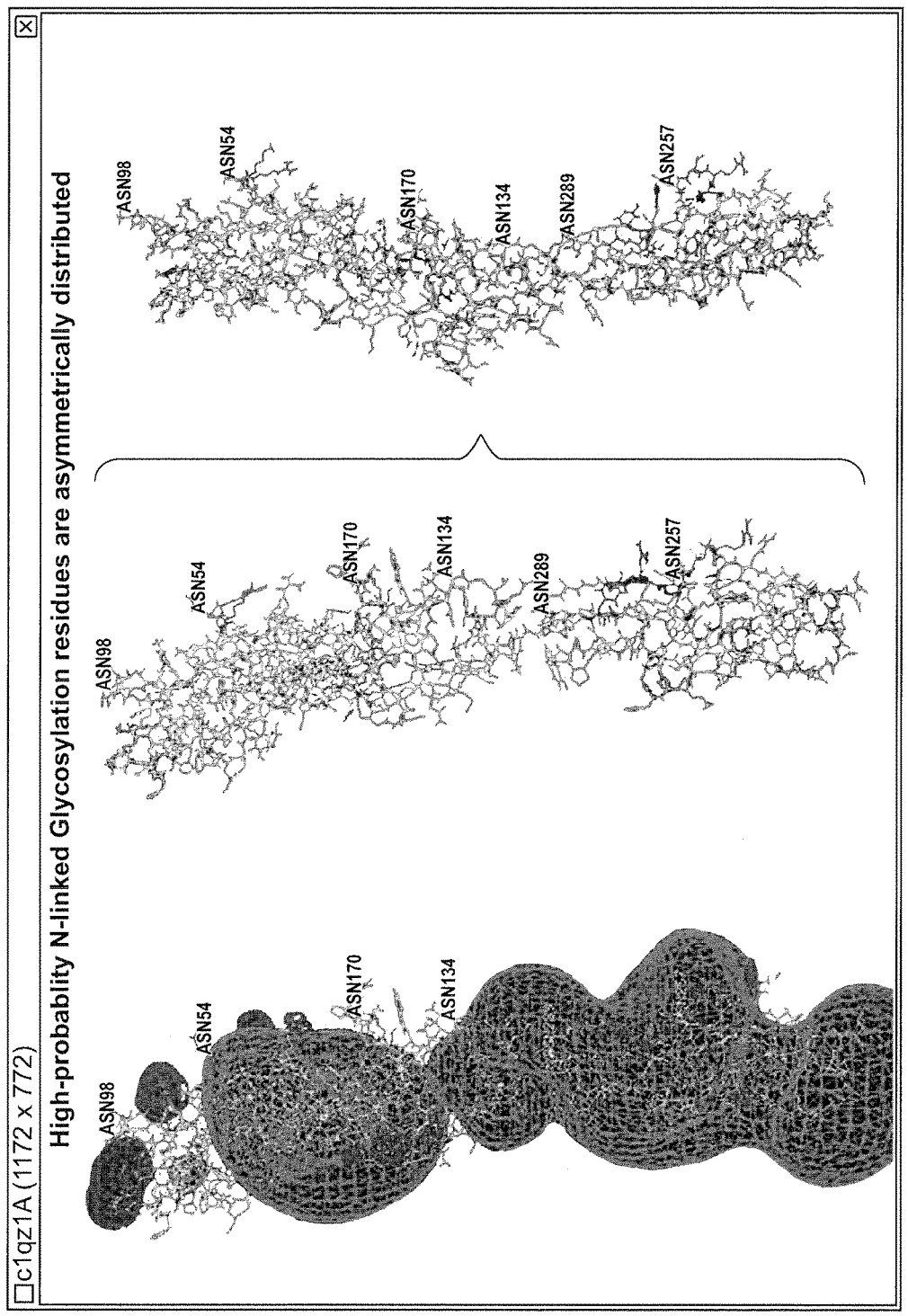
FIG. 24 shows a clockwise rotation of molecule shown in FIG. 23. It is apparent that all high-probability N-linked glycosylation sites are localized on one side of the molecule (to the right in this figure). The leftmost view shows a surface charge-distribution of molecule.

FIG. 24 shows the localization of the putative glycosylated asparagines shown in FIG. 24, with a rotation of the Betacam molecule. The two rightmost views display a one-sided, asymmetric localization of all of the Asparagine residues identified by the neural network prediction server. All of these were localized on the surface of the predicted fold. Suggestively, glycosylation protects one side of the Betacam protein. The other side is free to engage in protein/protein interactions. The leftmost view is identical to the middle representation of the Betacam molecule, except that surface-charge distribution has been visualized. It is clear that the D1/D2 area display an asymmetrical charge distribution.

Figure 25:
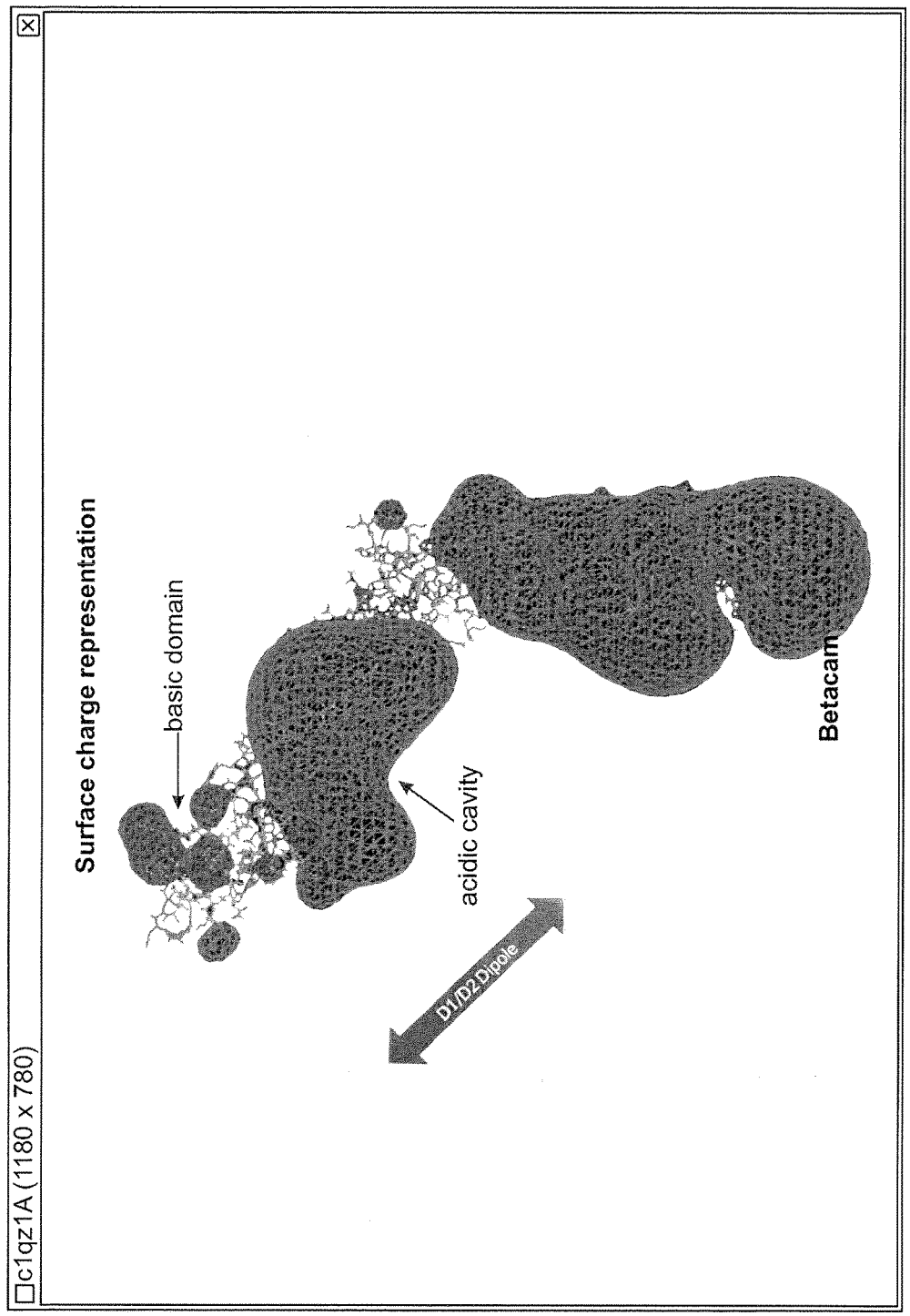
FIG. 25 is a surface charge representation of Betacam. Red corresponds to rich electron density, negative charge, whereas blue corresponds to positive charge. The D1-D2 region creates a dipole.

FIG. 25 is a side-view of the Betacam molecule in FIG. 23, leftmost. This view emphasizes the asymmetrical distribution of charge (blue corresponds to positively charged areas, red corresponds to negatively charged areas). A dipole exists that covers the D1/D2 region. In the following, reference is made to the "acidic groove" present at the D1/D2 bridge region.

Figure 26:
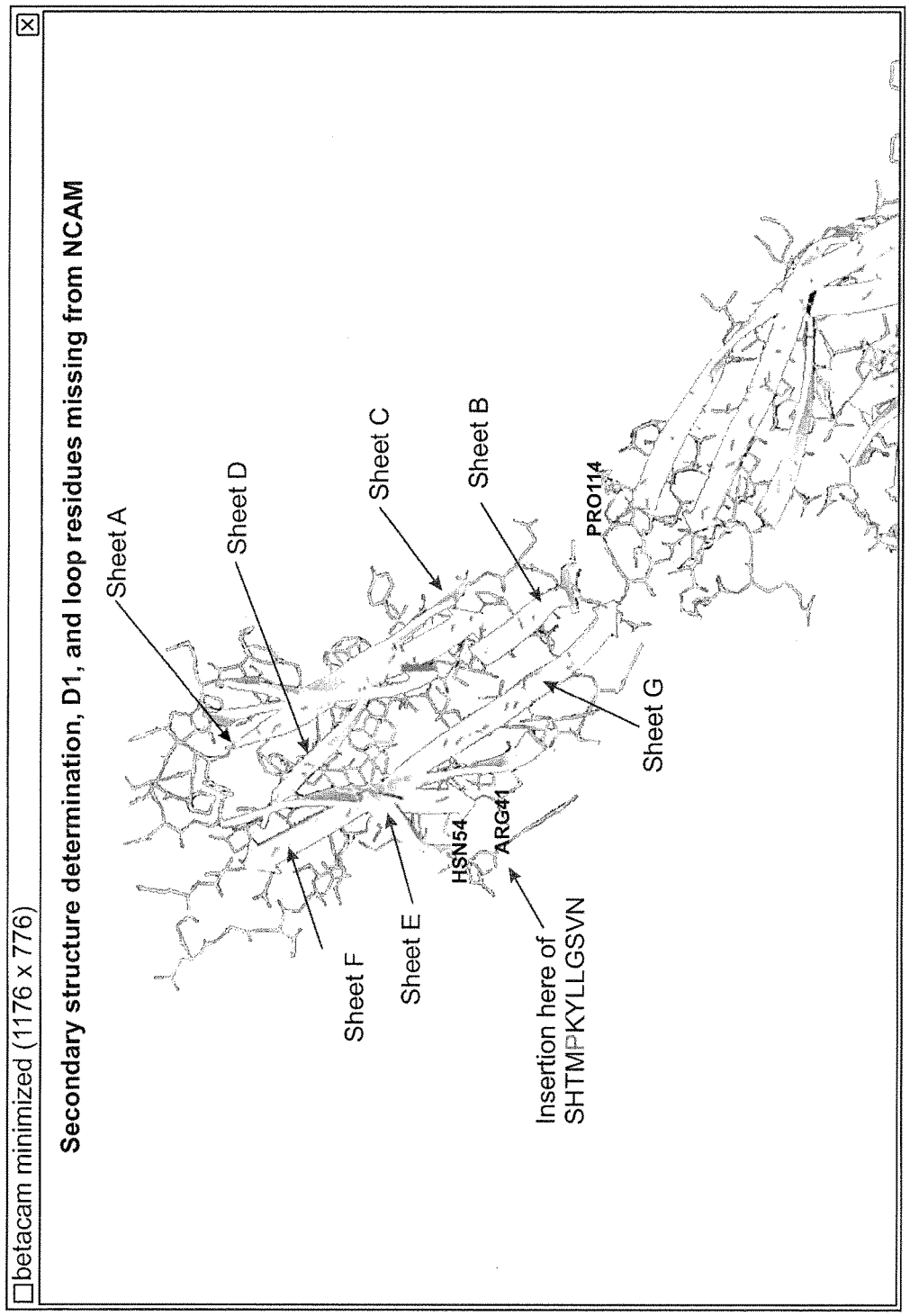
FIG. 26 is a secondary structure assignment of D1. A total of 7 beta-sheets is present in D1, naming as on the figure. With yellow is highlighted the Arg41 and Asn54 residues. A 13 amino-acid insertion exists between these two residues, not modeled in the present comparison to NCAM, which lacks such an amino acid stretch at the corresponding position.

FIG. 26 shows with higher magnification the secondary structure elements of Betacam D1. This Ig-type domain consists of 7 beta-sheets, named in the figure as A-G. On the left-most side of the domain, amino acids Arginine 41 and Asparagine 54 are shown in yellow. The D1 loop, present between these residues, on the surface of D1, is the same surface as the one containing the glycosylated residues. In fact, Asparagine 54 is one of the putative glycosylated residues. The D1 loop is therefore not considered to interfere with protein/protein interactions occurring at the opposite side of the domain.

Figure 27:
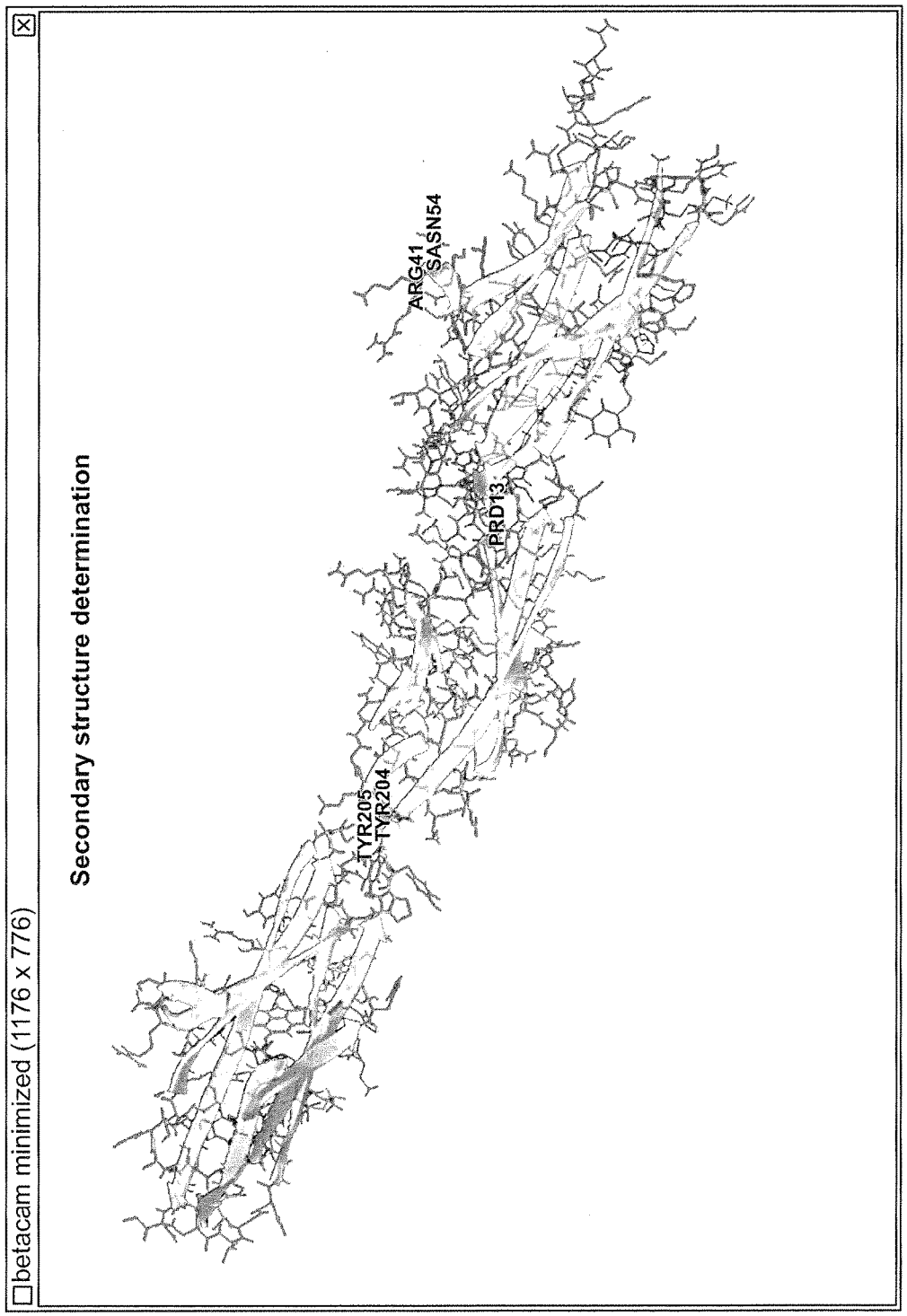
FIG. 27 is a secondary structure assignment of the full Betacam molecule. D1, D2, D3, all contain 7 beta-sheets, and all fold as Ig-type domains.

FIG. 27 shows the secondary structure of the Betacam molecule consisting of 3 Ig-domains, all of which consist of 7 beta-sheets. The bridging residues proline 114, and tyrosines 207-208 are shown.

Figure 28:
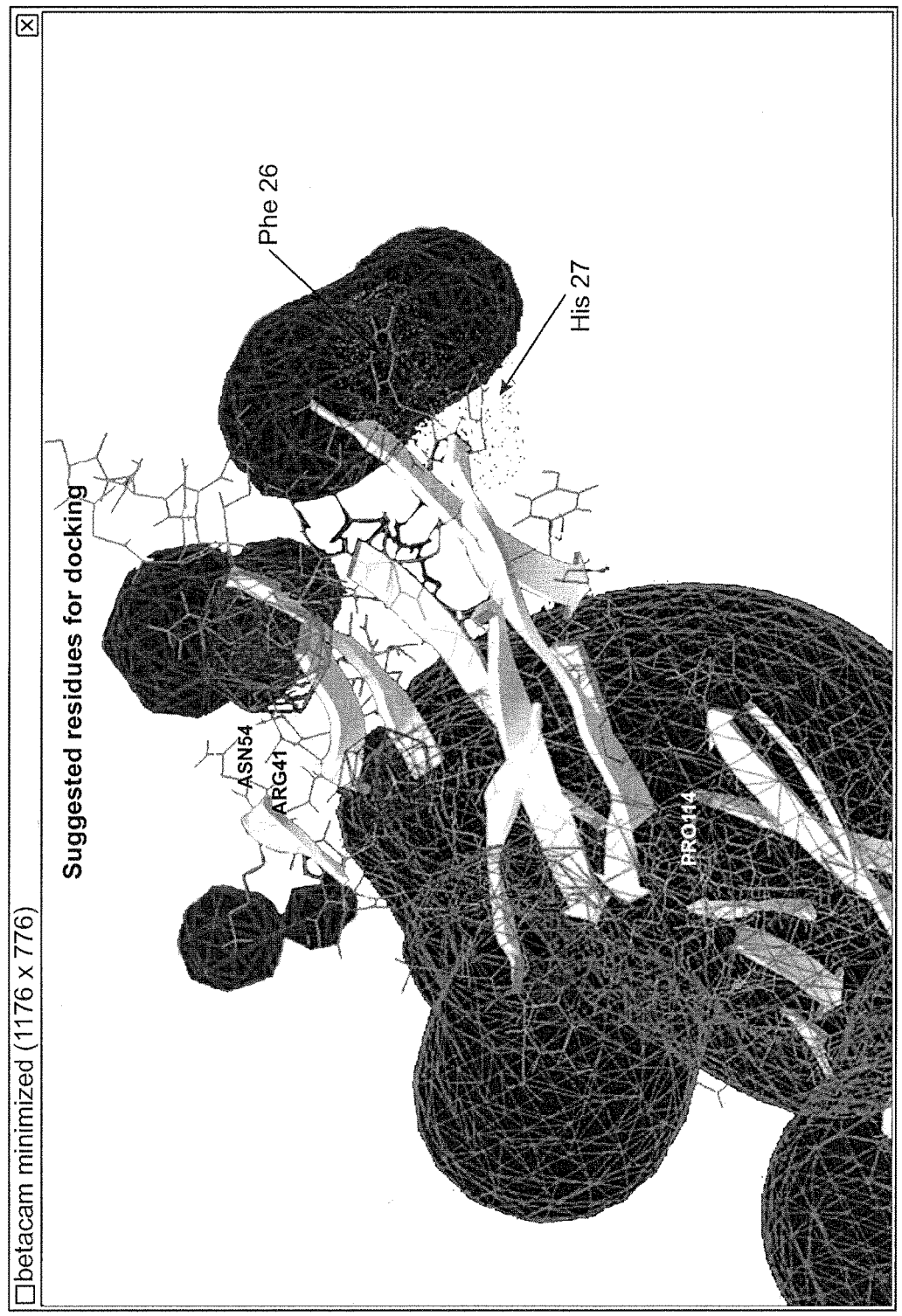
FIG. 28 is a magnified view of Domain 1, highlighting two residues (Phe26, His27) expected to insert into the acidic groove.

FIG. 28 shows a magnified view of the basic region of D1, which is referred to as the "docking motif". Two residues expected to insert into the acidic groove (Phenylalanine 26 and Histidine 27) are highlighted.

Figure 29:
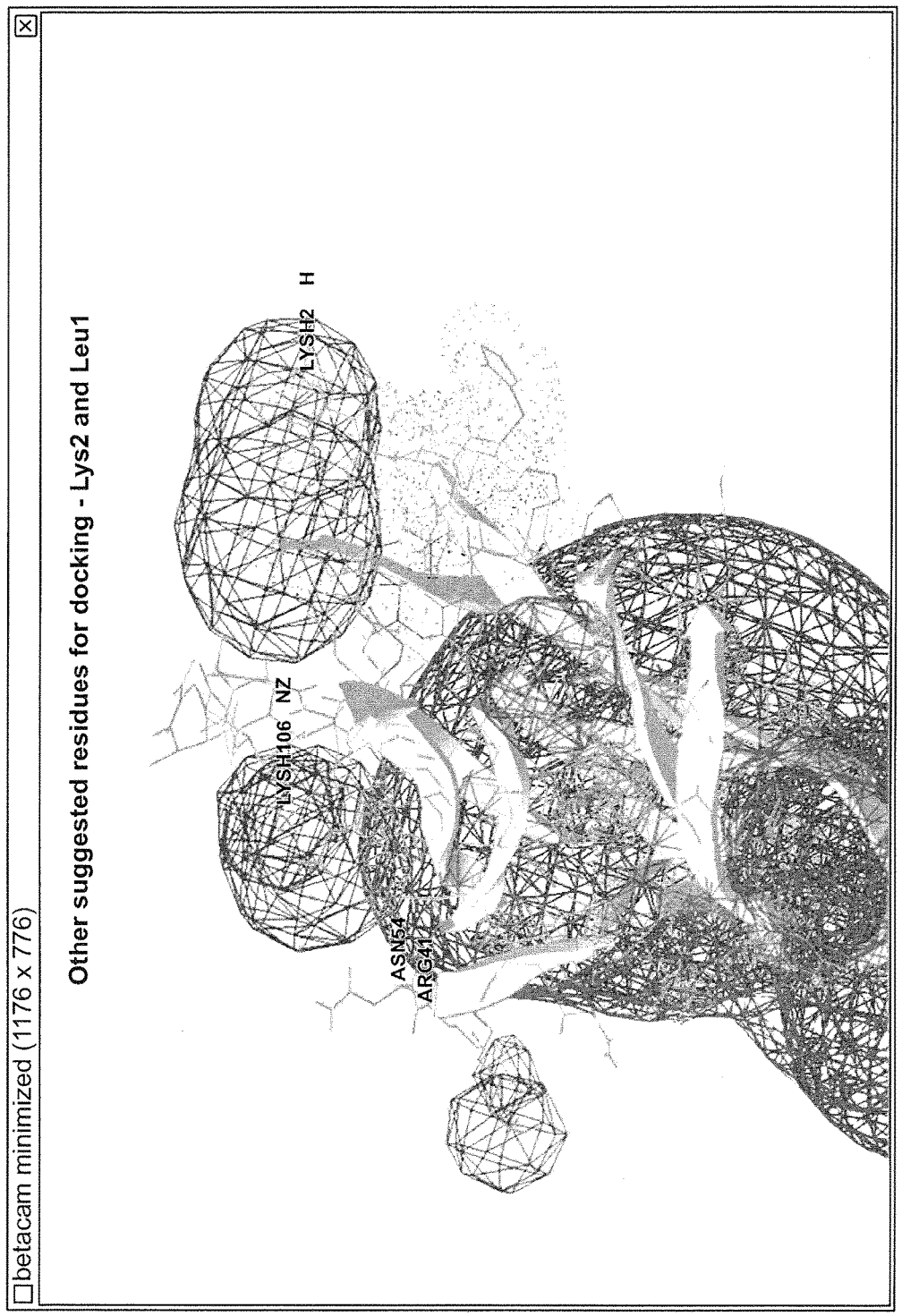
FIG. 29 is a magnified view of Domain 1, highlighting two residues (Leu33 (Leu1 in the molecule after SP cleavage), Lys34 (Lys2 in the molecule after SP cleavage) also expected to insert into the acidic groove. Lys2 is expected to contact glutamic acids 132 and 133.

FIG. 29 shows a magnified view of the basic region of D1, which is referred to as the "docking motif". Two residues, immediately neighboring those of Phenylalanine 26 and Histidine 27, Leucine 1 and Lysine 2, are highlighted. The Lysine 2 is positioned to contact the acidic residues (Aspartic acid 112, Aspartic acid 113) located in the acidic groove.

Figure 30:
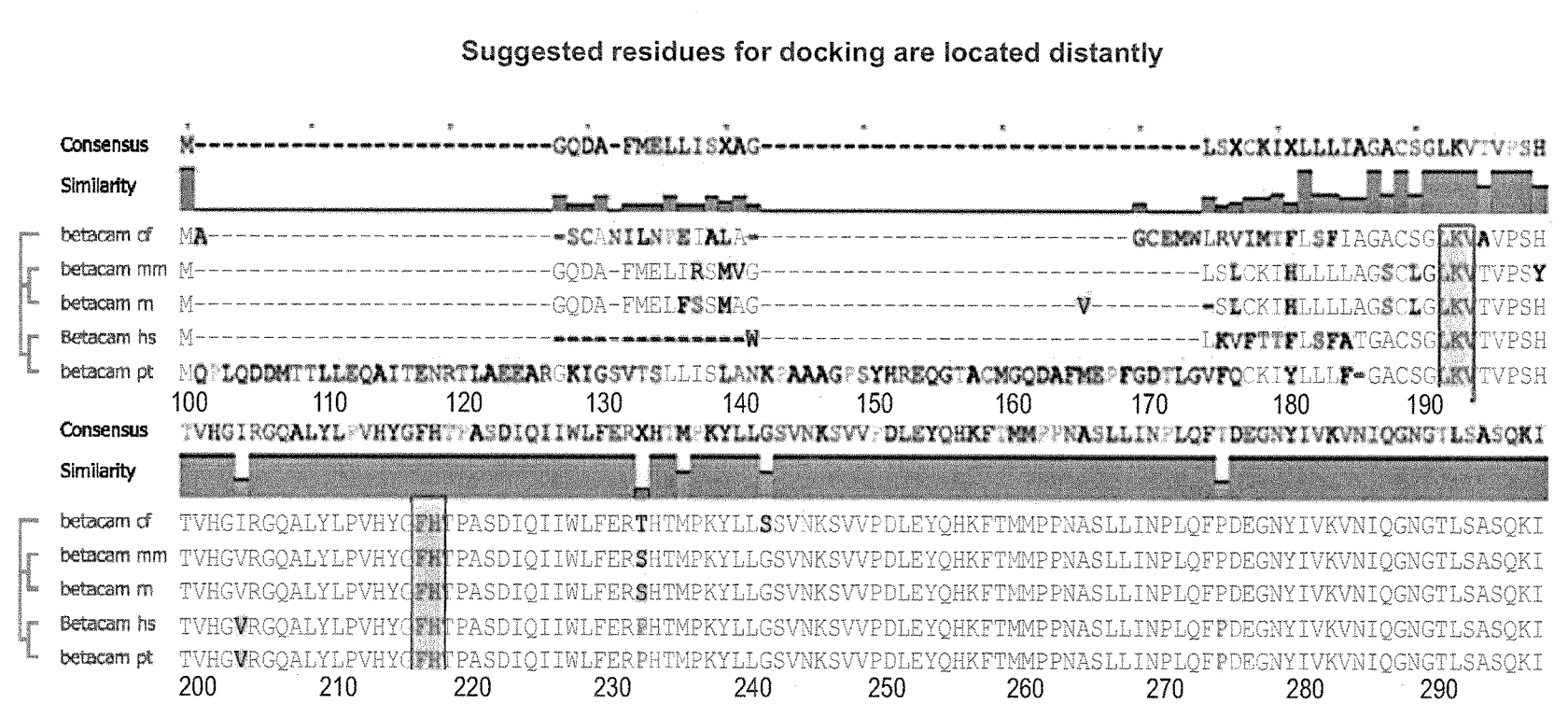

FIG. 30 shows the separation of the suggested docking residues (Leu1, Lys2, Phe26, His27) on the primary sequence of Betacam. These residues combinations are distantly located on the primary sequence, but proximal to each other in space.

Figure 31:
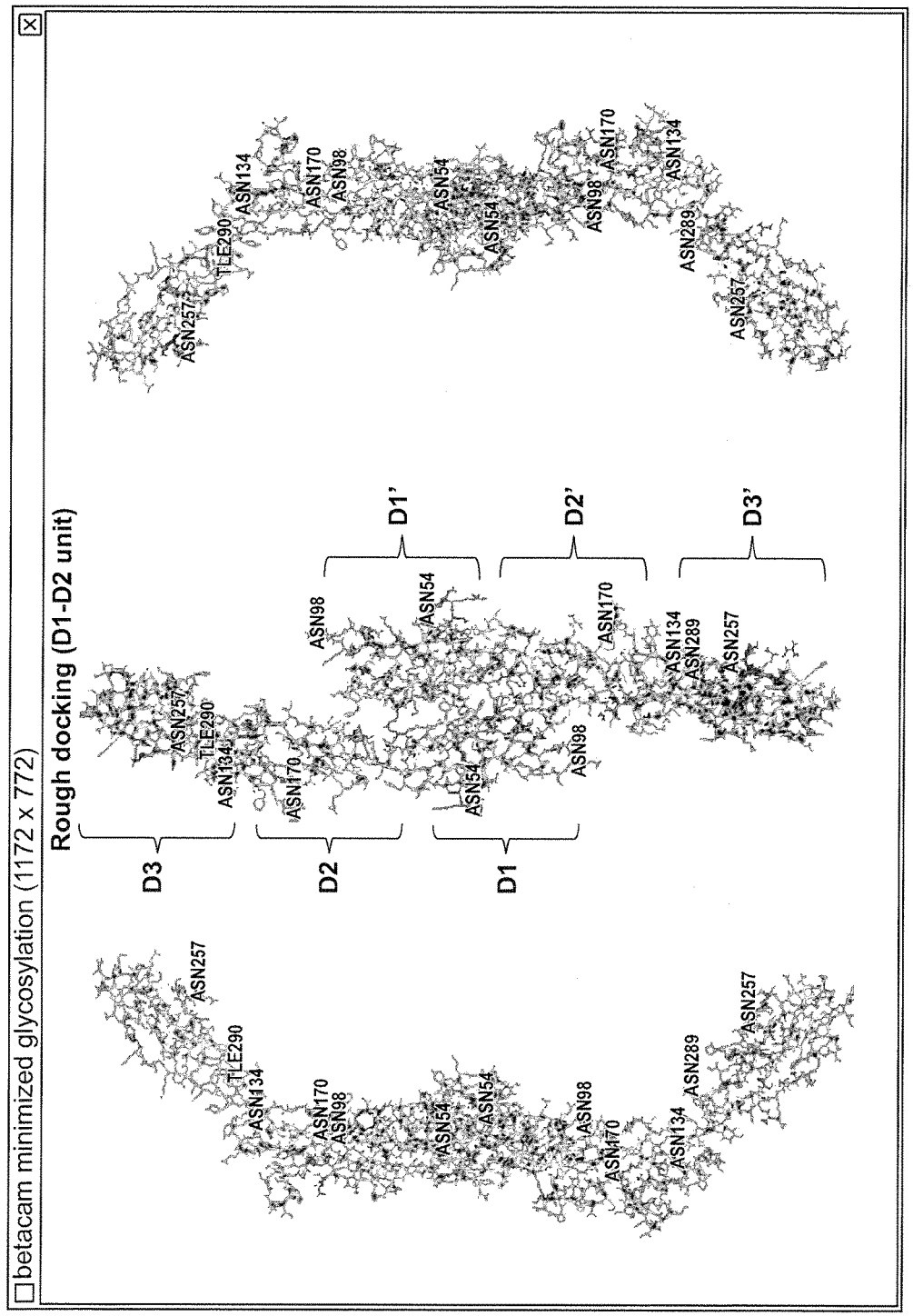
FIG. 31 is an anti-parallel docking of two Betacam molecules, in which D1 docking residues insert into the acidic groove created by D1'/D2', and D1' docking residues insert into the acidic groove D1/D2. A resulting half-domain offset is visible in the interaction region. For both molecules, all N-linked glycosylation residues are facing outward, and will not interfere with the docking. The resulting dimers form a semi-circle, which is viewed (left and right) using 90-degree rotations.

FIG. 31 shows the docking of two molecules of Betacam, engaged in homotypic, anti parallel interaction. The docking involves interactions between the two molecules on the exposed, non-glycosylated sides, and assumes opposing dipole interactions, which buries the docking residues in the acidic groove region. The resulting dimer is offset by one-half Ig-domain. The consequence of this docking would be to create a dimer, in which two molecules of Betacam, attached to the cell surface of adjacent beta cells become closely connected.

Figure 32:
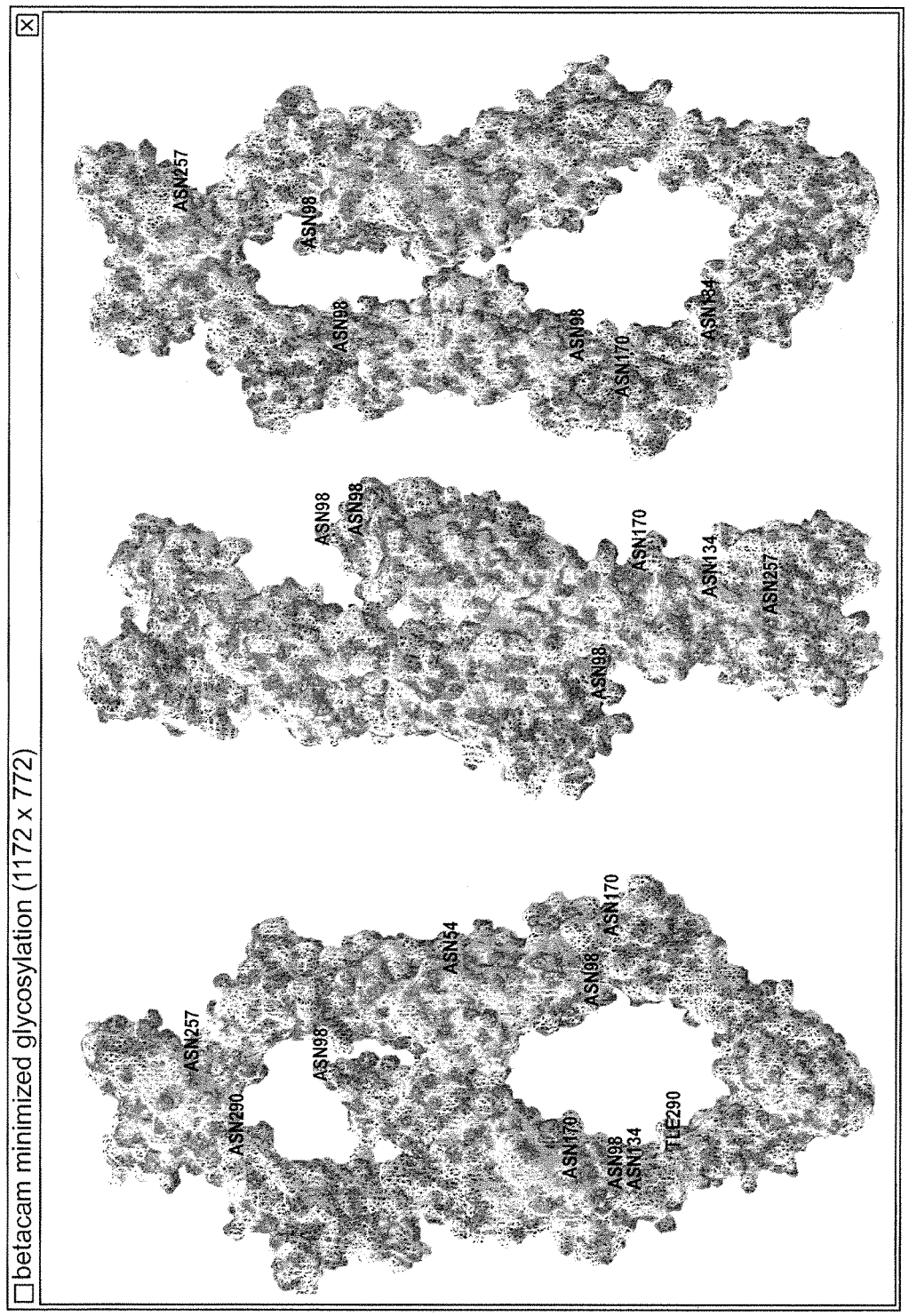
FIG. 32 shows surface renditions of a total of 4 Betacam molecules docked using one D1/D1:D1'/D2' interaction in the middle, and adding two additional Betacam molecules docking as D3/D3' interactions. The resulting molecule will take the form of a spiral, in which the central region of the extended circle is pinched together, creating a figure-8 shape. The top and bottom of the figure-8 would be attached to the membrane of two interacting cells.

FIG. 32 shows the docking of 4 molecules of Betacam, using D1/D2 interactions, and D3-D3 interactions. The model assumes D3-D3 homotypic interactions using the non-glycosylated face of the D3 domain.

Figure 33:
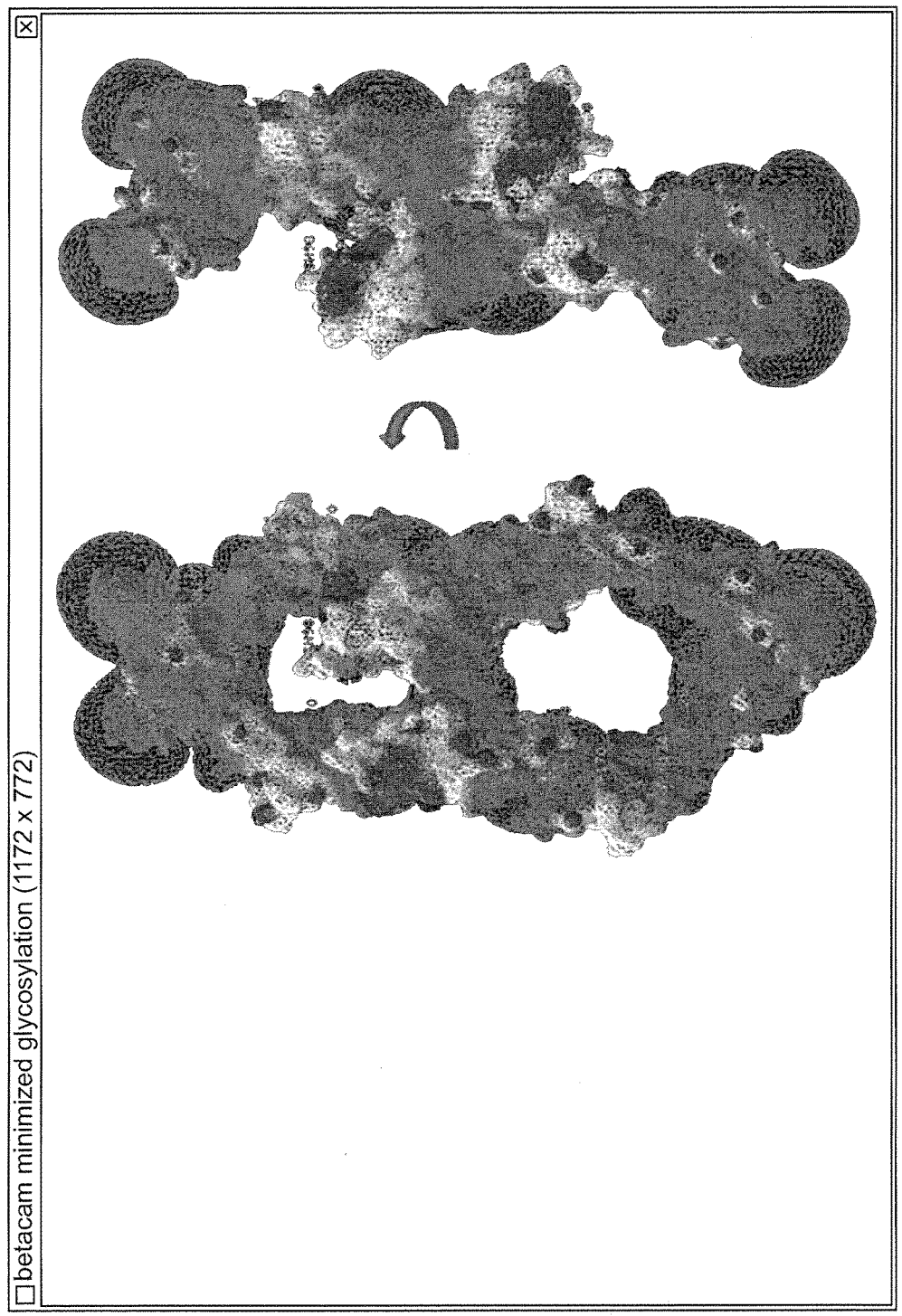
FIG. 33 shows surface renditions of a total of 4 Betacam molecules docked using one D1/D1:D1'/D2' interaction in the middle, and adding two additional Betacam molecules docking as D3/D3' interactions. Surface charge overlaid. Only two basic-regions (D1) of the molecule are present, those of the two Betacam molecules engaged in D3/D3' interactions. Connecting additional Betacam molecules to these using anti-parallel D1/D2 regions would extend the spiral, and neutralize the surface charges.

Referring now to the invention in more detail, if one considers the capacity of D3-D3 homotypic interactions, the molecule will be capable of forming a multimeric structure between two Betacam-expressing cells. The iteration of the model described in FIG. 33 can be extended in either direction through the addition of Betacam molecules, which will extend the free ends of the D1/D2 domains. Under those circumstances, a multimeric Betacam structure forms with the shape of a spiral, the apexes of which will be connected by two interacting D3-domain at the surface of the cell. It is believed that such a structure allows for strong homotypic cell-cell interaction, and the formation of a tight-junction type complex between interacting cells. The model therefore posits that Betacam is a tight-junction molecule, expressed by certain cells of both higher and lower vertebrates.

Figure 34:
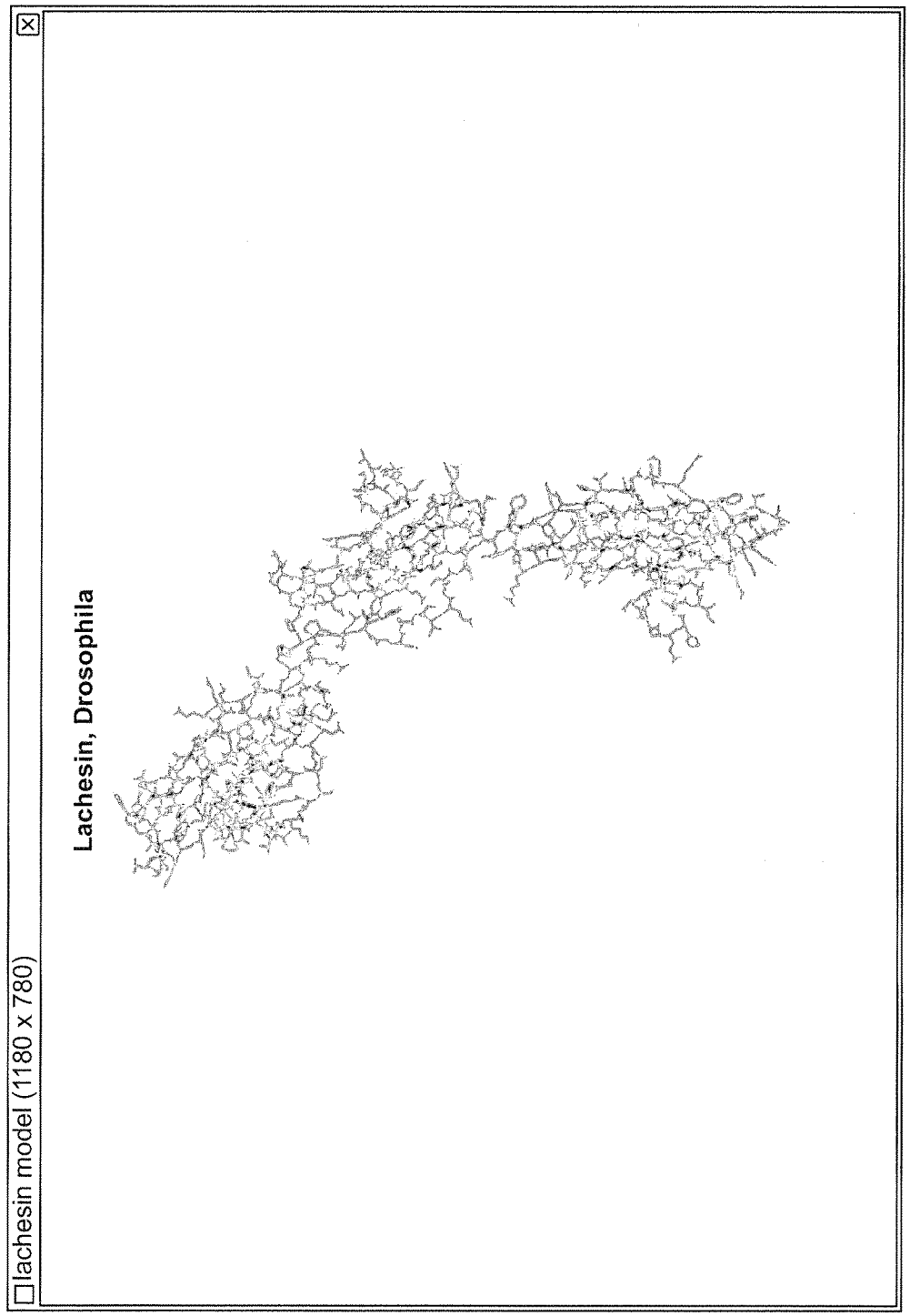
FIG. 34 shows threading results of *Drosophila* Lachesin onto the NCAM fold structure.

In a comparative perspective related to a predicted physiological involvement of Betacam, FIG. 34 displays the threading results of the *Drosophila melanogaster* Lachesin protein GeneID: 36363, Flybase link FLYBASE: FBgn0010238 against mammalian NCAM. The prediction score is 100%. Lachesin is the closest homologue to Betacam in flies. Lachesin (Lac), a cell surface protein, is required for the proper morphogenesis of the *Drosophila* tracheal system. Data suggest that Lac regulates organ size by influencing cell length rather than cell number, and cell detachments, indicating a role for Lac in cell adhesion. Results from an in vitro assay further support that Lac behaves as a homophilic cell adhesion molecule. Lac co-localizes with Septate Junction (SJ) proteins, and ultrastructural analysis confirms that it accumulates specifically at this type of cellular junction (Development. 2004 January; 131 (1):181-90). Although not described in detail in mammals, in the mammalian peripheral nervous system, nerve insulation depends on the integrity of paranodal junctions between axons and their ensheathing glia. Ultrastructurally, these junctions are similar to the septate junctions (SJ) of invertebrates. In *Drosophila*, SJ are found in epithelia and in the glia that form the blood-brain barrier (BBB). It has been described that *Drosophila* Lachesin (Lac), which is a SJ component, is required for a functional BBB in that organism. It is generally recognized that tight junctions regulate the barrier to paracellular permeability in chordate epithelia, including mammals; examples of another non-vertebrate organism such as the sea urchin, it has been shown that at its blastula stage, its epithelium lacks tight junctions and instead possesses septate junctions. Septate junctions are unique to non-chordate invertebrate cell layers and have a characteristic ladder-like appearance whereby adjacent cells are connected by septa. The similarity between Lachesin and Betacam, indicates that Betacam may be involved in formation of a septate-like adherens complex between pancreatic beta cells, which may help in forming proper beta-cell structure.

Figure 35:
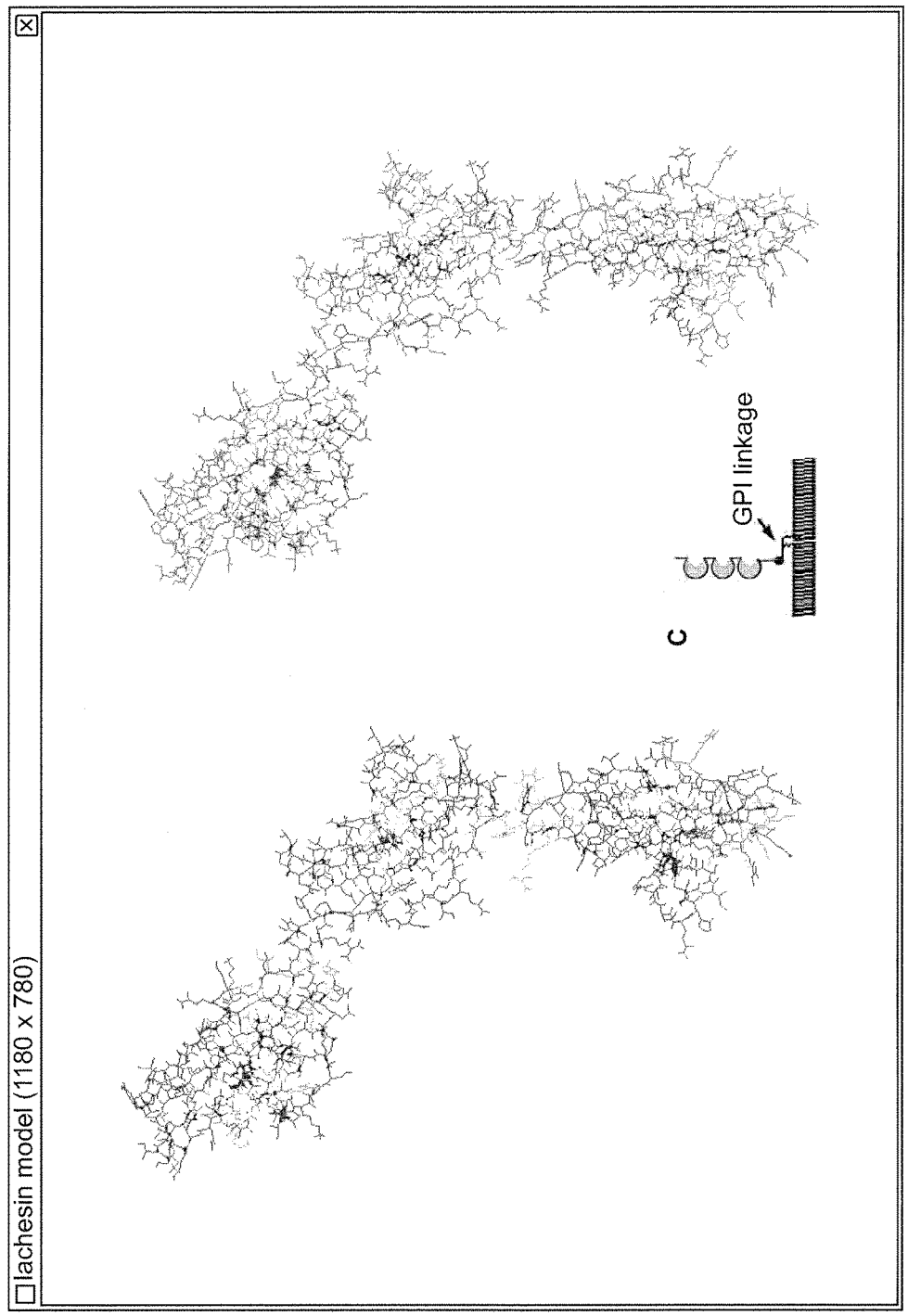
FIG. 35 is a view of *Drosophila* Lachesin following energy minimization. The insert depicts Lachesin binding to the membrane using a GPI anchor.
Figure 36:
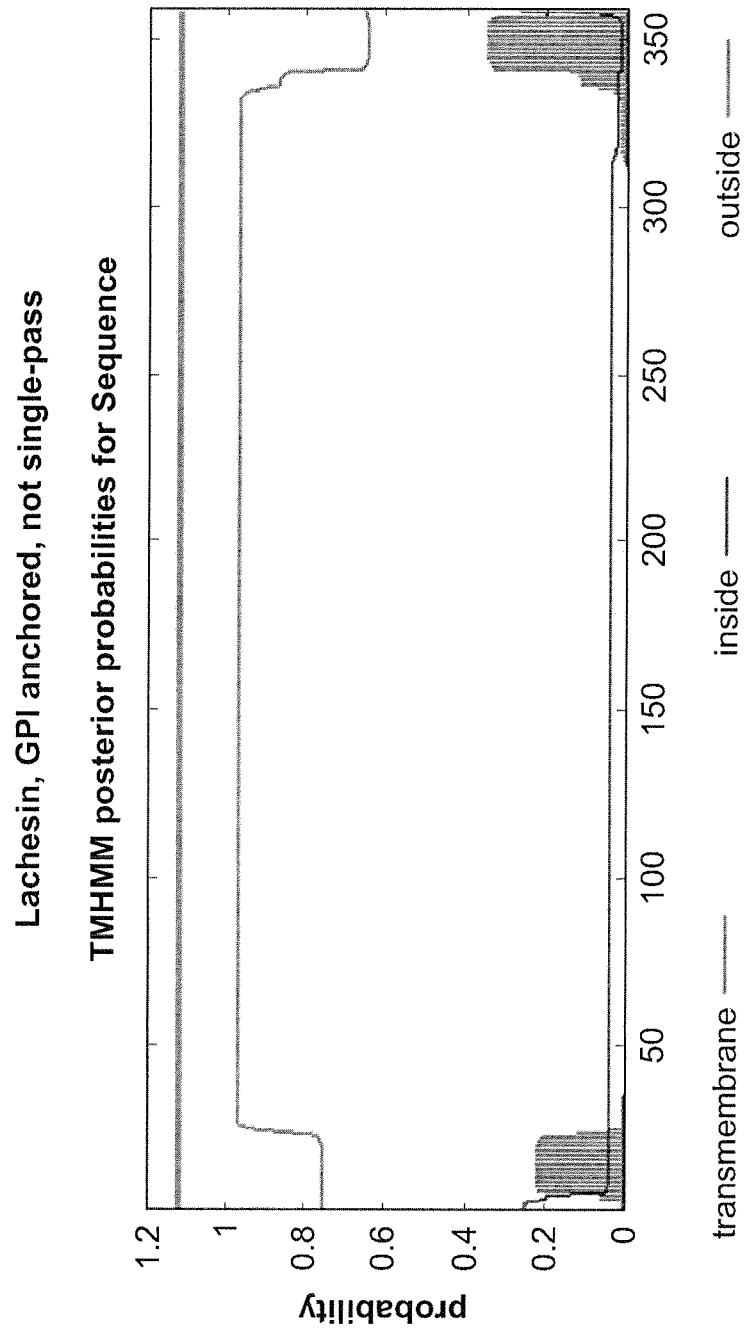
FIG. 36 is a detection result of trans-membrane regions in Lachesin.

Again, in a comparative perspective to the invention related to a predicted physiological involvement of Betacam, FIG. 35 displays predicted membrane attachment of lachesin to the cell membrane using a GPI-anchor. As is shown in FIG. 36, lachesin does not contain a membrane spanning region. The entire molecule is present on the outside of the cell surface.

Figure 37:
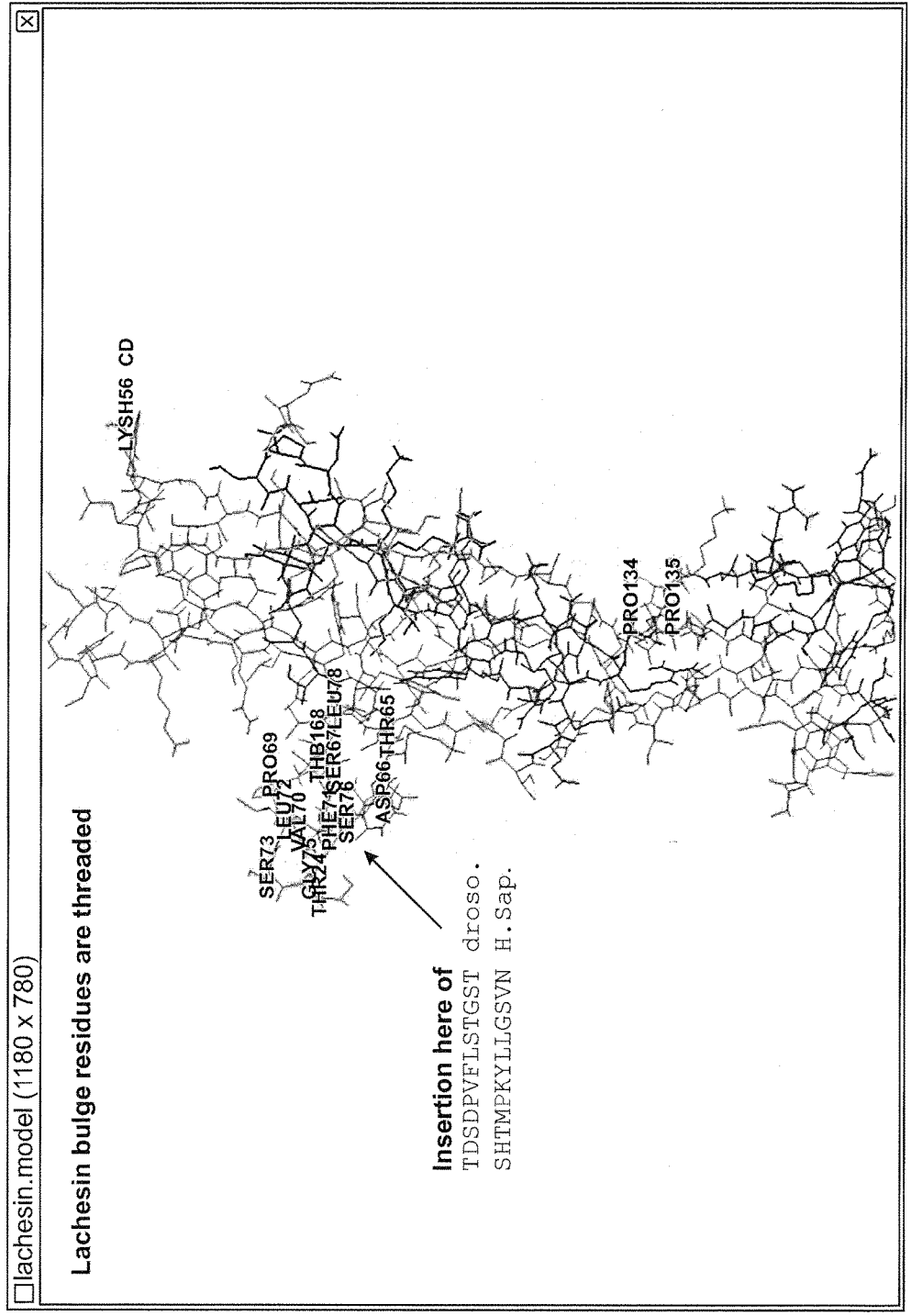
FIG. 37 is a magnified view of *Drosophila* Lachesin, Ig-domain 1. D1-bulge residues are shown (SEQ ID NO: 45, SEQ ID NO: 46).

Again in a comparative perspective to the invention, a magnified view of lachesin is shown in FIG. 37, in which D1 has been enlarged. Annotation of amino acid sequence TDSTPVFLSTGST (SEQ ID NO: 53) present in Lachesin is shown. This linker corresponds to the D1-bulge residues in Betacam, and is here modeled on the surface of Lachesin opposite to that of the likely interaction side. It is noteworthy that the linker presence is a conserved feature between fly Lachesin and vertebrate Betacam.

Figure 38:
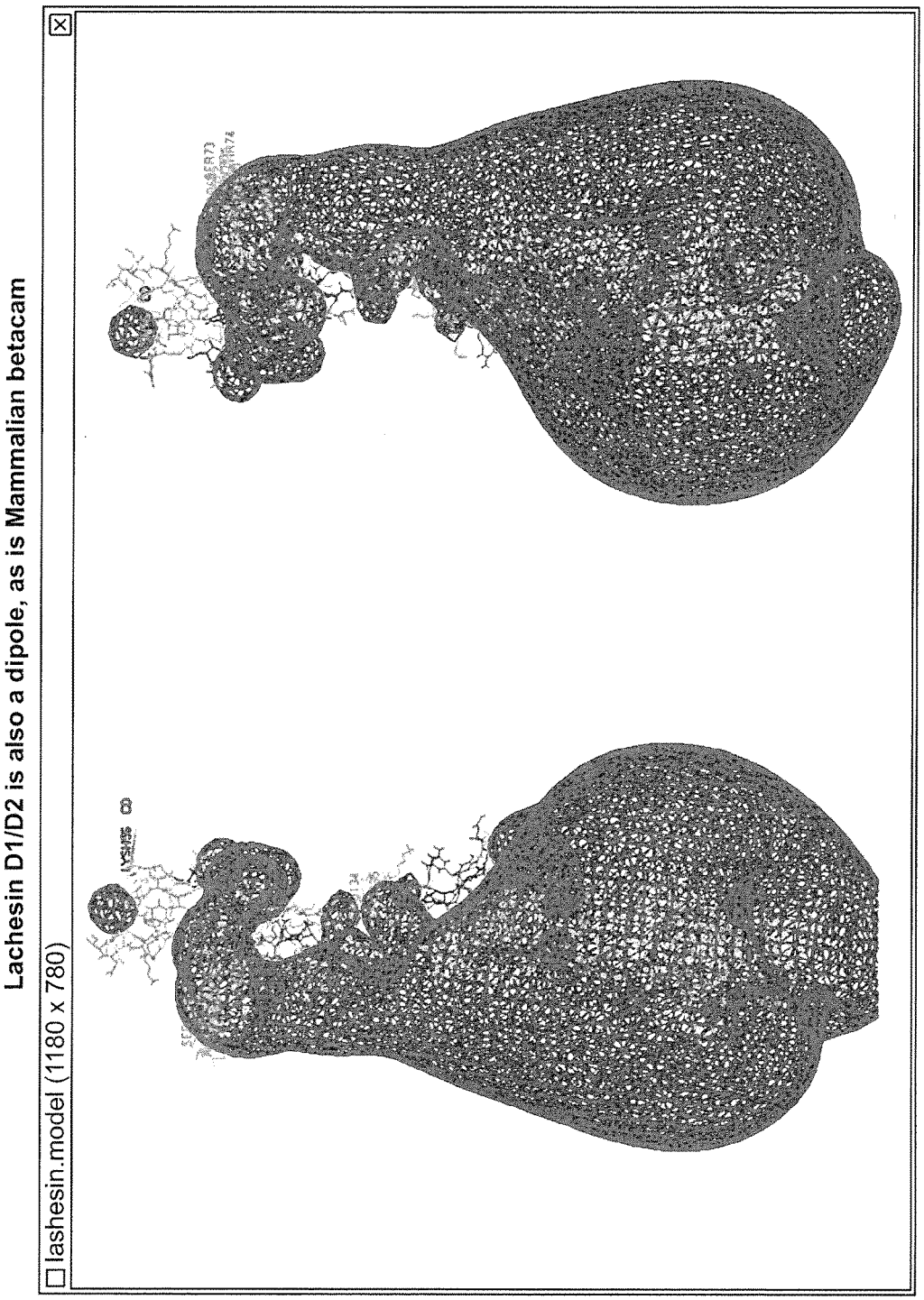
FIG. 38 is a surface charge representation of Lachesin. The D1-D2 region contains an electric dipole.

Again in a comparative perspective to the invention, the charge-distribution of lachesin is shown in FIG. 38. Similar to Betacam, the D1-D2 region of lachesin displays a similar electric dipole as that observed in Betacam. An acidic groove is present. This is conferred by Asp41 and Asp102. Lys56 is localized in position close to that represented by Betacam Lys2, and the N-terminal end of the molecule. Consequently, a model of lachesin homotypic interactions can be predicted following the exact geometry of that proposed for Betacam, involving a basic-residue docking into an acidic groove present at the D1-D2 link region.

Figure 39:
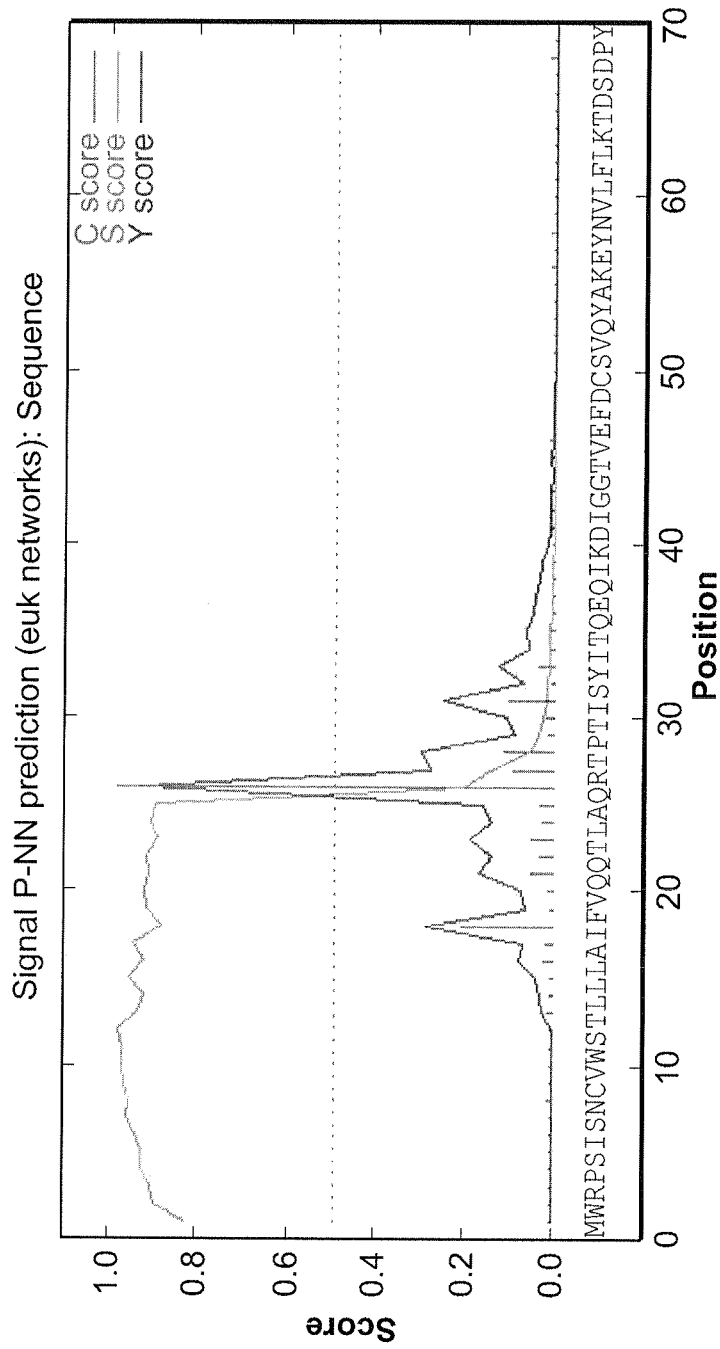
FIG. 39 shows prediction of a signal peptide cleavage (SEQ ID NO: 47) in Lachesin. Cleavage is predicted to occur after residue Alanine 25.

Again, in a comparative perspective to the invention related to a predicted physiological involvement of Betacam, FIG. 39 displays the detection of a signal peptide in lachesin with high confidence.

EXAMPLE 4

Figure 40:
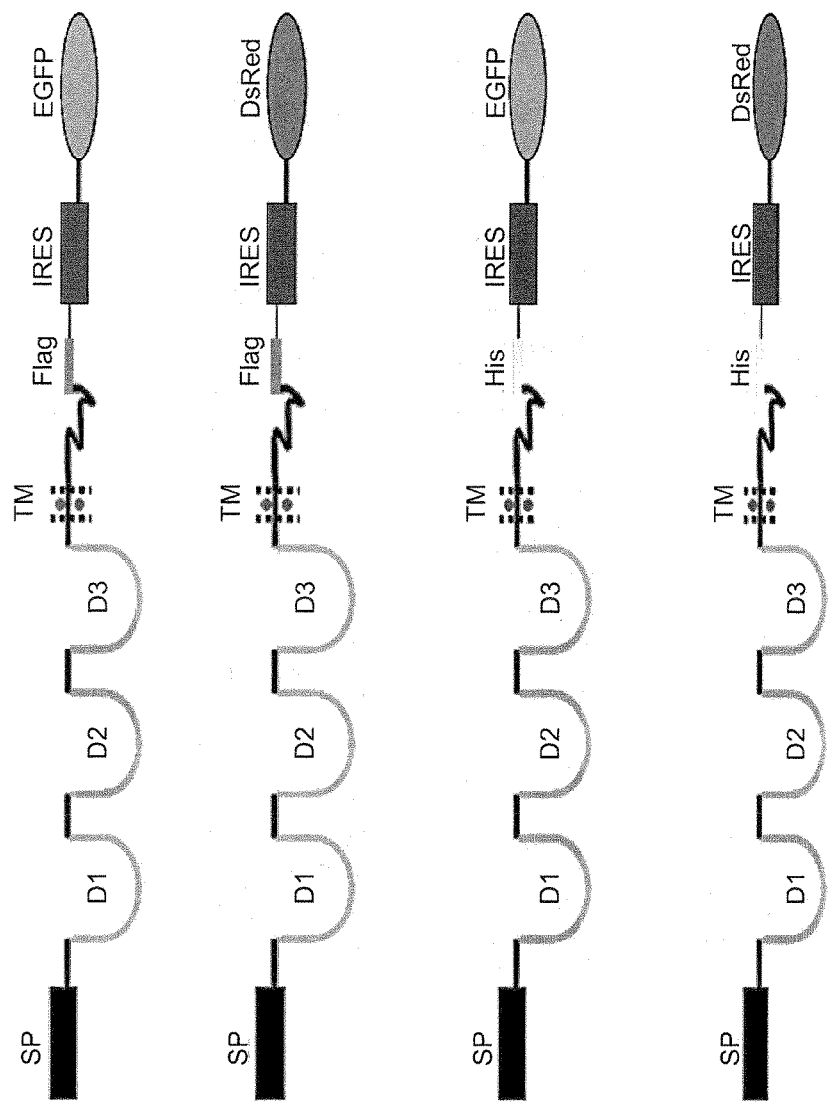
FIG. 40 is a schematic description of chimeric molecules generated for the experimental assessment of Betacam function. C-terminal Flag (or His)-tagged full-length murine Betacam (mBetacam) (including signal peptide, D1, D2, D3 domains, transmembrane domain and the intracellular domain) was subcloned into pIRES vectors so that it also expressed green fluorescent protein (EGFP) or red fluorescent protein (DsRed) in a bicistronic mRNA messenger.
Figure 41:
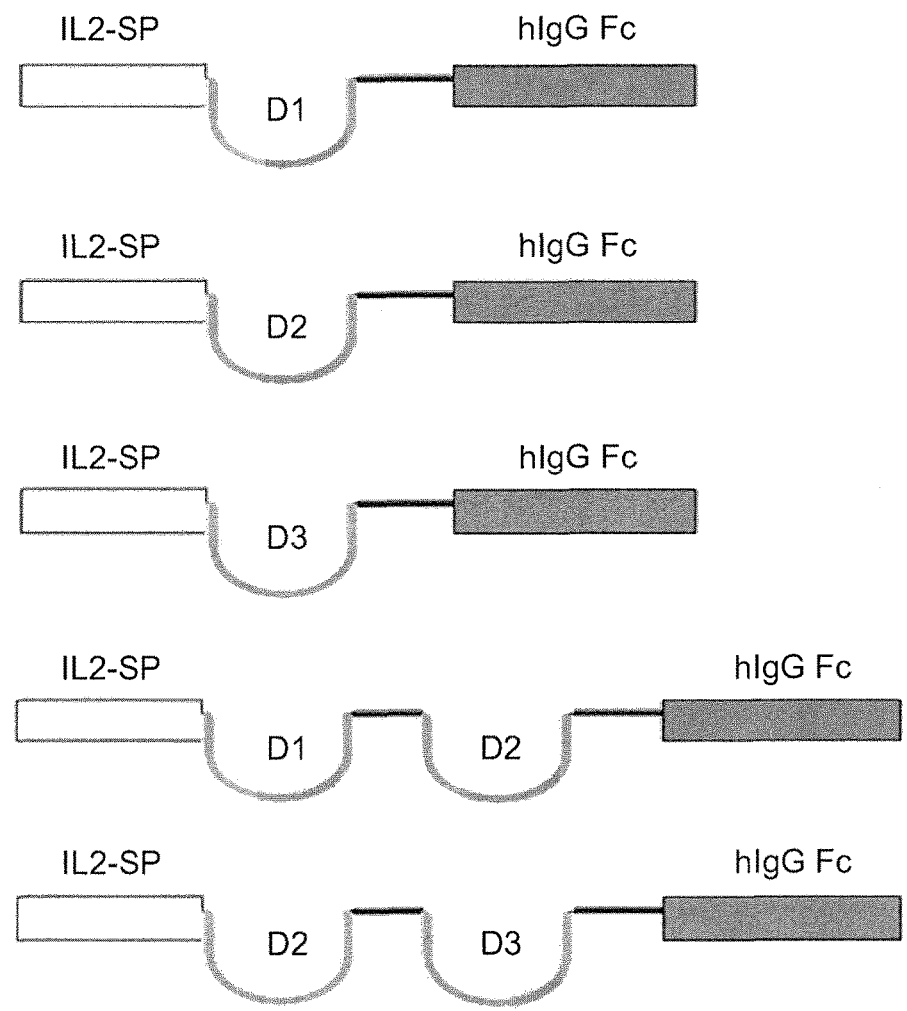
FIG. 41 is a schematic description of chimeric molecules generated for the experimental assessment of Betacam function. Generation of mBetacam domain-specific-Fc recombinant proteins. mBetacam D1 domain (aa 33-146), D2 domain (aa 146-239), D3 domain (aa 240-335), D1-D2 domain (aa 33-239), D2-D3 (146-335) were amplified by PCR and subcloned into vector pFUSE-hIgG1-Fc2 to facilitate the construction of Fc-fusion proteins.

Generation of Antibodies Reacting to Betacam Peptides and Detection of Betacam Expressing Cells Referring now to the invention in more detail, FIG. 40 and FIG. 41 display a schematic outline of various molecular forms of Betacam, designed and created by the inventors, and used in the following to functionally define the properties of the Betacam protein in relation to the specific claims of the invention. The generation of the various forms of Betacam were done by molecular biology techniques involving cloning DNA fragments into bacterially-propagated vectors, also known as plasmids. The vectors used for these particular purposes are commercially-available products, not uniquely designed for the functional analysis of Betacam, and derived polypeptides. More specifically, the vectors employed took advantage of multiple favorable features for analyzing membrane-type components.

Figure 42:
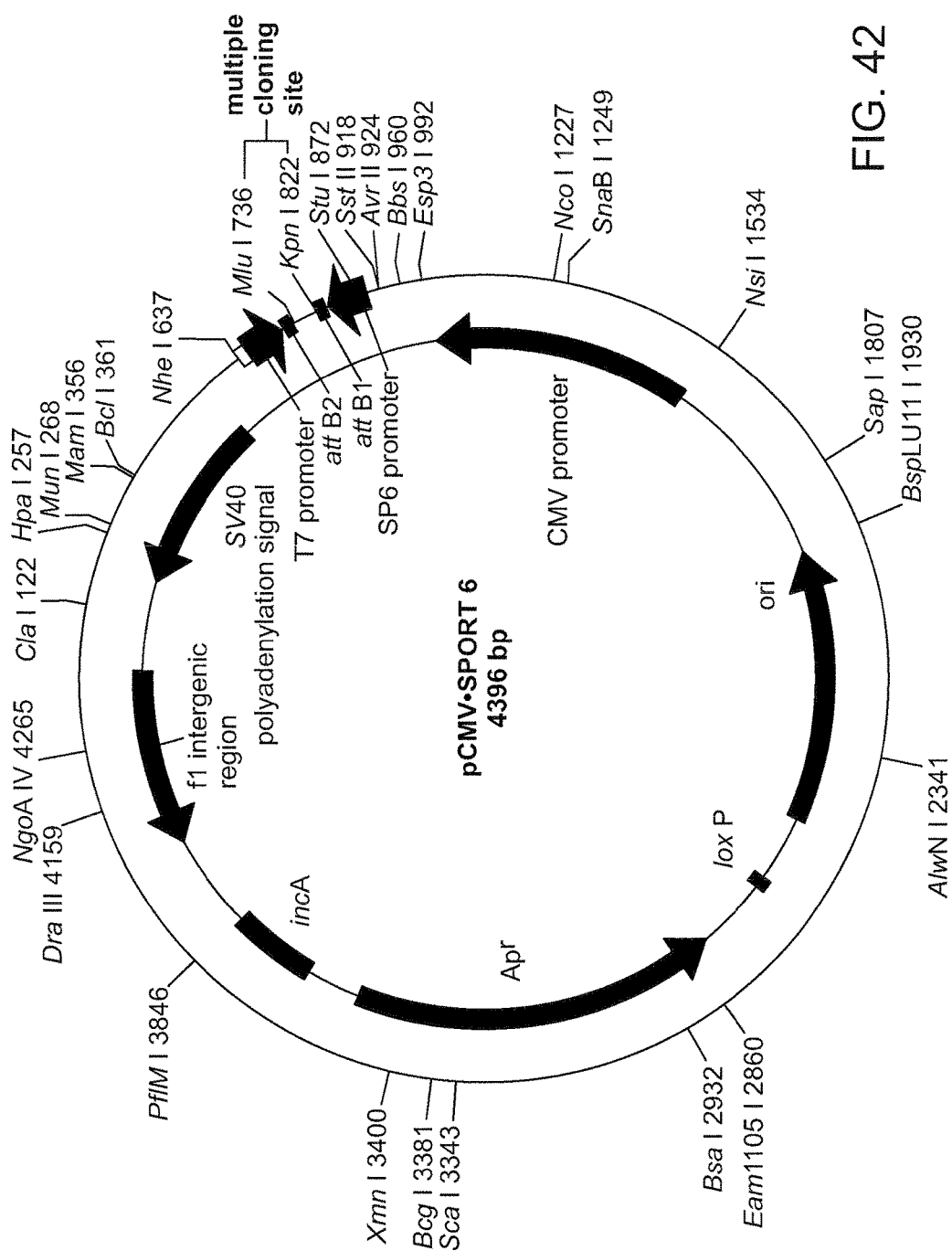
FIG. 42 is a graphical presentation of the cloning vector pCMV-SPORT6.
Figure 43:
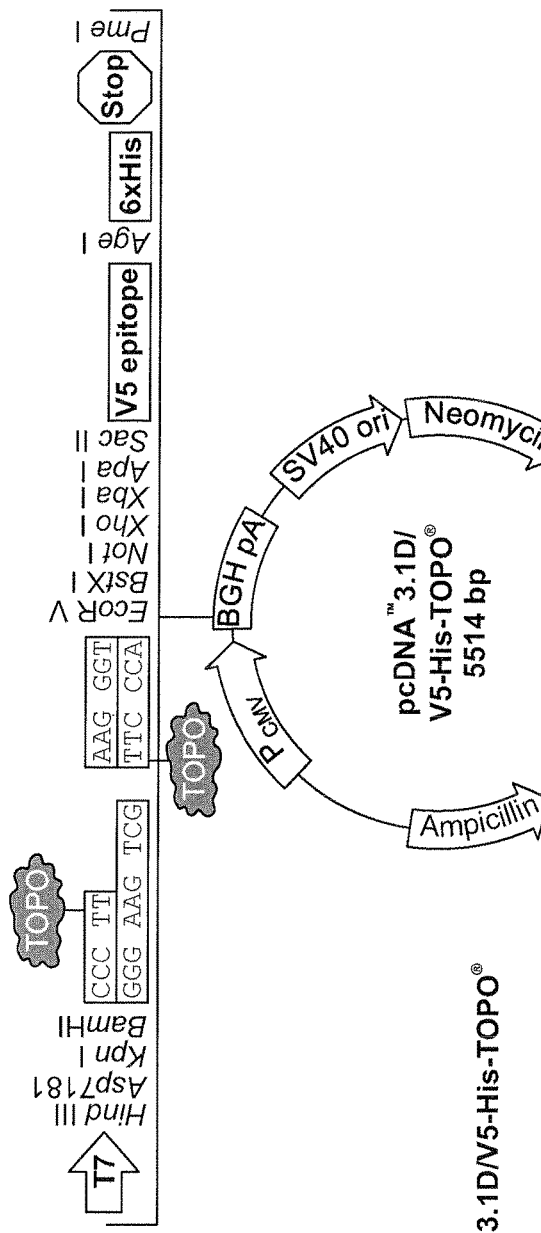
FIG. 43 is a graphical presentation of the cloning vector pcDNA3.1D-V5-His-TOPO.
Figure 45:
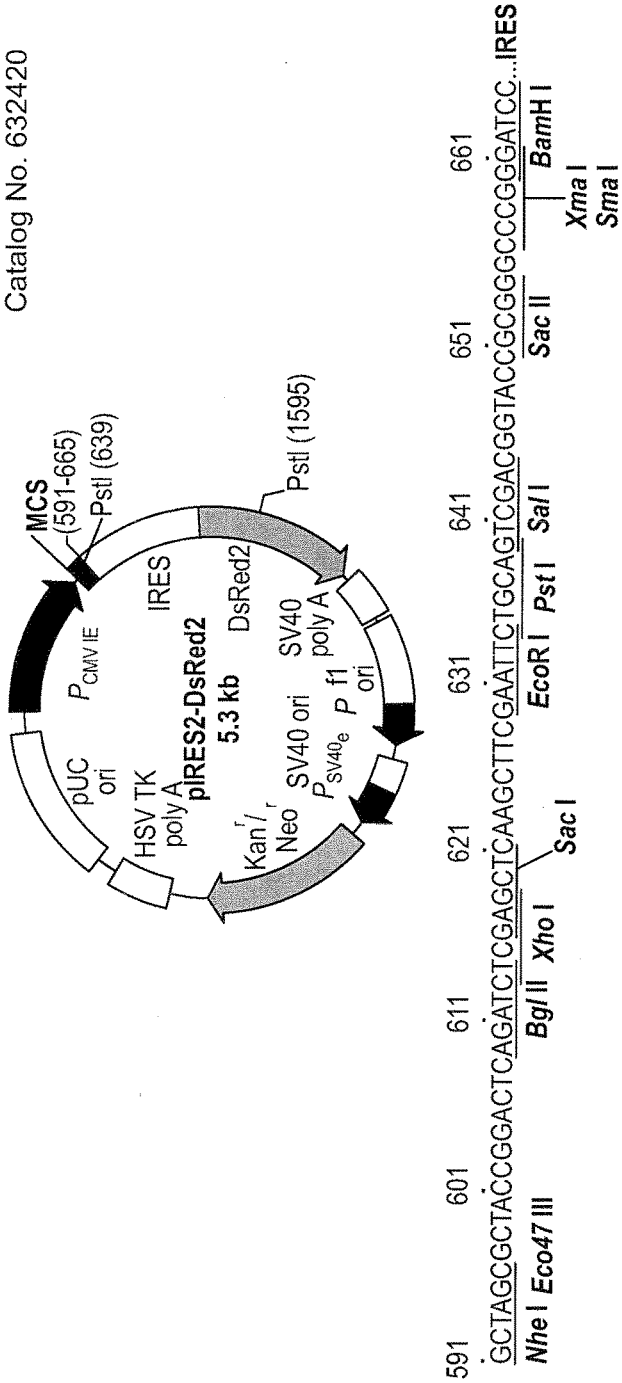
FIG. 45 is a graphical presentation of the cloning vector pIRES2-DsRed2 (SEQ ID NO: 48).
Figure 46:
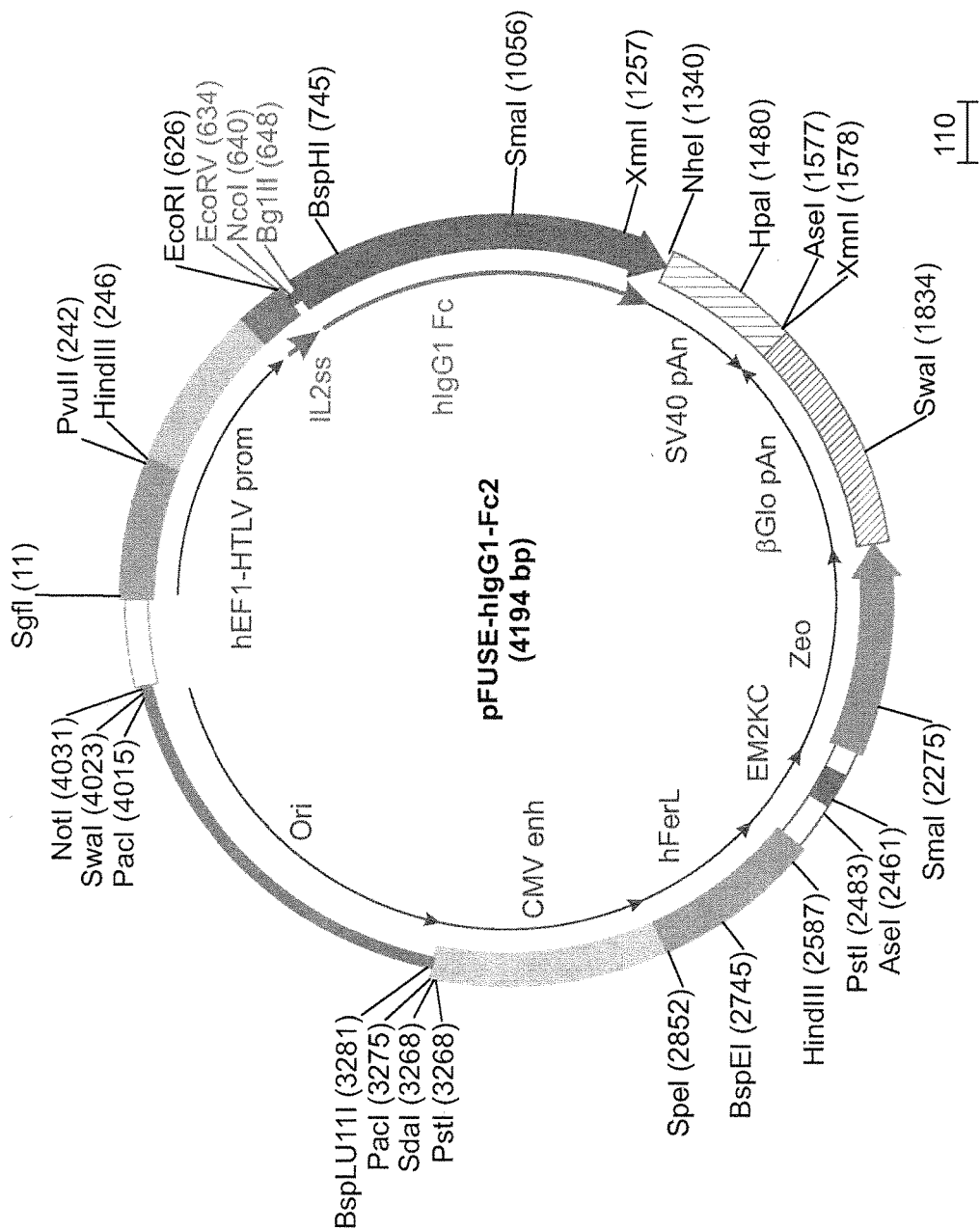
FIG. 46 is a graphical presentation of the cloning vector pFUSE-hIgG1-Fc2.
Figure 47:
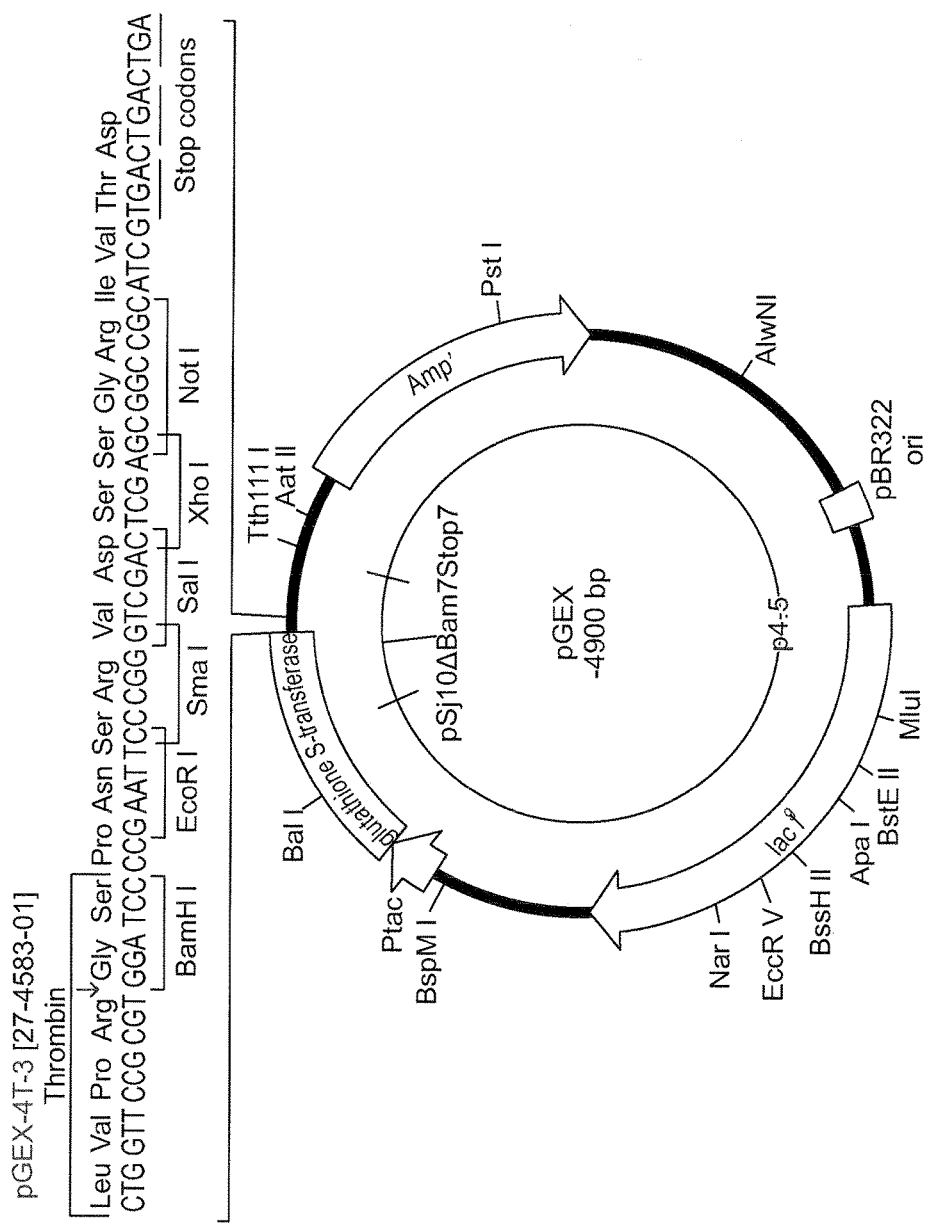
FIG. 47 is a graphical presentation of the cloning vector pGEX-4T3 (SEQ ID NO: 49, SEQ ID NO: 50).

The following plasmid backbones were applied to perform various functional assessments of Betacam. FIG. 42 is a vector map for pCMV-SPORT6. This vector allows for eukaryotic expression. FIG. 43 is a vector map for pCDNA13.1D/V5-His-TOPO, this vector allows for generation of V5- and His-tagged versions of Betacam, which then can be tracked by virtue of the added fusion protein tags. FIG. 44 is a vector map of pIRES2-EGFP. This vector provides a non-fused IRES-driven EGFP reporter that allows non-invasive tracking of expressing cells. It also allows for eukaryotic expression. FIG. 45 is a vector map of pIRES2-DsRED2. This vector provides a non-fused IRES-driven DsRed red fluorescent reporter that allows non-invasive tracking of expressing cells. It also allows for eukaryotic expression. FIG. 46 is a vector map of pFUSE-hIgG1-Fc2. This vector allows for the construction of Fc-fusion proteins. Such proteins are secreted due to the N-terminal presence of a signal peptide derived from the Interleukin2 protein. It allows for eukaryotic expression based on the presence of a hEF1/HTLV promoter. FIG. 47 is a map of pGEX-4T3. This plasmid allows for the generation of GST-fusion proteins, which can be purified by glutathione-conjugated column material. The vector is optimized for bacterial expression. The inventors inserted various defined nucleotide sequences from human Betacam into the above vectors as described in the following examples.

Figure 48:
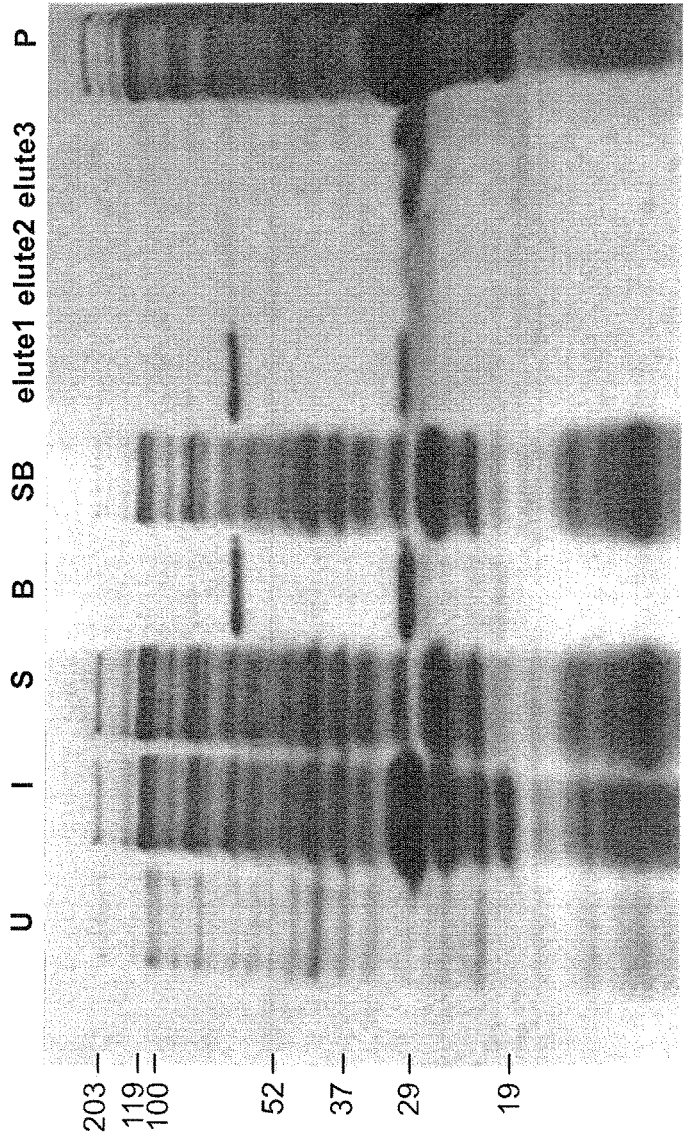
FIG. 48 shows the result of production of GST-Betacam33-80 using bacterial cells. Coomassie-stained protein gel is shown.

Referring now to the invention in more detail, FIG. 48 illustrates the production of an N-terminal fragment of Betacam as a GST-fusion protein (GST-Betacam33-80) in bacteria. The GST portion (Glutathione-S-transferase) is capable of binding Glutathione, hereby facilitating detection and purification of the fusion protein using commercial-type products. In the particular example, GST-Betacam33-80 was expressed in bacteria, using the pGEX-4T3 vector, and production was induced by IPTG. Protein samples from the lysed bacteria were analyzed using denaturing SDS-PAGE gel analysis, stained using a coomassie-based blue stain of the resulting gel. The uninduced bacteria (U) showed a background level of bacterial protein bands. Following induction (I), a prominent band at 30 kDa appeared, which corresponds to GST-Betacam33-80. This lysate was incubated with Glutathione-conjugated sepharose beads, which allowed binding of the GST-Betacam33-80. The fusion protein was excluded from the supernatant (SB), and detected with high specificity on the bead fraction (B). Incubation of the Bead fraction with free Glutathione released a minor fraction of the bead-bound GST-Betacam33-80. Three eluates revealed a similar results (eluate 1, 2, 3). The majority of GST-Betacam33-80 remained bound to the Bead fraction, and was deemed relatively insoluble. Given that purity was achieved, the Bead/GST-Betacam33-80 fraction was used to immunize rabbits against GST-Betacam33-80.

Figure 49:
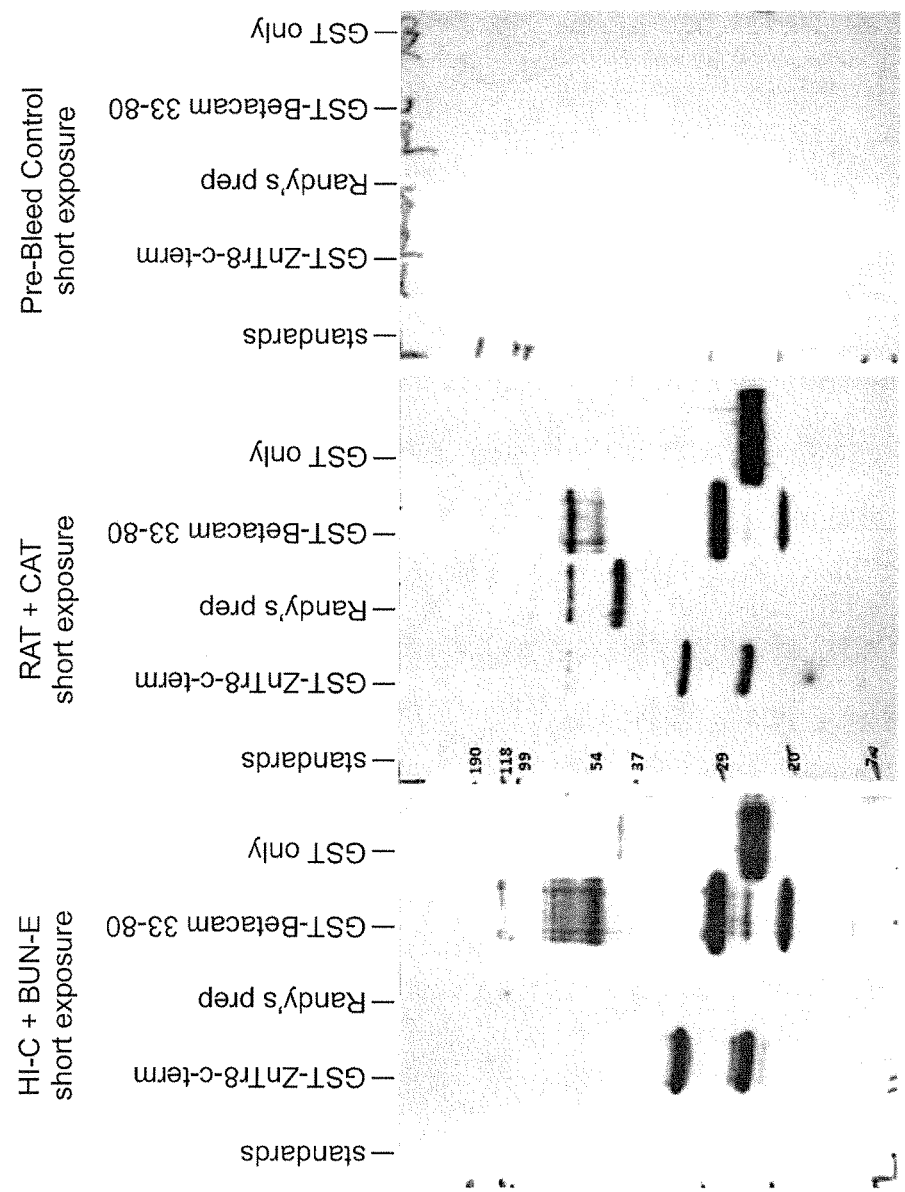
FIG. 49 shows testing of rabbit anti-sera raised against GST-Betacam33-80 using Western blotting against GST-fusion proteins.

Referring now to the invention in more detail, FIG. 49 describes results using combinations of antisera from immunized rabbits. Hi-C and Bun-E are two independent rabbits immunized with GST-Znt8, another molecule unrelated to GST-Betacam33-80. RAT and CAT are two independent rabbits immunized with GST-Betacam33-80. "Randy's prep" is a third GST-fusion protein preparation. Pre-immune bleeds are the RAT and CAT animal sera, obtained prior to immunization. They were expected not to be able to react. The inventors observed that Hi-C and Bun-E rabbits react to GST-type protein of both GST-Znt8 and GST-Betacam forms. Similarly, rabbits CAT and RAT reacted to both GST-Znt8 and GST-Betacam forms. This was due to the presence of the GST moiety in both fusion proteins. This was validated by the reactivity of either rabbit to GST-only, last lane.

Figure 50:
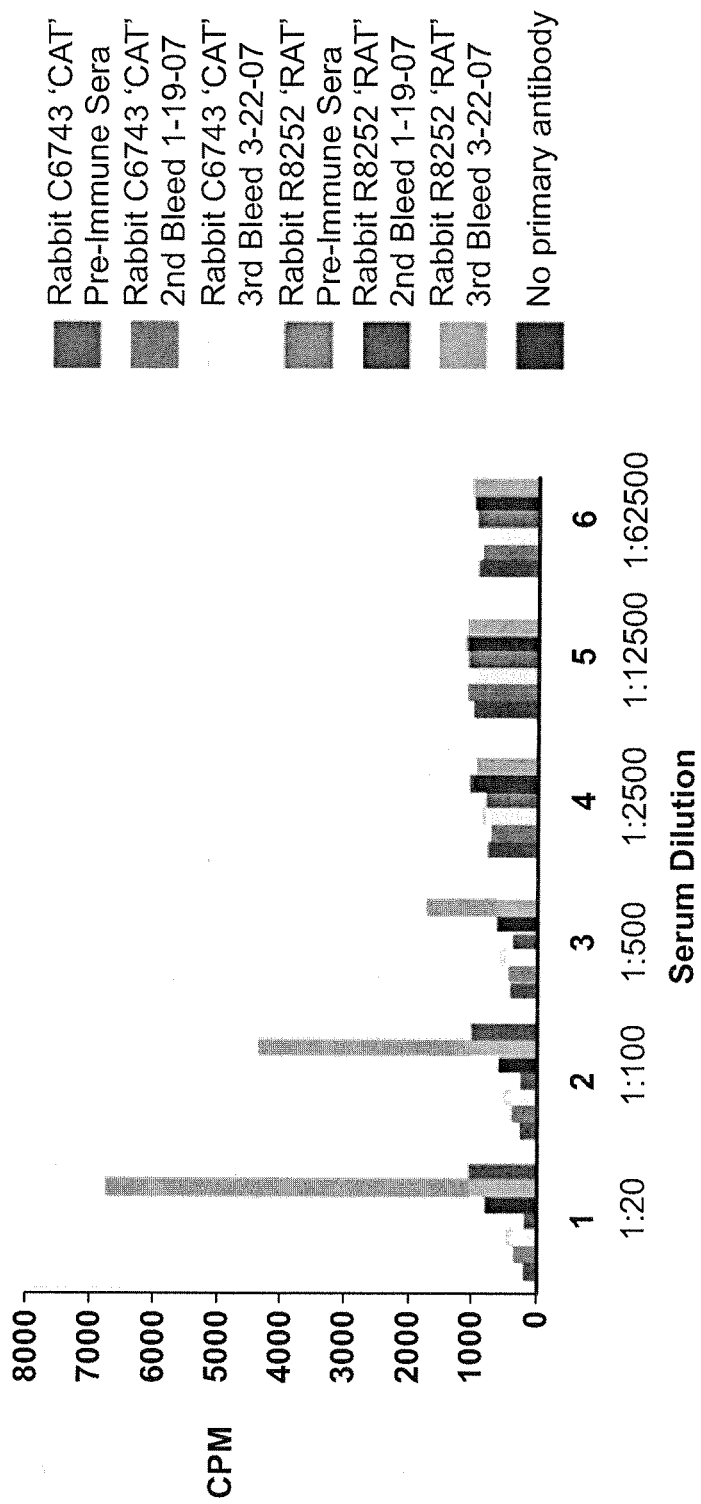
FIG. 50 shows testing of rabbit anti-sera raised against GST-Betacam33-80 using ELISA.

Referring now to the invention in more detail, FIG. 50 describes results using individual antisera obtained from the rabbits "CAT" (C6743) and "RAT" (R8252), analysed using ELISA for reactivity and binding to GST-Betacam33-80. In this assay, "RAT" antisera reacted with increasing titers upon later bleeds, whereas rabbit "CAT" did not react.

Figure 51:
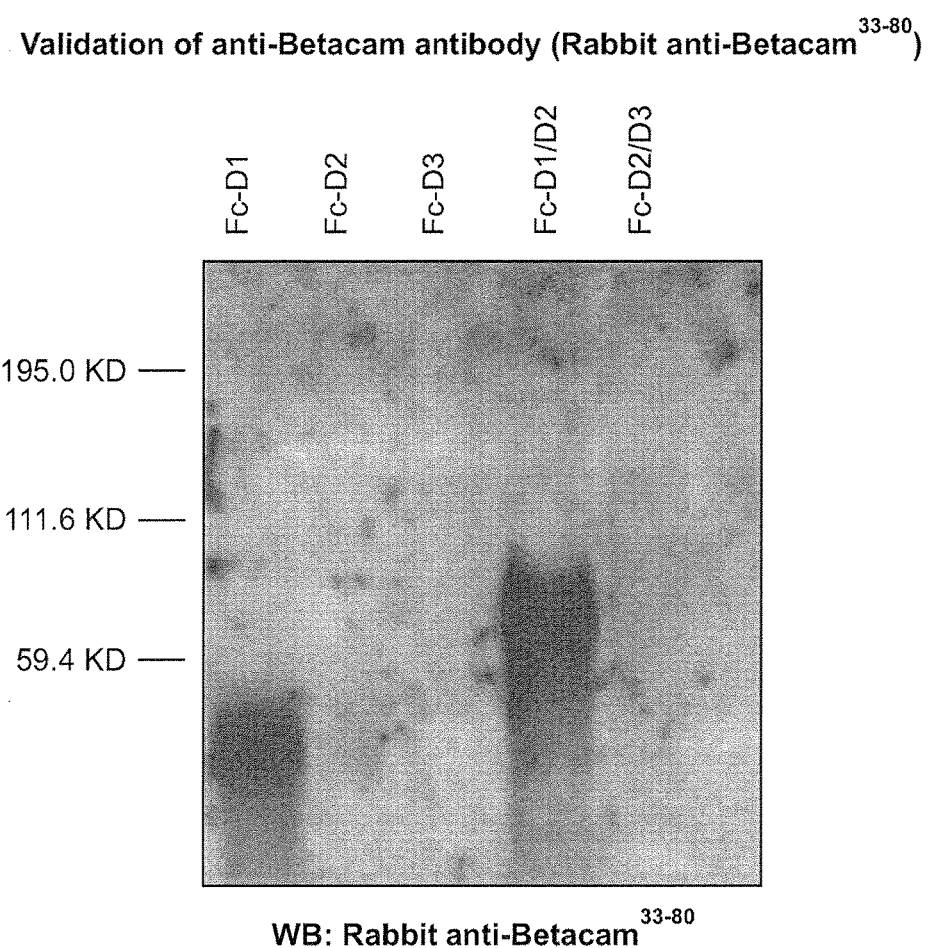
FIG. 51 shows testing of the "RAT" rabbit anti-sera raised against GST-Betacam33-80 using Western blotting against Fc-Betacam fusion proteins.

Referring now to the invention in more detail, FIG. 51 is a western blot showing that anti-betacam antibodies raised against GST-Betacam33-80 detected Fc-D1 and FcD1/D2, but not Fc forms of Betacam lacking D1. This confirmed that the antibodies raised reacted against D1. The construction and production of Fc-betacam proteins are described in Example 5.

Figure 52:
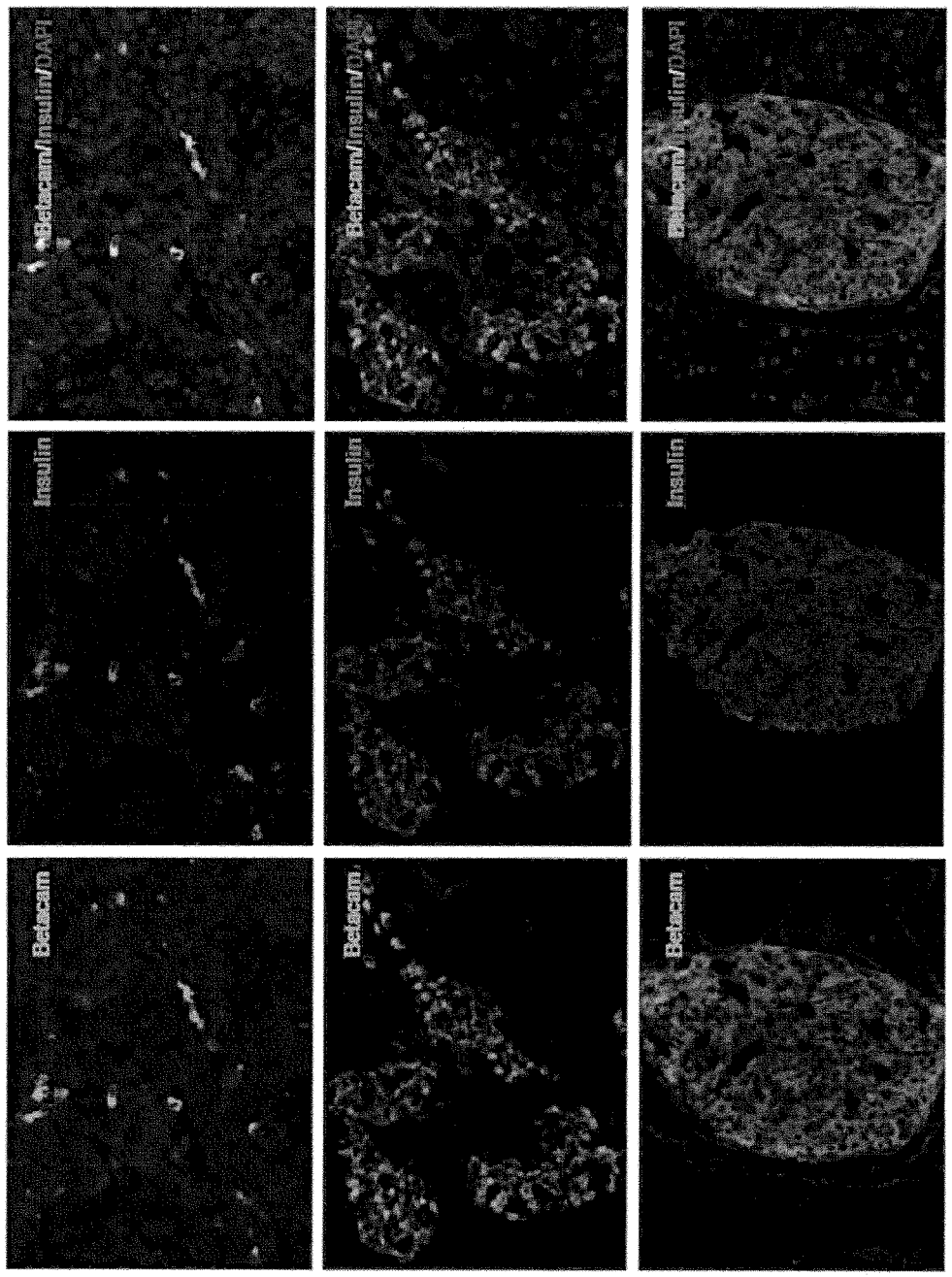
FIG. 52 shows immunohistochemistry of anti-Betacam antisera against sections of embryonic (E14.5 (top), E18.5 (middle)) and adult (2M) mouse pancreas (bottom), performed as a double-staining to insulin.

Referring now to the invention in more detail, FIG. 52 describes results using the "RAT" antisera as primary detection antibody for Betacam, on frozen sections obtained from CD1 mouse pancreas, or embryonic tissue. The analysis was performed as a co-staining of Betacam with Insulin. Embryonic expression of Betacam was detected at E14.5 in individually scattered cells, also expressing insulin (top row). At the later embryonic stage, E18.5, at which pancreatic beta cells have aggregated, expression of Betacam was detected only in the insulin-producing cells (middle row). There was a general congruency between Betacam and insulin at this stage. In the adult islet (2 months old mice), Betacam was detected with complete congruency to insulin-producing beta cells (lower row). All pancreatic insulin-producing cells reacted with the anti-GST-Betacam33-80 antibody; all anti-GST-Betacam33-80 reacting cells also expressed insulin.

EXAMPLE 5

Creation and Detection of Fc-Betacam Fusion Proteins

Construction details for the generation of Fc-fusion construct plasmids is outlined in the following. Various Betacam domains (e.g. D1, D2, D3, D1/D2, D2/D3) were amplified by using appropriate primer pairs. The amplified fragments were purified and digested by using the corresponding restriction enzyme sites, and ligated into the vector pFUSE-hIgG1-Fc2. The primer pairs used for amplification are as following:

```
D1 sense:
                                    (SEQ ID NO: 54)
AATTCCATGGCTCTGAAGGTGACCGTGCCGTC
    NcoI D1 antisense:
                                    (SEQ ID NO: 55)
CACCAGATCTAGGATCATCGACAGTGACTT
    BglII D2 sense:
                                    (SEQ ID NO: 56)
AATTCCATGGCTCCTGTCATGAAGCCAATGGT
    NcoI D2 antisense:
                                    (SEQ ID NO: 57)
CACCAGATCTATATATGGTGGGCATAATGA
    BglII D3 sense:
                                    (SEQ ID NO: 58)
GGCCGATATCTTATGGACCTTATGGACTTCA
    EcoRV D3 antisense:
                                    (SEQ ID NO: 59)
GACGCCATGGCTATGATGACTGTGAATCGAG
    NcoI D1/D2 sense:
                                    (SEQ ID NO: 60)
AATTCCATGGCTCTGAAGGTGACCGTGCCGTC
    NcoI D1/D2 antisense:
                                    (SEQ ID NO: 61)
CACCAGATCTATATATGGTGGGCATAATGA
    BglII D2/D3 sense:
                                    (SEQ ID NO: 62)
GGCCAGGCCTTCCTGTCATGAAGCCAATGGT
    StuI D2/D3 antisense:
                                    (SEQ ID NO: 63)
GACGCCATGGCTATGATGACTGTGAATCGAG
    NcoI
```

The following describes the methods applied by the inventors to prepare Fc-betacam fusion proteins using transient transfected Cos7 cells. The calcium-phosphate transfection method was used for introduction of DNA into mammalian cells and was based on the formation of a calcium phosphate-DNA precipitate. The calcium phosphate facilitates the binding of the DNA to the cell surface. It is believed that the DNA then enters the cell by endocytosis. The procedure is routinely used to transfect a wide variety of cell types for either transient expression or for the production of stable transformants. The DNA is mixed directly with a concentrated solution of $CaCl_2$. This is then added dropwise to a phosphate buffer to form a fine precipitate. Aeration of the phosphate buffer while adding the DNA-$CaCl_2$ solution helps to ensure that the precipitate which forms is as fine as possible. This is important because clumped DNA will not adhere to or enter the cell as efficiently. Generally, a final $CaCl_2$ concentration of 60 mM is used for calcium phosphate transfections. The final volume of DNA-$CaCl_2$ should not exceed 1/10th of the volume of media in which the cells are plated. Cells should be seeded at a density such that on the day of transfection they are no more than 50% confluent. The optimal seeding density produces a nearly confluent dish of cells when they are harvested or split into selective media 48 hours after the transfection. This will vary for each cell line and is dependent upon their doubling time. Generally, cells are seeded at a density of $5\times10^5$/60 mm dish or $1\text{-}2\times10^6$/100 mm dish. Between 10 and 100 µg of DNA may be transfected.

Calcium Phosphate Transfection Procedure was performed as follows. Cos7 cells were prepared for Transfection, by plating cells in 100 mm or 60 mm dishes at the required density. Generally, cells were seeded at a density of 1-2×106/100 mm dish or 5×107/150 mm dish. Cells were incubated overnight at 37° C. in a humidified CO2 incubator. On the following day, transfection was performed by 3-4 hours prior to transfection, the media was changed. At time of transfection, a transfection mixture was added to cells.

Specifically, as an example: For a 100 mm dish containing 10 ml of media, a transfection mix was made as in the following: To a 1.5 ml tube, add 62 µl of 2M CaCl2, adjust total Volume to 500 µl with sterile ddH2O, and mix gently. Add 10 µg DNA (Fc-betacam fusion constructs of various types), mix gently. On vortex, using a pasteur pipette, slowly add 500 µl 2×HBSS drop-wise. The transfection mix was hereafter incubated at room temperature for 15-20 minutes.

Subsequently, the precipitate was added dropwise to the media to the cells in dish. Cells were next incubated overnight at 37° C. in a humidified CO2 incubator.

Two days following Conditioned Media (CM) was isolated from the tissue culture dishes.

Fresh medium was added in a few cases for further production of Fc-betacam fusion protein.

Fc-fused Betacam Purification using HiTrap Protein A HP columns, GE Healthcare was done as follows, according to manufacturer's instructions:

1. Prepare working buffers:

| Buffer | Stock solution | ddH2O | Final Volume |
|---|---|---|---|
| Binding Buffer | 5 ml | 45 ml | 50 ml |
| Elution Buffer | 0.5 ml | 4.5 ml | 5 ml |

2. Fill up the 5 ml syringe with working Binding Buffer. Remove the stopper and connect the column to the syringe with the provided adaptor.

3. Wash the column with Binding Buffer at 1 ml/min. Wash two times. 'drop to drop" to avoid introducing air into the column.

4. Apply the corresponding samples of Conditioned Fc-Betacam Cos7 Media, using a new 5 ml syringe fitted to the adaptor by pumping it onto the column, at 1 ml/min.

5. Wash the column with Binding Buffer at 1 ml/min. Wash two times, until no material appears in the effluent.

6. Prepare a collection tube by adding 30 µl of Neutralizing Buffer. Elute with 400 ul of working Elution Buffer.

7. Re-load the flow-through onto the column for another elution, collect into the same collection tube.

Analysis of produced Betacam polypeptides by Western Blotting was done as follows. First, samples were prepared for SDS-PAGE analysis, by mixing 40 µl protein sample, 5 µl sample reducing reagent and 5 µl sample buffer (5× Sample Buffer: 10% w/v SDS, 10 mM beta-mercaptoethanol, 20% w/v glycerol, 0.2 M Tris-HCl, pH 6.8, 0.05% w/v bromophenol blue). Samples were mixed gently, spun down, and subsequently boiled for 10 minutes to denature the protein. A cooling step on ice for 3-5 min was followed by spinning the sample down briefly. Samples were loaded onto NuPAGE® Novex® Bis-Tris Mini gels (Invitrogen). A protein molecular weight marker was added. Gel was run at 120 until loading dye began to exit gel. For Blotting, fiber pads, filter papers, and PVDF membrane were initially soaked in transfer buffer (25 mM Tris, 192 mM glycine, 20% methanol, pH8.3). Bubbles trapped in the filters or filter pads were removed. The PVDF membrane was activated in methanol prior to soaking in transfer buffer. The top and bottom of the gel were cut off. The gel was equilibrated in transfer buffer for a few minutes. Hereafter, the transfer cassette was assembled, and loaded in transfer apparatus. The transfer apparatus was filled with transfer buffer prior to turning on the power supply. Proteins were transferred at 200 mA per transfer apparatus for 1 hr. After transfer, membranes were rinsed in ddH2O and placed in 5% milk solution (5% non-fat milk in 1×TBST) for 60 minutes at room temperature on a shaker to block non-specific binding. Following blocking, the membrane was soaked in primary antibody solution (example: goat anti-human IgG Fc specific, 1:500) on a shaker for overnight at 4° C. Hereafter the membrane was rinsed in ddH2O and washed 3 times for 10 min/wash. To detect the primary antibody binding, membranes were incubated in secondary antibody solution (donkey anti goat IgG-HRP, 1:5,000) for 60 min at room temperature on a shaker. Hereafter, the membrane was rinsed in ddH2O. Followed by three washes at 10 min/wash. Detection of signaling was performed using the ECL western blotting detection system (Amersham™ ECL™ Western Blotting Detection Reagents, GE Healthcare). 1 mL of solution A and 1 mL solution B was mixed. Membranes were incubated for various lengths of time, more preferably at 2 min. The reportable exposures differed, e.g. 30 sec, 1 min, 2 min, given optimal detection.

Figure 53:
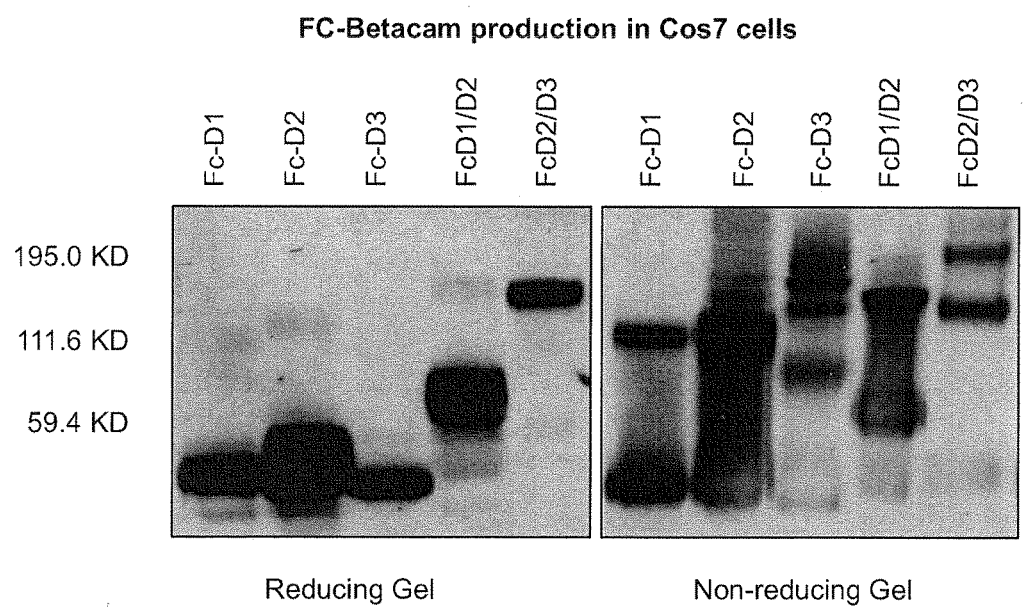
FIG. 53 shows purification of various forms of Fc-fragment fusion proteins to Betacam, during reducing and non-reducing conditions. The slower migration under non-reducing conditions signify the presence of disulfide bridges. Such are observed in Ig-domain1, -domain 2 and -domain 3 of Betacam.
Figure 54:
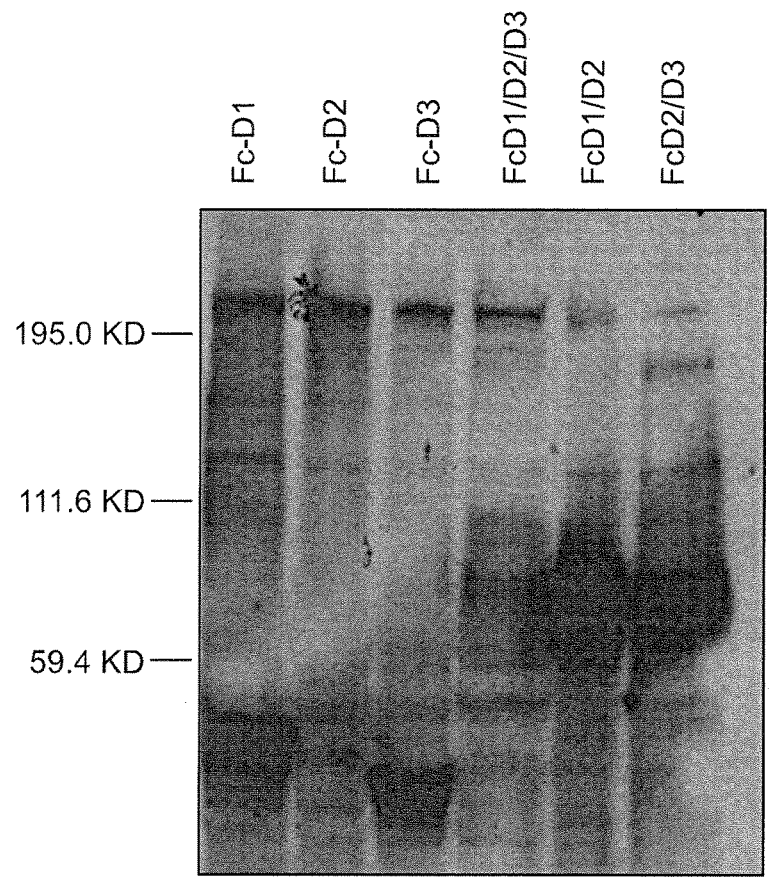
FIG. 54 shows western blotting detection using anti-human Fc-antibodies, the presence of Fc-Betacam fusion proteins in the lysate of transiently transfected CHO cells.

A result of production of Fc-Betacam proteins is shown in FIG. 53. By western blotting, using anti human-Fc, individual proteins of Fc-D1, FcD2, Fc-D3, Fc-D1/D2 and Fc-D2/D3 were detected under reducing conditions (left picture) and non-reducing conditions (no beta-mercaptoethanol, no boiling prior to gel loading). For all fusion proteins a single band of the expected size was observed (left most gel image). In all cases, these proteins migrated with a slower-forming complex under non-reducing conditions (right-most gel). This signified the presence of the disulfide bridges predicted to exist in both D1, D2 and D3. The inventors sought to purify a Fc-D1/D2/D3 fragment of Betacam as well. This was unsuccessful following multiple attempts. As shown in subsequent examples the formation of intra-cellular aggrosomes was observed commonly during the expression of the full extracellular domain in eukaryotic cells. This problem was likely due to the formation of multi-protein aggregates in the endoplasmatic reticulum. This indicated that the protein may not be either produced, or secreted. To test for the latter possibility, the inventors performed a western blot of the COS7, Fc-expressing cells, in which protein lysates were obtained rather than secreted media. An image is shown in FIG. 54, revealing retention of various forms of Fc-Betacam in the COS7 cells. Most notably, retention is observed for D1/D2 and D2/D3.

EXAMPLE 6

Binding of Betacam-Derived Polypeptides to the Cell Surface of Pancreatic Beta Cells Bead adhesion and recruitment assay. To detect Betacam-derived polypeptides directly binding to the cell surface of pancreatic insulin producing cells, a single-step binding assay was developed, referred to as the recruitment assay. The assay takes advantage of pre-binding Fc-Betacam fusion proteins to fluorescent beads which have been pre-coated by protein A by the vendor (Bangs Laboratories, Inc.). The beads were subsequently washed and added to Betacam-expressing cells and control cells. Imaging was done to assess adhesion of the fluorescent beads to the cell surface of the cells after exhaustive washing.

A specific experiment was done as follows. First, beads were coated with Fc-Betacam fusion proteins. Twenty microliters of Protein A coated microspheres (Dragon Green dyed) were washed three times in 200 µl of 50 mM sodium borate (pH 8.2), resuspended in 50 µl borate buffer 0.2 M pH 8.5, and incubated with 20 µg goat anti-human Fc fragment specific antibody with gentle mixing overnight at 4° C. Beads were washed three times by centrifugation at 9,000 rpm for 10 min with borate buffer containing 0.3% immunoglobulin-free BSA (Sigma), and hereafter incubated with 50 µl of purified various Fc-fused Betacam versions (e.g. Fc-D1, Fc-D2, Fc-D3, Fc-D1/D2, Fc-D2/D3) during 3 hr at room temperature with gentle mixing. The concentration of the Fc-betacam fusion proteins ranged typically from (0.05-0.09 ug/ul). Beads were finally washed three times in 0.3% BSA borate buffer and resuspended in 100 µl of this buffer. Immediately before loading on the cells, any possible bead aggregates were disrupted with a 1 s ultrasound pulse using a probe sonicator (Vibracell, Bioblock). The microsphere adhesion and recruitment assay was done as follows. βTC6 cells were cultured in a 12-well plate, and 10 µl of bead solution was added per well. After a 1 hr incubation time, three washes with PBS-BSA 0.3% were performed. Hereafter, the cells were photographed under the fluorescence microscopy.

Figure 55:
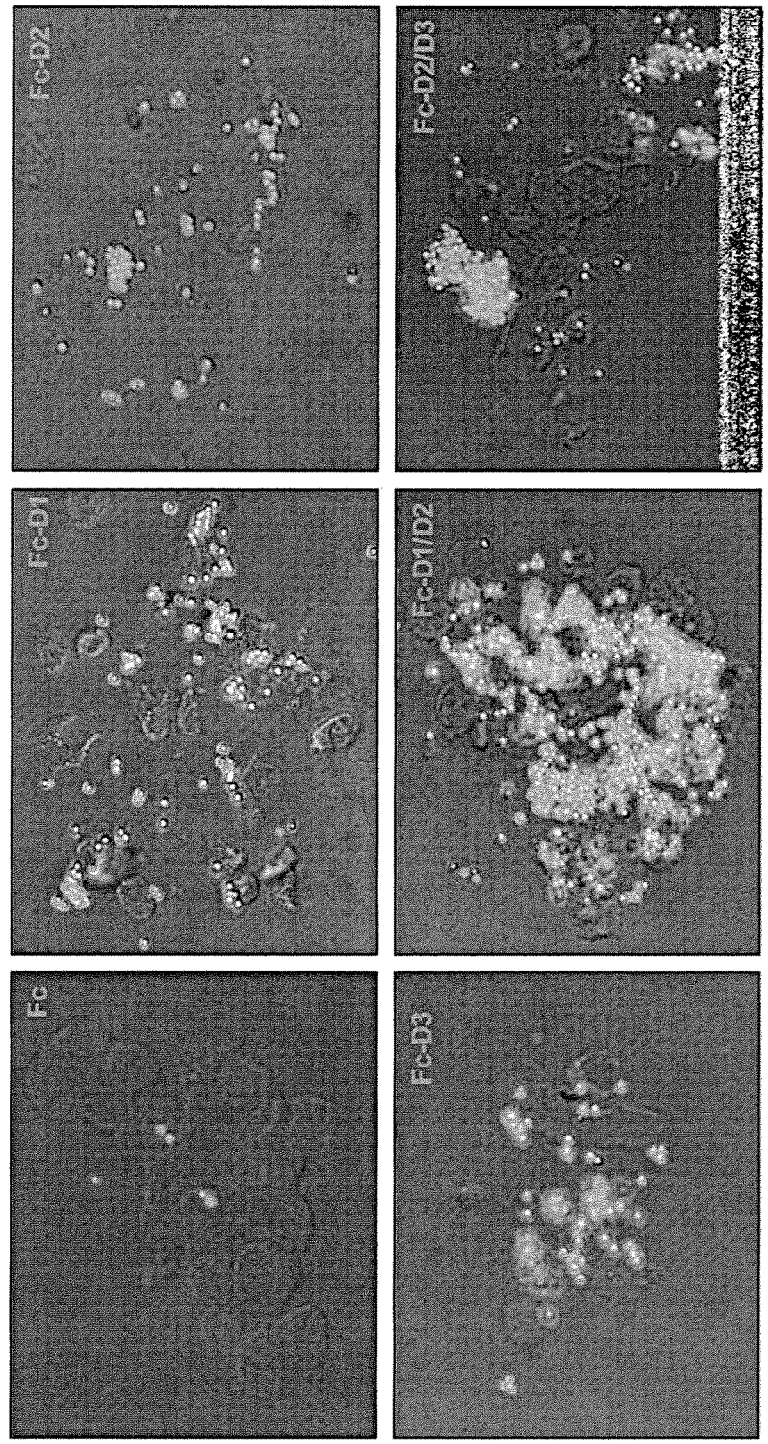
FIG. 55 shows direct, one-step cell surface live labeling of pancreatic insulinoma cells (bTC) using fluorescent beads bound to Fc-Betacam fusion proteins.

FIG. 55 describes results using various Fc-conjugated Betacam versions, bound to fluorescent beads, which were added to the media of growing bTC (insulinoma) cells, followed by repeated washing, and imaging. Fc-only beads do not attach to the surface of bTC cells. However, Fc-D1, Fc-D2, Fc-D2, Fc-D1/D2, Fc-D2/D3 conjugated fluorescent beads attach effectively to the surface of pancreatic insulinoma cells.

Surface binding of Fc-Betacam to insulinoma cells. The inventors tested for direct binding of Fc-Betacam to the surface of pancreatic insulinoma cells, bTC6. The bTC6 cell line was found to express Betacam mRNA, as outlined in Example 2. The specific experimental conditions for the results shown in FIG. 57 were as follows. βTC6 cells grown as adherent cells were washed 3 times with 1×PBS, 5 min/wash. Hereafter, cells were incubated with 50 µl purified various Fc-fused Betacam versions (e.g. Fc-D1, Fc-D2, Fc-D3, Fc-D1/D2, Fc-D2/D3) and Fc (as control) (or 1:5 dilutions), 1 hr at RT. Cells were then washed 3× in 1×PBS for 5 min at RT. Next, cells were fixed with 4% PFA, 15 min at RT. Hereafter, a subsequent series of washes, 3× in 1×PBS for 5 min at RT, were performed to remove fixative. Primary antibody (goat anti-human IgG Fc-FITC, 1:100) were dispersed onto cells, and left 0/N at room temp. Next morning, primary Ab were drained off, Cells were washed in 1×PBS, 3 times 5 min/wash, at RT. Following mounting, using cover slips in mounting media w/DAPI, imaging was performed. The inventors found that Fc-domain only did not bind to the surface of bTC6 cells whereas Fc-D1, Fc-D2, Fc-D3, Fc-D1/D2, Fc-D2/D3 were all capable of surface retention. This experiment was not capable of resolving affinity differences between the various forms tested.

EXAMPLE 7

Definition of Homotypic Adhesion Properties of Betacam

Development and application of a fluorescent bead aggregation assay. Bead aggregation assays. The beads used in this assay were Protein A-conjugated polystyrene microspheres, fluorescent yellow-green (YG) (excitation maximum of 445 nm and emission maximum of 500 nm, the fluorescent emission is observed green) and fluorescent blue (excitation maximum of 475 nm and 600 nm & emission maximum of 663 nm, the fluorescent emission is observed red), 1.0 um (Polysciences, Inc.).

To coat fluorescent beads with Fc-Betacam proteins, the following procedure was applied by the inventors. 100 μl of Protein A-conjugated microspheres were added to a 1.5 ml microcentrifuge tube. The microspheres were washed once in sodium acetate 100 mM, pH3.9 (which is a pH at which any impurities coupled to protein A will be eluted) and twice in 10 mM Hepes, 50 mM NaCl, pH 7.2, by mixing the buffer, centrifuging in a micro-centrifuge for 5-6 min at 10,000×g, and then removing the supernatant. The Fc-Betacam proteins were bound to the beads at a ratio of 5 μg of protein per 40 μl of beads suspension in 10 mM Hepes, 50 mM NaCl, pH7.2, 1 mM CaCl2 for overnight at 4° C. on an Eppendorf shaker (1,400 rpm). Hereafter, the coated beads were pelleted, washed twice, and resuspended in 100 μl of 10 mM Hepes, 50 mM NaCl, pH 7.2. The suspension was briefly (~30 sec) sonicated to obtain single beads, as determined by microscopy. Pictures were obtained recording the dissociation. The amount of protein coupled to the beads was determined by taking an aliquot and pelleting it and resuspending in 2×SDS sample buffer, boiling for 10 min. The beads were subsequently pelleted, and the supernatant was immunoblotted with the anti-human IgG (Fc specific)-HRP conjugate after SDS-PAGE.

An assay for establishing domain-specific interactions of Betacam-derived polypeptides was developed based on flow automated cell/bead sorting analysis. The detection of fluorescent beads allowed integer bead count assessment using fluorescence intensity as measured through FACS analysis. Such integer measurements therefore allowed the detection of bead aggregation as it may be mediated through conjugation of specific protein interaction domains. Beads were conjugated O/N. Prior to aggregation, sonication of the individual beads/mixtures was performed to achieve initial disaggregation. Hereafter, beads were incubated for 90 minutes, and subsequently analyzed by FACS analysis for multimer-formation. Following the FACS analysis, a spread of the bead mixture was performed on a microscope slide, and digital imaging using epifluorescence microscopy was done to assess visually the presence/absence of bead aggregates.

Figure 57:
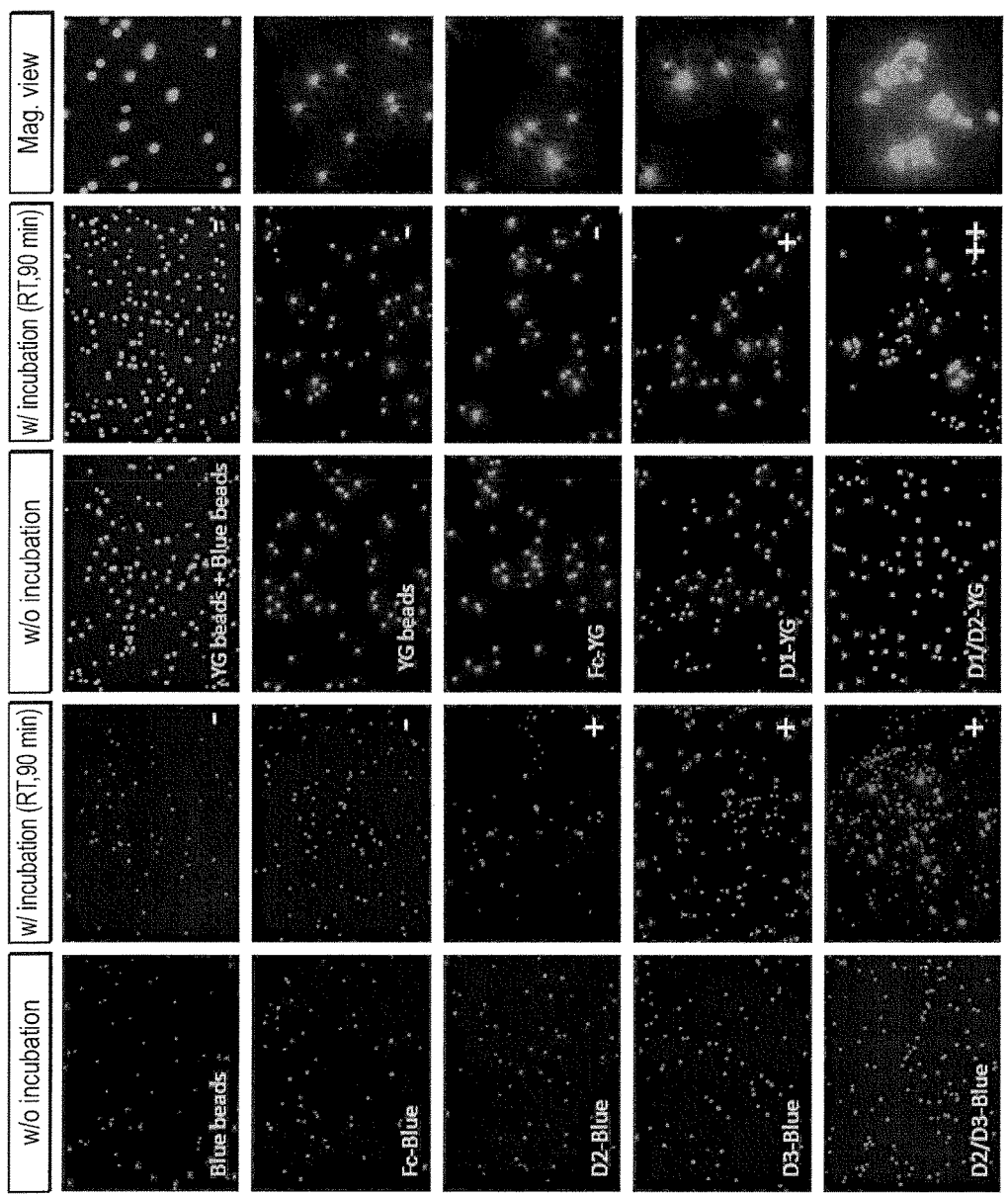
FIG. 57 shows digital images of bead-aggregation of Fc-conjugates fluorescent beads.

For the aggregation assay, Blue beads and YG beads were then mixed (equal volume of each) appropriately for a final volume of 100 μl and 1 mM $CaCl_2$ was added to initiate aggregation. The samples were incubated at room temperature on an Eppendorf shaker (1,400 rpm), and at various time points, 10 μl aliquots were removed and diluted 30-fold with 10 mM Hepes, 50 mM NaCl, pH7.2, 1 mM $CaCl_2$, and analyzed with the BD LSR II flow cytometer, or under the fluorescent microscopy for image acquisition. FIG. 57 shows images of various combinations of fluorescent beads. In the following, these images were compared to quantitative assessment of protein interactions based on flow cytometry.

The extent of aggregation, as determined by the aggregate size and aggregate composition, was quantified with a BD LSR II flow Cytometer. A 2D density plot of the intensity of red fluorescence versus green fluorescence in each aggregate revealed the size distribution and composition of the aggregates. The percentage of aggregates containing more than one red or green bead indicated the propensity for heterophilic binding.

Figure 58:
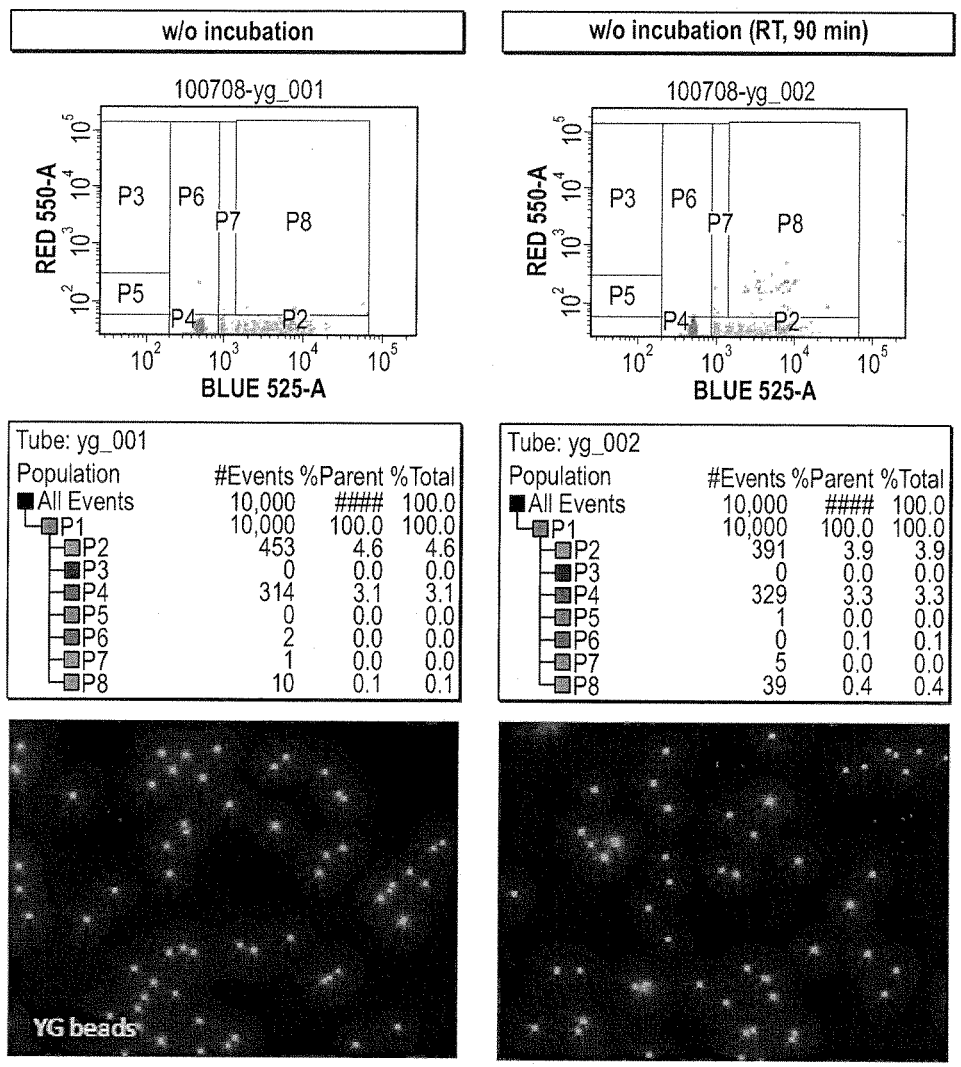
FIG. 58 shows flow cytometry analysis of pre- and post-incubation, testing for YG-beads only aggregation. An image is shown below representing the same experiment.
Figure 59:
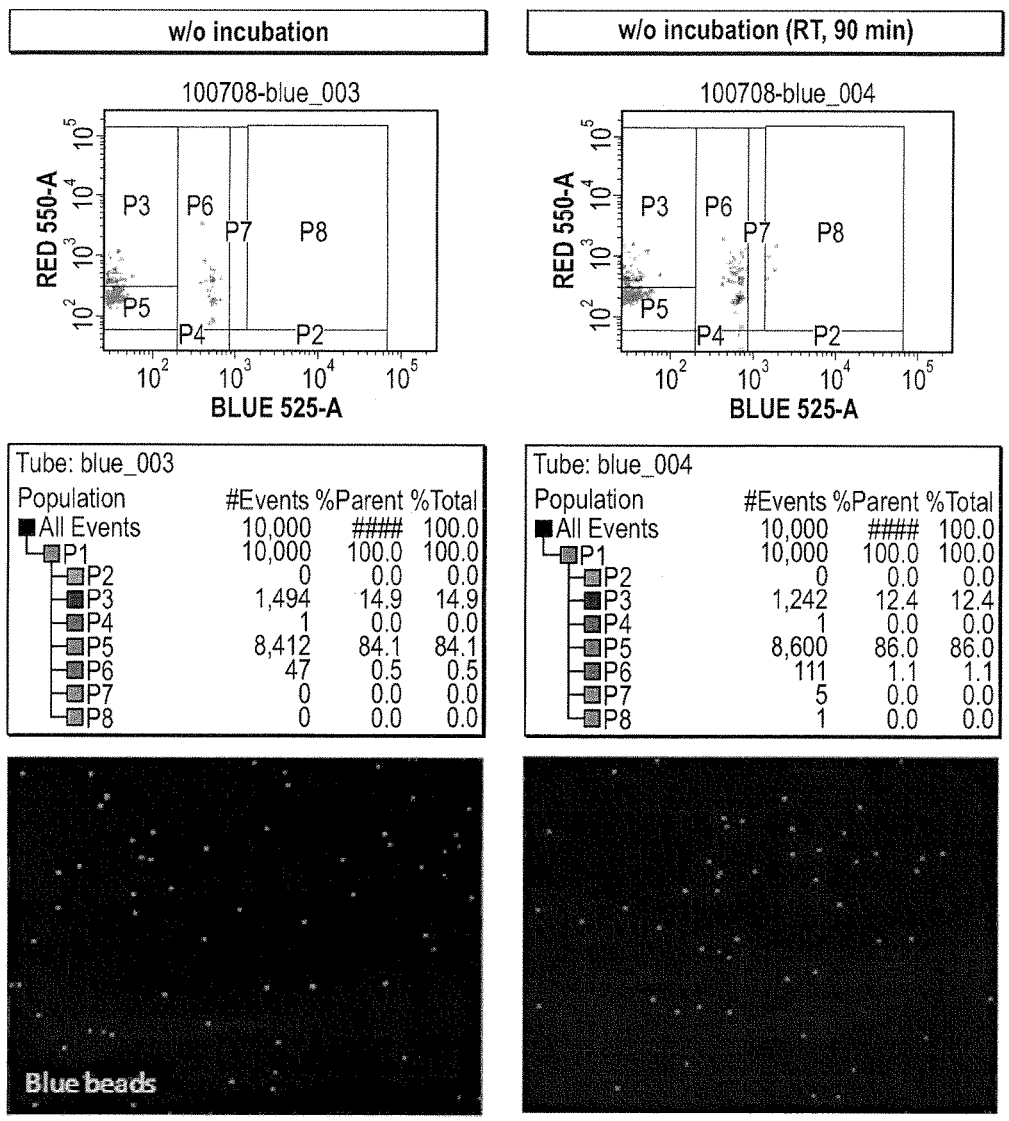
FIG. 59 shows flow cytometry analysis of pre- and post-incubation, testing for Blue-beads only aggregation. An image is shown below representing the same experiment.
Figure 60:
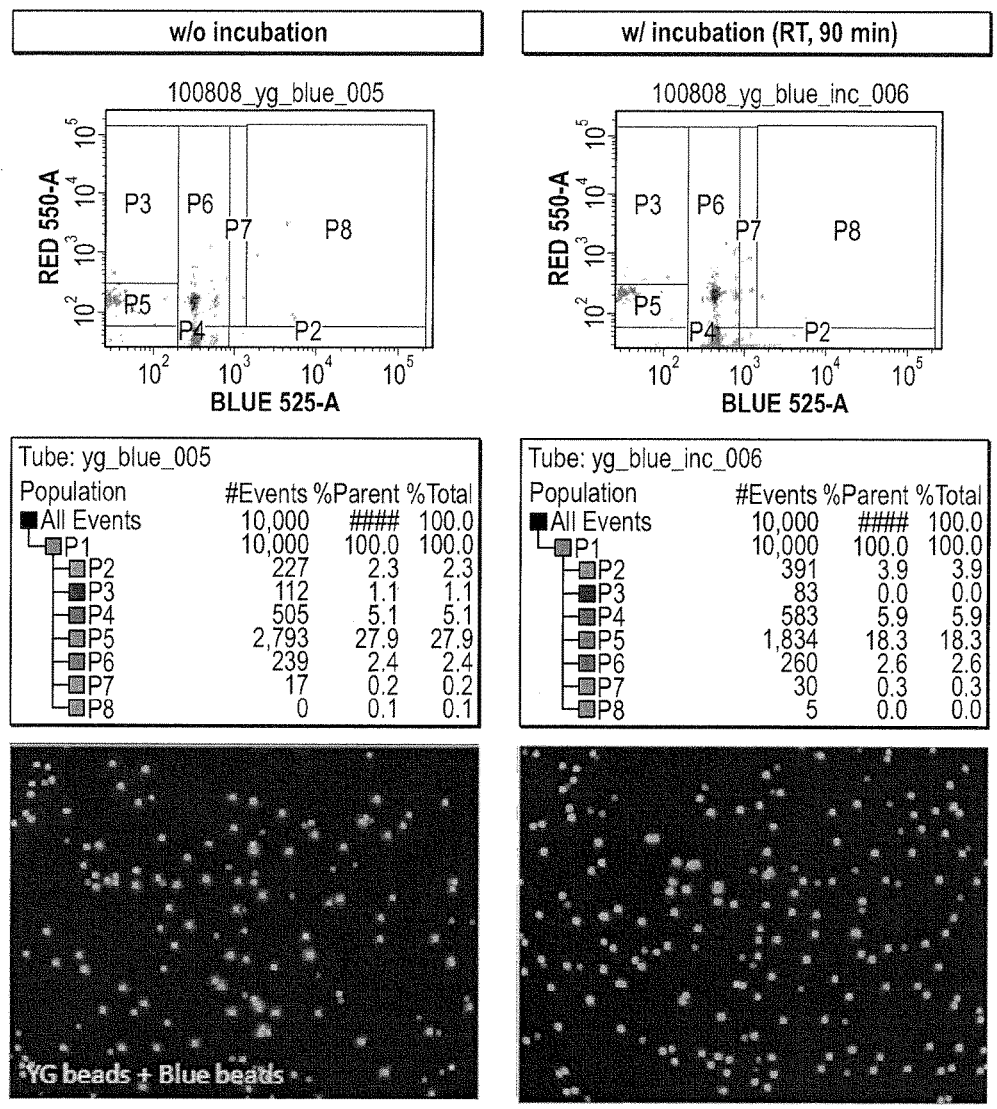
FIG. 60 shows flow cytometry analysis of pre- and post-incubation, for YG-beads and Blue-beads only, followed by aggregation. An image is shown below representing the same experiment.
Figure 61:
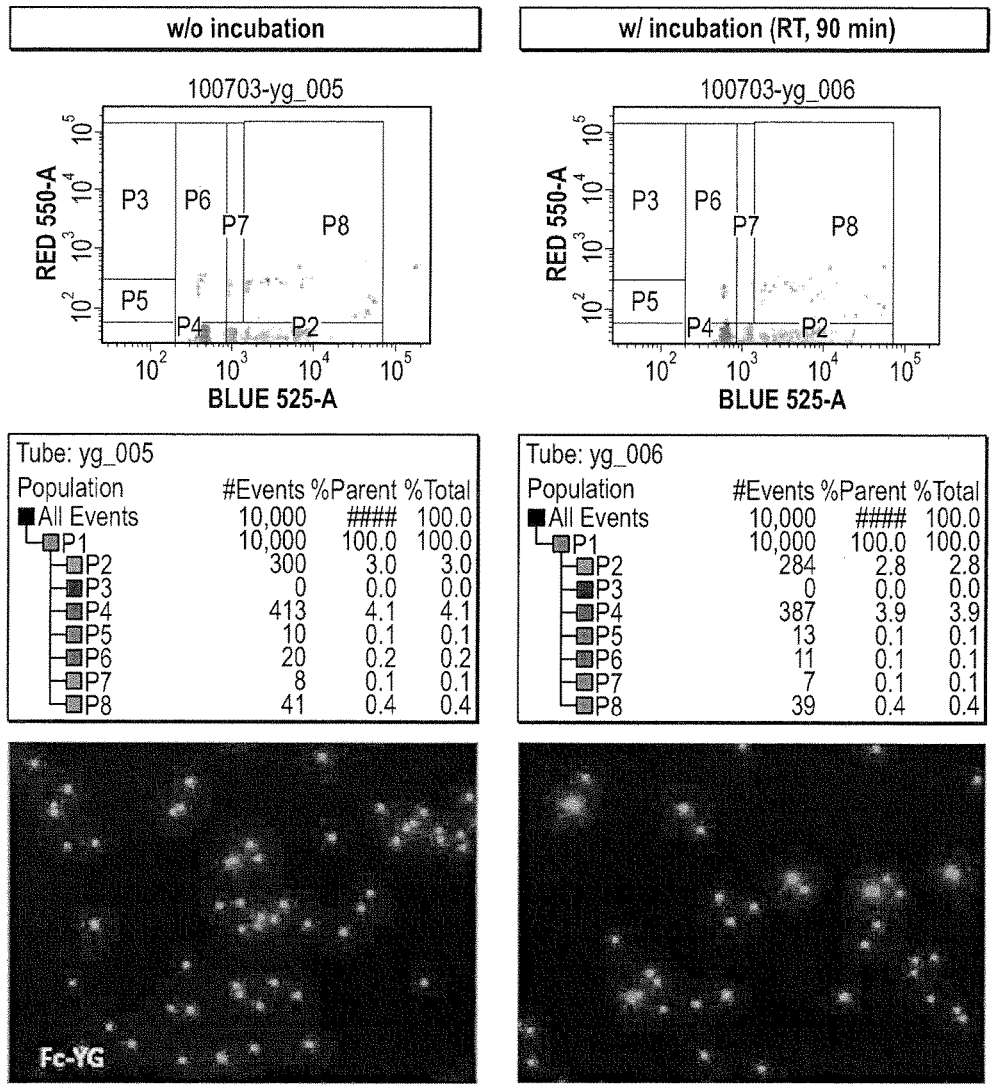
FIG. 61 shows flow cytometry analysis of pre- and post-incubation, mixing for Fc-conjugated YG-beads, followed by aggregation. An image is shown below representing the same experiment.
Figure 62:
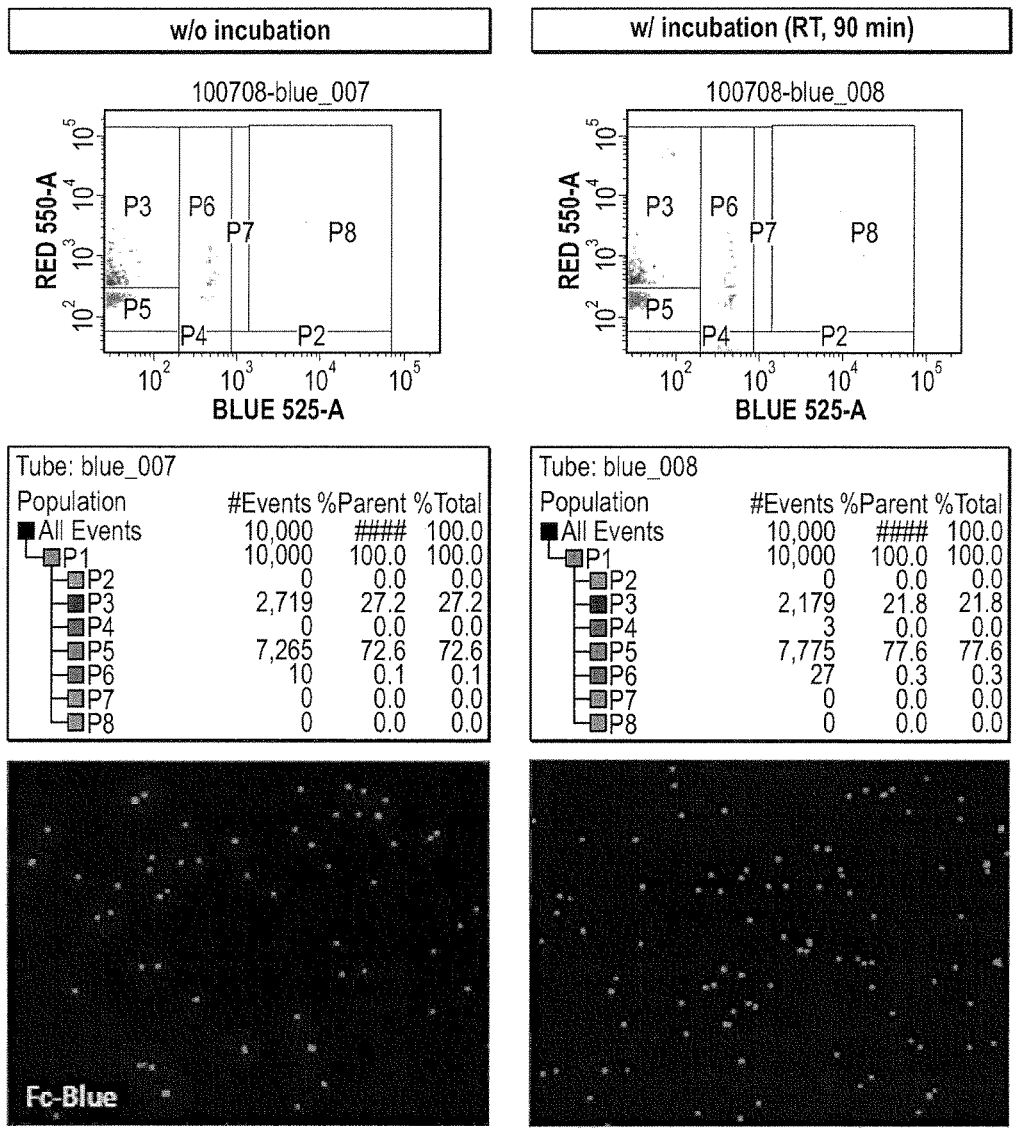
FIG. 62 shows flow cytometry analysis of pre- and post-incubation, testing for Fc-conjugated Blue-beads aggregation. An image is shown below representing the same experiment.
Figure 63:
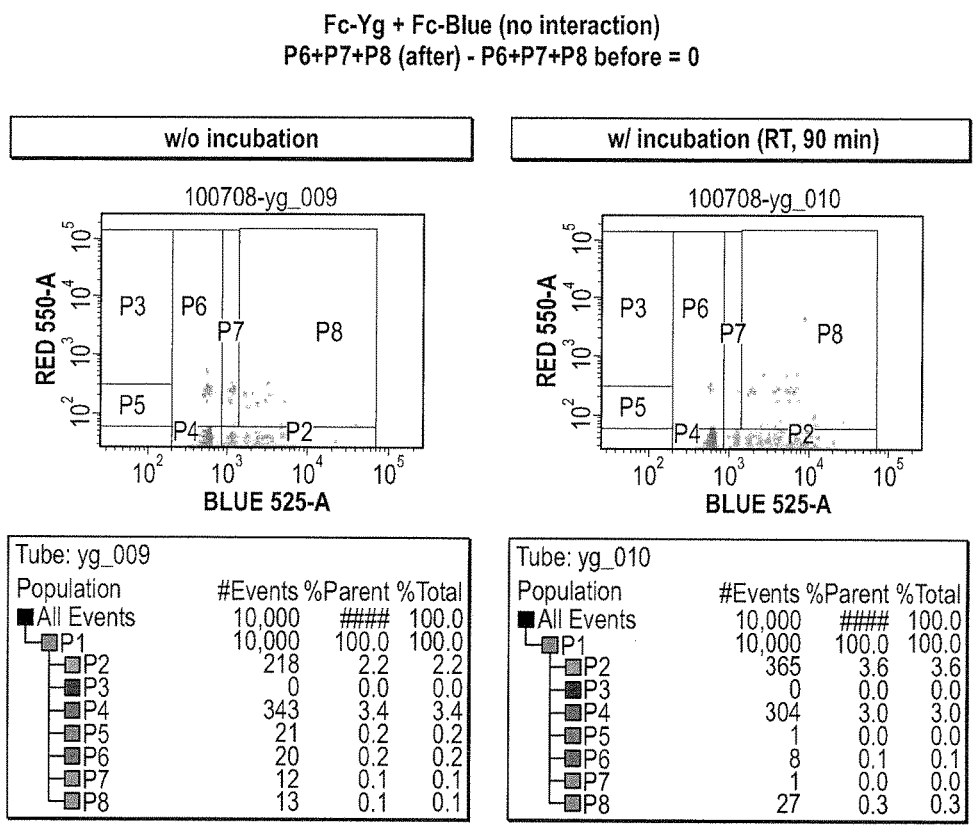
FIG. 63 shows flow cytometry analysis of pre- and post-incubation, testing for Fc-conjugated Blue-beads and YG-beads aggregation.
Figure 64:
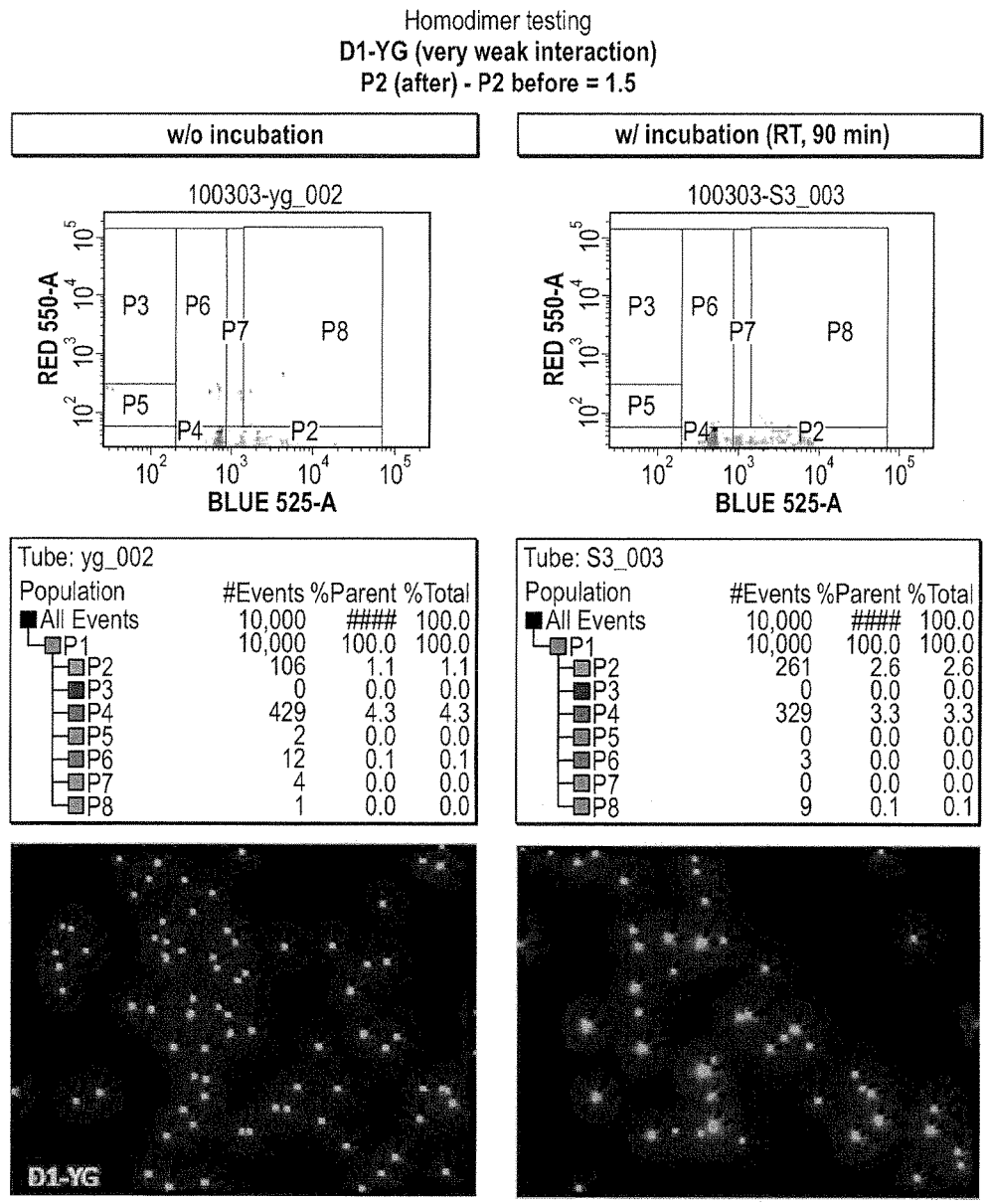
FIG. 64 shows flow cytometry analysis of pre- and post-incubation, testing for D1-Fc-conjugated YG-beads aggregation. An image is shown below representing the same experiment.
Figure 65:
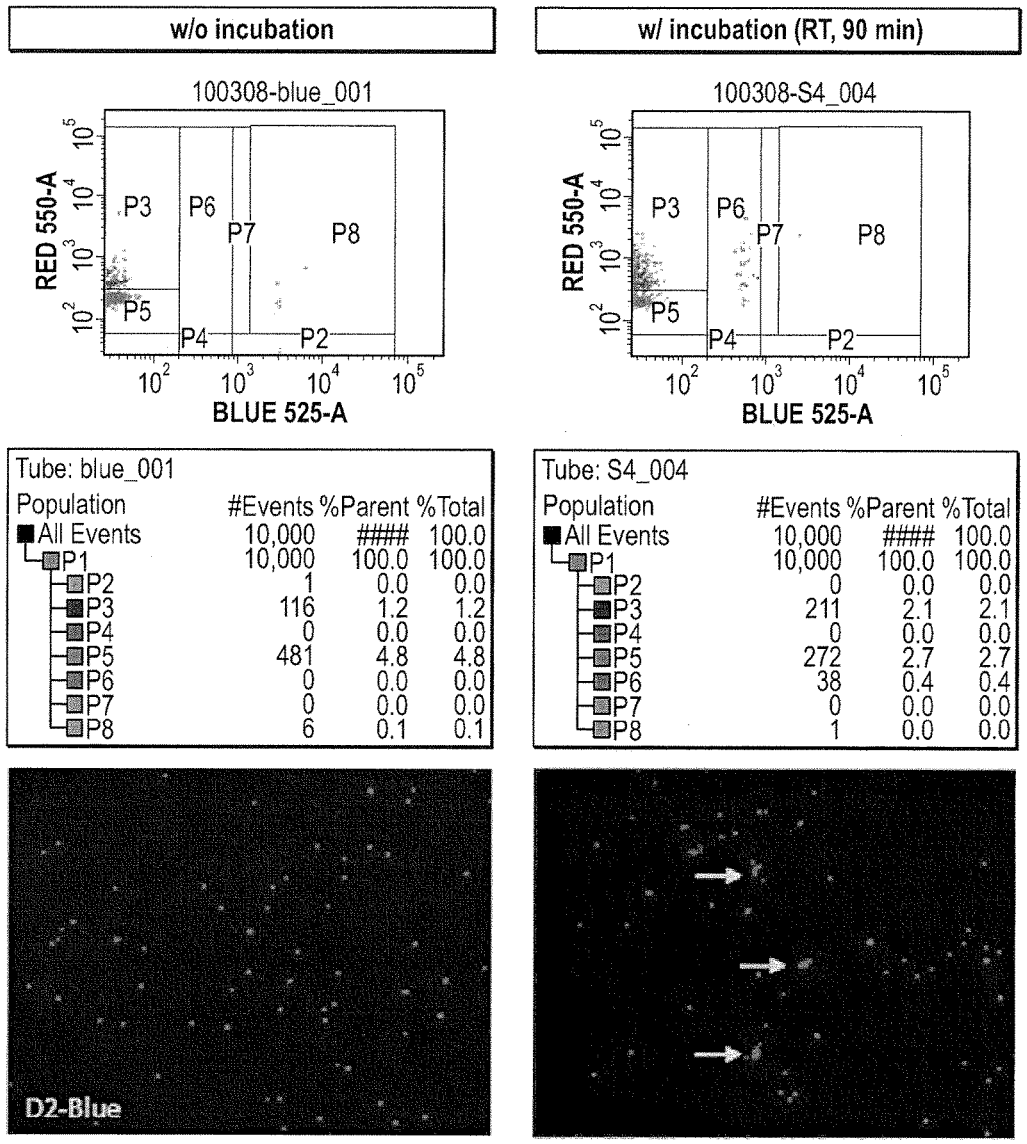
FIG. 65 shows flow cytometry analysis of pre- and post-incubation, testing for D2-Fc-conjugated Blue-beads aggregation. An image is shown below representing the same experiment.
Figure 66:
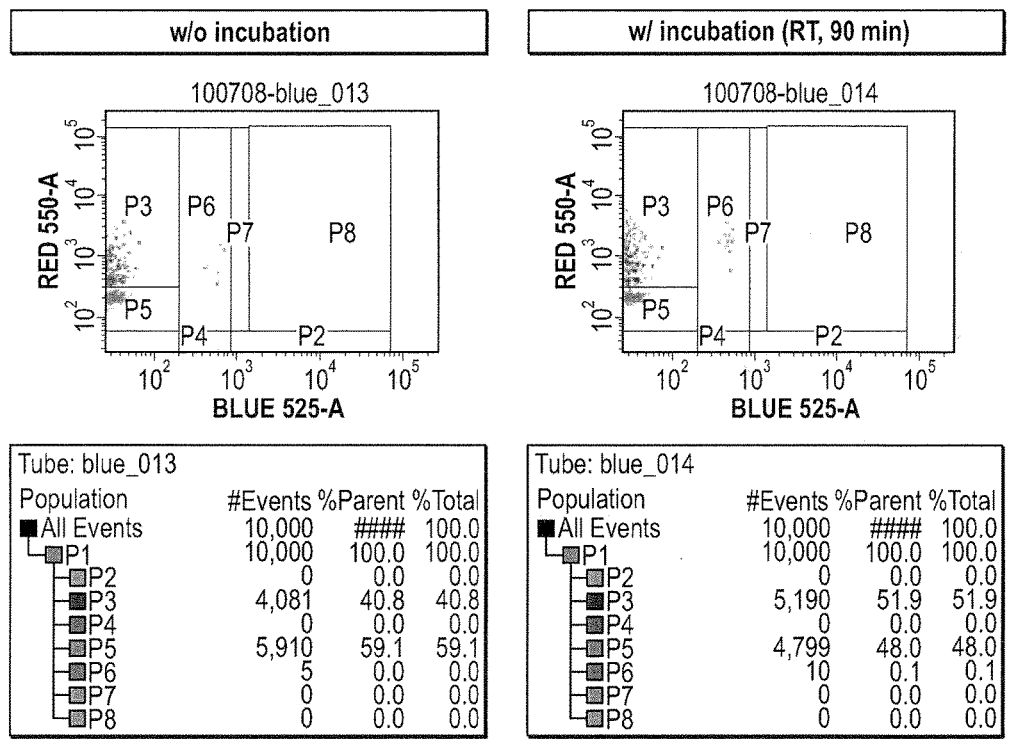
FIG. 66 shows flow cytometry analysis of pre- and post-incubation, testing for D3-Fc-conjugated Blue-beads aggregation, experiment 1. A significant number of aggregates is observed prior to incubation (P3 prior to incubation is 40.8%).
Figure 67:
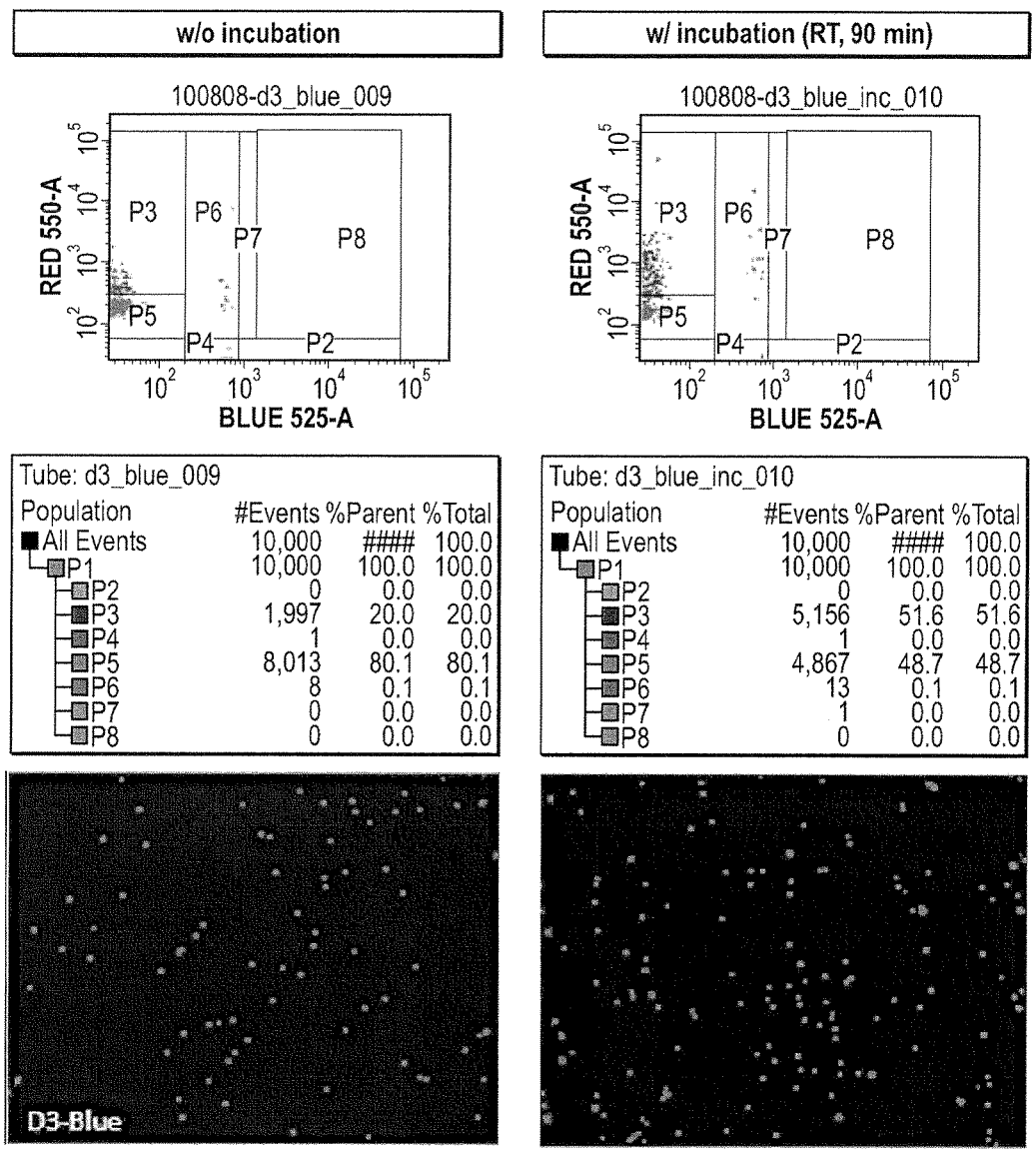
FIG. 67 shows flow cytometry analysis of pre- and post-incubation, testing for D3-Fc-conjugated Blue-beads aggregation, experiment 2. An image is shown below representing the same experiment.
Figure 68:
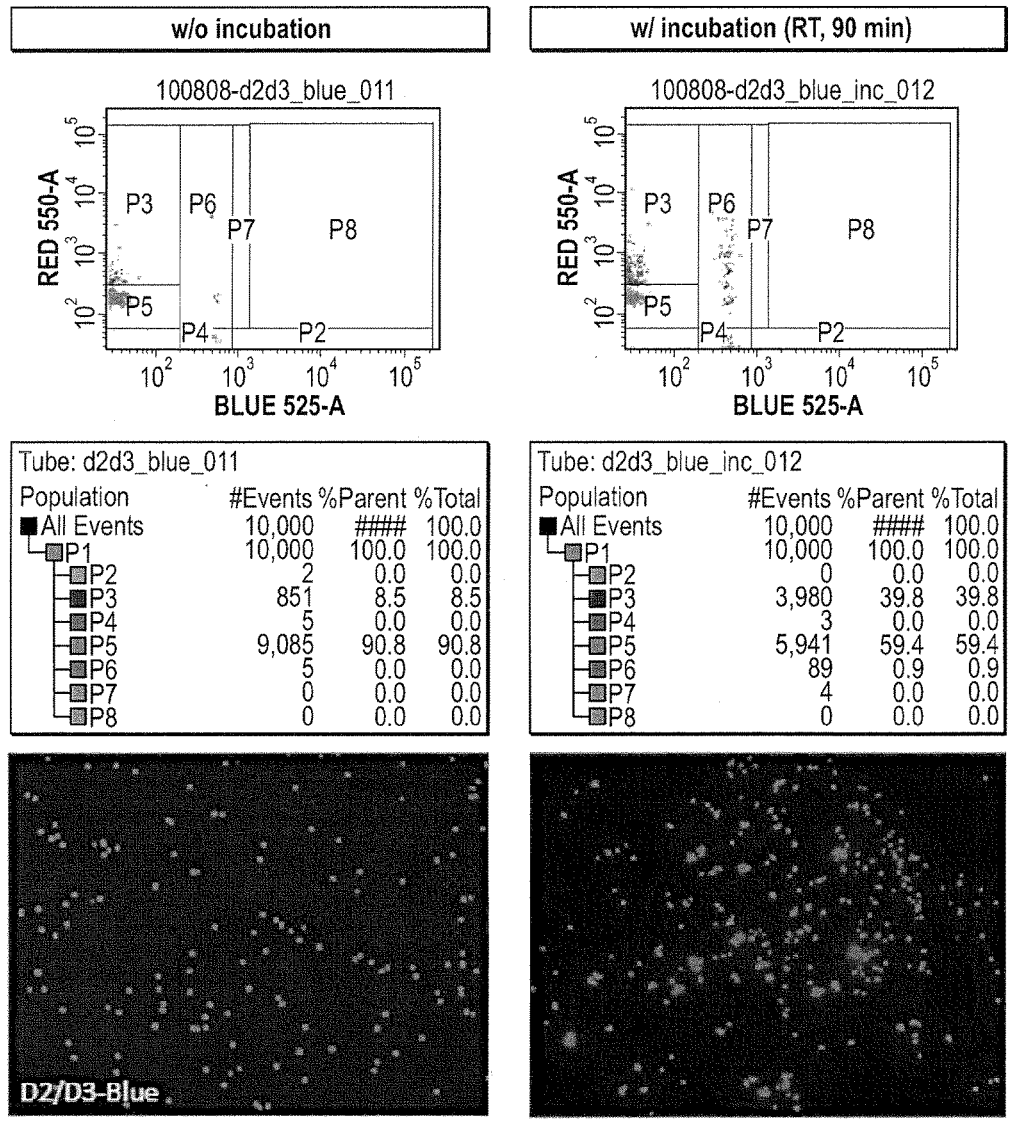
FIG. 68 shows flow cytometry analysis of pre- and post-incubation, testing for D2/D3-Fc-conjugated Blue-beads aggregation. An image is shown below representing the same experiment.
Figure 69:
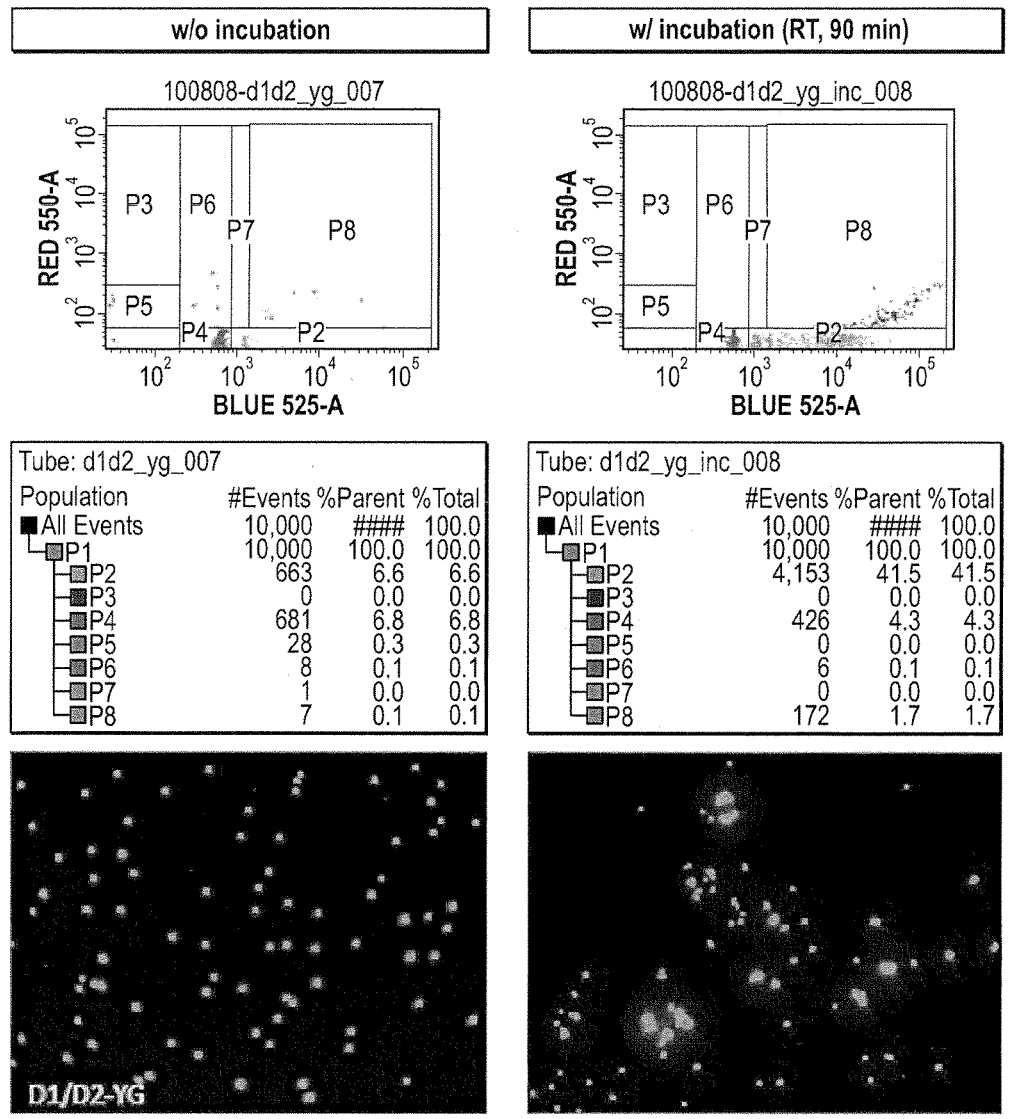
FIG. 69 shows flow cytometry analysis of pre- and post-incubation, testing for D1/D2-Fc-conjugated YG-beads aggregation. An image is shown below representing the same experiment.
Figure 70:
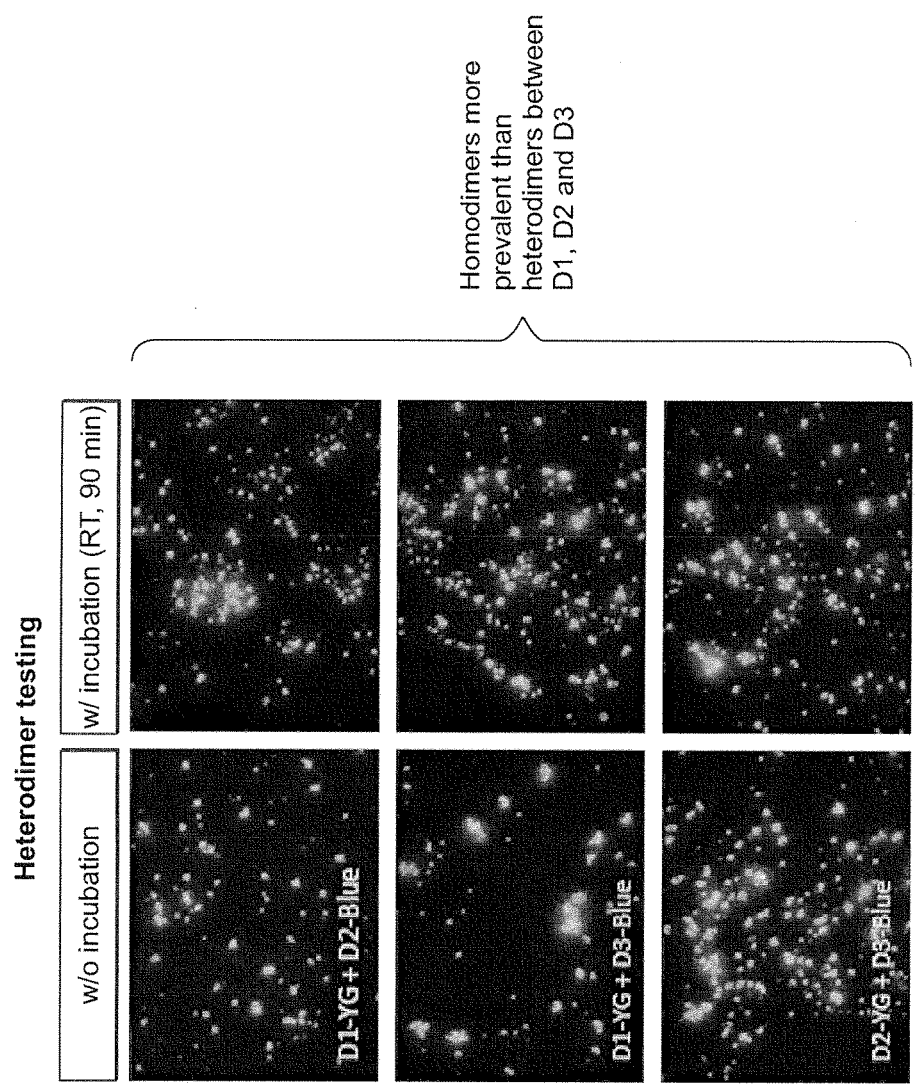
FIG. 70 shows imaging analysis of pre- and post-incubation, testing for heterodimer formation between D1 and D2, D1 and D3, D2 and D3.
Figure 71:
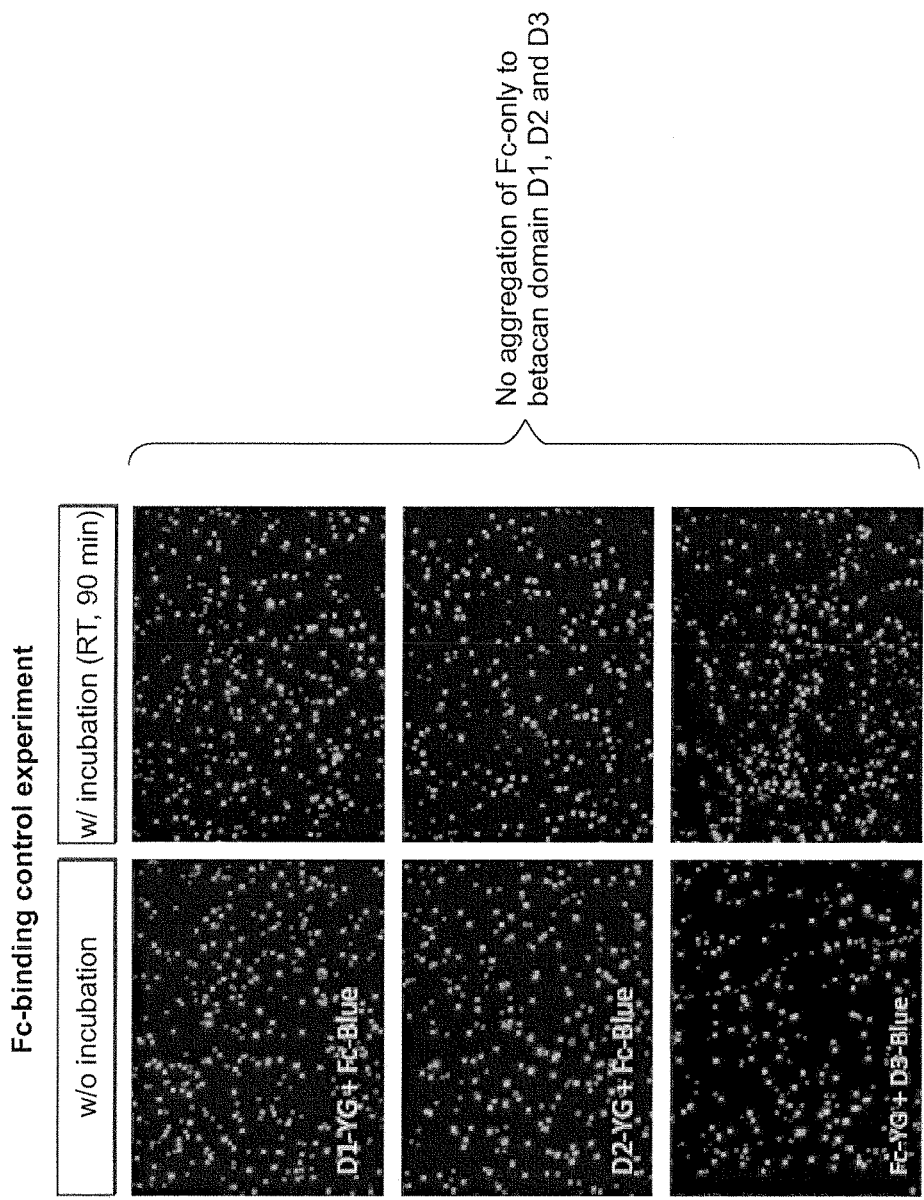
FIG. 71 shows imaging analysis of pre- and post-incubation, testing for involvement of the Fc-domain in any interactions between D1, D2 and D3.

The inventors first tested for intrinsic abilities of the fluorescent beads to bind as homodimers, or heterodimers. YG-beads (green fluorescent) showed no intrinsic capacity for aggregation (FIG. 58). Blue beads (red fluorescent) showed no intrinsic capacity for aggregation (FIG. 59). Mixing YG and Blue beads showed no intrinsic capacity for heterotypic aggregates (FIG. 60). Conjugation of Fc-only to the YG-bead fraction did not allow for aggregation (FIG. 61). Conjugation of Fc-only to the Blue bead fraction did not allow for aggregation (FIG. 62). Mixing Fc-conjugated YG- and Blue-type beads did not lead to aggregation (FIG. 63). Testing for homodimer formation between individual Betacam immunoglobulin domains was next performed. D1-YG conjugated beads revealed a very weak interaction suggesting D1-D1 homodimers may form (FIG. 64). Similarly, D2-D2 weak interactions were detected (FIG. 65). In contrast, D3-D3 homodimers are prominent (FIG. 66), and exist even prior to sonication, suggesting intrinsic capacity of D3-conjugated beads to aggregate in a homotypic fashion. A second experiment was performed at which the sonication process was extended, reducing the presence of pre-formed D3-D3 homodimers. It was observed that the 90 minute aggregation period leads to a dramatic increase in numbers of D3-D3 homotypic aggregates (FIG. 67). Testing D2/D3 in a similar manner yields similar results as those observed for the D3-D3 interactions, arguing that homotypic interactions between D2/D3 is mediated through the D3 domain, and that D2 contributes little, if any, to the observed aggregation (FIG. 68). D1/D2 homotypic aggregates were similarly analysed, and the inventors here observed a dramatic formation of very large aggregates, following incubation. This interaction appears stronger than the observed D3-D3 interaction. Aggregates of >100 beads were observed during immunofluorescence detection (FIG. 69). The inventors next tested for heterodimeric binding of the various Imnunoglubulin domains from Betacam. In no case did the inventors observe strongly forming heterotypic aggregates between D1 to D2 or D3, or D2 to D3 (FIG. 70). A control experiment in which Fc-conjugated blue beads were tested for binding to YG-beads conjugated to D1, D2 or D3 revealed no heterotypic interactions forming, providing evidence that the observed interactions are mediated by the D1/D2 and D3 domains (FIG. 71). The inventors concluded that the extracellular domains of Betacam exhibit two individual models in homotypic interactions, one involving the D1/D2 fragment, which is explained by antiparallel interactions, which are stronger than any D1-D2 interactions individually analyzed. The other interaction mode is based on D3-D3 homotypic interactions, which do not interfere with D1/D2 homotypic interactions.

The combined evidence of these interactions is strongly supportive of the proposed theoretical models of Betacam higher-order interactions as outlined in Example 2.

EXAMPLE 8

Figure 72:
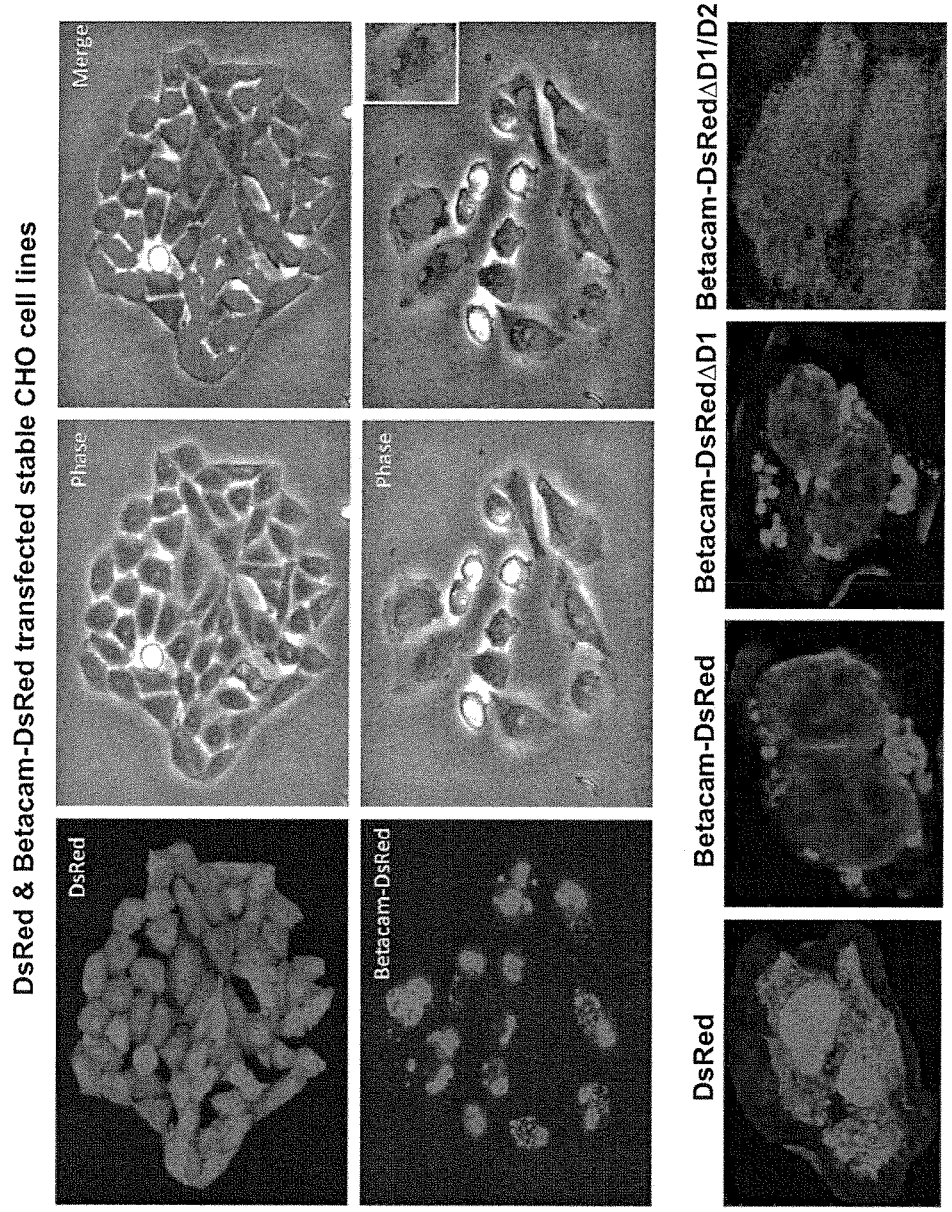
FIG. 72 shows analysis of stably transfected CHO cells overexpressing DsRed only (control) and Betacam-DsRed fusion proteins. The lower row of images contain a series of comparative pictures of cells overexpressing DsRed only, Betacam-DsRed, BetacamΔD1-DsRed (lacking Betacam domain D1) and BetacamΔD1/D2-DsRed (lacking Betacam domain D1-D2).

Generation of Mammalian Cells Stably Expressing Betacam, and Analysis of Cell Surface Expression of Betacam Referring now to the invention in more detail, FIG. 72 describes results from production of stably expressing cell lines for a Betacam-DsRED fusion protein. CHO (Chinese hamster ovary) cells were transfected with pCMV-DsRED or pCMV-Betacam-DsRED. Selection of clones stably expressing the constructs was performed using G418 (neomycin). It was noted that loss of Betacam-DsRed colonies during the culture phase was prominent. Clonal homogeneity is apparent in both cases. DsRED distributes throughout the cell, whereas Betacam-DsRED becomes localized to strongly fluorescent aggregates, predominantly in a perinuclear location. Such localization is commonly observed if proteins form intracellular aggregates, and generate "aggrosomes", which a eukaryotic version of bacterial inclusion bodies. The formation of aggrosomes is a result of ER-stress. Often, apoptotic death is associated with this, and the cells are impaired in growth. The inventors subsequently produced stable clones expressing N-terminally truncated versions of Betacam-DsREd fusions. CHO-cells expressing Betacam-DsRed-ΔD1 and Betacam-DsRed-ΔD1/D2 were similarly selected by G418 treatment. Such cells revealed that Aggrosome formation was observed in cells expressing Betacam-DsRed-ΔD1, but not in cells expressing Betacam-DsRed-ΔD1/D2. The Betacam-DsRed-ΔD1/D2 fusion protein distributes over the entire cell, and seems incapable of aggregation in this assay.

Figure 73:
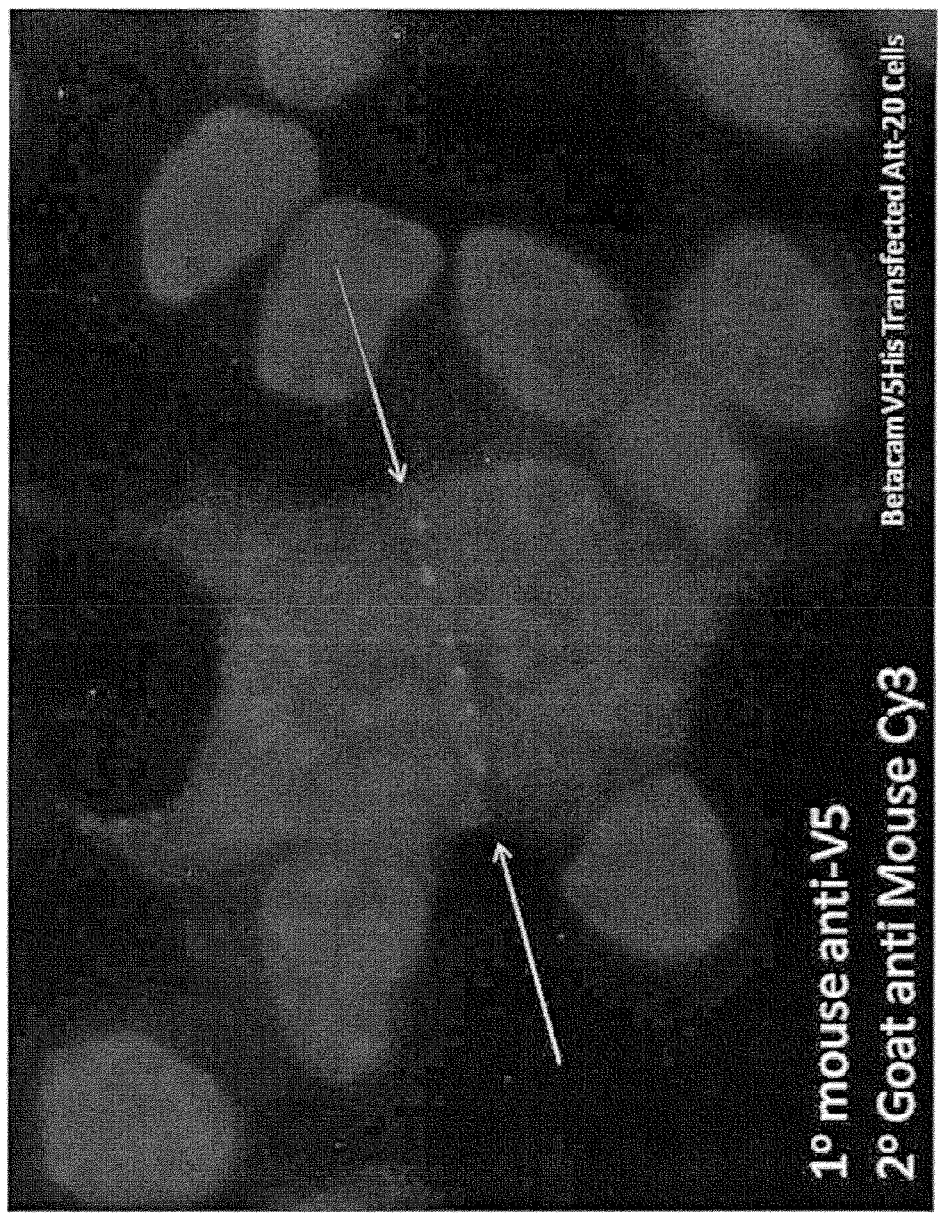
FIG. 73 shows fluorescent image of adjacent Att20-cells expressing Betacam-V5 his full length Betacam. Detection of signal was performed by immunofluorescence detection of the V5 epitope. Staining is observed at the membrane attachment zone of the two cells.

Referring now to the invention in more detail, FIG. 73 describes results transiently overexpressing a V5-tagged full length Betacam construct in Att20 (mouse anterior pituitary tumor) cells. The motivation for selecting the pituitary cell line was based on the fact that Att20 cells are of neuroendocrine type, and producing adrenocorticotropic hormone (ACTH), and consequently more resembling pancreatic b-cells as compared to CHO cells. A shorter detection tag (V5 epitope) was selected considering is smaller size, and lower likelihood of interfering with normal Betacam functions. Detection of the fusion protein was facilitated by using a monoclonal antibody binding to the V5 epitope. The full length Betacam construct contained the intact pre-peptide of Betacam. Two cells adjacent to, and contacting, each other, both expressing the V5-tagged Betacam protein are shown. The inventors note that formation of aggrosomes is minimal. The cell-cell connection interface between the cells is enriched for V5-reactivity. The inventors conclude that Betacam is expressed on the cell surface of either cell, and enriched at cell/cell junctions.

Figure 74:
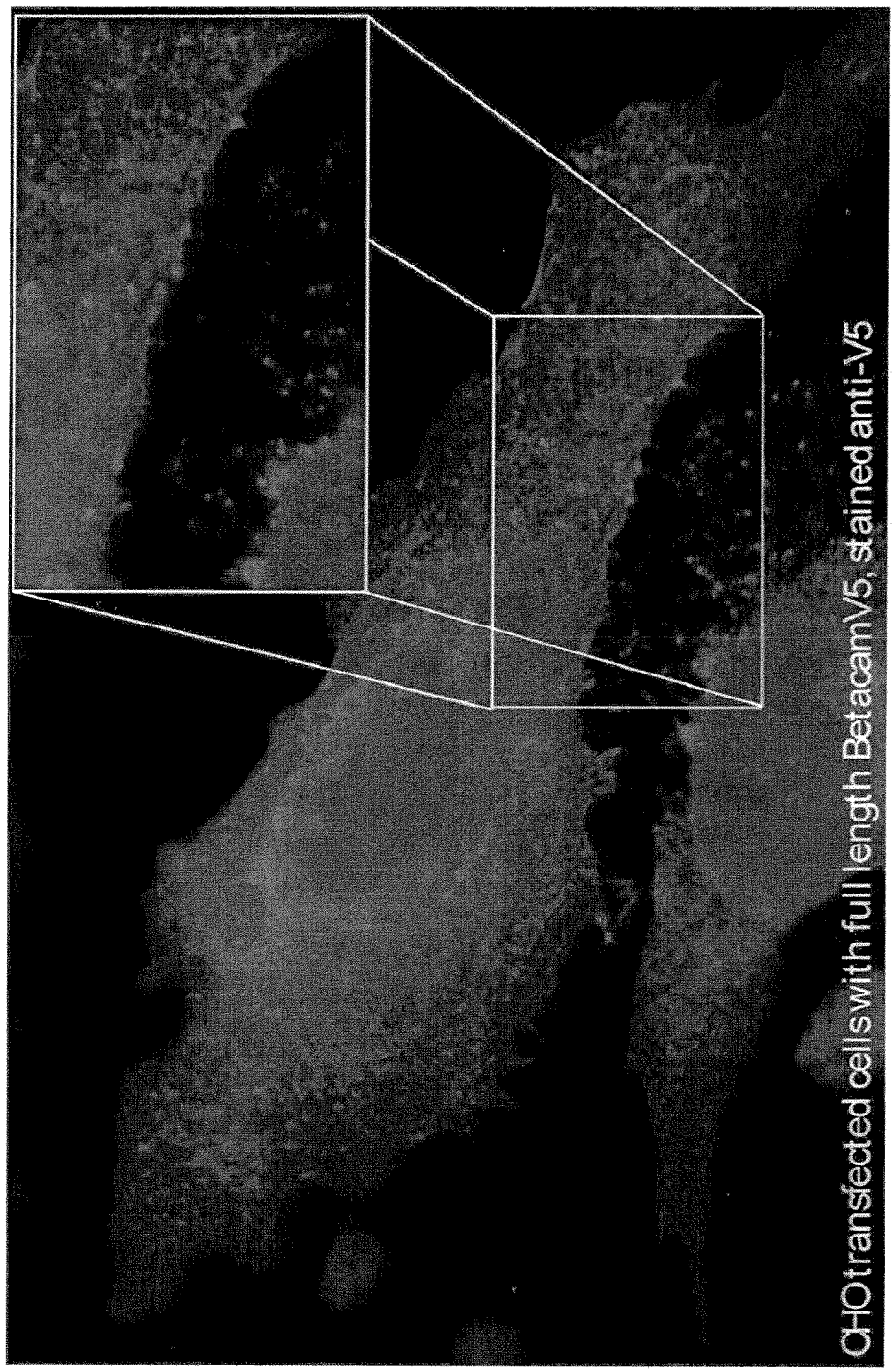
FIG. 74 shows confocal fluorescent image of CHO cells, expressing Betacam-V5. Staining is observed at points-of-contact.

Referring now to the invention in more detail, FIG. 74 describes results transiently overexpressing a V5-tagged full length Betacam construct in Chinese hamster ovary cells (CHO). Here, a confocal image scan was obtained better capable of resolving the interaction interface between two Betacam-expressing cells.

Figure 75:
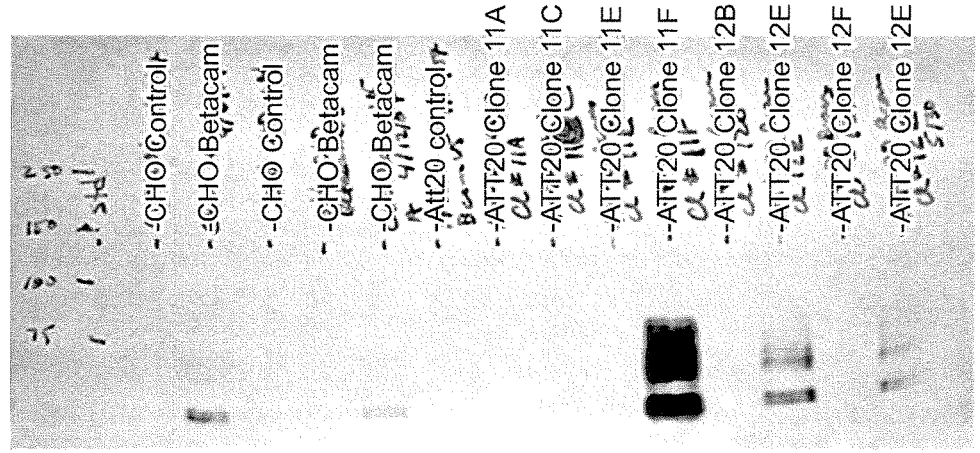
FIG. 75 shows western blot analysis for detecting Betacam protein stably expressed in multiple cell lines.
Figure 76:
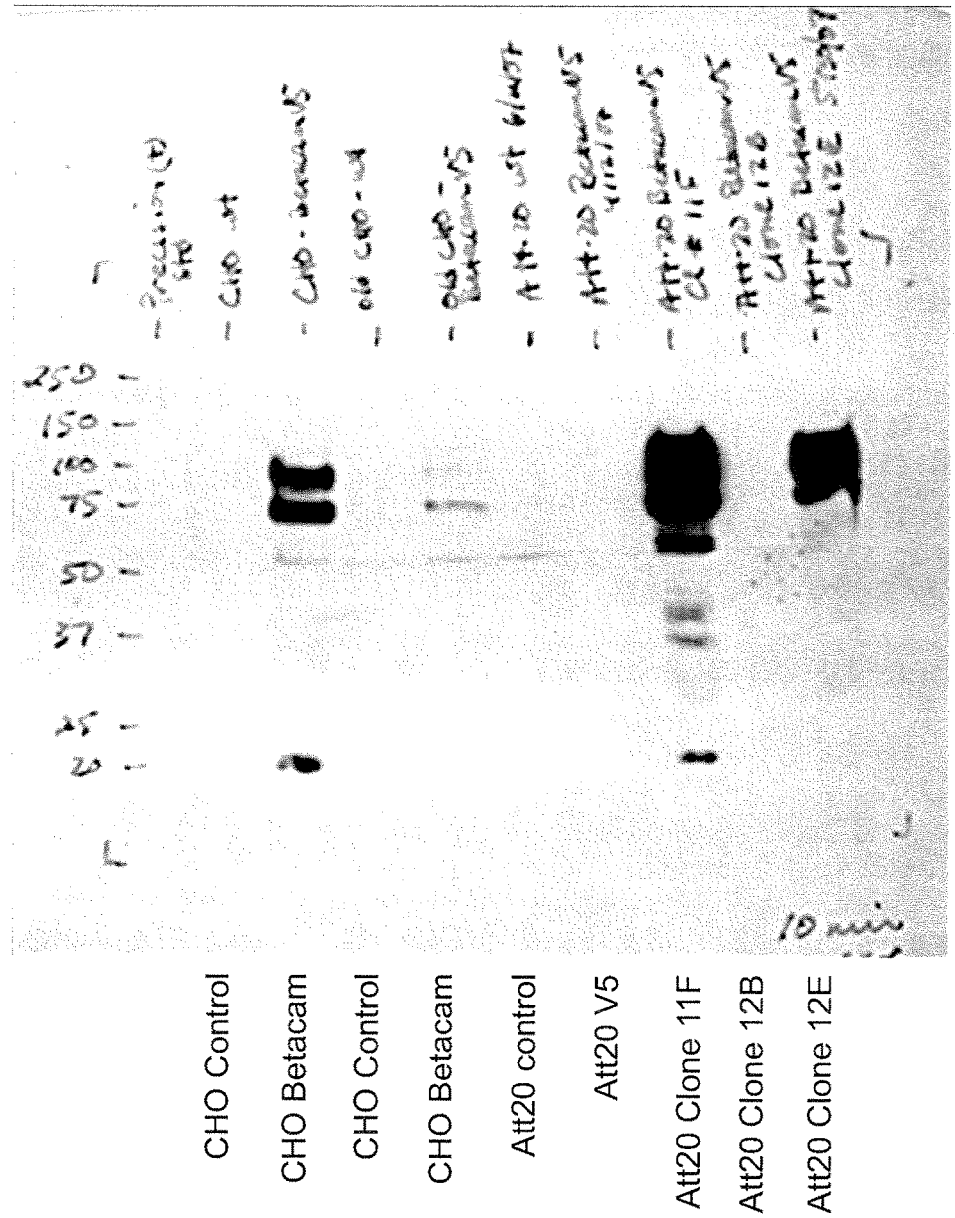
FIG. 76 shows western blot analysis for detecting Betacam protein stably expressed in multiple cell lines.

Referring now to the invention in more detail, FIGS. 75 and 76 describes results stably overexpressing a V5-tagged full length Betacam construct in both CHO and Att20 cells. A Western blot, using the V5 reacting monoclonal antibody, secondarily detected using HRP-conjugated anti-mouse antibodies is shown. Protein lysates from various independently selected stable clones of either cell line was loaded. Expression of Betacam varied, as expected, between individual clones. Results from the CHO expressing lines were not referred to in more detail. Att20 clones expressing Betacam-V5 were those named 11F and 12E, where 12E expressed lower total levels than 11F. Several G418 resistant clones did not express Betacam-V5 at detectable level (Clone 11A, 11C, 11F, 12B, 12F). Clone 12E was selected for further analysis.

Referring now to the invention in more detail, imaging of Att-20 clone 12E was performed using the V5 added tag to Betacam. Left image in FIG. 77 revealed widespread presence of immunofluorescence. This was most notable at cell/cell boundaries. The non-transfected control population (WT, rightmost) did not show a similar staining.

Another imaging result of Att20 clone 12E is shown in FIG. 78. This was represented in black/white to better reveal contrast. Brightly fluorescent specks were detected at cellular membrane/membrane connection points (both images of are of the Att20 transfected population, they represent different fields-of-view).

Figure 79:
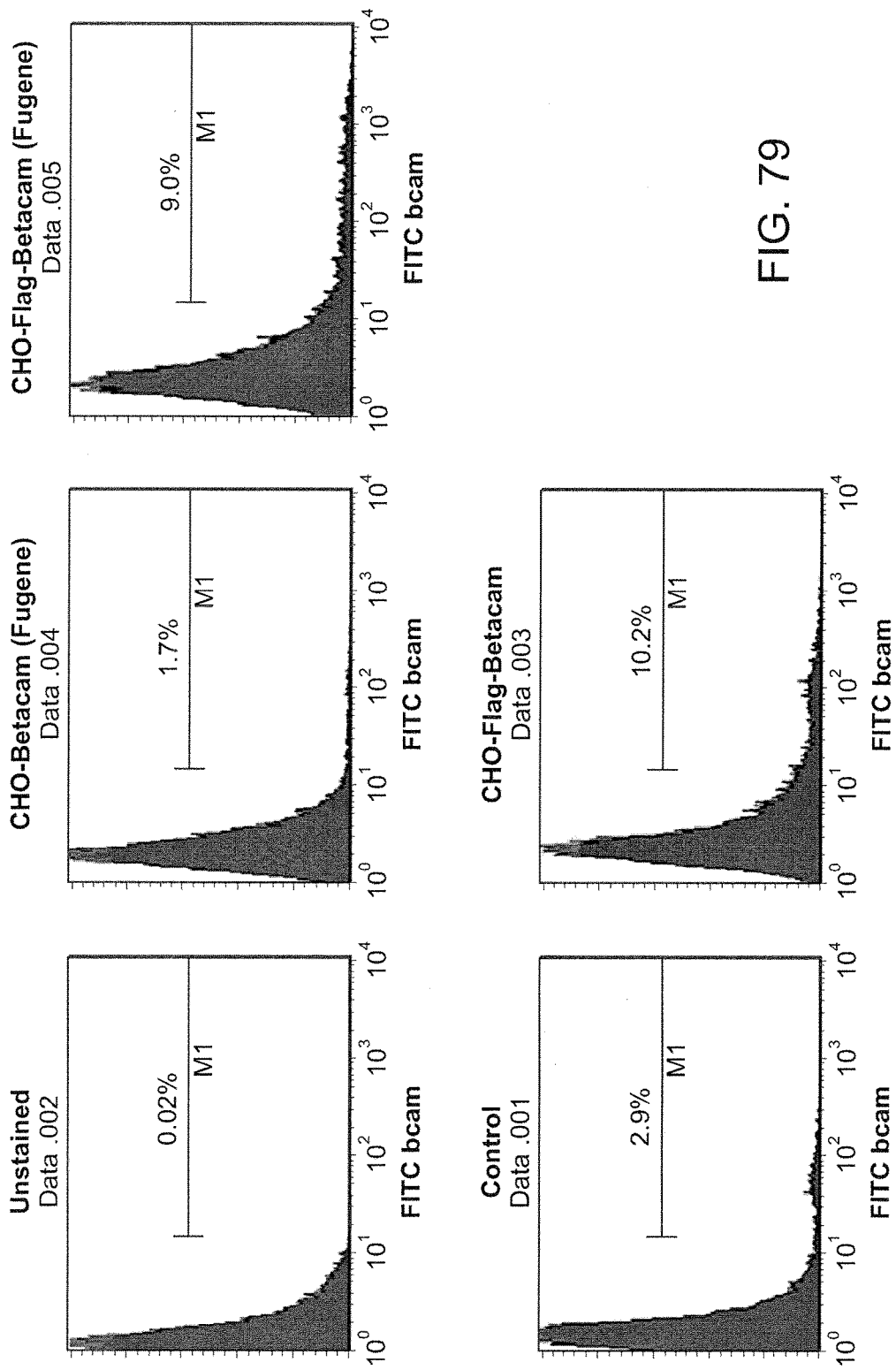
FIG. 79 shows flow cytometry analysis of CHO cells transiently transfected with Betacam forms, or control plasmid.

FIG. 79 shows FACS analysis of Betacam in CHO cells.

EXAMPLE 9

Cellular Aggregation Properties of Betacam

HEK 293FT cells were grown on culture dishes and washed three times with phosphate-buffered saline (PBS) without $Mg^{2+}$ or $Ca^{2+}$, and collected after brief exposure (1 min at 37° C.) to trypsin-EDTA (Sigma). After centrifugation, a single-cell suspension was obtained by passing cells through a cell strainer (40-μm pore size). The cells were suspended into DMEM medium containing 10% FCS at a density of $1\times10^6$ cells/ml. The single-cell suspension was placed in 24-well plates pre-coated with 2% bovine serum albumin (BSA) and then rotated on a shaker at 37 C for indicated periods (1 hr, 2 hr, 5 hr, overnight).

Figure 80:
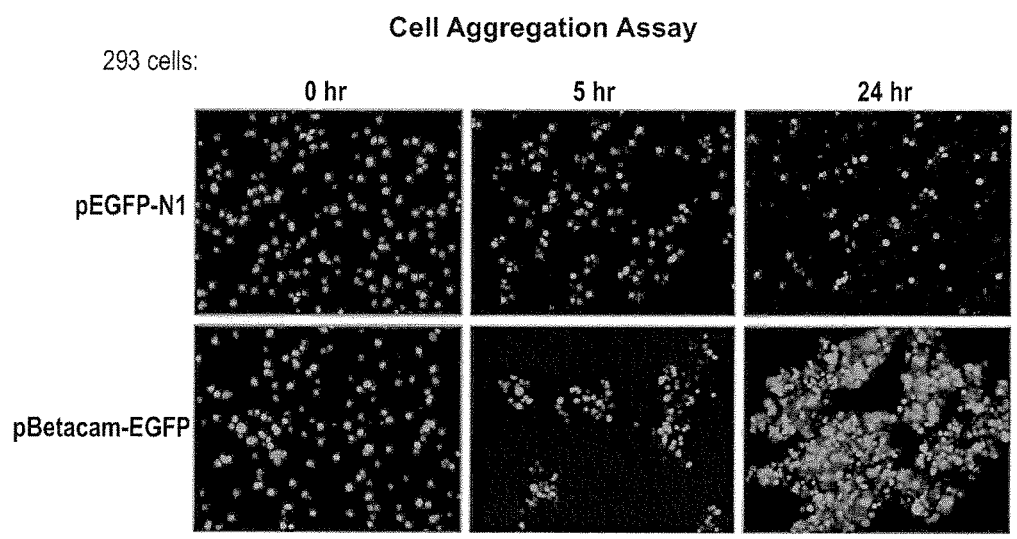
FIG. 80 shows cell aggregation assay, using HEK293 cells transiently transfected with EGFP control plasmid (top row) or Betacam-EGFP fusion protein (lower row). Over time, cell aggregates are detectable in Betacam-EGFP transfected cells, but not EGFP control cells.

In a selected experiment, cells were suspended in normal Hanks' balanced salt solution (HBSS) containing $Ca^{2+}$ and $Mg^{2+}$ (Sigma), or $Ca^{2+}$- and Mg2+-free HBSS (Sigma) containing 2 mM EDTA. Both HBSS solutions were supplemented with bovine serum albumin (BSA) at a final concentration of 2%. FIG. 80 shows a result in which pBETA-CAM-EGFP expression led to cell aggregation, detectable at 5 h, whereas transfection with pEGFP resulted in no difference in aggregation properties.

Figure 81:
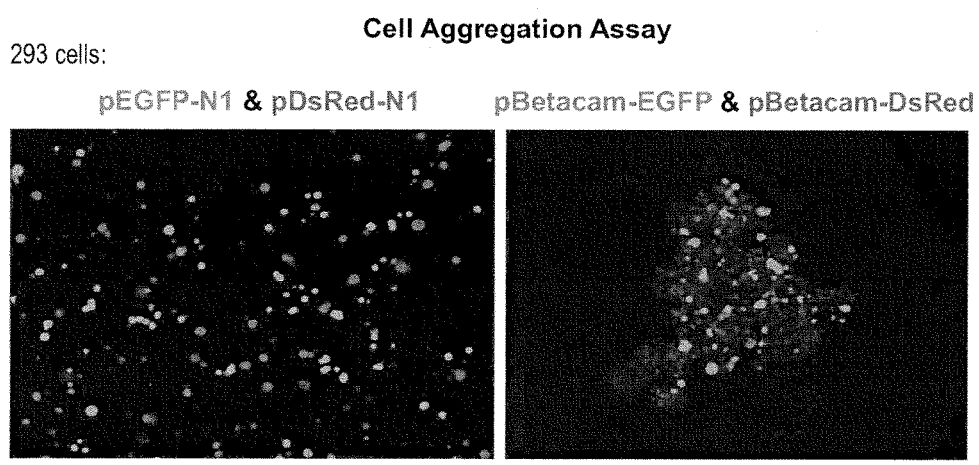
FIG. 81 shows cell aggregation assay, using HEK293 cells individually transiently transfected with a combination of EGFP and DsRed plasmids (left) or Betacam-EGFP and Betacam-DsRed fusion proteins (Right). Aggregation of Red/Green cells occur in the Betacam fusion protein transfected populations only.

In a selected experiment, two individual labeled Betacam forms (pBetacam-EGFP and pBetacam-DsRed) were transfected into HEK293FT cells; control transfections were performed using pEGFP-N1 and pDsRed-N1. The individual cells were subjected to the aggregation protocol as described earlier. FIG. 81 shows the aggregation of both red, and green, labeled Betacam-expressing cells. No aggregation was observed using the EGFP and DsRED proteins.

Referring now to the invention related to embodiments based on the Betacam peptide, an alternative method could be considered if a similar, but different gene as compared to Betacam exists which creates, upon its transcription and translation of its mRNA, a surface epitope present with high selectivity on the beta-cell surface. However, the inventors have reason to claim such a molecule is unlikely to exist. These claims are based on the following observations. 1. The genomics-based bioinformatics analysis was performed using the MOE-430v2 Affymetrix platform, which covers >90% of the transcribed genome (>40000 features are present on the platform). 2. The definition of tissue-specific expression towards pancreatic b-cells, also having selective expression of genes within the endocrine compartment of the pancreas was performed to lead to a much-reduced subset of genes (<200). 3. Within this list, all genes were manually curated for membrane localization, presumed function and novelty. 4. Only a single gene emerged, Betacam, consequently being the one exhibiting the highest degree of tissue-specificity for the pancreatic islet, beta-cells in particular, also being expressed on the surface of such cells, and representing a novel, uncharacterized gene. These criteria were fulfilled for both the mouse, and human Betacam genes and their translated products.

The embodiments of the invention are related to the utilization of Betacam as a novel, surface-expressed epitope, which normal pancreatic beta cells have. When combined with the predicted function of Betacam as a novel homotypic cell adhesion molecule, the various embodiments described are reagent definitions and formulations based on the advantageous features that such a unique component present on such cells provide.

The advantages of the present invention include, without limitation, the formulation of a reagent set capable of tracking a normal, as well as dysfunctional beta cells under several varying conditions. The advantage of the present invention is provided by our findings that a similar molecule is not known to exist. Our bioinformatics analysis suggests that an alternative molecule is unlikely to exist.

The advantages of the present invention lie in the recognition that there is no method to detect islet cells following transplantation in-vivo in a non-invasive manner.

The advantages of the present invention lies in the recognition that there is no specific purification step of the pancreatic beta cell type included current islet transplantation, as this is based on gradient purification of total islets, and results in quite crude cell populations.

The advantages of the present invention lie in the recognition that there is no non-invasive method to purify pancreatic beta cells from e.g. forward-differentiated human ES cells.

```
                                                                SEQUENCE ID: 1
hypothetical protein LOC253012 isoform 1 [Homo sapiens] (Human).
RED SEQUENCE CORRESPOND TO Predicted pre-peptide.
1         10        20        30        40        50
|         |         |         |         |         |
MGQDAPMEPFGDTLGVFQCKIYLLLFGACSGLKVTVPSHTVHGVRGQALY

LPVHYGEHTPASDIQIIWLFERPHTMPKYLLGSVNKSVVPDLEYQHKFTM

MPPNASLLINPLQFPDEGNYIVKVNIQGNGTLSASQKIQVTVDDPVTKPV

VQIHPPSGAVEYVGNMTLTCHVEGGTRLAYQWLKNGRPVHTSSTYSFSPQ

NNTLHIAPVTKEDIGNYSCLVRNPVSEMESDIIMPIIYYGPYGLQVNSDK

GLKVGEVFTVDLGEAILFDCSADSHPPNTYSWIRRTDNTTYIIKHGPRLE

VASEKVAQKTMDYVCCAYNNITGRQDETHFTVIITSVGLEKLAQKGKSLS

PLASITGISLFLIISMCLLFLWKKYQPYKVIKQKLEGRPETEYRKAQTFS

GHEDALDDEGIYEFVAFPDVSGVSRIPSRSVPASDCVSGQDLHSTVYEVI

QHIPAQQQDHPE

SEQUENCE ID: 2
hypothetical protein LOC253012 isoform 2 [Homo sapiens] (human)
RED SEQUENCE CORRESPOND TO Predicted pre-peptide.
1         10        20        30        40        50
|         |         |         |         |         |
MWLVKFTTFLSFATGACSGLKVTVPSHTVHGVRGQALYLPVHYGFHTPAS

DIQIIWLFERPHTMPKYLLGSVNKSVVPDLEYQHKFTMMPPNASLLINPL

QFPDEGNYIVKVNIQGNGTLSASQKIQVTVDDPVTKPVVQIHPPSGAVEY

VGNMTLTCHVEGGTRLAYQWLKNGRPVHTSSTYSFSPQNNTLHIAPVTKE

DIGNYSCLVRNPVSEMESDIIMPIIYYGPYGLQVNSDKGLKVGEVFTVDL

GEAILFDCSADSHPPNTYSWIRRTDNTTYIIKHGPRLEVASEKVAQKTMD

YVCCAYNNITGRQDETHFTVIITSVGLEKLAQKGKSLSPLASITGISLFL

IISMCLLFLWKKYQPYKVIKQKLEGRPETEYRKAQTFSGHEDALDDFGIY

EFVAFPDVSGVSRIPSRSVPASDCVSGQDLHSTVYEVIQHIPAQQQDHPE

SEQUENCE ID: 3
hypothetical protein LOC101202 [Mus musculus]
RED SEQUENCE CORRESPOND TO Predicted pre-peptide.
1         10        20        30        40        50
|         |         |         |         |         |
MGQDAFMELLRSMVGLSLCKIHLLLIAGSCLGLKVTVPSYTVHGIRGQAL

YLPVHYGFHTPASDIQIIWLFERSHTMPKYLLGSVNKSVVPDLEYQHKFT
```

```
MMPPNASLLINPLQFTDEGNYIVKVNIQGNGTLSASQKIQVTVDDPVMKP

MVQFHPASGAVEYVGNITLTCQVEGGTRLVYQWRKSGKPISINSSHSFSP

QNNTLWIVPVTKEDIGNYTCLVSNPVSEMESDIIMPTIYYGPYGLQVNSD

KGLKVGEVFTVDLGEAVLFDCSADSYPPNTYSWIQRSDNTTHVIKHGPHL

EVASEKVAQKTADYVCCAYNNITGRRDETRFTVIITSVGLEKLAQRGKSL

SPLASITGISLFLIISMCLLFLWKKYQPYKAIRQKLEGRPESEYRKAQTF

SGHEDALSDFGIYEFVTFPDASGVSRMSSRSSPASDGVTGQDIHGTIYEV

IQHIPEQQQENTE
```

SEQUENCE ID: 4
hypothetical protein LOC296846 [*Rattus norvegicus*] (rat)
RED SEQUENCE CORRESPOND TO Predicted pre-peptide.
```
        1         10        20        30        40        50
        |         |         |         |         |         |
MGQDAFMELFSSMAGVSLCKIHLLLIAGSCLGLKVTVPSHTVHGIRGQAL

YLPVHYGFHTPASDIQIIWLFERSHTTPKYLLGSVNKSVVPDLEYQHKFT

MMPPNASLLINPLQFTDEGNYIVKVNIQGNGTLSASQKIQVTVDDPVMKP

MVQFHPASGAVEYVGNITLTCRVEGGTRLVYQWRKNGKPININSSHSFSP

QNHTLRIVPATKEDIGNYTCLVSNPVSEMESDIIIPTIYYGPYGLQVNSD

KGLKVGEVFTVDLGEAVLFDCSADSYPPNTYSWIRRSANTTRVIKHGPRL

EVASDKVAQKTADYVCCAYNNITGRRDETHFTVIITSVGLEKLAQRGKSL

SPLASITGISLFFIISMCLLFLWKKFQPYKAIRQKLEGRPESEYRKAQSF

SGHEDALGDFGIYEFVAFPDASAVPRMSSRSAPASDGVTGQDFQGTIYEV

IQHIPAQQQDDTE
```

SEQUENCE ID: 5
hypothetical protein LOC513430 [*Bos taurus*] .(Cow)
RED SEQUENCE CORRESPOND TO Predicted pre-peptide
```
        1         10        20        30        40        50
        |         |         |         |         |         |
MWLRVFTAFLSFTAGACSGLKVAVPSHTVHGIRGQALYLPVHYGEHTPAS

DIQVIWLFERPHTMPKYLLGSVNKSVVPDLEYQHKFTMMPPNASLLINPL

QFTDEGNYIVKVNIQGNGTLSASQKIQVTVDDPVTKPVVQIQPSSGAVEY

VGNMTLTCLVEGGSRRVYQWLKNGRPVHTSSTNSFSLQNSSLHIAPVTKE

DIGNYSCLVKNPVSRMESDIIMPTIYYGPYGLRVNSDRGLKVGEVFTVDI

GEAILFDCSADSYPPNTYSWIQRTNNATYVIKHGPRLEVASEKIAQKTTD

YMCCAYNNITGRRDETHFTVIITSVGIEKLAQKGKSLSPLASITGISLFL

IISMCLLFLWKKFQPYKVIKQKLEGRPETEYRKARTFSGHEDALDDFGIY

EFVAFPDASGVARMPARSVPACDGVPGQDLHSTIYEVIHHIPAQQQDHPE

SSSQDGEEDACLDRHDEAGLQELGHCKEQDKGKHSRAKQCI
```

SEQUENCE ID: 6
similar to CG12369-PA, isoform A [*Canis familiaris*] (Dog)
RED SEQUENCE CORRESPOND TO Predicted pre-peptide
```
        1         10        20        30        40        50
        |         |         |         |         |         |
MASCANILNPEIALAGCEMWLRVIMTFLSFIAGACSGLKVAVPSHTVHGI

RGQALYLPVHYGFHTPASDIQIIWLFERTHTMPKYLLSSVNKSVVPDLEY

QHKFTMMPPNASLLINPLQFTDEGNYIVKVNIQGNGTLSASQKIQVTVDD

PVTKPVVQTQPSSGAVEYVGNMTLTCLVEGGTRLVYQWLKNERPVHSSST

TSFSLQNNTLHIAPVTKEDIGNYSCLVKNPVSEMESDIIMPTIYYGPYGL
```

```
RVNSDKGLKVGEVFTVDIGEAILFYCSADSYPPNTYSWIQRTDNTTYVIK

HGPHLEVASEKVAQKTTDYVCCAYNNVTGRRDEAHFTVIITSVGLEKLAQ

KGKSLSPLASITGVSLFLIISMCLLFLWKKYQPYKVIKQKLEGRPETEYR

KAQTLSGHEDALDDFGIYEFVAFPDASGVPRMPSRSVPASDGVSGQDFHS

TIYEVIQHIPAQQHDHPE
```

SEQUENCE ID: 7
PREDICTED: hypothetical protein [*Danio rerio*], Zebrafish
RED SEQUENCE CORRESPOND TO Predicted pre-peptide

```
1         10        20        30        40        50
|         |         |         |         |         |
MECVEVTMILLICSLFVIISGSDPEYIRLQPTQHGRKGESMNLRVETLFN

VKDVPFQGSWFKTRPKVTPLVTFQFSPSTTSSIPNLLVKNITMQELPDVS

LRFVNLDEDTKGEYELQVNIVFDENAPPVSVTKTVTVTVSVPVSTPVISK

TPESELVEDRDNVTLTCSALHGTEIRYKWLKDNMLVSPSDRHTFSEDNGT

LFINPVRKEDMGQYICEAHNQISSEQSQQTDLSVFYGPYNLAVNCDQALK

TEGVFTVNPGELAFFECNADSNPPNTFLWISKTGNGTEIVMTGPRLEVKT

YELPQGKEFLCRAFNNATKKQDETKFTLVVARLHRGKAKFLQEGSVMSPL

ALVTVTSVVIIVCMMFVLLRKSCHPKRVVKNFCRRTMTEQRGLHRSGHES

ATEDFGIYEFVSVGGKMESTQASCRSLTRLDSVRDLHTTIYDVIRHVPET

PTLSLLK
```

SEQUENCE ID: 8
PREDICTED: hypothetical protein [*Equus caballus*] (Horse)
RED SEQUENCE CORRESPOND TO Predicted pre-peptide

```
1         10        20        30        40        50
|         |         |         |         |         |
MGQDAFMDPFSNTVGVFQCKIYLLLLAGACSGLKVAVPSHTIHGIRGQAL

YLPVHYGFHTPASDIQIIWLFERPHTMPKYLLGSVNKSVVPDLEYQHKFT

MMPPNASLLINPLQFTDEGNYIVKVNIQGNGTLSASQKIQVTVDDPVTKP

VVQTQPLSGAVEYVGNMTLTCIVEGGTRLIYQWLKNGRPVHTTSTNSFSP

QNNTLHIAPVTKEDIGNYSCLVKNPVSKMESDITMPIIYYGPYGLRVNSD

KGLKVGEVFTVDIGEAILFDCSADSYPPNTYSWIRRTDNTTYVIKHGPHL

EVASEKVAQKTTDYVCCAYNNVTGRQDETHFTVIITSVGLEKLAQKGKSL

SPLASITGISLFLIISMCLLLLWKKYQPYKIIRQKLESRPKMEYRKARTF

SGHEDALDDFGIYEFVAFPDASGVPRMPRSVPASDSISGQDLHSTIYEVI

QHIPAQQQDHPE
```

SEQUENCE ID: 9
PREDICTED: hypothetical protein [*Gallus gallus*] (chicken)
RED SEQUENCE CORRESPOND TO Predicted pre-peptide

```
1         10        20        30        40        50
|         |         |         |         |         |
MLSWSPLASLFCDLNCHIYFLLVGICSALKLTVPSHTIHGVEGQPLQLTV

DYNFNTTACEIQIIWLFEKPQSNPKYLLGSVNQTVVPDLEYQHKFTLIPP

NASLMINLLRTSDEGNYIVKVNVRGNGTIAASERIHVAVDVPVTQPIVQT

EPSSGVVEYVGNITLKCTVGKGTRVVYQWMKNGKPLHAGPNYTFSSNNAT

LLIVPVAKEDIGNYSCLVSNPVSAMESERIVPTIYYGPYGLRVKSDKGLN

VGAVFTVNVGEAVLEDCSADSNPPNTYSWIQRADNTTHVIQYGPHLEVVS

DAVAQKTRDYVCRAFNNMTGKRDETHFTVIITSAGLEKLAQKGKSLSSLA

VITGISLFLILVMSFLFIWKRYKPLQVIQQKLRRRPEADYRKAQTFSGHE
```

-continued
```
SALDDFGIYEFVAIPDHASGSRVSSQPVHTSDSASGQDMLSTVYEVIQHI

PNQQQQDHQQ
```

```
                                                    SEQUENCE ID: 10
PREDICTED: hypothetical protein [Pan troglodytes] (monkey)
RED SEQUENCE CORRESPOND TO n-TERMINAL EXTENSION NOT CONTAINING A PRE-
PEPTIDE
1        10        20        30        40        50
|        |         |         |         |         |
MQPLQDDMTTLLEQAITENRTLAEEARGKIGSVTSLLISLANKPAAAGPS

YHREQGTACMGQDAFMEPFGDTLGVFQCKIYLLLFGACSGLKVTVPSHTV

HGVRGQALYLPVHYGFHTPASDIQIIWLFERPHTMPKYLLGSVNKSVVPD

LEYQHKFTMMPPNASLLINPLQFPDEGNYIVKVNIQGNGTLSASQKIQVT

VDDPVTKPVVQIHPPSGAVEYVGNMTLTCHVEGGTRLAYQWLKNGRPVHT

SSTYSFSPQNNTLHIAPVTKEDIGNYSCLVRNPVSETESDIIMPIIYYGP

YGLQVNSDKGLKVGEVFTVDLGEAILFDCSADSHPPNTYSWIRRTDNTTY

IIKHGPRLEVASEKVAQKTMDYVCCAYNNITGRQDETHFTVIITSVGLEK

LAQKGKSLSPLASITGISLFLIISMCLLFLWKKYQPYKVIKQKLEGRPET

EYRKAQTFSGHEDALDDFGIYEFVAFPDASGVSRIPSRSVPASDCVSGQD

LHSTVYEVIQHIPAQQQDHPE
```

```
                                                    SEQUENCE ID: 11
PREDICTED: hypothetical protein [Macaca mulatta] (Monkey)
RED SEQUENCE CORRESPOND TO n-TERMINAL EXTENSION NOT CONTAINING A PRE-
PEPTIDE
1        10        20        30        40        50
|        |         |         |         |         |
MQPLQDDMTTFLEQAITENRSLVKEARGKIGSVTSLLISLANKPAAAGPS

YHREQVTACMGQDAFMEPFGDTLGVFQCKLYLLLFGACSGLKVTVPSHTV

HGIRGQALYLPVHYGFHTPASDIQIIWLFERPHTMPKYLLGSVNKSVVPD

LEYQHKFTMMPPNASLLINPLQFSDEGNYIVKVNIQGNGTLSSSQKIQVT

VDDPVTKPVVQIHPPSGSVEYVGNMTLTCQVEGGTRLVYQWLKNGRPAHT

SSTYSFSPQNNTLHIAPVTKEDIGNYSCLVRNPVSEMESDIIMPIIYYGP

YGLQVNSDKGLKVGEVFTVDLGEAILFDCSADSYPPNTYSWIRRTDNTTY

IIKHGPRLEVASEKVAQKTTDYVCCAYNNITGRQDETHFTVIITSVGLEK

LAQKGKSLSPLASITGISLFLIISMCLLFLWKKYQPYKVIKQKLEGRPET

EYRKAQTFSGHEDALDDFGIYEFVAFPDASGVSRIPSRSVPVSDGISGQD

LHSTIYEVIQHIPAQQQDQPE
```

```
                                                    SEQUENCE ID: 12
unnamed protein product [Tetraodon nigroviridis] (pufferfish)
1        10        20        30        40        50
|        |         |         |         |         |
MGATGGTLLCLFSVLFILTETDCEFIHVPSLVHHGIEGKPLHLSVETHFL

LDEAEIQGTWSHTSPGGVRVTLVTFNKDSTITDMTYRERLVFEVPDVSLT

IKRLRAEDEGEYHLNLNMEFHNKTGLVTKEERIVRVTVDVPVSVPVVARS

PPHAVVEDQANVTWSCAVERGTRVTFQWLRDGAPLGHSDRFRFSEDNSTL

VISPVRKEDRGSYRCVASNAVSYGRHSKAAELTVYYGPYNLEVNSVQGLR

TGEVFTINPGELVFFECQADSNPPNSYAWIAKSHNATQVITEGPRLEVRS

YKLAQAEEYLCRAFNNVTKKQDEAQFTLVVASLGTGKEKHVQEDKSMSFL

TAIIVCSLFIIGCMLLFLIRRTCHPKRGHEDATEDFGIYEFVSIPGKMES

AQASCRSLARLESAPDMHTTIYDVIRHVPEMQSHSLLK
```

```
                                                    SEQUENCE ID: 13
Lachesin, Drosophila melanogaster (fruit fly)
1         10        20        30        40        50
|         |         |         |         |         |
MWRPSISNCVWSTLLLAIFVQQTLAQRTPTISYITQEQIKDIGGTVEFDC

SVQYAKEYNVLFLKTDSDPVFLSTGSTLVIKDSRFSLRYDPNSSTYKLQI

KDIQETDAGTYTCQVVISTVHKVSAEVKLSVRRPPVISDNSTQSVVASEG

SEVQMECYASGYPTPTITWRRENNAILPTDSATYVGNTLRIKSVKKEDRG

TYYCVADNGVSKGDRRNINVEVEFAPVITVPRPRLGQALQYDMDLECHIE

AYPPPAIVWTKDDIQLANNQHYSISHFATADEYTDSTLRVITVEKRQYGD

YVCKATNRFGEAEARVNLFETIIPVCPPACGQAYIAGAEDVSATSFALVG

ILAALLFAR

SEQUENCE ID: 14
Extracellular domain of Betacam [Mus Musculus] (Mouse)
1         10        20        30        40        50
|         |         |         |         |         |
GLKVTVPSYTVHGIRGQALYLPVHYGFHTPASDIQIIWLFERSHTMPKYL

LGSVNKSVVPDLEYQHKFTMMPPNASLLINPLQFTDEGNYIVKVNIQGNG

TLSASQKIQVTVDDPVMKPMVQFHPASGAVEYVGNITLTCQVEGGTRLVY

QWRKSGKPISINSSHSFSPQNNTLWIVPVTKEDIGNYTCLVSNPVSEMES

DIIMPTIYYGPYGLQVNSDKGLKVGEVFTVDLGEAVLFDCSADSYPPNTY

SWIQRSDNTTHVIKHGPHLEVASEKVAQKTADYVCCAYNNITGRRDETRF

TVIITSVGLEKLAQRGKSLS

SEQUENCE ID: 15
Extracellular domain of Betacam [Homo sapiens] (Human)
1         10        20        30        40        50
|         |         |         |         |         |
GLKVTVPSHTVHGVRGQALYLPVHYGFHTPASDIQIIWLFERPHTMPKYL

LGSVNKSVVPDLEYQHKFTMMPPNASLLINPLQFPDEGNYIVKVNIQGNG

TLSASQKIQVTVDDPVTKPVVQIHPPSGAVEYVGNMTLTCHVEGGTRLAY

QWLKNGRPVHTSSTYSFSPQNNTLHIAPVTKEDIGNYSCLVRNPVSEMES

DIIMPIIYYGPYGLQVNSDKGLKVGEVFTVDLGEAILFDCSADSHPPNTY

SWIRRTDNTTYIIKHGPRLEVASEKVAQKTMDYVCCAYNNITGRQDETH

FTVIITSVGLEKLAQKGKSLS

SEQUENCE ID: 16
Betacam-DsRed2 [Mouse] as in pIRES2-DsRED2
BLUE SEQUENCE: Betacam portion
BLACK SEQUENCE: linker peptide
RED SEQUENCE: DsRED2 sequence
1         10        20        30        40        50
|         |         |         |         |         |
MGQDAFMELLRSMVGTSLCKIHLLLIAGSCLGLKVTVPSYTVHGIRGQAL

YLPVHYGFHTPASDIQIIWLFERSHTMPKYLLGSVNKSVVPDLEYQHKFT

MMPPNASLLINPLQFTDEGNYIVKVNIQGNGTLSASQKIQVTVDDPVMKP

MVQFHPASGAVEYVGNITLTCQVEGGTRLVYQWRKSGKPISINSSHSFSP

QNNTLWIVPVTKEDIGNYTCLVSNPVSEMESDIIMPTIYYGPYGLQVNSD

KGLKVGEVFTVDLGEAVLFDCSADSYPPNTYSWIQRSDNTTHVIKHGPHL

EVASEKVAQKTADYVCCAYNNITGRRDETRFTVIITSVGLEKLAQRGKSL

SPLASITGISLFLIISMCLLFLWKKYQPYKAIRQKLEGRPESEYRKAQTF

SGHEDALSDPGIYEFVTFPDASGVSRMSSRSSPASDGVTGQDIHGTIYEV
```

IQHIPEQQQENTERILQSTVPRARDPPVATMASSEDVIKEFMRFKVRMEG

SVNGHEFEIEGEGEGRPYEGTQTAKLKVTKGGPLPFAWDILSPQFQYGSK

VYVKHPADIPDYKKLSFPEGFKWERVMNFEDGGVVTVTQDSSLQDGSFIY

KVKFIGVNFPSDGPVMQKKTMGWEASTERLYPRDGVLKGEIHKALKLKDG

GHYLVEFKSIYMAKKPVQLPGYYYVDSKLDITSHNEDYTIVEQYERAEGR

HHLFL*

SEQUENCE ID: 17

Betacam-nEGFP [Mouse] as in pIRES2-EGFP
BLUE SEQUENCE: Betacam portion
BLACK SEQUENCE: linker peptide
RED SEQUENCE: EGFP sequence

```
1         10        20        30        40        50
|         |         |         |         |         |
```
MGQDAFMELLRSMVGLSLCKIHLLLIAGSCLGLKVTVPSYTVHGIRGQAL

YLPVHYGFHTPASDIQIIWLFERSHTMPKYLLGSVNKSVVPDLEYQHKFT

MMPPNASLLINPLQFTDEGNYIVKVNIQGNGTLSASQKIQVTVDDPVMKP

MVQFHPASGAVEYVGNITLTCQVEGGTRLVYQWRKSGKPISINSSHSFSP

QNNTLWIVPVTKEDIGNYTCLVSNPVSEMESDIIMPTIYYGPYGLQVNSD

KGLKVGEVFTVDLGEAVLFDCSADSYPPNTYSWIQRSDNTTHVIKHGPHL

EVASEKVAQKTADYVCCAYNNITGRRDETRFTVITTSVGLEKLAQRGKSL

SPLASITGISLFLIISMCLLFLWKKYQPYKAIRQKLEGRPESEYRKAQTF

SGHEDALSDFGIYEFVTFPDASGVSRMSSRSSPASDGVTGQDIHGTIYEV

IQHIPEQQQENTERILQSTVPRARDPPVATMVSKGEELFTGVVPILVELD

GDVNGHKFSVSGEGEGDATYGKLTLKFICTTGKLPVPWPTLVTTLTYGVQ

CFSRYPDHMKQHDFFKSAMPEGYVQERTIFFKDDGNYKTRAEVKFEGDTL

VNRIELKGIDFKEDGNILGHKLEYNYNSHNVYIMADKQKNGIKVNFKIRH

NIEDGSVQLADHYQQNTPIGDGPVLLPDNHYLSTQSALSKDPNEKRDHMV

LLEFVTAAGITLGMDELYK*

SEQUENCE ID: 18 pFUSE-FcOnly, BLUE SEQUENCE IS Glutahione S-transferase, Red sequence
is IL2R signal peptide.
```
1         10        20        30        40        50
|         |         |         |         |         |
```
MTAMGLLSCIALSLALVTASPSAMGTSALTHTCPPCPAPGLLGGPSVPLP

PPLPLATLMISATPGVTCVVVAVSHGAPGVLPATTVAGVGVHAALTLPAG

GGTASTTAVVSVLTVLHGATLAGLGTLCLVSALALPAPIGLTISLALGGP

AGPGVTTLPPSAGGMTLAGVSLTCLVLGPTPSAIAVGTGSAGGPGAATLT

TPPVLASAGSPPLTSLLTVALSATGGGAVPSCSVMHGALHAHTTGLSLSL

S

SEQUENCE ID: 19 pFUSE-Fc-D1, BLUE SEQUENCE IS Glutahione S-transferase, Red sequence
is IL2R signal peptide, GREEN SEQUENCE IS BETACAM DERIVED.
```
1         10        20        30        40        50
|         |         |         |         |         |
```
MTAMGLLSCIALSLALVTASPSAMSLKVTVPSYTVHGIRGQALYLPVHYG

FHTPASDIQIIWLFERSHTMPKYLLGSVNKSVVPDLEYQHKFTMMPPNAS

LLINPLQFTDEGNYIVKVNIQGNGTLSASQKIQVTVDDPVALTPPCPAPG

LLGGPSVPLPPPLPLATLMISATPGVTCVVVAVSHGAPGVLPATTVAGVG

VHAALTLPAGGCGASTTAVVSVLTVLHGATLAGLGTLCLVSALALPAPIG

```
LTISLALGGPAGPGVTTLPPSAGGMTLAGVSLTCLVLGPTPSAIAVGTGS

AGGPGAATLTTPPVLASAGSPPLTSLLTVALSATGGGAVPSCSVMHGALH

AHTTGLSLSLSPGL
```

SEQUENCE ID: 20
pFUSE-Fc-D2 BLUE SEQUENCE IS Glutahione S-transferase, Red sequence is
IL2R signal peptide, GREEN SEQUENCE IS BETACAM DERIVED.

```
1         10        20        30        40        50
|         |         |         |         |         |
MTAMGLLSCIALSLALVTASPSAMSPVMKPMVQFHPASGAVEYVGNITLT

CQVEGGTRLVYQWRKSGKPISINSSHSFSPQNNTLWIVPVTKEDIGNYTC

LVSNPVSEMESDIIMPTIYYGALTPPCPAPGLLGGPSVPLPPPLPLATLM

ISATPGVTCVVVAVSHGAPGVLPATTVAGVGVHAALTLPAGGGTASTTAV

VSVLTVLHGATLAGLGTLCLVSALALPAPIGLTISLALGGPAGPGVTTLP

PSAGGMTLAGVSLTCLVLGPTPSAIAVGTGSAGGPGAATLTTPPVLASAG

SPPLTSLLTVALSATGGGAVPSCSVMHGALHAHTTGLSLSLSPGL
```

SEQUENCE ID: 21
pFUSE-Fc-D3 BLUE SEQUENCE IS Glutahione S-transferase, Red sequence is
IL2R signal peptide, GREEN SEQUENCE IS BETACAM DERIVED.

```
1         10        20        30        40        50
|         |         |         |         |         |
MTAMGLLSCIALSLALVTASSAMGTSYGPYGLQVNSDKGLKVGEVFTVDL

GEAVLFDCSADSYPPNTYSWIQRSDNTTHVIKHGPHLEVASEDVAQKTAD

YVCCAYNNITGRRDETRFTVIIALTHTCPPCPAPGLLGGPSVPLPPPLPL

ATLMISATPGVTCVVVAVSHGAPGVLPATTVAGVGVHAALTLPAGGGTAS

TTAVVSVLTVLHGATLAGLGTLCLVSALALPAPIGLTISLALGGPAGPGV

TTLPPSAGGMTLAGVSLTCLVLGPTPSAIAVGTGSAGGPGAATLTTPPVL

ASAGSPPLTSLLTVALSATGGGAVPSCSVMHGALHAHTTGLSLSLS
```

SEQUENCE ID: 22
pFUSE-Fc-D1/D2 BLUE SEQUENCE IS Glutahione S-transferase, Red sequence
is IL2R signal peptide, GREEN SEQUENCE IS BETACAM DERIVED.

```
1         10        20        30        40        50
|         |         |         |         |         |
MTAMGLLSCIALSLALVTASPSAMSLKVTVPSYTVHGIRGQALYLPVHYG

FHTPASDIQIIWLFERSHTMPKYLLGSVNKSVVPDLEYQHKFTMMPPNAS

LLINPLQFTDEGNYIVKVNIQGNGTLSASQKIQVTVDDPVMKPMVQFHPA

SGAVEYVGNITLTCQVEGGTRLVYQWRKSGKPISINSSHSFSPQNNTLWI

VPVTKEDIGNYTCLVSNPVSEMESDIIMPTIYALTHTCPPCPAPGLLGGP

SVPLPPPLPLATLMISATPGVTCVVVAVSHGAPGVLPATTVAGVGVHAAL

TLPAGGGTASTTAVVSVLTVLHGATLAGLGTLCLVSALALPAPIGLTISL

ALGGPAGPGVTTLPPSAGGMTLAGVSLTCLVLGPTPSAIAVGTGSAGGPG

AATLTTPPVLASAGSPPLTSLLTVALSATGGGAVPSCSVMHGALHAHTTG

LSLSLS
```

SEQUENCE ID: 23
pFUSE-Fc-D2/D3 BLUE SEQUENCE IS Glutahione S-transferase, Red sequence
is IL2R signal peptide, GREEN SEQUENCE IS BETACAM DERIVED.

```
1         10        20        30        40        50
|         |         |         |         |         |
MTAMGLLSCIALSLSLVTASSAMGTSPVMKPMVQFHPASGAVEYVGNITL

TCQVEGGTRLVYQWRKSGKPISINSSHSFSPQNNTLWIVPVTKEDIGNYT

CLVSNPVSEMESDIIMPTIYYGPYGLQVNSDKGLKVGEVFTVDLGEAVLF
```

```
DCSADSYPPNTYSWIQRSDNTTHVIKHGPHLEVASEKVAQKTADYVCCAY

NNITGRRDETRFTVIIALTHTCPPCPAPGLLGGPSVPLPPPLPLATLMIS

ATPGVTCVVVAVSHGAPGVLPATTVAGVGVHAALTLPAGGGTASTTAVVS

VLTVLHGATLAGLGTLCLVSALALPAPIGLTISLALGGPAGPGVTTLPPS

AGGMTLAGVSLTCLVLGPTPSAIAVGTGSAGGPGAATLTTPPVLASAGSP

PLTSLLTVALSATGGGAVPSCSVMHGALHAHTTGLSLSLS
```

SEQUENCE ID: 24
pFUSE-Fc-D1/D2/D3 BLUE SEQUENCE IS Glutahione S-transferase, Red
sequence is IL2R signal peptide, GREEN SEQUENCE IS BETACAM DERIVED.

```
1         10        20        30        40        50
|         |         |         |         |         |
MTAMGLLSCIALSLALVTASSAMG

ALTHTCPPCPAPGLLGGPSVPLPPPLPLATLMIS

ATPGVTCVVVAVSHGAPGVLPATTVAGVGVHAALTLPAGGGTASTTAVVS

VLTVLHGATLAGLGTLCLVSALALPAPIGLTISLALGGPAGPGVTTLPPS

AGGMTLADVSLTCLVLGPTPSAIAVGTGSAGGPGAATLTTPPVLASAGSP

PLTSLLTVALSATGGGAVPSCSVMHGALHAHTTGLSLSLS
```

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

---

What is claimed is:

1. A method of detecting beta cells in a mixture of pancreatic cells comprising detecting the presence of a polypeptide on the surface of the cells, wherein the polypeptide comprises SEQ ID NO: 14, SEQ ID NO: 15, an amino acid sequence that has at least 50% identity to SEQ ID NO: 14 or an amino acid sequence that has at least 50% identity to SEQ ID NO: 15, and detection of expression of the polypeptide on the surface of the cells indicates that the cells are pancreatic beta cells.

2. The method of claim 1 further comprising isolating the pancreatic beta cells from the mixture of cells.

3. The method of claim 2 wherein the pancreatic beta cells are isolated from a biological sample.

4. The method of claim 1 wherein the biological sample is pancreatic tissue.

5. The method of claim 4 wherein the pancreatic tissue is obtained from a cadaver.

6. The method of claim 1 wherein expression of the polypeptide is detected using an antibody that has binding affinity for the polypeptide.

7. An in vivo method of detecting pancreatic beta cells in an individual in need thereof, comprising administering to the individual a molecule labeled with a positron emission tomography (PET) tracer that detects the presence of a polypeptide on the surface of the pancreatic beta cells, wherein the polypeptide comprises SEQ ID NO: 14, SEQ ID NO: 15, an amino acid sequence that has at least 50% identity to SEQ ID NO: 14 or an amino acid sequence that has at least 50% identity to SEQ ID NO: 15, wherein upon binding of said molecule to the surface of the pancreatic beta cells and the emittance of a signal from said PET tracer, the pancreatic beta cells are detected with a PET scanner.

8. The method of claim 7 wherein the individual is being screened for a risk of developing diabetes.

9. The method of claim 7 wherein the individual has diabetes.

10. The method of claim 9 wherein the diabetes is Type I diabetes or Type II diabetes.

11. The method of claim 7 wherein the individual has had an islet cell transplantation.

12. A method of isolating pancreatic beta cells from a mixture of pancreatic cells comprising:
  a) contacting the mixture with a reagent that specifically binds to a polypeptide present on the surface of pancreatic beta cells, wherein the polypeptide comprises SEQ ID NO: 14, SEQ ID NO: 15, an amino acid sequence that has at least 50% identity to SEQ ID NO: 14 or an amino acid sequence that has at least 50% identity to SEQ ID NO: 15, thereby producing a combination;
  b) maintaining the combination under conditions in which the reagent binds to the polypeptide present on the surface of the pancreatic beta cells, thereby producing a complex of pancreatic beta cells bound to the reagent; and c) separating the complex from the combination, thereby isolating pancreatic beta cells from the mixture of pancreatic cells.

13. The method of claim 12 further comprising d) separating the pancreatic beta cells from the reagent.

14. The method of claim 12 wherein the mixture of pancreatic beta cells is pancreatic tissue.

15. The method of claim 14 wherein the pancreatic tissue is obtained from a cadaver.

16. The method of claim 12 wherein the reagent is an antibody that has binding affinity for the polypeptide.

* * * * *

SEQUENCE LISTING

```
<160> NUMBER OF SEQ ID NOS: 63

<210> SEQ ID NO 1
<211> LENGTH: 462
<212> TYPE: PRT
<213> ORGANISM: Unknown
<220> FEATURE:
<223> OTHER INFORMATION: hypothetical protein LOC253012 isoform 1 [Homo
      sapiens] (Human)

<400> SEQUENCE: 1

Met Gly Gln Asp Ala Phe Met Glu Pro Phe Gly Asp Thr Leu Gly Val
1               5                   10                  15

Phe Gln Cys Lys Ile Tyr Leu Leu Phe Gly Ala Cys Ser Gly Leu
            20                  25                  30

Lys Val Thr Val Pro Ser His Thr Val His Gly Val Arg Gly Gln Ala
        35                  40                  45

Leu Tyr Leu Pro Val His Tyr Gly Phe His Thr Pro Ala Ser Asp Ile
    50                  55                  60

Gln Ile Ile Trp Leu Phe Glu Arg Pro His Thr Met Pro Lys Tyr Leu
65                  70                  75                  80

Leu Gly Ser Val Asn Lys Ser Val Val Pro Asp Leu Glu Tyr Gln His
                85                  90                  95

Lys Phe Thr Met Met Pro Pro Asn Ala Ser Leu Leu Ile Asn Pro Leu
            100                 105                 110

Gln Phe Pro Asp Glu Gly Asn Tyr Ile Val Lys Val Asn Ile Gln Gly
        115                 120                 125

Asn Gly Thr Leu Ser Ala Ser Gln Lys Ile Gln Val Thr Val Asp Asp
    130                 135                 140

Pro Val Thr Lys Pro Val Val Gln Ile His Pro Pro Ser Gly Ala Val
```

```
            145                 150                 155                 160
        Glu Tyr Val Gly Asn Met Thr Leu Thr Cys His Val Glu Gly Thr
                        165                 170                 175
        Arg Leu Ala Tyr Gln Trp Leu Lys Asn Gly Arg Pro Val His Thr Ser
                        180                 185                 190
        Ser Thr Tyr Ser Phe Ser Pro Gln Asn Asn Thr Leu His Ile Ala Pro
                        195                 200                 205
        Val Thr Lys Glu Asp Ile Gly Asn Tyr Ser Cys Leu Val Arg Asn Pro
            210                 215                 220
        Val Ser Glu Met Glu Ser Asp Ile Ile Met Pro Ile Ile Tyr Tyr Gly
        225                 230                 235                 240
        Pro Tyr Gly Leu Gln Val Asn Ser Asp Lys Gly Leu Lys Val Gly Glu
                        245                 250                 255
        Val Phe Thr Val Asp Leu Gly Glu Ala Ile Leu Phe Asp Cys Ser Ala
                        260                 265                 270
        Asp Ser His Pro Pro Asn Thr Tyr Ser Trp Ile Arg Arg Thr Asp Asn
                        275                 280                 285
        Thr Thr Tyr Ile Ile Lys His Gly Pro Arg Leu Glu Val Ala Ser Glu
            290                 295                 300
        Lys Val Ala Gln Lys Thr Met Asp Tyr Val Cys Cys Ala Tyr Asn Asn
        305                 310                 315                 320
        Ile Thr Gly Arg Gln Asp Glu Thr His Phe Thr Val Ile Ile Thr Ser
                        325                 330                 335
        Val Gly Leu Glu Lys Leu Ala Gln Lys Gly Lys Ser Leu Ser Pro Leu
                        340                 345                 350
        Ala Ser Ile Thr Gly Ile Ser Leu Phe Leu Ile Ile Ser Met Cys Leu
                        355                 360                 365
        Leu Phe Leu Trp Lys Lys Tyr Gln Pro Tyr Lys Val Ile Lys Gln Lys
                        370                 375                 380
        Leu Glu Gly Arg Pro Glu Thr Glu Tyr Arg Lys Ala Gln Thr Phe Ser
        385                 390                 395                 400
        Gly His Glu Asp Ala Leu Asp Asp Phe Gly Ile Tyr Glu Phe Val Ala
                        405                 410                 415
        Phe Pro Asp Val Ser Gly Val Ser Arg Ile Pro Ser Arg Ser Val Pro
                        420                 425                 430
        Ala Ser Asp Cys Val Ser Gly Gln Asp Leu His Ser Thr Val Tyr Glu
                        435                 440                 445
        Val Ile Gln His Ile Pro Ala Gln Gln Gln Asp His Pro Glu
            450                 455                 460

<210> SEQ ID NO 2
<211> LENGTH: 450
<212> TYPE: PRT
<213> ORGANISM: Uknown
<220> FEATURE:
<223> OTHER INFORMATION: hypothetical protein LOC253012 isoform 2 [Homo
      sapiens] (human)

<400> SEQUENCE: 2

Met Trp Leu Lys Val Phe Thr Thr Phe Leu Ser Phe Ala Thr Gly Ala
        1                   5                   10                  15
        Cys Ser Gly Leu Lys Val Thr Val Pro Ser His Thr Val His Gly Val
                        20                  25                  30
        Arg Gly Gln Ala Leu Tyr Leu Pro Val His Tyr Gly Phe His Thr Pro
                        35                  40                  45
```

```
Ala Ser Asp Ile Gln Ile Ile Trp Leu Phe Glu Arg Pro His Thr Met
     50                  55                  60
Pro Lys Tyr Leu Leu Gly Ser Val Asn Lys Ser Val Val Pro Asp Leu
 65                  70                  75                  80
Glu Tyr Gln His Lys Phe Thr Met Met Pro Pro Asn Ala Ser Leu Leu
                 85                  90                  95
Ile Asn Pro Leu Gln Phe Pro Asp Glu Gly Asn Tyr Ile Val Lys Val
            100                 105                 110
Asn Ile Gln Gly Asn Gly Thr Leu Ser Ala Ser Gln Lys Ile Gln Val
                115                 120                 125
Thr Val Asp Asp Pro Val Thr Lys Pro Val Val Gln Ile His Pro Pro
130                 135                 140
Ser Gly Ala Val Glu Tyr Val Gly Asn Met Thr Leu Thr Cys His Val
145                 150                 155                 160
Glu Gly Gly Thr Arg Leu Ala Tyr Gln Trp Leu Lys Asn Gly Arg Pro
                165                 170                 175
Val His Thr Ser Ser Thr Tyr Ser Phe Ser Pro Gln Asn Asn Thr Leu
                180                 185                 190
His Ile Ala Pro Val Thr Lys Glu Asp Ile Gly Asn Tyr Ser Cys Leu
            195                 200                 205
Val Arg Asn Pro Val Ser Glu Met Glu Ser Asp Ile Ile Met Pro Ile
210                 215                 220
Ile Tyr Tyr Gly Pro Tyr Gly Leu Gln Val Asn Ser Asp Lys Gly Leu
225                 230                 235                 240
Lys Val Gly Glu Val Phe Thr Val Asp Leu Gly Glu Ala Ile Leu Phe
                245                 250                 255
Asp Cys Ser Ala Asp Ser His Pro Pro Asn Thr Tyr Ser Trp Ile Arg
            260                 265                 270
Arg Thr Asp Asn Thr Thr Tyr Ile Ile Lys His Gly Pro Arg Leu Glu
            275                 280                 285
Val Ala Ser Glu Lys Val Ala Gln Lys Thr Met Asp Tyr Val Cys Cys
290                 295                 300
Ala Tyr Asn Asn Ile Thr Gly Arg Gln Asp Glu Thr His Phe Thr Val
305                 310                 315                 320
Ile Ile Thr Ser Val Gly Leu Glu Lys Leu Ala Gln Lys Gly Lys Ser
                325                 330                 335
Leu Ser Pro Leu Ala Ser Ile Thr Gly Ile Ser Leu Phe Leu Ile Ile
            340                 345                 350
Ser Met Cys Leu Leu Phe Leu Trp Lys Lys Tyr Gln Pro Tyr Lys Val
            355                 360                 365
Ile Lys Gln Lys Leu Glu Gly Arg Pro Glu Thr Glu Tyr Arg Lys Ala
370                 375                 380
Gln Thr Phe Ser Gly His Glu Asp Ala Leu Asp Asp Phe Gly Ile Tyr
385                 390                 395                 400
Glu Phe Val Ala Phe Pro Asp Val Ser Gly Val Ser Arg Ile Pro Ser
                405                 410                 415
Arg Ser Val Pro Ala Ser Asp Cys Val Ser Gly Gln Asp Leu His Ser
            420                 425                 430
Thr Val Tyr Glu Val Ile Gln His Ile Pro Ala Gln Gln Gln Asp His
            435                 440                 445
Pro Glu
450
```

```
<210> SEQ ID NO 3
<211> LENGTH: 463
<212> TYPE: PRT
<213> ORGANISM: Unknown
<220> FEATURE:
<223> OTHER INFORMATION: hypothetical protein LOC101202 [Mus musculus]

<400> SEQUENCE: 3

Met Gly Gln Asp Ala Phe Met Glu Leu Leu Arg Ser Met Val Gly Leu
1               5                   10                  15

Ser Leu Cys Lys Ile His Leu Leu Ile Ala Gly Ser Cys Leu Gly
            20                  25                  30

Leu Lys Val Thr Val Pro Ser Tyr Thr Val His Gly Ile Arg Gly Gln
        35                  40                  45

Ala Leu Tyr Leu Pro Val His Tyr Gly Phe His Thr Pro Ala Ser Asp
    50                  55                  60

Ile Gln Ile Ile Trp Leu Phe Glu Arg Ser His Thr Met Pro Lys Tyr
65                  70                  75                  80

Leu Leu Gly Ser Val Asn Lys Ser Val Val Pro Asp Leu Glu Tyr Gln
                85                  90                  95

His Lys Phe Thr Met Met Pro Pro Asn Ala Ser Leu Leu Ile Asn Pro
            100                 105                 110

Leu Gln Phe Thr Asp Glu Gly Asn Tyr Ile Val Lys Val Asn Ile Gln
        115                 120                 125

Gly Asn Gly Thr Leu Ser Ala Ser Gln Lys Ile Gln Val Thr Val Asp
    130                 135                 140

Asp Pro Val Met Lys Pro Met Val Gln Phe His Pro Ala Ser Gly Ala
145                 150                 155                 160

Val Glu Tyr Val Gly Asn Ile Thr Leu Thr Cys Gln Val Glu Gly Gly
                165                 170                 175

Thr Arg Leu Val Tyr Gln Trp Arg Lys Ser Gly Lys Pro Ile Ser Ile
            180                 185                 190

Asn Ser Ser His Ser Phe Ser Pro Gln Asn Asn Thr Leu Trp Ile Val
        195                 200                 205

Pro Val Thr Lys Glu Asp Ile Gly Asn Tyr Thr Cys Leu Val Ser Asn
    210                 215                 220

Pro Val Ser Glu Met Glu Ser Asp Ile Ile Met Pro Thr Ile Tyr Tyr
225                 230                 235                 240

Gly Pro Tyr Gly Leu Gln Val Asn Ser Asp Lys Gly Leu Lys Val Gly
                245                 250                 255

Glu Val Phe Thr Val Asp Leu Gly Glu Ala Val Leu Phe Asp Cys Ser
            260                 265                 270

Ala Asp Ser Tyr Pro Pro Asn Thr Tyr Ser Trp Ile Gln Arg Ser Asp
        275                 280                 285

Asn Thr Thr His Val Ile Lys His Gly Pro His Leu Glu Val Ala Ser
    290                 295                 300

Glu Lys Val Ala Gln Lys Thr Ala Asp Tyr Val Cys Cys Ala Tyr Asn
305                 310                 315                 320

Asn Ile Thr Gly Arg Arg Asp Glu Thr Arg Phe Thr Val Ile Ile Thr
                325                 330                 335

Ser Val Gly Leu Glu Lys Leu Ala Gln Arg Gly Lys Ser Leu Ser Pro
            340                 345                 350

Leu Ala Ser Ile Thr Gly Ile Ser Leu Phe Leu Ile Ile Ser Met Cys
        355                 360                 365

Leu Leu Phe Leu Trp Lys Lys Tyr Gln Pro Tyr Lys Ala Ile Arg Gln
```

```
                   370                 375                 380
Lys Leu Glu Gly Arg Pro Glu Ser Gly Tyr Arg Lys Ala Gln Thr Phe
385                 390                 395                 400

Ser Gly His Glu Asp Ala Leu Ser Asp Phe Gly Ile Tyr Glu Phe Val
                405                 410                 415

Thr Phe Pro Asp Ala Ser Gly Val Ser Arg Met Ser Arg Ser Ser
                420                 425                 430

Pro Ala Ser Asp Gly Val Thr Gly Gln Asp Ile His Gly Thr Ile Tyr
            435                 440                 445

Glu Val Ile Gln His Ile Pro Glu Gln Gln Gln Glu Asn Thr Glu
    450                 455                 460
```

<210> SEQ ID NO 4
<211> LENGTH: 463
<212> TYPE: PRT
<213> ORGANISM: Unknown
<220> FEATURE:
<223> OTHER INFORMATION: hypothetical protein LOC296846 [Rattus norvegicus] (rat)

<400> SEQUENCE: 4

```
Met Gly Gln Asp Ala Phe Met Glu Leu Phe Ser Ser Met Ala Gly Val
1               5                   10                  15

Ser Leu Cys Lys Ile His Leu Leu Ile Ala Gly Ser Cys Leu Gly
            20                  25                  30

Leu Lys Val Thr Val Pro Ser His Thr Val His Gly Ile Arg Gly Gln
            35                  40                  45

Ala Leu Tyr Leu Pro Val His Tyr Gly Phe His Thr Pro Ala Ser Asp
    50                  55                  60

Ile Gln Ile Ile Trp Leu Phe Glu Arg Ser His Thr Thr Pro Lys Tyr
65                  70                  75                  80

Leu Leu Gly Ser Val Asn Lys Ser Val Val Pro Asp Leu Glu Tyr Gln
                85                  90                  95

His Lys Phe Thr Met Met Pro Pro Asn Ala Ser Leu Leu Ile Asn Pro
            100                 105                 110

Leu Gln Phe Thr Asp Glu Gly Asn Tyr Ile Val Lys Val Asn Ile Gln
        115                 120                 125

Gly Asn Gly Thr Leu Ser Ala Ser Gln Lys Ile Gln Val Thr Val Asp
130                 135                 140

Asp Pro Val Met Lys Pro Met Val Gln Phe His Pro Ala Ser Gly Ala
145                 150                 155                 160

Val Glu Tyr Val Gly Asn Ile Thr Leu Thr Cys Arg Val Glu Gly Gly
                165                 170                 175

Thr Arg Leu Val Tyr Gln Trp Arg Lys Asn Gly Lys Pro Ile Asn Ile
            180                 185                 190

Asn Ser Ser His Ser Phe Ser Pro Gln Asn His Thr Leu Arg Ile Val
        195                 200                 205

Pro Ala Thr Lys Glu Asp Ile Gly Asn Tyr Thr Cys Leu Val Ser Asn
    210                 215                 220

Pro Val Ser Glu Met Glu Ser Asp Ile Ile Pro Thr Ile Tyr Tyr
225                 230                 235                 240

Gly Pro Tyr Gly Leu Gln Val Asn Ser Asp Lys Gly Leu Lys Val Gly
                245                 250                 255

Glu Val Phe Thr Val Asp Leu Gly Glu Ala Val Leu Phe Asp Cys Ser
            260                 265                 270
```

Ala Asp Ser Tyr Pro Pro Asn Thr Tyr Ser Trp Ile Arg Arg Ser Ala
            275                 280                 285

Asn Thr Thr Arg Val Ile Lys His Gly Pro Arg Leu Glu Val Ala Ser
        290                 295                 300

Asp Lys Val Ala Gln Lys Thr Ala Asp Tyr Val Cys Cys Ala Tyr Asn
305                 310                 315                 320

Asn Ile Thr Gly Arg Arg Asp Glu Thr His Phe Thr Val Ile Ile Thr
                325                 330                 335

Ser Val Gly Leu Glu Lys Leu Ala Gln Arg Gly Lys Ser Leu Ser Pro
            340                 345                 350

Leu Ala Ser Ile Thr Gly Ile Ser Leu Phe Phe Ile Ile Ser Met Cys
        355                 360                 365

Leu Leu Phe Leu Trp Lys Lys Phe Gln Pro Tyr Lys Ala Ile Arg Gln
    370                 375                 380

Lys Leu Glu Gly Arg Pro Glu Ser Glu Tyr Arg Lys Ala Gln Ser Phe
385                 390                 395                 400

Ser Gly His Glu Asp Ala Leu Gly Asp Phe Gly Ile Tyr Glu Phe Val
                405                 410                 415

Ala Phe Pro Asp Ala Ser Ala Val Pro Arg Met Ser Ser Arg Ser Ala
            420                 425                 430

Pro Ala Ser Asp Gly Val Thr Gly Gln Asp Phe Gln Gly Thr Ile Tyr
        435                 440                 445

Glu Val Ile Gln His Ile Pro Ala Gln Gln Gln Asp Asp Thr Glu
    450                 455                 460

<210> SEQ ID NO 5
<211> LENGTH: 491
<212> TYPE: PRT
<213> ORGANISM: Unknown
<220> FEATURE:
<223> OTHER INFORMATION: hypothetical protein LOC513430 [Bos taurus]
      (Cow)

<400> SEQUENCE: 5

Met Trp Leu Arg Val Phe Thr Ala Phe Leu Ser Phe Thr Ala Gly Ala
1               5                   10                  15

Cys Ser Gly Leu Lys Val Ala Val Pro Ser His Thr Val His Gly Ile
            20                  25                  30

Arg Gly Gln Ala Leu Tyr Leu Pro Val His Tyr Gly Phe His Thr Pro
        35                  40                  45

Ala Ser Asp Ile Gln Val Ile Trp Leu Phe Glu Arg Pro His Thr Met
    50                  55                  60

Pro Lys Tyr Leu Leu Gly Ser Val Asn Lys Ser Val Val Pro Asp Leu
65                  70                  75                  80

Glu Tyr Gln His Lys Phe Thr Met Met Pro Pro Asn Ala Ser Leu Leu
                85                  90                  95

Ile Asn Pro Leu Gln Phe Thr Asp Glu Gly Asn Tyr Ile Val Lys Val
            100                 105                 110

Asn Ile Gln Gly Asn Gly Thr Leu Ser Ala Ser Gln Lys Ile Gln Val
        115                 120                 125

Thr Val Asp Asp Pro Val Thr Lys Pro Val Val Gln Ile Gln Pro Ser
    130                 135                 140

Ser Gly Ala Val Glu Tyr Val Gly Asn Met Thr Leu Thr Cys Leu Val
145                 150                 155                 160

Glu Gly Gly Ser Arg Arg Val Tyr Gln Trp Leu Lys Asn Gly Arg Pro
                165                 170                 175

Val His Thr Ser Ser Thr Asn Ser Phe Ser Leu Gln Asn Ser Ser Leu
            180                 185                 190

His Ile Ala Pro Val Thr Lys Glu Asp Ile Gly Asn Tyr Ser Cys Leu
            195                 200                 205

Val Lys Asn Pro Val Ser Arg Met Glu Ser Asp Ile Met Pro Thr
210                 215                 220

Ile Tyr Tyr Gly Pro Tyr Gly Leu Arg Val Asn Ser Asp Arg Gly Leu
225                 230                 235                 240

Lys Val Gly Glu Val Phe Thr Val Asp Ile Gly Glu Ala Ile Leu Phe
            245                 250                 255

Asp Cys Ser Ala Asp Ser Tyr Pro Pro Asn Thr Tyr Ser Trp Ile Gln
            260                 265                 270

Arg Thr Asn Asn Ala Thr Tyr Val Ile Lys His Gly Pro Arg Leu Glu
            275                 280                 285

Val Ala Ser Glu Lys Ile Ala Gln Lys Thr Thr Asp Tyr Met Cys Cys
            290                 295                 300

Ala Tyr Asn Asn Ile Thr Gly Arg Arg Asp Glu Thr His Phe Thr Val
305                 310                 315                 320

Ile Ile Thr Ser Val Gly Ile Glu Lys Leu Ala Gln Lys Gly Lys Ser
            325                 330                 335

Leu Ser Pro Leu Ala Ser Ile Thr Gly Ile Ser Leu Phe Leu Ile Ile
            340                 345                 350

Ser Met Cys Leu Leu Phe Leu Trp Lys Lys Phe Gln Pro Tyr Lys Val
            355                 360                 365

Ile Lys Gln Lys Leu Glu Gly Arg Pro Glu Thr Glu Tyr Arg Lys Ala
370                 375                 380

Arg Thr Phe Ser Gly His Glu Asp Ala Leu Asp Asp Phe Gly Ile Tyr
385                 390                 395                 400

Glu Phe Val Ala Phe Pro Asp Ala Ser Gly Val Ala Arg Met Pro Ala
            405                 410                 415

Arg Ser Val Pro Ala Cys Asp Gly Val Pro Gly Gln Asp Leu His Ser
            420                 425                 430

Thr Ile Tyr Glu Val Ile His His Ile Pro Ala Gln Gln Gln Asp His
            435                 440                 445

Pro Glu Ser Ser Ser Gln Asp Gly Glu Glu Asp Ala Cys Leu Asp Arg
450                 455                 460

His Asp Glu Ala Gly Leu Gln Glu Leu Gly His Cys Lys Glu Gln Asp
465                 470                 475                 480

Lys Gly Lys His Ser Arg Ala Lys Gln Cys Ile
            485                 490

<210> SEQ ID NO 6
<211> LENGTH: 468
<212> TYPE: PRT
<213> ORGANISM: Unknown
<220> FEATURE:
<223> OTHER INFORMATION: similar to CG12369-PA, isoform A [Canis
      familiaris] (Dog)

<400> SEQUENCE: 6

Met Ala Ser Cys Ala Asn Ile Leu Asn Pro Glu Ile Ala Leu Ala Gly
1               5                   10                  15

Cys Glu Met Trp Leu Arg Val Ile Met Thr Phe Leu Ser Phe Ile Ala
            20                  25                  30

Gly Ala Cys Ser Gly Leu Lys Val Ala Val Pro Ser His Thr Val His

```
                35                  40                  45
Gly Ile Arg Gly Gln Ala Leu Tyr Leu Pro Val His Tyr Gly Phe His
         50                  55                  60
Thr Pro Ala Ser Asp Ile Gln Ile Ile Trp Leu Phe Glu Arg Thr His
65                  70                  75                  80
Thr Met Pro Lys Tyr Leu Leu Ser Ser Val Asn Lys Ser Val Val Pro
                85                  90                  95
Asp Leu Glu Tyr Gln His Lys Phe Thr Met Met Pro Pro Asn Ala Ser
            100                 105                 110
Leu Leu Ile Asn Pro Leu Gln Phe Thr Asp Glu Gly Asn Tyr Ile Val
            115                 120                 125
Lys Val Asn Ile Gln Gly Asn Gly Thr Leu Ser Ala Ser Gln Lys Ile
            130                 135                 140
Gln Val Thr Val Asp Asp Pro Val Thr Lys Pro Val Val Gln Thr Gln
145                 150                 155                 160
Pro Ser Ser Gly Ala Val Glu Tyr Val Gly Asn Met Thr Leu Thr Cys
                165                 170                 175
Leu Val Glu Gly Gly Thr Arg Leu Val Tyr Gln Trp Leu Lys Asn Glu
            180                 185                 190
Arg Pro Val His Ser Ser Ser Thr Ser Phe Ser Leu Gln Asn Asn
            195                 200                 205
Thr Leu His Ile Ala Pro Val Thr Lys Glu Asp Ile Gly Asn Tyr Ser
            210                 215                 220
Cys Leu Val Lys Asn Pro Val Ser Glu Met Glu Ser Asp Ile Ile Met
225                 230                 235                 240
Pro Thr Ile Tyr Tyr Gly Pro Tyr Gly Leu Arg Val Asn Ser Asp Lys
                245                 250                 255
Gly Leu Lys Val Gly Glu Val Phe Thr Val Asp Ile Gly Glu Ala Ile
            260                 265                 270
Leu Phe Tyr Cys Ser Ala Asp Ser Tyr Pro Pro Asn Thr Tyr Ser Trp
            275                 280                 285
Ile Gln Arg Thr Asp Asn Thr Thr Tyr Val Ile Lys His Gly Pro His
            290                 295                 300
Leu Glu Val Ala Ser Glu Lys Val Ala Gln Lys Thr Thr Asp Tyr Val
305                 310                 315                 320
Cys Cys Ala Tyr Asn Asn Val Thr Gly Arg Arg Asp Glu Ala His Phe
                325                 330                 335
Thr Val Ile Ile Thr Ser Val Gly Leu Glu Lys Leu Ala Gln Lys Gly
            340                 345                 350
Lys Ser Leu Ser Pro Leu Ala Ser Ile Thr Gly Val Ser Leu Phe Leu
            355                 360                 365
Ile Ile Ser Met Cys Leu Leu Phe Leu Trp Lys Lys Tyr Gln Pro Tyr
            370                 375                 380
Lys Val Ile Lys Gln Lys Leu Glu Gly Arg Pro Glu Thr Glu Tyr Arg
385                 390                 395                 400
Lys Ala Gln Thr Leu Ser Gly His Glu Asp Ala Leu Asp Asp Phe Gly
                405                 410                 415
Ile Tyr Glu Phe Val Ala Phe Pro Asp Ala Ser Gly Val Pro Arg Met
            420                 425                 430
Pro Ser Arg Ser Val Pro Ala Ser Asp Gly Val Ser Gly Gln Asp Phe
            435                 440                 445
His Ser Thr Ile Tyr Glu Val Ile Gln His Ile Pro Ala Gln Gln His
            450                 455                 460
```

Asp His Pro Glu
465

<210> SEQ ID NO 7
<211> LENGTH: 457
<212> TYPE: PRT
<213> ORGANISM: Unknown
<220> FEATURE:
<223> OTHER INFORMATION: hypothetical protein [Danio rerio], Zebrafish

<400> SEQUENCE: 7

Met Glu Cys Val Glu Val Thr Met Ile Leu Leu Ile Cys Ser Leu Phe
1               5                   10                  15

Val Ile Ile Ser Gly Ser Asp Pro Glu Tyr Ile Arg Leu Gln Pro Thr
            20                  25                  30

Gln His Gly Arg Lys Gly Glu Ser Met Asn Leu Arg Val Glu Thr Leu
        35                  40                  45

Phe Asn Val Lys Asp Val Pro Phe Gln Gly Ser Trp Phe Lys Thr Arg
50                  55                  60

Pro Lys Val Thr Pro Leu Val Thr Phe Gln Phe Ser Pro Ser Thr Thr
65                  70                  75                  80

Ser Ser Ile Pro Asn Leu Leu Val Lys Asn Ile Thr Met Gln Glu Leu
                85                  90                  95

Pro Asp Val Ser Leu Arg Phe Val Asn Leu Asp Glu Asp Thr Lys Gly
            100                 105                 110

Glu Tyr Glu Leu Gln Val Asn Ile Val Phe Asp Glu Asn Ala Pro Pro
        115                 120                 125

Val Ser Val Thr Lys Thr Val Thr Val Thr Val Ser Val Pro Val Ser
130                 135                 140

Thr Pro Val Ile Ser Lys Thr Pro Glu Ser Gly Leu Val Glu Asp Arg
145                 150                 155                 160

Asp Asn Val Thr Leu Thr Cys Ser Ala Leu His Gly Thr Glu Ile Arg
                165                 170                 175

Tyr Lys Trp Leu Lys Asp Asn Met Leu Val Ser Pro Ser Asp Arg His
            180                 185                 190

Thr Phe Ser Glu Asp Asn Gly Thr Leu Phe Ile Asn Pro Val Arg Lys
        195                 200                 205

Glu Asp Met Gly Gln Tyr Ile Cys Glu Ala His Asn Gln Ile Ser Ser
210                 215                 220

Glu Gln Ser Gln Gln Thr Asp Leu Ser Val Phe Tyr Gly Pro Tyr Asn
225                 230                 235                 240

Leu Ala Val Asn Cys Asp Gln Ala Leu Lys Thr Gly Val Phe Thr
                245                 250                 255

Val Asn Pro Gly Glu Leu Ala Phe Phe Glu Cys Asn Ala Asp Ser Asn
            260                 265                 270

Pro Pro Asn Thr Phe Leu Trp Ile Ser Lys Thr Gly Asn Gly Thr Glu
        275                 280                 285

Ile Val Met Thr Gly Pro Arg Leu Glu Val Lys Thr Tyr Glu Leu Pro
290                 295                 300

Gln Gly Lys Glu Phe Leu Cys Arg Ala Phe Asn Asn Ala Thr Lys Lys
305                 310                 315                 320

Gln Asp Glu Thr Lys Phe Thr Leu Val Val Ala Arg Leu His Arg Gly
                325                 330                 335

Lys Ala Lys Phe Leu Gln Glu Gly Ser Val Met Ser Pro Leu Ala Leu
            340                 345                 350

-continued

Val Thr Val Thr Ser Val Val Ile Val Cys Met Met Phe Val Leu
            355                 360                 365

Leu Arg Lys Ser Cys His Pro Lys Arg Val Val Lys Asn Phe Cys Arg
370                 375                 380

Arg Thr Met Thr Glu Gln Arg Gly Leu His Arg Ser Gly His Glu Ser
385                 390                 395                 400

Ala Thr Glu Asp Phe Gly Ile Tyr Glu Phe Val Ser Val Gly Gly Lys
            405                 410                 415

Met Glu Ser Thr Gln Ala Ser Cys Arg Ser Leu Thr Arg Leu Asp Ser
            420                 425                 430

Val Arg Asp Leu His Thr Thr Ile Tyr Asp Val Ile Arg His Val Pro
            435                 440                 445

Glu Thr Pro Thr Leu Ser Leu Leu Lys
            450                 455

<210> SEQ ID NO 8
<211> LENGTH: 462
<212> TYPE: PRT
<213> ORGANISM: Unknown
<220> FEATURE:
<223> OTHER INFORMATION: hypothetical protein [Equus caballus] (Horse)

<400> SEQUENCE: 8

Met Gly Gln Asp Ala Phe Met Asp Pro Phe Ser Asn Thr Val Gly Val
1               5                   10                  15

Phe Gln Cys Lys Ile Tyr Leu Leu Leu Ala Gly Ala Cys Ser Gly
                20                  25                  30

Leu Lys Val Ala Val Pro Ser His Thr Ile His Gly Ile Arg Gly Gln
            35                  40                  45

Ala Leu Tyr Leu Pro Val His Tyr Gly Phe His Thr Pro Ala Ser Asp
        50                  55                  60

Ile Gln Ile Ile Trp Leu Phe Glu Arg Pro His Thr Met Pro Lys Tyr
65                  70                  75                  80

Leu Leu Gly Ser Val Asn Lys Ser Val Val Pro Asp Leu Glu Tyr Gln
                85                  90                  95

His Lys Phe Thr Met Met Pro Pro Asn Ala Ser Leu Leu Ile Asn Pro
            100                 105                 110

Leu Gln Phe Thr Asp Glu Gly Asn Tyr Ile Val Lys Val Asn Ile Gln
        115                 120                 125

Gly Asn Gly Thr Leu Ser Ala Ser Gln Lys Ile Gln Val Thr Val Asp
130                 135                 140

Asp Pro Val Thr Lys Pro Val Gln Thr Gln Pro Leu Ser Gly Ala
145                 150                 155                 160

Val Glu Tyr Val Gly Asn Met Thr Leu Thr Cys Ile Val Glu Gly Gly
                165                 170                 175

Thr Arg Leu Ile Tyr Gln Trp Leu Lys Asn Gly Arg Pro Val His Thr
            180                 185                 190

Thr Ser Thr Asn Ser Phe Ser Pro Gln Asn Asn Thr Leu His Ile Ala
        195                 200                 205

Pro Val Thr Lys Glu Asp Ile Gly Asn Tyr Ser Cys Leu Val Lys Asn
210                 215                 220

Pro Val Ser Lys Met Glu Ser Asp Ile Thr Met Pro Ile Ile Tyr Tyr
225                 230                 235                 240

Gly Pro Tyr Gly Leu Arg Val Asn Ser Asp Lys Gly Leu Lys Val Gly
                245                 250                 255

Glu Val Phe Thr Val Asp Ile Gly Glu Ala Ile Leu Phe Asp Cys Ser
                260                 265                 270

Ala Asp Ser Tyr Pro Pro Asn Thr Tyr Ser Trp Ile Arg Arg Thr Asp
            275                 280                 285

Asn Thr Thr Tyr Val Ile Lys His Gly Pro His Leu Glu Val Ala Ser
        290                 295                 300

Glu Lys Val Ala Gln Lys Thr Thr Asp Tyr Val Cys Cys Ala Tyr Asn
305                 310                 315                 320

Asn Val Thr Gly Arg Gln Asp Glu Thr His Phe Thr Val Ile Ile Thr
                325                 330                 335

Ser Val Gly Leu Glu Lys Leu Ala Gln Lys Gly Lys Ser Leu Ser Pro
            340                 345                 350

Leu Ala Ser Ile Thr Gly Ile Ser Leu Phe Leu Ile Ile Ser Met Cys
        355                 360                 365

Leu Leu Leu Leu Trp Lys Lys Tyr Gln Pro Tyr Lys Ile Ile Arg Gln
370                 375                 380

Lys Leu Glu Ser Arg Pro Lys Met Glu Tyr Arg Lys Ala Arg Thr Phe
385                 390                 395                 400

Ser Gly His Glu Asp Ala Leu Asp Asp Phe Gly Ile Tyr Glu Phe Val
                405                 410                 415

Ala Phe Pro Asp Ala Ser Gly Val Pro Arg Met Pro Arg Ser Val Pro
            420                 425                 430

Ala Ser Asp Ser Ile Ser Gly Gln Asp Leu His Ser Thr Ile Tyr Glu
        435                 440                 445

Val Ile Gln His Ile Pro Ala Gln Gln Gln Asp His Pro Glu
    450                 455                 460

<210> SEQ ID NO 9
<211> LENGTH: 460
<212> TYPE: PRT
<213> ORGANISM: Unknown
<220> FEATURE:
<223> OTHER INFORMATION: hypothetical protein [Gallus gallus] (chicken)

<400> SEQUENCE: 9

Met Leu Ser Trp Ser Pro Leu Ala Ser Leu Phe Cys Asp Leu Asn Cys
1               5                   10                  15

His Ile Tyr Phe Leu Leu Val Gly Ile Cys Ser Ala Leu Lys Leu Thr
            20                  25                  30

Val Pro Ser His Thr Ile His Gly Val Glu Gly Gln Pro Leu Gln Leu
        35                  40                  45

Thr Val Asp Tyr Asn Phe Asn Thr Thr Ala Cys Glu Ile Gln Ile Ile
    50                  55                  60

Trp Leu Phe Glu Lys Pro Gln Ser Asn Pro Lys Tyr Leu Leu Gly Ser
65                  70                  75                  80

Val Asn Gln Thr Val Pro Asp Leu Glu Tyr Gln His Lys Phe Thr
                85                  90                  95

Leu Ile Pro Pro Asn Ala Ser Leu Met Ile Asn Leu Leu Arg Thr Ser
            100                 105                 110

Asp Glu Gly Asn Tyr Ile Val Lys Val Asn Val Arg Gly Asn Gly Thr
        115                 120                 125

Ile Ala Ala Ser Glu Arg Ile His Val Ala Val Asp Val Pro Val Thr
    130                 135                 140

Gln Pro Ile Val Gln Thr Glu Pro Ser Ser Gly Val Val Glu Tyr Val
145                 150                 155                 160

```
Gly Asn Ile Thr Leu Lys Cys Thr Val Gly Lys Gly Thr Arg Val Val
                165                 170                 175

Tyr Gln Trp Met Lys Asn Gly Lys Pro Leu His Ala Gly Pro Asn Tyr
            180                 185                 190

Thr Phe Ser Ser Asn Asn Ala Thr Leu Leu Ile Val Pro Val Ala Lys
        195                 200                 205

Glu Asp Ile Gly Asn Tyr Ser Cys Leu Val Ser Asn Pro Val Ser Ala
    210                 215                 220

Met Glu Ser Glu Arg Ile Val Pro Thr Ile Tyr Tyr Gly Pro Tyr Gly
225                 230                 235                 240

Leu Arg Val Lys Ser Asp Lys Gly Leu Asn Val Gly Ala Val Phe Thr
                245                 250                 255

Val Asn Val Gly Glu Ala Val Leu Phe Asp Cys Ser Ala Asp Ser Asn
            260                 265                 270

Pro Pro Asn Thr Tyr Ser Trp Ile Gln Arg Ala Asp Asn Thr Thr His
        275                 280                 285

Val Ile Gln Tyr Gly Pro His Leu Glu Val Val Ser Asp Ala Val Ala
    290                 295                 300

Gln Lys Thr Arg Asp Tyr Val Cys Arg Ala Phe Asn Asn Met Thr Gly
305                 310                 315                 320

Lys Arg Asp Glu Thr His Phe Thr Val Ile Ile Thr Ser Ala Gly Leu
                325                 330                 335

Glu Lys Leu Ala Gln Lys Gly Lys Ser Leu Ser Leu Ala Val Ile
            340                 345                 350

Thr Gly Ile Ser Leu Phe Leu Ile Leu Val Met Ser Phe Leu Phe Ile
        355                 360                 365

Trp Lys Arg Tyr Lys Pro Leu Gln Val Ile Gln Gln Lys Leu Arg Arg
    370                 375                 380

Arg Pro Glu Ala Asp Tyr Arg Lys Ala Gln Thr Phe Ser Gly His Glu
385                 390                 395                 400

Ser Ala Leu Asp Asp Phe Gly Ile Tyr Glu Phe Val Ala Ile Pro Asp
                405                 410                 415

His Ala Ser Gly Ser Arg Val Ser Ser Gln Pro Val His Thr Ser Asp
            420                 425                 430

Ser Ala Ser Gly Gln Asp Met Leu Ser Thr Val Tyr Glu Val Ile Gln
        435                 440                 445

His Ile Pro Asn Gln Gln Gln Gln Asp His Gln Gln
    450                 455                 460

<210> SEQ ID NO 10
<211> LENGTH: 521
<212> TYPE: PRT
<213> ORGANISM: Unknown
<220> FEATURE:
<223> OTHER INFORMATION: hypothetical protein [Pan troglodytes] (monkey)

<400> SEQUENCE: 10

Met Gln Pro Leu Gln Asp Asp Met Thr Thr Leu Leu Glu Gln Ala Ile
1               5                   10                  15

Thr Glu Asn Arg Thr Leu Ala Glu Glu Ala Arg Gly Lys Ile Gly Ser
            20                  25                  30

Val Thr Ser Leu Leu Ile Ser Leu Ala Asn Lys Pro Ala Ala Ala Gly
        35                  40                  45

Pro Ser Tyr His Arg Glu Gln Gly Thr Ala Cys Met Gly Gln Asp Ala
    50                  55                  60
```

-continued

```
Phe Met Glu Pro Phe Gly Asp Thr Leu Gly Val Phe Gln Cys Lys Ile
 65                  70                  75                  80

Tyr Leu Leu Leu Phe Gly Ala Cys Ser Gly Leu Lys Val Thr Val Pro
                 85                  90                  95

Ser His Thr Val His Gly Val Arg Gly Gln Ala Leu Tyr Leu Pro Val
            100                 105                 110

His Tyr Gly Phe His Thr Pro Ala Ser Asp Ile Gln Ile Ile Trp Leu
            115                 120                 125

Phe Glu Arg Pro His Thr Met Pro Lys Tyr Leu Leu Gly Ser Val Asn
130                 135                 140

Lys Ser Val Val Pro Asp Leu Glu Tyr Gln His Lys Phe Thr Met Met
145                 150                 155                 160

Pro Pro Asn Ala Ser Leu Leu Ile Asn Pro Leu Gln Phe Pro Asp Glu
                165                 170                 175

Gly Asn Tyr Ile Val Lys Val Asn Ile Gln Gly Asn Gly Thr Leu Ser
            180                 185                 190

Ala Ser Gln Lys Ile Gln Val Thr Val Asp Asp Pro Val Thr Lys Pro
            195                 200                 205

Val Val Gln Ile His Pro Pro Ser Gly Ala Val Glu Tyr Val Gly Asn
210                 215                 220

Met Thr Leu Thr Cys His Val Glu Gly Gly Thr Arg Leu Ala Tyr Gln
225                 230                 235                 240

Trp Leu Lys Asn Gly Arg Pro Val His Thr Ser Ser Thr Tyr Ser Phe
                245                 250                 255

Ser Pro Gln Asn Asn Thr Leu His Ile Ala Pro Val Thr Lys Glu Asp
            260                 265                 270

Ile Gly Asn Tyr Ser Cys Leu Val Arg Asn Pro Val Ser Glu Thr Glu
            275                 280                 285

Ser Asp Ile Ile Met Pro Ile Ile Tyr Tyr Gly Pro Tyr Gly Leu Gln
290                 295                 300

Val Asn Ser Asp Lys Gly Leu Lys Val Gly Glu Val Phe Thr Val Asp
305                 310                 315                 320

Leu Gly Glu Ala Ile Leu Phe Asp Cys Ser Ala Asp Ser His Pro Pro
                325                 330                 335

Asn Thr Tyr Ser Trp Ile Arg Arg Thr Asp Asn Thr Thr Tyr Ile Ile
            340                 345                 350

Lys His Gly Pro Arg Leu Glu Val Ala Ser Glu Lys Val Ala Gln Lys
            355                 360                 365

Thr Met Asp Tyr Val Cys Cys Ala Tyr Asn Asn Ile Thr Gly Arg Gln
370                 375                 380

Asp Glu Thr His Phe Thr Val Ile Ile Thr Ser Val Gly Leu Glu Lys
385                 390                 395                 400

Leu Ala Gln Lys Gly Lys Ser Leu Ser Pro Leu Ala Ser Ile Thr Gly
                405                 410                 415

Ile Ser Leu Phe Leu Ile Ile Ser Met Cys Leu Leu Phe Leu Trp Lys
            420                 425                 430

Lys Tyr Gln Pro Tyr Lys Val Ile Lys Gln Lys Leu Glu Gly Arg Pro
            435                 440                 445

Glu Thr Glu Tyr Arg Lys Ala Gln Thr Phe Ser Gly His Glu Asp Ala
            450                 455                 460

Leu Asp Asp Phe Gly Ile Tyr Glu Phe Val Ala Phe Pro Asp Ala Ser
465                 470                 475                 480
```

```
Gly Val Ser Arg Ile Pro Ser Arg Ser Val Pro Ala Ser Asp Cys Val
                485                 490                 495
Ser Gly Gln Asp Leu His Ser Thr Val Tyr Glu Val Ile Gln His Ile
            500                 505                 510
Pro Ala Gln Gln Gln Asp His Pro Glu
        515                 520

<210> SEQ ID NO 11
<211> LENGTH: 521
<212> TYPE: PRT
<213> ORGANISM: Unknown
<220> FEATURE:
<223> OTHER INFORMATION: hypothetical protein [Macaca mulatta] (Monkey)

<400> SEQUENCE: 11

Met Gln Pro Leu Gln Asp Asp Met Thr Thr Phe Leu Glu Gln Ala Ile
  1               5                  10                  15
Thr Glu Asn Arg Ser Leu Val Lys Glu Ala Arg Gly Lys Ile Gly Ser
                 20                  25                  30
Val Thr Ser Leu Leu Ile Ser Leu Ala Asn Lys Pro Ala Ala Ala Gly
             35                  40                  45
Pro Ser Tyr His Arg Gln Val Thr Ala Cys Met Gly Gln Asp Ala
     50                  55                  60
Phe Met Glu Pro Phe Gly Asp Thr Leu Gly Val Phe Gln Cys Lys Leu
 65                  70                  75                  80
Tyr Leu Leu Leu Phe Gly Ala Cys Ser Gly Leu Lys Val Thr Val Pro
                 85                  90                  95
Ser His Thr Val His Gly Ile Arg Gly Gln Ala Leu Tyr Leu Pro Val
            100                 105                 110
His Tyr Gly Phe His Thr Pro Ala Ser Asp Ile Gln Ile Ile Trp Leu
        115                 120                 125
Phe Glu Arg Pro His Thr Met Pro Lys Tyr Leu Leu Gly Ser Val Asn
    130                 135                 140
Lys Ser Val Val Pro Asp Leu Glu Tyr Gln His Lys Phe Thr Met Met
145                 150                 155                 160
Pro Pro Asn Ala Ser Leu Leu Ile Asn Pro Leu Gln Phe Ser Asp Glu
                165                 170                 175
Gly Asn Tyr Ile Val Lys Val Asn Ile Gln Gly Asn Gly Thr Leu Ser
            180                 185                 190
Ser Ser Gln Lys Ile Gln Val Thr Val Asp Asp Pro Val Thr Lys Pro
        195                 200                 205
Val Val Gln Ile His Pro Pro Ser Gly Ser Val Glu Tyr Val Gly Asn
    210                 215                 220
Met Thr Leu Thr Cys Gln Val Glu Gly Gly Thr Arg Leu Val Tyr Gln
225                 230                 235                 240
Trp Leu Lys Asn Gly Arg Pro Ala His Thr Ser Ser Thr Tyr Ser Phe
                245                 250                 255
Ser Pro Gln Asn Asn Thr Leu His Ile Ala Pro Val Thr Lys Glu Asp
            260                 265                 270
Ile Gly Asn Tyr Ser Cys Leu Val Arg Asn Pro Val Ser Glu Met Glu
        275                 280                 285
Ser Asp Ile Ile Met Pro Ile Ile Tyr Tyr Gly Pro Tyr Gly Leu Gln
    290                 295                 300
Val Asn Ser Asp Lys Gly Leu Lys Val Gly Glu Val Phe Thr Val Asp
305                 310                 315                 320
```

Leu Gly Glu Ala Ile Leu Phe Asp Cys Ser Ala Asp Ser Tyr Pro Pro
                325                 330                 335

Asn Thr Tyr Ser Trp Ile Arg Arg Thr Asp Asn Thr Thr Tyr Ile Ile
            340                 345                 350

Lys His Gly Pro Arg Leu Glu Val Ala Ser Glu Lys Val Ala Gln Lys
        355                 360                 365

Thr Thr Asp Tyr Val Cys Cys Ala Tyr Asn Asn Ile Thr Gly Arg Gln
    370                 375                 380

Asp Glu Thr His Phe Thr Val Ile Ile Thr Ser Val Gly Leu Glu Lys
385                 390                 395                 400

Leu Ala Gln Lys Gly Lys Ser Leu Ser Pro Leu Ala Ser Ile Thr Gly
                405                 410                 415

Ile Ser Leu Phe Leu Ile Ile Ser Met Cys Leu Leu Phe Leu Trp Lys
            420                 425                 430

Lys Tyr Gln Pro Tyr Lys Val Ile Lys Gln Lys Leu Glu Gly Arg Pro
        435                 440                 445

Glu Thr Gly Tyr Arg Lys Ala Gln Thr Phe Ser Gly His Glu Asp Ala
    450                 455                 460

Leu Asp Asp Phe Gly Ile Tyr Glu Phe Val Ala Phe Pro Asp Ala Ser
465                 470                 475                 480

Gly Val Ser Arg Ile Pro Ser Arg Ser Val Pro Val Ser Asp Gly Ile
                485                 490                 495

Ser Gly Gln Asp Leu His Ser Thr Ile Tyr Glu Val Ile Gln His Ile
            500                 505                 510

Pro Ala Gln Gln Gln Asp Gln Pro Glu
        515                 520

<210> SEQ ID NO 12
<211> LENGTH: 438
<212> TYPE: PRT
<213> ORGANISM: Unknown
<220> FEATURE:
<223> OTHER INFORMATION: unnamed protein product [Tetraodon
      nigroviridis] (pufferfish)

<400> SEQUENCE: 12

Met Gly Ala Thr Gly Gly Thr Leu Leu Cys Leu Phe Ser Val Leu Phe
1               5                   10                  15

Ile Leu Thr Glu Thr Asp Cys Glu Phe Ile His Val Pro Ser Leu Val
            20                  25                  30

His His Gly Ile Glu Gly Lys Pro Leu His Leu Ser Val Glu Thr His
        35                  40                  45

Phe Leu Leu Asp Glu Ala Glu Ile Gln Gly Thr Trp Ser His Thr Ser
    50                  55                  60

Pro Gly Gly Val Arg Val Thr Leu Val Thr Phe Asn Lys Asp Ser Thr
65                  70                  75                  80

Ile Thr Asp Met Thr Tyr Arg Glu Arg Leu Val Phe Glu Val Pro Asp
                85                  90                  95

Val Ser Leu Thr Ile Lys Arg Leu Arg Ala Glu Asp Glu Gly Glu Tyr
            100                 105                 110

His Leu Asn Leu Asn Met Glu Phe His Asn Lys Thr Gly Leu Val Thr
        115                 120                 125

Lys Glu Glu Arg Ile Val Arg Val Thr Val Asp Val Pro Val Ser Val
    130                 135                 140

Pro Val Val Ala Arg Ser Pro Pro His Ala Val Val Glu Asp Gln Ala
145                 150                 155                 160

Asn Val Thr Trp Ser Cys Ala Val Glu Arg Gly Thr Arg Val Thr Phe
                165                 170                 175

Gln Trp Leu Arg Asp Gly Ala Pro Leu Gly His Ser Asp Arg Phe Arg
            180                 185                 190

Phe Ser Glu Asp Asn Ser Thr Leu Val Ile Ser Pro Val Arg Lys Glu
        195                 200                 205

Asp Arg Gly Ser Tyr Arg Cys Val Ala Ser Asn Ala Val Ser Tyr Gly
    210                 215                 220

Arg His Ser Lys Ala Ala Glu Leu Thr Val Tyr Tyr Gly Pro Tyr Asn
225                 230                 235                 240

Leu Glu Val Asn Ser Val Gln Gly Leu Arg Thr Gly Glu Val Phe Thr
                245                 250                 255

Ile Asn Pro Gly Glu Leu Val Phe Phe Glu Cys Gln Ala Asp Ser Asn
            260                 265                 270

Pro Pro Asn Ser Tyr Ala Trp Ile Ala Lys Ser His Asn Ala Thr Gln
        275                 280                 285

Val Ile Thr Glu Gly Pro Arg Leu Glu Val Arg Ser Tyr Lys Leu Ala
    290                 295                 300

Gln Ala Glu Glu Tyr Leu Cys Arg Ala Phe Asn Asn Val Thr Lys Lys
305                 310                 315                 320

Gln Asp Glu Ala Gln Phe Thr Leu Val Val Ala Ser Leu Gly Thr Gly
                325                 330                 335

Lys Glu Lys His Val Gln Glu Asp Lys Ser Met Ser Phe Leu Thr Ala
            340                 345                 350

Ile Ile Val Cys Ser Leu Phe Ile Gly Cys Met Leu Leu Phe Leu
        355                 360                 365

Ile Arg Arg Thr Cys His Pro Lys Arg Gly His Glu Asp Ala Thr Glu
    370                 375                 380

Asp Phe Gly Ile Tyr Glu Phe Val Ser Ile Pro Gly Lys Met Glu Ser
385                 390                 395                 400

Ala Gln Ala Ser Cys Arg Ser Leu Ala Arg Leu Glu Ser Ala Pro Asp
                405                 410                 415

Met His Thr Thr Ile Tyr Asp Val Ile Arg His Val Pro Glu Met Gln
            420                 425                 430

Ser His Ser Leu Leu Lys
        435

<210> SEQ ID NO 13
<211> LENGTH: 359
<212> TYPE: PRT
<213> ORGANISM: Unknown
<220> FEATURE:
<223> OTHER INFORMATION: Lachesin, Drosophila melanogaster (fruit fly)

<400> SEQUENCE: 13

Met Trp Arg Pro Ser Ile Ser Asn Cys Val Trp Ser Thr Leu Leu Leu
1               5                   10                  15

Ala Ile Phe Val Gln Gln Thr Leu Ala Gln Arg Thr Pro Thr Ile Ser
                20                  25                  30

Tyr Ile Thr Gln Glu Gln Ile Lys Asp Ile Gly Gly Thr Val Glu Phe
            35                  40                  45

Asp Cys Ser Val Gln Tyr Ala Lys Glu Tyr Asn Val Leu Phe Leu Lys
        50                  55                  60

Thr Asp Ser Asp Pro Val Phe Leu Ser Thr Gly Ser Thr Leu Val Ile
65                  70                  75                  80

```
Lys Asp Ser Arg Phe Ser Leu Arg Tyr Asp Pro Asn Ser Ser Thr Tyr
                85                  90                  95

Lys Leu Gln Ile Lys Asp Ile Gln Glu Thr Asp Ala Gly Thr Tyr Thr
            100                 105                 110

Cys Gln Val Val Ile Ser Thr Val His Lys Val Ser Ala Glu Val Lys
        115                 120                 125

Leu Ser Val Arg Arg Pro Pro Val Ile Ser Asp Asn Ser Thr Gln Ser
    130                 135                 140

Val Val Ala Ser Glu Gly Ser Glu Val Gln Met Glu Cys Tyr Ala Ser
145                 150                 155                 160

Gly Tyr Pro Thr Pro Thr Ile Thr Trp Arg Arg Glu Asn Asn Ala Ile
                165                 170                 175

Leu Pro Thr Asp Ser Ala Thr Tyr Val Gly Asn Thr Leu Arg Ile Lys
            180                 185                 190

Ser Val Lys Lys Glu Asp Arg Gly Thr Tyr Tyr Cys Val Ala Asp Asn
        195                 200                 205

Gly Val Ser Lys Gly Asp Arg Arg Asn Ile Asn Val Glu Val Glu Phe
    210                 215                 220

Ala Pro Val Ile Thr Val Pro Arg Pro Arg Leu Gly Gln Ala Leu Gln
225                 230                 235                 240

Tyr Asp Met Asp Leu Glu Cys His Ile Glu Ala Tyr Pro Pro Pro Ala
                245                 250                 255

Ile Val Trp Thr Lys Asp Asp Ile Gln Leu Ala Asn Asn Gln His Tyr
            260                 265                 270

Ser Ile Ser His Phe Ala Thr Ala Asp Glu Tyr Thr Asp Ser Thr Leu
        275                 280                 285

Arg Val Ile Thr Val Glu Lys Arg Gln Tyr Gly Asp Tyr Val Cys Lys
    290                 295                 300

Ala Thr Asn Arg Phe Gly Glu Ala Glu Ala Arg Val Asn Leu Phe Glu
305                 310                 315                 320

Thr Ile Ile Pro Val Cys Pro Pro Ala Cys Gly Gln Ala Tyr Ile Ala
                325                 330                 335

Gly Ala Glu Asp Val Ser Ala Thr Ser Phe Ala Leu Val Gly Ile Leu
            340                 345                 350

Ala Ala Leu Leu Phe Ala Arg
        355

<210> SEQ ID NO 14
<211> LENGTH: 320
<212> TYPE: PRT
<213> ORGANISM: Unknown
<220> FEATURE:
<223> OTHER INFORMATION: Extracellular domain of Betacam [Mus Musculus]
      (Mouse)

<400> SEQUENCE: 14

Gly Leu Lys Val Thr Val Pro Ser Tyr Thr Val His Gly Ile Arg Gly
1               5                   10                  15

Gln Ala Leu Tyr Leu Pro Val His Tyr Gly Phe His Thr Pro Ala Ser
            20                  25                  30

Asp Ile Gln Ile Ile Trp Leu Phe Glu Arg Ser His Thr Met Pro Lys
        35                  40                  45

Tyr Leu Leu Gly Ser Val Asn Lys Ser Val Pro Asp Leu Glu Tyr
    50                  55                  60

Gln His Lys Phe Thr Met Met Pro Pro Asn Ala Ser Leu Leu Ile Asn
```

```
                65                  70                  75                  80
Pro Leu Gln Phe Thr Asp Glu Gly Asn Tyr Ile Val Lys Val Asn Ile
                    85                  90                  95

Gln Gly Asn Gly Thr Leu Ser Ala Ser Gln Lys Ile Gln Val Thr Val
                100                 105                 110

Asp Asp Pro Val Met Lys Pro Met Val Gln Phe His Pro Ala Ser Gly
                115                 120                 125

Ala Val Glu Tyr Val Gly Asn Ile Thr Leu Thr Cys Gln Val Glu Gly
                130                 135                 140

Gly Thr Arg Leu Val Tyr Gln Trp Arg Lys Ser Gly Lys Pro Ile Ser
145                 150                 155                 160

Ile Asn Ser Ser His Ser Phe Ser Pro Gln Asn Asn Thr Leu Trp Ile
                165                 170                 175

Val Pro Val Thr Lys Glu Asp Ile Gly Asn Tyr Thr Cys Leu Val Ser
                180                 185                 190

Asn Pro Val Ser Glu Met Glu Ser Asp Ile Ile Met Pro Thr Ile Tyr
                195                 200                 205

Tyr Gly Pro Tyr Gly Leu Gln Val Asn Ser Asp Lys Gly Leu Lys Val
                210                 215                 220

Gly Glu Val Phe Thr Val Asp Leu Gly Glu Ala Val Leu Phe Asp Cys
225                 230                 235                 240

Ser Ala Asp Ser Tyr Pro Pro Asn Thr Tyr Ser Trp Ile Gln Arg Ser
                245                 250                 255

Asp Asn Thr Thr His Val Ile Lys His Gly Pro His Leu Glu Val Ala
                260                 265                 270

Ser Glu Lys Val Ala Gln Lys Thr Ala Asp Tyr Val Cys Cys Ala Tyr
                275                 280                 285

Asn Asn Ile Thr Gly Arg Arg Asp Glu Thr Arg Phe Thr Val Ile Ile
                290                 295                 300

Thr Ser Val Gly Leu Glu Lys Leu Ala Gln Arg Gly Lys Ser Leu Ser
305                 310                 315                 320

<210> SEQ ID NO 15
<211> LENGTH: 320
<212> TYPE: PRT
<213> ORGANISM: Unknown
<220> FEATURE:
<223> OTHER INFORMATION: Extracellular domain of Betacam [Homo sapiens]
      (Human)

<400> SEQUENCE: 15

Gly Leu Lys Val Thr Val Pro Ser His Thr Val His Gly Val Arg Gly
1                   5                   10                  15

Gln Ala Leu Tyr Leu Pro Val His Tyr Gly Phe His Thr Pro Ala Ser
                20                  25                  30

Asp Ile Gln Ile Ile Trp Leu Phe Glu Arg Pro His Thr Met Pro Lys
                35                  40                  45

Tyr Leu Leu Gly Ser Val Asn Lys Ser Val Val Pro Asp Leu Glu Tyr
                50                  55                  60

Gln His Lys Phe Thr Met Met Pro Pro Asn Ala Ser Leu Leu Ile Asn
65                  70                  75                  80

Pro Leu Gln Phe Pro Asp Glu Gly Asn Tyr Ile Val Lys Val Asn Ile
                85                  90                  95

Gln Gly Asn Gly Thr Leu Ser Ala Ser Gln Lys Ile Gln Val Thr Val
                100                 105                 110
```

Asp Asp Pro Val Thr Lys Pro Val Gln Ile His Pro Pro Ser Gly
            115                 120                 125

Ala Val Glu Tyr Val Gly Asn Met Thr Leu Thr Cys His Val Glu Gly
        130                 135                 140

Gly Thr Arg Leu Ala Tyr Gln Trp Leu Lys Asn Gly Arg Pro Val His
145                 150                 155                 160

Thr Ser Ser Thr Tyr Ser Phe Ser Pro Gln Asn Asn Thr Leu His Ile
                165                 170                 175

Ala Pro Val Thr Lys Glu Asp Ile Gly Asn Tyr Ser Cys Leu Val Arg
            180                 185                 190

Asn Pro Val Ser Glu Met Glu Ser Asp Ile Ile Met Pro Ile Ile Tyr
        195                 200                 205

Tyr Gly Pro Tyr Gly Leu Gln Val Asn Ser Asp Lys Gly Leu Lys Val
210                 215                 220

Gly Glu Val Phe Thr Val Asp Leu Gly Glu Ala Ile Leu Phe Asp Cys
225                 230                 235                 240

Ser Ala Asp Ser His Pro Pro Asn Thr Tyr Ser Trp Ile Arg Arg Thr
                245                 250                 255

Asp Asn Thr Thr Tyr Ile Ile Lys His Gly Pro Arg Leu Glu Val Ala
            260                 265                 270

Ser Glu Lys Val Ala Gln Lys Thr Met Asp Tyr Val Cys Cys Ala Tyr
        275                 280                 285

Asn Asn Ile Thr Gly Arg Gln Asp Glu Thr His Phe Thr Val Ile Ile
        290                 295                 300

Thr Ser Val Gly Leu Glu Lys Leu Ala Gln Lys Gly Lys Ser Leu Ser
305                 310                 315                 320

<210> SEQ ID NO 16
<211> LENGTH: 705
<212> TYPE: PRT
<213> ORGANISM: Unknown
<220> FEATURE:
<223> OTHER INFORMATION: Betacam-DsRed2 [Mouse] as in plasmid
      pIRES2-DsRED2

<400> SEQUENCE: 16

Met Gly Gln Asp Ala Phe Met Glu Leu Leu Arg Ser Met Val Gly Leu
1               5                   10                  15

Ser Leu Cys Lys Ile His Leu Leu Leu Ile Ala Gly Ser Cys Leu Gly
            20                  25                  30

Leu Lys Val Thr Val Pro Ser Tyr Thr Val His Gly Ile Arg Gly Gln
        35                  40                  45

Ala Leu Tyr Leu Pro Val His Tyr Gly Phe His Thr Pro Ala Ser Asp
    50                  55                  60

Ile Gln Ile Ile Trp Leu Phe Glu Arg Ser His Thr Met Pro Lys Tyr
65                  70                  75                  80

Leu Leu Gly Ser Val Asn Lys Ser Val Val Pro Asp Leu Glu Tyr Gln
                85                  90                  95

His Lys Phe Thr Met Met Pro Pro Asn Ala Ser Leu Leu Ile Asn Pro
            100                 105                 110

Leu Gln Phe Thr Asp Glu Gly Asn Tyr Ile Val Lys Val Asn Ile Gln
        115                 120                 125

Gly Asn Gly Thr Leu Ser Ala Ser Gln Lys Ile Gln Val Thr Val Asp
    130                 135                 140

Asp Pro Val Met Lys Pro Met Val Gln Phe His Pro Ala Ser Gly Ala
145                 150                 155                 160

```
Val Glu Tyr Val Gly Asn Ile Thr Leu Thr Cys Gln Val Glu Gly Gly
                165                 170                 175

Thr Arg Leu Val Tyr Gln Trp Arg Lys Ser Gly Lys Pro Ile Ser Ile
            180                 185                 190

Asn Ser Ser His Ser Phe Ser Pro Gln Asn Asn Thr Leu Trp Ile Val
        195                 200                 205

Pro Val Thr Lys Glu Asp Ile Gly Asn Tyr Thr Cys Leu Val Ser Asn
210                 215                 220

Pro Val Ser Glu Met Glu Ser Asp Ile Ile Met Pro Thr Ile Tyr Tyr
225                 230                 235                 240

Gly Pro Tyr Gly Leu Gln Val Asn Ser Asp Lys Gly Leu Lys Val Gly
            245                 250                 255

Glu Val Phe Thr Val Asp Leu Gly Glu Ala Val Leu Phe Asp Cys Ser
        260                 265                 270

Ala Asp Ser Tyr Pro Pro Asn Thr Tyr Ser Trp Ile Gln Arg Ser Asp
    275                 280                 285

Asn Thr Thr His Val Ile Lys His Gly Pro His Leu Glu Val Ala Ser
290                 295                 300

Glu Lys Val Ala Gln Lys Thr Ala Asp Tyr Val Cys Cys Ala Tyr Asn
305                 310                 315                 320

Asn Ile Thr Gly Arg Arg Asp Glu Thr Arg Phe Thr Val Ile Ile Thr
            325                 330                 335

Ser Val Gly Leu Glu Lys Leu Ala Gln Arg Gly Lys Ser Leu Ser Pro
        340                 345                 350

Leu Ala Ser Ile Thr Gly Ile Ser Leu Phe Leu Ile Ile Ser Met Cys
    355                 360                 365

Leu Leu Phe Leu Trp Lys Lys Tyr Gln Pro Tyr Lys Ala Ile Arg Gln
370                 375                 380

Lys Leu Glu Gly Arg Pro Glu Ser Glu Tyr Lys Ala Gln Thr Phe
385                 390                 395                 400

Ser Gly His Glu Asp Ala Leu Ser Asp Phe Gly Ile Tyr Glu Phe Val
            405                 410                 415

Thr Phe Pro Asp Ala Ser Gly Val Ser Arg Met Ser Ser Arg Ser Ser
        420                 425                 430

Pro Ala Ser Asp Gly Val Thr Gly Gln Asp Ile His Gly Thr Ile Tyr
    435                 440                 445

Glu Val Ile Gln His Ile Pro Glu Gln Gln Glu Asn Thr Glu Arg
450                 455                 460

Ile Leu Gln Ser Thr Val Pro Arg Ala Arg Asp Pro Pro Val Ala Thr
465                 470                 475                 480

Met Ala Ser Ser Glu Asp Val Ile Lys Glu Phe Met Arg Phe Lys Val
            485                 490                 495

Arg Met Glu Gly Ser Val Asn Gly His Glu Phe Glu Ile Glu Gly Glu
        500                 505                 510

Gly Glu Gly Arg Pro Tyr Glu Gly Thr Gln Thr Ala Lys Leu Lys Val
    515                 520                 525

Thr Lys Gly Gly Pro Leu Pro Phe Ala Trp Asp Ile Leu Ser Pro Gln
530                 535                 540

Phe Gln Tyr Gly Ser Lys Val Tyr Val Lys His Pro Ala Asp Ile Pro
545                 550                 555                 560

Asp Tyr Lys Lys Leu Ser Phe Pro Glu Gly Phe Lys Trp Glu Arg Val
            565                 570                 575
```

```
Met Asn Phe Glu Asp Gly Gly Val Val Thr Val Thr Gln Asp Ser Ser
            580                 585                 590

Leu Gln Asp Gly Ser Phe Ile Tyr Lys Val Lys Phe Ile Gly Val Asn
            595                 600                 605

Phe Pro Ser Asp Gly Pro Val Met Gln Lys Lys Thr Met Gly Trp Glu
            610                 615                 620

Ala Ser Thr Glu Arg Leu Tyr Pro Arg Asp Gly Val Leu Lys Gly Glu
625                 630                 635                 640

Ile His Lys Ala Leu Lys Leu Lys Asp Gly Gly His Tyr Leu Val Glu
                645                 650                 655

Phe Lys Ser Ile Tyr Met Ala Lys Lys Pro Val Gln Leu Pro Gly Tyr
            660                 665                 670

Tyr Tyr Val Asp Ser Lys Leu Asp Ile Thr Ser His Asn Glu Asp Tyr
            675                 680                 685

Thr Ile Val Glu Gln Tyr Glu Arg Ala Glu Gly Arg His His Leu Phe
            690                 695                 700

Leu
705

<210> SEQ ID NO 17
<211> LENGTH: 719
<212> TYPE: PRT
<213> ORGANISM: Unknown
<220> FEATURE:
<223> OTHER INFORMATION: Betacam-nEGFP [Mouse] as in plasmid pIRES2-EGFP

<400> SEQUENCE: 17

Met Gly Gln Asp Ala Phe Met Glu Leu Leu Arg Ser Met Val Gly Leu
  1               5                  10                  15

Ser Leu Cys Lys Ile His Leu Leu Ile Ala Gly Ser Cys Leu Gly
            20                  25                  30

Leu Lys Val Thr Val Pro Ser Tyr Thr Val His Gly Ile Arg Gly Gln
            35                  40                  45

Ala Leu Tyr Leu Pro Val His Tyr Gly Phe His Thr Pro Ala Ser Asp
 50                  55                  60

Ile Gln Ile Ile Trp Leu Phe Glu Arg Ser His Thr Met Pro Lys Tyr
 65                  70                  75                  80

Leu Leu Gly Ser Val Asn Lys Ser Val Val Pro Asp Leu Glu Tyr Gln
                85                  90                  95

His Lys Phe Thr Met Met Pro Pro Asn Ala Ser Leu Leu Ile Asn Pro
            100                 105                 110

Leu Gln Phe Thr Asp Glu Gly Asn Tyr Ile Val Lys Val Asn Ile Gln
            115                 120                 125

Gly Asn Gly Thr Leu Ser Ala Ser Gln Lys Ile Gln Val Thr Val Asp
            130                 135                 140

Asp Pro Val Met Lys Pro Met Val Gln Phe His Pro Ala Ser Gly Ala
145                 150                 155                 160

Val Glu Tyr Val Gly Asn Ile Thr Leu Thr Cys Gln Val Glu Gly Gly
                165                 170                 175

Thr Arg Leu Val Tyr Gln Trp Arg Lys Ser Gly Lys Pro Ile Ser Ile
            180                 185                 190

Asn Ser Ser His Ser Phe Ser Pro Gln Asn Asn Thr Leu Trp Ile Val
            195                 200                 205

Pro Val Thr Lys Glu Asp Ile Gly Asn Tyr Thr Cys Leu Val Ser Asn
            210                 215                 220
```

-continued

```
Pro Val Ser Glu Met Glu Ser Asp Ile Ile Met Pro Thr Ile Tyr Tyr
225                 230                 235                 240

Gly Pro Tyr Gly Leu Gln Val Asn Ser Asp Lys Gly Leu Lys Val Gly
            245                 250                 255

Glu Val Phe Thr Val Asp Leu Gly Glu Ala Val Leu Phe Asp Cys Ser
        260                 265                 270

Ala Asp Ser Tyr Pro Pro Asn Thr Tyr Ser Trp Ile Gln Arg Ser Asp
    275                 280                 285

Asn Thr Thr His Val Ile Lys His Gly Pro His Leu Glu Val Ala Ser
290                 295                 300

Glu Lys Val Ala Gln Lys Thr Ala Asp Tyr Val Cys Cys Ala Tyr Asn
305                 310                 315                 320

Asn Ile Thr Gly Arg Arg Asp Glu Thr Arg Phe Thr Val Ile Ile Thr
            325                 330                 335

Ser Val Gly Leu Glu Lys Leu Ala Gln Arg Gly Lys Ser Leu Ser Pro
        340                 345                 350

Leu Ala Ser Ile Thr Gly Ile Ser Leu Phe Leu Ile Ile Ser Met Cys
    355                 360                 365

Leu Leu Phe Leu Trp Lys Lys Tyr Gln Pro Tyr Lys Ala Ile Arg Gln
370                 375                 380

Lys Leu Glu Gly Arg Pro Glu Ser Glu Tyr Arg Lys Ala Gln Thr Phe
385                 390                 395                 400

Ser Gly His Glu Asp Ala Leu Ser Asp Phe Gly Ile Tyr Glu Phe Val
            405                 410                 415

Thr Phe Pro Asp Ala Ser Gly Val Ser Arg Met Ser Ser Arg Ser Ser
        420                 425                 430

Pro Ala Ser Asp Gly Val Thr Gly Gln Asp Ile His Gly Thr Ile Tyr
    435                 440                 445

Glu Val Ile Gln His Ile Pro Glu Gln Gln Gln Asn Thr Glu Arg
450                 455                 460

Ile Leu Gln Ser Thr Val Pro Arg Ala Arg Asp Pro Pro Val Ala Thr
465                 470                 475                 480

Met Val Ser Lys Gly Glu Glu Leu Phe Thr Gly Val Val Pro Ile Leu
            485                 490                 495

Val Glu Leu Asp Gly Asp Val Asn Gly His Lys Phe Ser Val Ser Gly
        500                 505                 510

Glu Gly Glu Gly Asp Ala Thr Tyr Gly Lys Leu Thr Leu Lys Phe Ile
    515                 520                 525

Cys Thr Thr Gly Lys Leu Pro Val Pro Trp Pro Thr Leu Val Thr Thr
530                 535                 540

Leu Thr Tyr Gly Val Gln Cys Phe Ser Arg Tyr Pro Asp His Met Lys
545                 550                 555                 560

Gln His Asp Phe Phe Lys Ser Ala Met Pro Glu Gly Tyr Val Gln Glu
            565                 570                 575

Arg Thr Ile Phe Phe Lys Asp Asp Gly Asn Tyr Lys Thr Arg Ala Glu
        580                 585                 590

Val Lys Phe Glu Gly Asp Thr Leu Val Asn Arg Ile Glu Leu Lys Gly
    595                 600                 605

Ile Asp Phe Lys Glu Asp Gly Asn Ile Leu Gly His Lys Leu Glu Tyr
610                 615                 620

Asn Tyr Asn Ser His Asn Val Tyr Ile Met Ala Asp Lys Gln Lys Asn
625                 630                 635                 640

Gly Ile Lys Val Asn Phe Lys Ile Arg His Asn Ile Glu Asp Gly Ser
```

```
                   645                 650                 655
Val Gln Leu Ala Asp His Tyr Gln Gln Asn Thr Pro Ile Gly Asp Gly
            660                 665                 670

Pro Val Leu Leu Pro Asp Asn His Tyr Leu Ser Thr Gln Ser Ala Leu
        675                 680                 685

Ser Lys Asp Pro Asn Glu Lys Arg Asp His Met Val Leu Leu Glu Phe
    690                 695                 700

Val Thr Ala Ala Gly Ile Thr Leu Gly Met Asp Glu Leu Tyr Lys
705                 710                 715
```

<210> SEQ ID NO 18
<211> LENGTH: 251
<212> TYPE: PRT
<213> ORGANISM: Unknown
<220> FEATURE:
<223> OTHER INFORMATION: plasmid pFUSE-FcOnly

<400> SEQUENCE: 18

```
Met Thr Ala Met Gly Leu Leu Ser Cys Ile Ala Leu Ser Leu Ala Leu
1               5                   10                  15

Val Thr Ala Ser Pro Ser Ala Met Gly Thr Ser Ala Leu Thr His Thr
            20                  25                  30

Cys Pro Pro Cys Pro Ala Pro Gly Leu Leu Gly Gly Pro Ser Val Pro
        35                  40                  45

Leu Pro Pro Leu Pro Leu Ala Thr Leu Met Ile Ser Ala Thr Pro
    50                  55                  60

Gly Val Thr Cys Val Val Ala Val Ser His Gly Ala Pro Gly Val
65                  70                  75                  80

Leu Pro Ala Thr Thr Val Ala Gly Val Gly Val His Ala Ala Leu Thr
            85                  90                  95

Leu Pro Ala Gly Gly Gly Thr Ala Ser Thr Thr Ala Val Val Ser Val
        100                 105                 110

Leu Thr Val Leu His Gly Ala Thr Leu Ala Gly Leu Gly Thr Leu Cys
    115                 120                 125

Leu Val Ser Ala Leu Ala Leu Pro Ala Pro Ile Gly Leu Thr Ile Ser
130                 135                 140

Leu Ala Leu Gly Gly Pro Ala Gly Pro Gly Val Thr Thr Leu Pro Pro
145                 150                 155                 160

Ser Ala Gly Gly Met Thr Leu Ala Gly Val Ser Leu Thr Cys Leu Val
            165                 170                 175

Leu Gly Pro Thr Pro Ser Ala Ile Ala Val Gly Thr Gly Ser Ala Gly
        180                 185                 190

Gly Pro Gly Ala Ala Thr Leu Thr Thr Pro Pro Val Leu Ala Ser Ala
    195                 200                 205

Gly Ser Pro Pro Leu Thr Ser Leu Leu Thr Val Ala Leu Ser Ala Thr
210                 215                 220

Gly Gly Gly Ala Val Pro Ser Cys Ser Val Met His Gly Ala Leu His
225                 230                 235                 240

Ala His Thr Thr Gly Leu Ser Leu Ser Leu Ser
            245                 250
```

<210> SEQ ID NO 19
<211> LENGTH: 364
<212> TYPE: PRT
<213> ORGANISM: Unknown
<220> FEATURE:
<223> OTHER INFORMATION: plasmid pFUSE-Fc-D1

<400> SEQUENCE: 19

Met Thr Ala Met Gly Leu Leu Ser Cys Ile Ala Leu Ser Leu Ala Leu
1               5                   10                  15

Val Thr Ala Ser Pro Ser Ala Met Ser Leu Lys Val Thr Val Pro Ser
            20                  25                  30

Tyr Thr Val His Gly Ile Arg Gly Gln Ala Leu Tyr Leu Pro Val His
        35                  40                  45

Tyr Gly Phe His Thr Pro Ala Ser Asp Ile Gln Ile Ile Trp Leu Phe
    50                  55                  60

Glu Arg Ser His Thr Met Pro Lys Tyr Leu Leu Gly Ser Val Asn Lys
65              70                  75                  80

Ser Val Val Pro Asp Leu Glu Tyr Gln His Lys Phe Thr Met Met Pro
                85                  90                  95

Pro Asn Ala Ser Leu Leu Ile Asn Pro Leu Gln Phe Thr Asp Glu Gly
            100                 105                 110

Asn Tyr Ile Val Lys Val Asn Ile Gln Gly Asn Gly Thr Leu Ser Ala
        115                 120                 125

Ser Gln Lys Ile Gln Val Thr Val Asp Asp Pro Val Ala Leu Thr Pro
    130                 135                 140

Pro Cys Pro Ala Pro Gly Leu Leu Gly Gly Pro Ser Val Pro Leu Pro
145                 150                 155                 160

Pro Pro Leu Pro Leu Ala Thr Leu Met Ile Ser Ala Thr Pro Gly Val
                165                 170                 175

Thr Cys Val Val Val Ala Val Ser His Gly Ala Pro Gly Val Leu Pro
            180                 185                 190

Ala Thr Thr Val Ala Gly Val Gly Val His Ala Ala Leu Thr Leu Pro
        195                 200                 205

Ala Gly Gly Gly Thr Ala Ser Thr Thr Ala Val Val Ser Val Leu Thr
    210                 215                 220

Val Leu His Gly Ala Thr Leu Ala Gly Leu Gly Thr Leu Cys Leu Val
225                 230                 235                 240

Ser Ala Leu Ala Leu Pro Ala Pro Ile Gly Leu Thr Ile Ser Leu Ala
                245                 250                 255

Leu Gly Gly Pro Ala Gly Pro Gly Val Thr Thr Leu Pro Pro Ser Ala
            260                 265                 270

Gly Gly Met Thr Leu Ala Gly Val Ser Leu Thr Cys Leu Val Leu Gly
        275                 280                 285

Pro Thr Pro Ser Ala Ile Ala Val Gly Thr Gly Ser Ala Gly Gly Pro
    290                 295                 300

Gly Ala Ala Thr Leu Thr Thr Pro Pro Val Leu Ala Ser Ala Gly Ser
305                 310                 315                 320

Pro Pro Leu Thr Ser Leu Leu Thr Val Ala Leu Ser Ala Thr Gly Gly
                325                 330                 335

Gly Ala Val Pro Ser Cys Ser Val Met His Gly Ala Leu His Ala His
            340                 345                 350

Thr Thr Gly Leu Ser Leu Ser Leu Ser Pro Gly Leu
        355                 360

<210> SEQ ID NO 20
<211> LENGTH: 345
<212> TYPE: PRT
<213> ORGANISM: Unknown
<220> FEATURE:
<223> OTHER INFORMATION: plasmid pFUSE-Fc-D2

<400> SEQUENCE: 20

```
Met Thr Ala Met Gly Leu Leu Ser Cys Ile Ala Leu Ser Leu Ala Leu
 1               5                  10                  15

Val Thr Ala Ser Pro Ser Ala Met Ser Pro Val Met Lys Pro Met Val
             20                  25                  30

Gln Phe His Pro Ala Ser Gly Ala Val Glu Tyr Val Gly Asn Ile Thr
         35                  40                  45

Leu Thr Cys Gln Val Glu Gly Thr Arg Leu Val Tyr Gln Trp Arg
     50                  55                  60

Lys Ser Gly Lys Pro Ile Ser Ile Asn Ser Ser His Ser Phe Ser Pro
65               70                  75                  80

Gln Asn Asn Thr Leu Trp Ile Val Pro Val Thr Lys Glu Asp Ile Gly
                 85                  90                  95

Asn Tyr Thr Cys Leu Val Ser Asn Pro Val Ser Glu Met Glu Ser Asp
             100                 105                 110

Ile Ile Met Pro Thr Ile Tyr Tyr Gly Ala Leu Thr Pro Pro Cys Pro
             115                 120                 125

Ala Pro Gly Leu Leu Gly Gly Pro Ser Val Pro Leu Pro Pro Pro Leu
130                 135                 140

Pro Leu Ala Thr Leu Met Ile Ser Ala Thr Pro Gly Val Thr Cys Val
145                 150                 155                 160

Val Val Ala Val Ser His Gly Ala Pro Gly Val Leu Pro Ala Thr Thr
                 165                 170                 175

Val Ala Gly Val Gly Val His Ala Ala Leu Thr Leu Pro Ala Gly Gly
             180                 185                 190

Gly Thr Ala Ser Thr Thr Ala Val Val Ser Val Leu Thr Val Leu His
         195                 200                 205

Gly Ala Thr Leu Ala Gly Leu Gly Thr Leu Cys Leu Val Ser Ala Leu
     210                 215                 220

Ala Leu Pro Ala Pro Ile Gly Leu Thr Ile Ser Leu Ala Leu Gly Gly
225                 230                 235                 240

Pro Ala Gly Pro Gly Val Thr Thr Leu Pro Pro Ser Ala Gly Gly Met
                 245                 250                 255

Thr Leu Ala Gly Val Ser Leu Thr Cys Leu Val Leu Gly Pro Thr Pro
             260                 265                 270

Ser Ala Ile Ala Val Gly Thr Gly Ser Ala Gly Gly Pro Gly Ala Ala
             275                 280                 285

Thr Leu Thr Thr Pro Pro Val Leu Ala Ser Ala Gly Ser Pro Pro Leu
290                 295                 300

Thr Ser Leu Leu Thr Val Ala Leu Ser Ala Thr Gly Gly Gly Ala Val
305                 310                 315                 320

Pro Ser Cys Ser Val Met His Gly Ala Leu His Ala His Thr Thr Gly
                 325                 330                 335

Leu Ser Leu Ser Leu Ser Pro Gly Leu
                 340                 345
```

<210> SEQ ID NO 21
<211> LENGTH: 346
<212> TYPE: PRT
<213> ORGANISM: Unknown
<220> FEATURE:
<223> OTHER INFORMATION: plasmid pFUSE-Fc-D3

<400> SEQUENCE: 21

```
Met Thr Ala Met Gly Leu Leu Ser Cys Ile Ala Leu Ser Leu Ala Leu
1               5                   10                  15

Val Thr Ala Ser Ser Ala Met Gly Thr Ser Tyr Gly Pro Tyr Gly Leu
            20                  25                  30

Gln Val Asn Ser Asp Lys Gly Leu Lys Val Gly Glu Val Phe Thr Val
            35                  40                  45

Asp Leu Gly Glu Ala Val Leu Phe Asp Cys Ser Ala Asp Ser Tyr Pro
50                  55                  60

Pro Asn Thr Tyr Ser Trp Ile Gln Arg Ser Asp Asn Thr Thr His Val
65                  70                  75                  80

Ile Lys His Gly Pro His Leu Glu Val Ala Ser Glu Lys Val Ala Gln
                85                  90                  95

Lys Thr Ala Asp Tyr Val Cys Cys Ala Tyr Asn Asn Ile Thr Gly Arg
            100                 105                 110

Arg Asp Glu Thr Arg Phe Thr Val Ile Ala Leu Thr His Thr Cys
            115                 120                 125

Pro Pro Cys Pro Ala Pro Gly Leu Leu Gly Pro Ser Val Pro Leu
130                 135                 140

Pro Pro Pro Leu Pro Leu Ala Thr Leu Met Ile Ser Ala Thr Pro Gly
145                 150                 155                 160

Val Thr Cys Val Val Val Ala Val Ser His Gly Ala Pro Gly Val Leu
                165                 170                 175

Pro Ala Thr Thr Val Ala Gly Val Gly Val His Ala Ala Leu Thr Leu
            180                 185                 190

Pro Ala Gly Gly Gly Thr Ala Ser Thr Thr Ala Val Val Ser Val Leu
            195                 200                 205

Thr Val Leu His Gly Ala Thr Leu Ala Gly Leu Gly Thr Leu Cys Leu
210                 215                 220

Val Ser Ala Leu Ala Leu Pro Ala Pro Ile Gly Leu Thr Ile Ser Leu
225                 230                 235                 240

Ala Leu Gly Gly Pro Ala Gly Pro Gly Val Thr Thr Leu Pro Pro Ser
                245                 250                 255

Ala Gly Gly Met Thr Leu Ala Gly Val Ser Leu Thr Cys Leu Val Leu
            260                 265                 270

Gly Pro Thr Pro Ser Ala Ile Ala Val Gly Thr Gly Ser Ala Gly Gly
            275                 280                 285

Pro Gly Ala Ala Thr Leu Thr Thr Pro Pro Val Leu Ala Ser Ala Gly
            290                 295                 300

Ser Pro Pro Leu Thr Ser Leu Leu Thr Val Ala Leu Ser Ala Thr Gly
305                 310                 315                 320

Gly Gly Ala Val Pro Ser Cys Ser Val Met His Gly Ala Leu His Ala
                325                 330                 335

His Thr Thr Gly Leu Ser Leu Ser Leu Ser
                340                 345

<210> SEQ ID NO 22
<211> LENGTH: 456
<212> TYPE: PRT
<213> ORGANISM: Unknown
<220> FEATURE:
<223> OTHER INFORMATION: plasmid pFUSE-Fc-D1/D2

<400> SEQUENCE: 22

Met Thr Ala Met Gly Leu Leu Ser Cys Ile Ala Leu Ser Leu Ala Leu
1               5                   10                  15
```

-continued

```
Val Thr Ala Ser Pro Ser Ala Met Ser Leu Lys Val Thr Val Pro Ser
             20                  25                  30

Tyr Thr Val His Gly Ile Arg Gly Gln Ala Leu Tyr Leu Pro Val His
     35                  40                  45

Tyr Gly Phe His Thr Pro Ala Ser Asp Ile Gln Ile Ile Trp Leu Phe
 50                  55                  60

Glu Arg Ser His Thr Met Pro Lys Tyr Leu Leu Gly Ser Val Asn Lys
 65                  70                  75                  80

Ser Val Val Pro Asp Leu Glu Tyr Gln His Lys Phe Thr Met Met Pro
                 85                  90                  95

Pro Asn Ala Ser Leu Leu Ile Asn Pro Leu Gln Phe Thr Asp Glu Gly
             100                 105                 110

Asn Tyr Ile Val Lys Val Asn Ile Gln Gly Asn Gly Thr Leu Ser Ala
         115                 120                 125

Ser Gln Lys Ile Gln Val Thr Val Asp Asp Pro Val Met Lys Pro Met
     130                 135                 140

Val Gln Phe His Pro Ala Ser Gly Ala Val Glu Tyr Val Gly Asn Ile
145                 150                 155                 160

Thr Leu Thr Cys Gln Val Glu Gly Gly Thr Arg Leu Val Tyr Gln Trp
                165                 170                 175

Arg Lys Ser Gly Lys Pro Ile Ser Ile Asn Ser Ser His Ser Phe Ser
            180                 185                 190

Pro Gln Asn Asn Thr Leu Trp Ile Val Pro Val Thr Lys Glu Asp Ile
        195                 200                 205

Gly Asn Tyr Thr Cys Leu Val Ser Asn Pro Val Ser Glu Met Glu Ser
210                 215                 220

Asp Ile Ile Met Pro Thr Ile Tyr Ala Leu Thr His Thr Cys Pro Pro
225                 230                 235                 240

Cys Pro Ala Pro Gly Leu Leu Gly Gly Pro Ser Val Pro Leu Pro Pro
                245                 250                 255

Pro Leu Pro Leu Ala Thr Leu Met Ile Ser Ala Thr Pro Gly Val Thr
            260                 265                 270

Cys Val Val Val Ala Val Ser His Gly Ala Pro Gly Val Leu Pro Ala
        275                 280                 285

Thr Thr Val Ala Gly Val Gly Val His Ala Ala Leu Thr Leu Pro Ala
    290                 295                 300

Gly Gly Gly Thr Ala Ser Thr Thr Ala Val Val Ser Val Leu Thr Val
305                 310                 315                 320

Leu His Gly Ala Thr Leu Ala Gly Leu Gly Thr Leu Cys Leu Val Ser
                325                 330                 335

Ala Leu Ala Leu Pro Ala Pro Ile Gly Leu Thr Ile Ser Leu Ala Leu
            340                 345                 350

Gly Gly Pro Ala Gly Pro Gly Val Thr Thr Leu Pro Pro Ser Ala Gly
        355                 360                 365

Gly Met Thr Leu Ala Gly Val Ser Leu Thr Cys Leu Val Leu Gly Pro
    370                 375                 380

Thr Pro Ser Ala Ile Ala Val Gly Thr Gly Ser Ala Gly Gly Pro Gly
385                 390                 395                 400

Ala Ala Thr Leu Thr Thr Pro Pro Val Leu Ala Ser Ala Gly Ser Pro
                405                 410                 415

Pro Leu Thr Ser Leu Leu Thr Val Ala Leu Ser Ala Thr Gly Gly Gly
            420                 425                 430

Ala Val Pro Ser Cys Ser Val Met His Gly Ala Leu His Ala His Thr
```

```
                    435                 440                 445
Thr Gly Leu Ser Leu Ser Leu Ser
    450                 455

<210> SEQ ID NO 23
<211> LENGTH: 440
<212> TYPE: PRT
<213> ORGANISM: Unknown
<220> FEATURE:
<223> OTHER INFORMATION: plasmid pFUSE-Fc-D2/D3

<400> SEQUENCE: 23

Met Thr Ala Met Gly Leu Leu Ser Cys Ile Ala Leu Ser Leu Ala Leu
1               5                   10                  15

Val Thr Ala Ser Ser Ala Met Gly Thr Ser Pro Val Met Lys Pro Met
            20                  25                  30

Val Gln Phe His Pro Ala Ser Gly Ala Val Glu Tyr Val Gly Asn Ile
        35                  40                  45

Thr Leu Thr Cys Gln Val Glu Gly Gly Thr Arg Leu Val Tyr Gln Trp
    50                  55                  60

Arg Lys Ser Gly Lys Pro Ile Ser Ile Asn Ser Ser His Ser Phe Ser
65                  70                  75                  80

Pro Gln Asn Asn Thr Leu Trp Ile Val Pro Val Thr Lys Glu Asp Ile
                85                  90                  95

Gly Asn Tyr Thr Cys Leu Val Ser Asn Pro Val Ser Glu Met Glu Ser
            100                 105                 110

Asp Ile Ile Met Pro Thr Ile Tyr Tyr Gly Pro Tyr Gly Leu Gln Val
        115                 120                 125

Asn Ser Asp Lys Gly Leu Lys Val Gly Glu Val Phe Thr Val Asp Leu
    130                 135                 140

Gly Glu Ala Val Leu Phe Asp Cys Ser Ala Asp Ser Tyr Pro Pro Asn
145                 150                 155                 160

Thr Tyr Ser Trp Ile Gln Arg Ser Asp Asn Thr Thr His Val Ile Lys
                165                 170                 175

His Gly Pro His Leu Glu Val Ala Ser Glu Lys Val Ala Gln Lys Thr
            180                 185                 190

Ala Asp Tyr Val Cys Cys Ala Tyr Asn Asn Ile Thr Gly Arg Arg Asp
        195                 200                 205

Glu Thr Arg Phe Thr Val Ile Ile Ala Leu Thr His Thr Cys Pro Pro
    210                 215                 220

Cys Pro Ala Pro Gly Leu Leu Gly Gly Pro Ser Val Pro Leu Pro Pro
225                 230                 235                 240

Pro Leu Pro Leu Ala Thr Leu Met Ile Ser Ala Thr Pro Gly Val Thr
                245                 250                 255

Cys Val Val Ala Val Ser His Gly Ala Pro Gly Val Leu Pro Ala
            260                 265                 270

Thr Thr Val Ala Gly Val Gly Val His Ala Ala Leu Thr Leu Pro Ala
        275                 280                 285

Gly Gly Gly Thr Ala Ser Thr Thr Ala Val Val Ser Val Leu Thr Val
    290                 295                 300

Leu His Gly Ala Thr Leu Ala Gly Leu Gly Thr Leu Cys Leu Val Ser
305                 310                 315                 320

Ala Leu Ala Leu Pro Ala Pro Ile Gly Leu Thr Ile Ser Leu Ala Leu
                325                 330                 335

Gly Gly Pro Ala Gly Pro Gly Val Thr Thr Leu Pro Pro Ser Ala Gly
```

```
                    340                 345                 350
Gly Met Thr Leu Ala Gly Val Ser Leu Thr Cys Leu Val Leu Gly Pro
            355                 360                 365

Thr Pro Ser Ala Ile Ala Val Gly Thr Gly Ser Ala Gly Gly Pro Gly
            370                 375                 380

Ala Ala Thr Leu Thr Thr Pro Pro Val Leu Ala Ser Ala Gly Ser Pro
385                 390                 395                 400

Pro Leu Thr Ser Leu Leu Thr Val Ala Leu Ser Ala Thr Gly Gly Gly
                405                 410                 415

Ala Val Pro Ser Cys Ser Val Met His Gly Ala Leu His Ala His Thr
                420                 425                 430

Thr Gly Leu Ser Leu Ser Leu Ser
            435                 440

<210> SEQ ID NO 24
<211> LENGTH: 248
<212> TYPE: PRT
<213> ORGANISM: Unknown
<220> FEATURE:
<223> OTHER INFORMATION: plasmid pFUSE-Fc-D1/D2/D3

<400> SEQUENCE: 24

Met Thr Ala Met Gly Leu Leu Ser Cys Ile Ala Leu Ser Leu Ala Leu
1               5                   10                  15

Val Thr Ala Ser Ser Ala Met Gly Ala Leu Thr His Thr Cys Pro Pro
                20                  25                  30

Cys Pro Ala Pro Gly Leu Leu Gly Gly Pro Ser Val Pro Leu Pro Pro
            35                  40                  45

Pro Leu Pro Leu Ala Thr Leu Met Ile Ser Ala Thr Pro Gly Val Thr
        50                  55                  60

Cys Val Val Ala Val Ser His Gly Ala Pro Gly Val Leu Pro Ala
65                  70                  75                  80

Thr Thr Val Ala Gly Val Gly Val His Ala Ala Leu Thr Leu Pro Ala
                85                  90                  95

Gly Gly Gly Thr Ala Ser Thr Thr Ala Val Val Ser Val Leu Thr Val
            100                 105                 110

Leu His Gly Ala Thr Leu Ala Gly Leu Gly Thr Leu Cys Leu Val Ser
        115                 120                 125

Ala Leu Ala Leu Pro Ala Pro Ile Gly Leu Thr Ile Ser Leu Ala Leu
130                 135                 140

Gly Gly Pro Ala Gly Pro Gly Val Thr Thr Leu Pro Pro Ser Ala Gly
145                 150                 155                 160

Gly Met Thr Leu Ala Gly Val Ser Leu Thr Cys Leu Val Leu Gly Pro
                165                 170                 175

Thr Pro Ser Ala Ile Ala Val Gly Thr Gly Ser Ala Gly Gly Pro Gly
            180                 185                 190

Ala Ala Thr Leu Thr Thr Pro Pro Val Leu Ala Ser Ala Gly Ser Pro
        195                 200                 205

Pro Leu Thr Ser Leu Leu Thr Val Ala Leu Ser Ala Thr Gly Gly Gly
210                 215                 220

Ala Val Pro Ser Cys Ser Val Met His Gly Ala Leu His Ala His Thr
225                 230                 235                 240

Thr Gly Leu Ser Leu Ser Leu Ser
            245
```

<210> SEQ ID NO 25
<211> LENGTH: 1353
<212> TYPE: DNA
<213> ORGANISM: Unknown
<220> FEATURE:
<223> OTHER INFORMATION: Nucleotide Sequence of human Betacam, isoform 2

<400> SEQUENCE: 25

| | | | | | |
|---|---|---|---|---|---|
| atgtggctca | aggtcttcac | aactttcctt | tcctttgcaa | caggtgcttg | ctcggggctg | 60 |
| aaggtgacag | tgccatcaca | cactgtccat | ggcgtcagag | gtcaggccct | ctacctaccc | 120 |
| gtccactatg | gcttccacac | tccagcatca | gacatccaga | tcatatggct | atttgagaga | 180 |
| ccccacacaa | tgcccaaata | cttactgggc | tctgtgaata | agtctgtggt | tcctgacttg | 240 |
| gaataccaac | acaagttcac | catgatgcca | cccaatgcat | ctctgcttat | caacccactg | 300 |
| cagttccctg | atgaaggcaa | ttacatcgtg | aaggtcaaca | ttcagggaaa | tggaactcta | 360 |
| tctgccagtc | agaagataca | agtcacggtt | gatgatcctg | tcacaaagcc | agtggtgcag | 420 |
| attcatcctc | cctctggggc | tgtggagtat | gtggggaaca | tgaccctgac | atgccatgtg | 480 |
| gaaggggca | ctcggctagc | ttaccaatgg | ctaaaaatg | ggagacctgt | ccacaccagc | 540 |
| tccacctact | cctttctcc | ccaaaacaat | acccttcata | ttgctccagt | aaccaaggaa | 600 |
| gacattggga | attacagctg | cctggtgagg | aaccctgtca | gtgaaatgga | aagtgatatc | 660 |
| attatgccca | tcatatatta | tggacctat | ggacttcaag | tgaattctga | taaagggcta | 720 |
| aaagtagggg | aagtgtttac | tgttgacctt | ggagaggcca | tcctatttga | ttgttctgct | 780 |
| gattctcatc | cccccaacac | ctactcctgg | attaggagga | ctgacaatac | tacatatatc | 840 |
| attaagcatg | ggcctcgctt | agaagttgca | tctgagaaag | tagcccagaa | gacaatggac | 900 |
| tatgtgtgct | gtgcttacaa | caacataacc | ggcaggcaag | atgaaactca | tttcacagtt | 960 |
| atcatcactt | ccgtaggact | ggagaagctt | gcacagaaag | gaaaatcatt | gtcacccttta | 1020 |
| gcaagtataa | ctggaatatc | actatttttg | attatatcca | tgtgtcttct | cttcctatgg | 1080 |
| aaaaaatatc | aacccttacaa | agttataaaa | cagaaactag | aaggcaggcc | agaaacagaa | 1140 |
| tacaggaaag | ctcaaacatt | ttcaggccat | gaagatgctc | tggatgactt | cggaatatat | 1200 |
| gaatttgttg | cttttccaga | tgtttctggt | gtttccagga | tcccaagcag | gtctgttcca | 1260 |
| gcctctgatt | gtgtatcggg | gcaagatttg | cacagtacag | tgtatgaagt | tattcagcac | 1320 |
| atccctgccc | agcagcaaga | ccatccagag | tga | | | 1353 |

<210> SEQ ID NO 26
<211> LENGTH: 960
<212> TYPE: DNA
<213> ORGANISM: Unknown
<220> FEATURE:
<223> OTHER INFORMATION: Nucleotide Sequence of extracellular domain of Betacam

<400> SEQUENCE: 26

| | | | | | |
|---|---|---|---|---|---|
| gggctgaagg | tgacagtgcc | atcacacact | gtccatggcg | tcagaggtca | ggccctctac | 60 |
| ctacccgtcc | actatggctt | ccacactcca | gcatcagaca | tccagatcat | atggctattt | 120 |
| gagagacccc | acacaatgcc | caaatactta | ctgggctctg | tgaataagtc | tgtggttcct | 180 |
| gacttggaat | accaacacaa | gttcaccatg | atgccaccca | atgcatctct | gcttatcaac | 240 |
| ccactgcagt | tccctgatga | aggcaattac | atcgtgaagg | tcaacattca | gggaaatgga | 300 |
| actctatctg | ccagtcagaa | gatacaagtc | acggttgatg | atcctgtcac | aaagccagtg | 360 |
| gtgcagattc | atcctccctc | tggggctgtg | agtatgtgg | ggaacatgac | cctgacatgc | 420 |

```
catgtggaag gggcactcg gctagcttac caatggctaa aaaatgggag acctgtccac    480
accagctcca cctactcctt ttctccccaa aacaataccc ttcatattgc tccagtaacc    540
aaggaagaca ttgggaatta cagctgcctg gtgaggaacc ctgtcagtga aatggaaagt    600
gatatcatta tgcccatcat atattatgga ccttatggac ttcaagtgaa ttctgataaa    660
gggctaaaag tagggaagt gtttactgtt gaccttggag aggccatcct atttgattgt    720
tctgctgatt ctcatccccc caacacctac tcctggatta ggaggactga caatactaca    780
tatatcatta agcatgggcc tcgcttagaa gttgcatctg agaaagtagc ccagaagaca    840
atggactatg tgtgctgtgc ttacaacaac ataaccggca ggcaagatga aactcatttc    900
acagttatca tcacttccgt aggactggag aagcttgcac agaaaggaaa atcattgtca    960
```

<210> SEQ ID NO 27
<211> LENGTH: 277
<212> TYPE: PRT
<213> ORGANISM: Unknown
<220> FEATURE:
<223> OTHER INFORMATION: Amino acid sequence of pGEX-4T3-Betacam 33-80

<400> SEQUENCE: 27

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Asn Ser Leu Lys Val Thr Val Pro Ser Tyr Thr Val His
225                 230                 235                 240

Gly Ile Arg Gly Gln Ala Leu Tyr Leu Pro Val His Tyr Gly Phe His
                245                 250                 255

Thr Pro Ala Ser Asp Ile Gln Ile Ile Trp Leu Phe Glu Arg Ser His
            260                 265                 270
```

```
Thr Met Pro Lys Tyr
        275

<210> SEQ ID NO 28
<211> LENGTH: 70
<212> TYPE: PRT
<213> ORGANISM: Unknown
<220> FEATURE:
<223> OTHER INFORMATION: signal peptide in mouse Betacam

<400> SEQUENCE: 28

Met Gly Gln Asp Ala Phe Met Glu Leu Leu Arg Ser Met Val Gly Leu
 1               5                  10                  15

Ser Leu Cys Lys Ile His Leu Leu Ile Ala Gly Ser Cys Leu Gly
                20                  25                  30

Leu Lys Val Thr Val Pro Ser Tyr Thr Val His Gly Ile Arg Gly Gln
            35                  40                  45

Ala Leu Tyr Leu Pro Val His Tyr Gly Phe His Thr Pro Ala Ser Asp
        50                  55                  60

Ile Gln Ile Ile Trp Leu
65                  70

<210> SEQ ID NO 29
<211> LENGTH: 70
<212> TYPE: PRT
<213> ORGANISM: Unknown
<220> FEATURE:
<223> OTHER INFORMATION: signal peptide in human Betacam, isoform 1

<400> SEQUENCE: 29

Met Gly Gln Asp Ala Phe Met Glu Pro Phe Gly Asp Thr Leu Gly Val
 1               5                  10                  15

Phe Gln Cys Lys Ile Tyr Leu Leu Leu Phe Gly Ala Cys Ser Gly Leu
                20                  25                  30

Lys Val Thr Val Pro Ser His Thr Val His Gly Val Arg Gly Gln Ala
            35                  40                  45

Leu Tyr Leu Pro Val His Tyr Gly Phe His Thr Pro Ala Ser Asp Ile
        50                  55                  60

Gln Ile Ile Trp Leu Phe
65                  70

<210> SEQ ID NO 30
<211> LENGTH: 70
<212> TYPE: PRT
<213> ORGANISM: Unknown
<220> FEATURE:
<223> OTHER INFORMATION: signal peptide in human Betacam, isoform 2

<400> SEQUENCE: 30

Met Trp Leu Lys Val Phe Thr Thr Phe Leu Ser Phe Ala Thr Gly Ala
 1               5                  10                  15

Cys Ser Gly Leu Lys Val Thr Val Pro Ser His Thr Val His Gly Val
                20                  25                  30

Arg Gly Gln Ala Leu Tyr Leu Pro Val His Tyr Gly Phe His Thr Pro
            35                  40                  45

Ala Ser Asp Ile Gln Ile Ile Trp Leu Phe Glu Arg Pro His Thr Met
        50                  55                  60

Pro Lys Tyr Leu Leu Gly
65                  70
```

<210> SEQ ID NO 31
<211> LENGTH: 70
<212> TYPE: PRT
<213> ORGANISM: Unknown
<220> FEATURE:
<223> OTHER INFORMATION: signal peptide in macaca mulatta

<400> SEQUENCE: 31

Met Gln Pro Leu Gln Asp Asp Met Thr Thr Phe Leu Glu Gln Ala Ile
1               5                   10                  15

Thr Glu Asn Arg Ser Leu Val Lys Glu Ala Arg Gly Lys Ile Gly Ser
            20                  25                  30

Val Thr Ser Leu Leu Ile Ser Leu Ala Asn Lys Pro Ala Ala Ala Gly
        35                  40                  45

Pro Ser Tyr His Arg Glu Gln Val Thr Ala Cys Met Gly Gln Asp Ala
    50                  55                  60

Phe Met Glu Pro Phe Gly
65                  70

<210> SEQ ID NO 32
<211> LENGTH: 71
<212> TYPE: PRT
<213> ORGANISM: Unknown
<220> FEATURE:
<223> OTHER INFORMATION: signal peptide in macaca mulatta, short
      N-terminal

<400> SEQUENCE: 32

Met Glu Pro Phe Gly Asp Thr Leu Gly Val Phe Gln Cys Lys Leu Tyr
1               5                   10                  15

Leu Leu Leu Phe Gly Ala Cys Ser Gly Leu Lys Val Thr Val Pro Ser
            20                  25                  30

His Thr Val His Gly Ile Arg Gly Gln Ala Leu Leu Tyr Leu Pro Val
        35                  40                  45

His Tyr Gly Phe His Thr Pro Ala Ser Asp Ile Gln Ile Ile Trp Leu
    50                  55                  60

Phe Glu Arg Pro His Thr Met
65                  70

<210> SEQ ID NO 33
<211> LENGTH: 468
<212> TYPE: PRT
<213> ORGANISM: Unknown
<220> FEATURE:
<223> OTHER INFORMATION: canis familiaris Betacam

<400> SEQUENCE: 33

Met Ala Ser Cys Ala Asn Ile Leu Asn Pro Glu Ile Ala Leu Ala Gly
1               5                   10                  15

Cys Glu Met Trp Leu Arg Val Ile Met Thr Phe Ile Ser Phe Ile Ala
            20                  25                  30

Gly Ala Cys Ser Gly Leu Lys Val Ala Val Pro Ser His Thr Val His
        35                  40                  45

Gly Ile Arg Gly Gln Ala Leu Tyr Leu Pro Val His Tyr Gly Phe His
    50                  55                  60

Thr Pro Ala Ser Asp Ile Gln Ile Ile Trp Leu Phe Glu Arg Thr His
65                  70                  75                  80

Thr Met Pro Lys Tyr Leu Leu Ser Ser Val Asn Lys Ser Val Val Pro
                85                  90                  95

Asp Leu Glu Tyr Gln His Lys Phe Thr Met Met Pro Pro Asn Ala Ser
            100                 105                 110

Leu Leu Ile Asn Pro Leu Gln Phe Thr Asp Glu Gly Asn Tyr Ile Val
        115                 120                 125

Lys Val Asn Ile Gln Gly Asn Gly Thr Leu Ser Ala Ser Gln Lys Ile
    130                 135                 140

Gln Val Thr Val Asp Asp Pro Val Thr Lys Pro Val Val Gln Thr Gln
145                 150                 155                 160

Pro Ser Ser Gly Ala Val Glu Tyr Val Gly Asn Met Thr Leu Thr Cys
                165                 170                 175

Leu Val Glu Gly Gly Thr Arg Leu Val Tyr Gln Trp Leu Lys Asn Glu
            180                 185                 190

Arg Pro Val His Ser Ser Ser Thr Thr Ser Phe Ser Leu Gln Asn Asn
        195                 200                 205

Thr Leu His Ile Ala Pro Val Thr Lys Glu Asp Ile Gly Asn Tyr Ser
210                 215                 220

Cys Leu Val Lys Asn Pro Val Ser Glu Met Glu Ser Asp Ile Ile Met
225                 230                 235                 240

Pro Thr Ile Tyr Tyr Gly Pro Tyr Gly Leu Arg Val Asn Ser Asp Lys
                245                 250                 255

Gly Leu Lys Val Gly Glu Val Phe Thr Val Asp Ile Gly Glu Ala Ile
            260                 265                 270

Leu Phe Tyr Cys Ser Ala Asp Ser Tyr Pro Pro Asn Thr Tyr Ser Trp
        275                 280                 285

Ile Gln Arg Thr Asp Asn Thr Thr Tyr Val Ile Lys His Gly Pro His
290                 295                 300

Leu Glu Val Ala Ser Glu Lys Val Ala Gln Lys Thr Thr Asp Tyr Val
305                 310                 315                 320

Cys Cys Ala Tyr Asn Asn Val Thr Gly Arg Arg Asp Glu Ala His Phe
                325                 330                 335

Thr Val Thr Ile Thr Ser Val Gly Leu Glu Lys Leu Ala Gln Lys Gly
            340                 345                 350

Lys Ser Leu Ser Pro Leu Ala Ser Ile Thr Gly Val Ser Leu Phe Leu
        355                 360                 365

Ile Ile Ser Met Cys Leu Leu Phe Leu Trp Lys Lys Tyr Gln Pro Tyr
370                 375                 380

Lys Val Ile Lys Gln Lys Leu Glu Gly Arg Pro Glu Thr Glu Tyr Arg
385                 390                 395                 400

Lys Ala Gln Thr Leu Ser Gly His Glu Asp Ala Leu Asp Asp Phe Gly
                405                 410                 415

Ile Tyr Glu Phe Val Ala Phe Pro Asp Ala Ser Gly Val Pro Arg Met
            420                 425                 430

Pro Ser Arg Ser Val Pro Ala Ser Asp Gly Val Ser Gly Gln Asp Phe
        435                 440                 445

His Ser Thr Ile Tyr Glu Val Ile Gln His Ile Pro Ala Gln Gln His
450                 455                 460

Asp His Pro Glu
465

<210> SEQ ID NO 34
<211> LENGTH: 463
<212> TYPE: PRT
<213> ORGANISM: Unknown
<220> FEATURE:
<223> OTHER INFORMATION: macaca mulatta Betacam

<400> SEQUENCE: 34

Met Gly Gln Asp Ala Phe Met Glu Leu Leu Arg Ser Met Val Gly Leu
1               5                   10                  15

Ser Leu Cys Lys Ile His Leu Leu Ile Ala Gly Ser Cys Leu Gly
            20                  25                  30

Leu Lys Val Thr Val Pro Ser Tyr Thr Val His Gly Ile Arg Gly Gln
            35                  40                  45

Ala Leu Tyr Leu Pro Val His Tyr Gly Phe His Thr Pro Ala Ser Asp
        50                  55                  60

Ile Gln Ile Ile Trp Leu Phe Glu Arg Ser His Thr Met Pro Lys Tyr
65                  70                  75                  80

Leu Leu Gly Ser Val Asn Lys Ser Val Val Pro Asp Leu Glu Tyr Gln
                85                  90                  95

His Lys Phe Thr Met Met Pro Pro Asn Ala Ser Leu Leu Ile Asn Pro
            100                 105                 110

Leu Gln Phe Thr Asp Glu Gly Asn Tyr Ile Val Lys Val Asn Ile Gln
            115                 120                 125

Gly Asn Gly Thr Leu Ser Ala Ser Gln Lys Ile Gln Val Thr Val Asp
130                 135                 140

Asp Pro Val Met Lys Pro Met Val Gln Phe His Pro Ala Ser Gly Ala
145                 150                 155                 160

Val Glu Tyr Val Gly Asn Ile Thr Leu Thr Cys Gln Val Glu Gly Gly
                165                 170                 175

Thr Arg Leu Val Tyr Gln Trp Arg Lys Ser Gly Lys Pro Ile Ser Ile
            180                 185                 190

Asn Ser Ser His Ser Phe Ser Pro Gln Asn Asn Thr Leu Trp Ile Val
            195                 200                 205

Pro Val Thr Lys Glu Asp Ile Gly Asn Tyr Thr Cys Leu Val Ser Asn
210                 215                 220

Pro Val Ser Glu Met Glu Ser Asp Ile Ile Met Pro Thr Ile Tyr Tyr
225                 230                 235                 240

Gly Pro Tyr Gly Leu Gln Val Asn Ser Asp Lys Gly Leu Lys Val Gly
                245                 250                 255

Glu Val Phe Thr Val Asp Leu Gly Glu Ala Val Leu Phe Asp Cys Ser
            260                 265                 270

Ala Asp Ser Tyr Pro Pro Asn Thr Tyr Ser Trp Ile Gln Arg Ser Asp
            275                 280                 285

Asn Thr Thr His Val Ile Lys His Gly Pro His Leu Glu Val Ala Ser
290                 295                 300

Glu Lys Val Ala Gln Lys Ala Thr Asp Tyr Val Cys Cys Ala Tyr Asn
305                 310                 315                 320

Asn Ile Thr Gly Arg Arg Asp Glu Thr Arg Phe Thr Val Ile Ile Thr
                325                 330                 335

Ser Val Gly Leu Glu Lys Leu Ala Gln Arg Gly Lys Ser Leu Ser Pro
            340                 345                 350

Leu Ala Ser Ile Thr Gly Ile Ser Leu Phe Leu Ile Ile Ser Met Cys
            355                 360                 365

Leu Leu Phe Leu Trp Lys Lys Tyr Gln Pro Tyr Lys Ala Ile Lys Gln
            370                 375                 380

Lys Leu Glu Gly Arg Pro Glu Ser Glu Tyr Arg Lys Ala Gln Thr Phe
385                 390                 395                 400

Ser Gly His Glu Asp Ala Leu Ser Asp Phe Gly Ile Tyr Glu Phe Val

```
                    405                 410                 415
Thr Phe Pro Asp Ala Ser Gly Val Ser Arg Met Ser Arg Ser Ser
                420                 425                 430

Pro Ala Ser Asp Gly Val Thr Gly Gln Asp Ile His Gly Thr Ile Tyr
            435                 440                 445

Glu Val Ile Gln His Ile Pro Glu Gln Gln Gln Asn Thr Glu
    450                 455                 460
```

<210> SEQ ID NO 35
<211> LENGTH: 463
<212> TYPE: PRT
<213> ORGANISM: Unknown
<220> FEATURE:
<223> OTHER INFORMATION: mouse Betacam

<400> SEQUENCE: 35

```
Met Gly Gln Asp Ala Phe Met Glu Leu Phe Ser Ser Met Ala Gly Val
1               5                   10                  15

Ser Leu Cys Lys Ile His Leu Leu Ile Ala Gly Ser Cys Leu Gly
            20                  25                  30

Leu Lys Val Thr Val Pro Ser His Thr Val His Gly Ile Arg Gly Gln
            35                  40                  45

Ala Leu Tyr Leu Pro Val His Tyr Gly Phe His Thr Pro Ala Ser Asp
    50                  55                  60

Ile Gln Ile Ile Trp Leu Phe Glu Arg Ser His Thr Thr Pro Lys Tyr
65                  70                  75                  80

Leu Leu Gly Ser Val Asn Lys Ser Val Val Pro Asp Leu Glu Tyr Gln
                85                  90                  95

His Lys Phe Thr Met Met Pro Pro Asn Ala Ser Leu Leu Ile Asn Pro
            100                 105                 110

Leu Gln Phe Thr Asp Glu Gly Asn Tyr Ile Val Lys Val Asn Ile Gln
        115                 120                 125

Gly Asn Gly Thr Leu Ser Ala Ser Gln Lys Ile Gln Val Thr Val Asp
    130                 135                 140

Asp Pro Val Met Lys Pro Met Val Gln Phe His Pro Ala Ser Gly Ala
145                 150                 155                 160

Val Glu Tyr Val Gly Asn Ile Thr Leu Thr Cys Arg Val Glu Gly Gly
                165                 170                 175

Thr Arg Leu Val Tyr Gln Trp Arg Lys Asn Gly Lys Pro Ile Asn Ile
            180                 185                 190

Asn Ser Ser His Ser Phe Ser Pro Gln Asn His Thr Leu Arg Ile Val
        195                 200                 205

Pro Ala Thr Lys Glu Asp Ile Gly Asn Tyr Thr Cys Leu Val Ser Asn
    210                 215                 220

Pro Val Ser Glu Met Glu Ser Asp Ile Ile Pro Thr Ile Tyr Tyr
225                 230                 235                 240

Gly Pro Tyr Gly Leu Gln Val Asn Ser Asp Lys Gly Leu Lys Val Gly
                245                 250                 255

Glu Val Phe Thr Val Asp Leu Gly Glu Ala Val Leu Phe Asp Cys Ser
            260                 265                 270

Ala Asp Ser Tyr Pro Pro Asn Thr Tyr Ser Trp Ile Arg Arg Ser Ala
        275                 280                 285

Asn Thr Thr Arg Val Ile Lys His Gly Pro Arg Leu Glu Val Ala Ser
    290                 295                 300

Asp Lys Val Ala Gln Lys Thr Ala Asp Tyr Val Cys Cys Ala Tyr Asn
```

```
                305                 310                 315                 320
Asn Ile Thr Gly Arg Arg Asp Glu Thr His Phe Thr Val Ile Ile Thr
                325                 330                 335

Ser Val Gly Leu Glu Lys Leu Ala Gln Arg Gly Lys Ser Leu Ser Pro
                340                 345                 350

Leu Ala Ser Ile Thr Gly Ile Ser Leu Phe Phe Ile Ile Ser Met Cys
                355                 360                 365

Leu Leu Phe Leu Trp Lys Lys Phe Gln Pro Tyr Lys Ala Ile Arg Gln
                370                 375                 380

Lys Leu Glu Gly Arg Pro Glu Ser Glu Tyr Arg Lys Ala Gln Ser Phe
385                 390                 395                 400

Ser Gly His Glu Asp Ala Leu Gly Asp Phe Gly Ile Tyr Glu Phe Val
                405                 410                 415

Ala Phe Pro Asp Ala Ser Ala Val Pro Arg Met Ser Ser Arg Ser Ala
                420                 425                 430

Pro Ala Ser Asp Gly Val Thr Gly Gln Asp Phe Gln Gly Thr Ile Tyr
                435                 440                 445

Glu Val Ile Gln His Ile Pro Ala Gln Gln Gln Asp Asp Thr Glu
                450                 455                 460

<210> SEQ ID NO 36
<211> LENGTH: 449
<212> TYPE: PRT
<213> ORGANISM: Unknown
<220> FEATURE:
<223> OTHER INFORMATION: homo sapiens Betacam

<400> SEQUENCE: 36

Met Trp Leu Lys Val Phe Thr Thr Phe Leu Ser Phe Ala Thr Gly Ala
1               5                   10                  15

Cys Ser Gly Leu Lys Val Thr Val Pro Ser His Thr Val His Gly Val
                20                  25                  30

Arg Gly Gln Ala Leu Tyr Leu Pro Val His Tyr Gly Phe His Thr Pro
                35                  40                  45

Ala Ser Asp Ile Gln Ile Ile Trp Leu Phe Glu Arg Pro His Thr Met
                50                  55                  60

Pro Lys Tyr Leu Leu Gly Ser Val Asn Lys Ser Val Val Pro Asp Leu
65                  70                  75                  80

Glu Tyr Gln His Lys Phe Thr Met Met Pro Asn Ala Ser Leu Leu
                85                  90                  95

Ile Asn Pro Leu Gln Phe Pro Asp Glu Gly Asn Tyr Ile Val Lys Val
                100                 105                 110

Asn Ile Gln Gly Asn Gly Thr Leu Ser Ala Ser Gln Lys Ile Gln Val
                115                 120                 125

Thr Val Asp Asp Pro Val Thr Lys Pro Val Val Gln Ile His Pro Pro
                130                 135                 140

Ser Gly Ala Val Glu Tyr Val Gly Asn Met Thr Leu Thr Cys His Val
145                 150                 155                 160

Glu Gly Gly Thr Arg Leu Ala Tyr Gln Trp Leu Lys Asn Gly Arg Pro
                165                 170                 175

Val His Thr Ser Ser Thr Tyr Ser Phe Ser Pro Gln Asn Asn Thr Leu
                180                 185                 190

His Ile Ala Pro Val Thr Lys Glu Asp Ile Gly Asn Tyr Ser Cys Leu
                195                 200                 205

Val Arg Asn Pro Val Ser Glu Met Glu Ser Asp Ile Ile Met Pro Ile
```

-continued

```
            210                 215                 220
Ile Tyr Tyr Gly Pro Tyr Gly Leu Gln Val Asn Ser Asp Lys Gly Leu
225                 230                 235                 240

Lys Val Gly Glu Val Phe Thr Val Asp Leu Gly Glu Ala Val Leu Phe
                245                 250                 255

Asp Cys Ser Ala Asp Ser His Pro Asn Thr Tyr Ser Trp Ile Arg
                260                 265                 270

Arg Thr Ala Asn Thr Thr Tyr Ile Ile Lys His Gly Pro Arg Leu Glu
                275                 280                 285

Val Ala Ser Glu Lys Val Ala Gln Lys Thr Met Asp Tyr Val Cys Cys
                290                 295                 300

Ala Tyr Asn Asn Ile Thr Gly Arg Gln Asp Glu Thr His Phe Thr Val
305                 310                 315                 320

Ile Ile Thr Ser Val Gly Leu Glu Lys Leu Ala Gln Lys Gly Lys Ser
                325                 330                 335

Leu Ser Pro Leu Ala Ser Ile Thr Gly Ile Ser Leu Phe Leu Ile Ile
                340                 345                 350

Ser Met Cys Leu Leu Phe Leu Trp Lys Lys Tyr Gln Pro Tyr Lys Val
                355                 360                 365

Ile Lys Gln Lys Leu Glu Gly Arg Pro Glu Thr Glu Tyr Arg Lys Ala
                370                 375                 380

Gln Thr Phe Ser Gly His Glu Asp Ala Leu Asp Asp Phe Gly Ile Tyr
385                 390                 395                 400

Glu Phe Val Ala Phe Pro Asp Val Ser Gly Val Ser Arg Pro Ser Arg
                405                 410                 415

Ser Val Pro Ala Ser Asp Cys Val Ser Gly Gln Asp Leu His Ser Thr
                420                 425                 430

Val Tyr Glu Val Ile Gln His Ile Pro Ala Gln Gln Asp His Pro
                435                 440                 445

Glu

<210> SEQ ID NO 37
<211> LENGTH: 520
<212> TYPE: PRT
<213> ORGANISM: Unknown
<220> FEATURE:
<223> OTHER INFORMATION: pan troglodyte Betacam

<400> SEQUENCE: 37

Met Gln Pro Leu Gln Asp Asp Met Thr Thr Leu Leu Glu Gln Ala Ile
1               5                   10                  15

Thr Glu Asn Arg Thr Leu Ala Glu Glu Ala Arg Gly Lys Ile Gly Ser
                20                  25                  30

Val Thr Ser Leu Leu Ile Ser Leu Ala Asn Lys Pro Ala Ala Ala Gly
                35                  40                  45

Pro Ser Tyr His Arg Glu Gln Gly Thr Ala Cys Met Gly Gln Asp Ala
                50                  55                  60

Phe Met Glu Pro Phe Gly Asp Thr Leu Gly Val Phe Gln Cys Lys Ile
65              70                  75                  80

Tyr Leu Leu Leu Phe Gly Ala Cys Ser Gly Leu Lys Val Thr Val Pro
                85                  90                  95

Ser His Thr Val His Gly Val Arg Gly Gln Ala Leu Tyr Leu Pro Val
                100                 105                 110

His Tyr Gly Phe His Thr Pro Ala Ser Asp Ile Gln Ile Ile Trp Leu
                115                 120                 125
```

Phe Glu Arg Pro His Thr Met Pro Lys Tyr Leu Leu Gly Ser Val Asn
            130                 135                 140

Lys Ser Val Val Pro Asp Leu Glu Tyr Gln His Lys Phe Thr Met Met
145                 150                 155                 160

Pro Pro Asn Ala Ser Leu Leu Ile Asn Pro Leu Gln Phe Pro Asp Glu
                165                 170                 175

Gly Asn Tyr Ile Val Lys Val Asn Ile Gln Gly Asn Gly Thr Leu Ser
            180                 185                 190

Ala Ser Gln Lys Ile Gln Val Thr Val Asp Asp Pro Val Thr Lys Pro
        195                 200                 205

Val Val Gln Ile His Pro Pro Ser Gly Ala Val Glu Tyr Val Gly Asn
210                 215                 220

Met Thr Leu Thr Cys His Val Glu Gly Gly Thr Arg Leu Ala Tyr Gln
225                 230                 235                 240

Trp Leu Lys Asn Gly Arg Pro Val His Thr Ser Ser Thr Tyr Ser Phe
                245                 250                 255

Ser Pro Gln Asn Asn Thr Leu His Ile Ala Pro Val Thr Lys Glu Asp
                260                 265                 270

Ile Gly Asn Tyr Ser Cys Leu Val Arg Asn Pro Val Ser Glu Thr Glu
            275                 280                 285

Ser Asp Ile Ile Met Pro Ile Ile Tyr Tyr Gly Pro Tyr Gly Leu Gln
290                 295                 300

Val Asn Ser Asp Lys Gly Leu Lys Val Gly Glu Val Phe Thr Val Asp
305                 310                 315                 320

Leu Gly Glu Ala Ile Leu Phe Asp Cys Ser Ala Asp Ser His Pro Pro
                325                 330                 335

Asn Thr Tyr Ser Trp Ile Arg Arg Thr Asp Asn Thr Tyr Ile Ile
                340                 345                 350

Lys His Gly Pro Arg Leu Glu Val Ala Ser Glu Lys Val Ala Gln Lys
            355                 360                 365

Thr Met Asp Tyr Val Cys Cys Ala Tyr Asn Asn Ile Thr Gly Arg Gln
        370                 375                 380

Asp Glu Thr His Phe Thr Val Ile Ile Thr Ser Val Gly Leu Glu Lys
385                 390                 395                 400

Leu Ala Gln Lys Gly Lys Ser Leu Ser Pro Leu Ala Ser Ile Thr Gly
                405                 410                 415

Ile Ser Leu Phe Leu Ile Ile Ser Met Cys Leu Leu Phe Leu Trp Lys
                420                 425                 430

Lys Tyr Gln Pro Tyr Lys Val Ile Lys Gln Lys Leu Glu Gly Arg Pro
            435                 440                 445

Glu Thr Glu Tyr Arg Lys Ala Gln Thr Phe Ser Gly His Glu Asp Ala
        450                 455                 460

Leu Asp Asp Phe Gly Ile Tyr Glu Phe Val Ala Phe Pro Asp Ala Ser
465                 470                 475                 480

Gly Val Ser Arg Pro Ser Arg Ser Val Pro Ala Ser Asp Cys Val Ser
                485                 490                 495

Gly Gln Asp Leu His Ser Thr Val Tyr Glu Val Ile Gln His Ile Pro
            500                 505                 510

Ala Gln Gln Gln Asp His Pro Glu
            515                 520

<210> SEQ ID NO 38
<211> LENGTH: 463

<212> TYPE: PRT
<213> ORGANISM: Unknown
<220> FEATURE:
<223> OTHER INFORMATION: consensus Betacam
<220> FEATURE:
<221> NAME/KEY: VARIANT
<222> LOCATION: 13, 18, 22, 74, 154, 157, 192, 196, 223, 312, 443
<223> OTHER INFORMATION: Xaa = Any Amino Acid

<400> SEQUENCE: 38

Met Gly Gln Asp Ala Phe Met Glu Leu Leu Ile Ser Xaa Ala Gly Leu
 1               5                  10                  15

Ser Xaa Cys Lys Ile Xaa Leu Leu Ile Ala Gly Ala Cys Ser Gly
         20                  25                  30

Leu Lys Val Thr Val Pro Ser His Thr Val His Gly Ile Arg Gly Gln
             35                  40                  45

Ala Leu Tyr Leu Pro Val His Tyr Gly Phe His Thr Pro Ala Ser Asp
 50                  55                  60

Ile Gln Ile Ile Trp Leu Phe Glu Arg Xaa His Thr Met Pro Lys Tyr
 65                  70                  75                  80

Leu Leu Gly Ser Val Asn Lys Ser Val Val Pro Asp Leu Glu Tyr Gln
                 85                  90                  95

His Lys Phe Thr Met Met Pro Pro Asn Ala Ser Leu Leu Ile Asn Pro
             100                 105                 110

Leu Gln Phe Thr Asp Glu Gly Asn Tyr Ile Val Lys Val Asn Ile Gln
         115                 120                 125

Gly Asn Gly Thr Leu Ser Ala Ser Gln Lys Ile Gln Val Thr Val Asp
130                 135                 140

Asp Pro Val Thr Lys Pro Val Val Gln Xaa His Pro Xaa Ser Gly Ala
145                 150                 155                 160

Val Glu Tyr Val Gly Asn Met Thr Leu Thr Cys His Val Glu Gly Gly
                 165                 170                 175

Thr Arg Leu Val Tyr Gln Trp Leu Lys Asn Gly Arg Pro Val His Xaa
             180                 185                 190

Ser Ser Thr Xaa Ser Phe Ser Pro Gln Asn Asn Thr Leu His Ile Ala
         195                 200                 205

Pro Val Thr Lys Glu Asp Ile Gly Asn Tyr Ser Cys Leu Val Xaa Asn
210                 215                 220

Pro Val Ser Glu Met Glu Ser Asp Ile Ile Met Pro Thr Ile Tyr Tyr
225                 230                 235                 240

Gly Pro Tyr Gly Leu Gln Val Asn Ser Asp Lys Gly Leu Lys Val Gly
                 245                 250                 255

Glu Val Phe Thr Val Asp Leu Gly Glu Ala Ile Leu Phe Asp Cys Ser
             260                 265                 270

Ala Asp Ser Tyr Pro Pro Asn Thr Tyr Ser Trp Thr Arg Arg Thr Asp
         275                 280                 285

Asn Thr Thr Tyr Val Ile Lys His Gly Pro Arg Leu Glu Val Ala Ser
290                 295                 300

Glu Lys Val Ala Gln Lys Thr Xaa Asp Tyr Tyr Cys Cys Ala Tyr Asn
305                 310                 315                 320

Asn Ile Thr Gly Arg Arg Asp Glu Thr His Phe Thr Tyr Ile Ile Pro
                 325                 330                 335

Ser Val Gly Leu Glu Lys Leu Ala Gln Lys Gly Lys Ser Leu Ser Pro
             340                 345                 350

Leu Ala Ser Ile Thr Gly Ile Ser Leu Phe Leu Ile Ile Ser Met Cys
         355                 360                 365

```
Leu Leu Phe Leu Trp Lys Lys Tyr Gln Pro Tyr Lys Val Ile Lys Gln
    370                 375                 380

Lys Leu Glu Gly Arg Pro Glu Thr Glu Tyr Arg Lys Ala Gln Thr Phe
385                 390                 395                 400

Ser Gly His Glu Asp Ala Leu Asp Asp Phe Gly Ile Tyr Glu Phe Val
                405                 410                 415

Ala Phe Pro Asp Ala Ser Gly Val Ser Arg Met Pro Ser Arg Ser Val
            420                 425                 430

Pro Ala Ser Asp Gly Val Ser Gly Gln Asp Xaa His Ser Thr Ile Tyr
        435                 440                 445

Glu Val Ile Gln His Ile Pro Ala Gln Gln Gln Asp His Pro Glu
    450                 455                 460
```

<210> SEQ ID NO 39
<211> LENGTH: 144
<212> TYPE: PRT
<213> ORGANISM: Unknown
<220> FEATURE:
<223> OTHER INFORMATION: canis familiaris Betacam sequence with suggested residues for docking

<400> SEQUENCE: 39

```
Met Ala Ser Cys Ala Asn Ile Leu Asn Pro Glu Ile Ala Leu Ala Gly
 1               5                  10                  15

Cys Glu Met Trp Leu Arg Val Ile Met Thr Phe Leu Ser Phe Ile Ala
            20                  25                  30

Gly Ala Cys Ser Gly Leu Lys Val Ala Val Pro Ser His Thr Val His
        35                  40                  45

Gly Ile Arg Gly Gln Ala Leu Tyr Leu Pro Val His Tyr Cys Pro His
    50                  55                  60

Thr Pro Ala Ser Asp Ile Gln Ile Ile Trp Leu Phe Glu Arg Thr His
65                  70                  75                  80

Thr Met Pro Lys Tyr Leu Leu Ser Ser Val Asn Lys Ser Val Val Pro
                85                  90                  95

Asp Leu Glu Tyr Gln Arg Lys Phe Thr Met Met Pro Pro Asn Ala Ser
            100                 105                 110

Leu Leu Ile Asn Pro Leu Gln Phe Thr Asp Glu Gly Asn Tyr Ile Val
        115                 120                 125

Lys Val Asn Ile Gln Gly Asn Gly Thr Leu Ser Ala Ser Gln Lys Ile
    130                 135                 140
```

<210> SEQ ID NO 40
<211> LENGTH: 139
<212> TYPE: PRT
<213> ORGANISM: Unknown
<220> FEATURE:
<223> OTHER INFORMATION: macaca mulatta Betacam sequence with suggested residues for docking

<400> SEQUENCE: 40

```
Met Gly Gln Asp Ala Phe Met Glu Leu Leu Arg Ser Met Val Gly Leu
 1               5                  10                  15

Ser Leu Cys Lys Ile His Leu Leu Leu Ile Ala Gly Ser Cys Leu Gly
            20                  25                  30

Leu Lys Val Thr Val Pro Ser Tyr Thr Val His Gly Ile Arg Gly Gln
        35                  40                  45

Ala Leu Tyr Leu Pro Val His Tyr Cys Pro His Thr Pro Ala Ser Asp
    50                  55                  60
```

Ile Gln Ile Ile Trp Leu Phe Glu Arg Ser His Thr Met Pro Lys Tyr
65                  70                  75                  80

Leu Leu Gly Ser Val Asn Lys Ser Val Val Pro Asp Leu Glu Tyr Gln
                85                  90                  95

His Lys Phe Thr Met Met Pro Pro Asn Ala Ser Leu Leu Ile Asn Pro
            100                 105                 110

Leu Gln Phe Thr Asp Glu Gly Asn Tyr Ile Val Lys Val Asn Ile Gln
        115                 120                 125

Gly Asn Gly Thr Leu Ser Ala Ser Gln Lys Ile
    130                 135

<210> SEQ ID NO 41
<211> LENGTH: 139
<212> TYPE: PRT
<213> ORGANISM: Unknown
<220> FEATURE:
<223> OTHER INFORMATION: mouse Betacam sequence with suggested residues
      for docking

<400> SEQUENCE: 41

Met Gly Gln Asp Ala Phe Met Glu Leu Phe Ser Ser Met Ala Gly Val
1               5                   10                  15

Ser Leu Cys Lys Ile His Leu Leu Ile Ala Gly Ser Cys Leu Gly
            20                  25                  30

Leu Lys Val Thr Val Pro Ser His Thr Val His Gly Ile Arg Gly Gln
        35                  40                  45

Ala Leu Tyr Leu Pro Val His Tyr Cys Phe His Thr Pro Ala Ser Asp
50                  55                  60

Ile Gln Ile Ile Trp Leu Phe Glu Arg Ser His Thr Thr Pro Lys Tyr
65                  70                  75                  80

Leu Leu Gly Ser Val Asn Lys Ser Val Val Pro Asp Leu Glu Tyr Gln
                85                  90                  95

His Lys Phe Thr Met Met Pro Pro Asn Ala Ser Leu Leu Ile Asn Pro
            100                 105                 110

Leu Gln Phe Thr Asp Glu Gly Asn Tyr Ile Val Lys Val Asn Ile Gln
        115                 120                 125

Gly Asn Gly Thr Leu Ser Ala Ser Gln Lys Ile
    130                 135

<210> SEQ ID NO 42
<211> LENGTH: 126
<212> TYPE: PRT
<213> ORGANISM: Unknown
<220> FEATURE:
<223> OTHER INFORMATION: homo sapiens Betacam sequence with suggested
      residues for docking

<400> SEQUENCE: 42

Met Trp Leu Lys Val Phe Thr Thr Phe Leu Ser Phe Ala Thr Gly Ala
1               5                   10                  15

Cys Ser Gly Leu Lys Val Thr Val Pro Ser His Thr Val His Gly Val
            20                  25                  30

Arg Gly Gln Ala Leu Tyr Leu Pro Val His Tyr Cys Phe His Thr Pro
        35                  40                  45

Ala Ser Asp Ile Gln Ile Ile Trp Leu Phe Glu Arg Pro His Thr Met
50                  55                  60

Pro Lys Tyr Leu Leu Gly Ser Val Asn Lys Ser Val Val Pro Asp Leu
65                  70                  75                  80

```
Glu Tyr Gln Arg Lys Phe Thr Met Met Pro Pro Asn Ala Ser Leu Leu
                85                  90                  95

Ile Asn Pro Leu Gln Phe Pro Asp Glu Gly Asn Tyr Ile Val Lys Val
            100                 105                 110

Asn Ile Gln Gly Asn Gly Thr Leu Ser Ala Ser Gln Lys Ile
        115                 120                 125

<210> SEQ ID NO 43
<211> LENGTH: 197
<212> TYPE: PRT
<213> ORGANISM: Unknown
<220> FEATURE:
<223> OTHER INFORMATION: pan troglodyte Betacam sequence with suggested
      residues for docking

<400> SEQUENCE: 43

Met Gln Pro Leu Gln Asp Asp Met Thr Thr Leu Leu Glu Gln Ala Ile
1               5                   10                  15

Thr Glu Asn Arg Thr Leu Ala Glu Glu Ala Arg Gly Lys Ile Gly Ser
            20                  25                  30

Val Thr Ser Leu Leu Ile Ser Leu Ala Asn Lys Pro Ala Ala Ala Gly
        35                  40                  45

Pro Ser Tyr His Arg Glu Gln Gly Thr Ala Cys Met Gly Gln Asp Ala
    50                  55                  60

Phe Met Glu Pro Phe Gly Asp Thr Leu Gly Val Phe Gln Cys Lys Ile
65                  70                  75                  80

Tyr Leu Leu Leu Phe Gly Ala Cys Ser Gly Leu Lys Val Thr Val Pro
                85                  90                  95

Ser His Thr Val His Gly Val Arg Gly Gln Ala Leu Tyr Leu Pro Val
            100                 105                 110

His Tyr Cys Phe His Thr Pro Ala Ser Asp Ile Gln Ile Ile Trp Leu
        115                 120                 125

Phe Glu Arg Pro His Thr Met Pro Lys Tyr Leu Leu Gly Ser Val Asn
    130                 135                 140

Lys Ser Val Val Pro Asp Leu Glu Tyr Gln His Lys Phe Thr Met Met
145                 150                 155                 160

Pro Pro Asn Ala Ser Leu Leu Ile Asn Pro Leu Gln Phe Pro Asp Glu
                165                 170                 175

Gly Asn Tyr Ile Val Lys Val Asn Ile Gln Gly Asn Gly Thr Leu Ser
            180                 185                 190

Ala Ser Gln Lys Ile
        195

<210> SEQ ID NO 44
<211> LENGTH: 139
<212> TYPE: PRT
<213> ORGANISM: Unknown
<220> FEATURE:
<223> OTHER INFORMATION: consensus Betacam sequence with suggested
      residues for docking
<220> FEATURE:
<221> NAME/KEY: VARIANT
<222> LOCATION: 13, 18, 22, 74
<223> OTHER INFORMATION: Xaa = Any Amino Acid

<400> SEQUENCE: 44

Met Gly Gln Asp Ala Phe Met Glu Leu Leu Ile Ser Xaa Ala Gly Leu
1               5                   10                  15

Ser Xaa Cys Lys Ile Xaa Leu Leu Leu Ile Ala Gly Ala Cys Ser Gly
```

```
                20              25              30
Leu Lys Val Thr Val Pro Ser His Thr Val His Gly Ile Arg Gly Gln
            35                  40                  45

Ala Leu Tyr Leu Pro Val His Tyr Gly Phe His Thr Pro Ala Ser Asp
        50                  55                  60

Ile Gln Ile Ile Trp Leu Phe Glu Arg Xaa His Thr Met Pro Lys Tyr
 65                  70                  75                  80

Leu Leu Gly Ser Val Asn Lys Ser Val Val Pro Asp Leu Glu Tyr Gln
                85                  90                  95

His Lys Phe Thr Met Met Pro Pro Asn Ala Ser Leu Leu Ile Asn Pro
            100                 105                 110

Leu Gln Phe Thr Asp Glu Gly Asn Tyr Ile Val Lys Val Asn Ile Gln
        115                 120                 125

Gly Asn Gly Thr Leu Ser Ala Ser Gln Lys Ile
    130                 135

<210> SEQ ID NO 45
<211> LENGTH: 13
<212> TYPE: PRT
<213> ORGANISM: Unknown
<220> FEATURE:
<223> OTHER INFORMATION: D1 bulge residues in drosophila Betacam

<400> SEQUENCE: 45

Thr Asp Ser Asp Pro Val Phe Leu Ser Thr Gly Ser Thr
 1               5                  10

<210> SEQ ID NO 46
<211> LENGTH: 13
<212> TYPE: PRT
<213> ORGANISM: Unknown
<220> FEATURE:
<223> OTHER INFORMATION: D1 bulge residues in homo sapiens Betacam

<400> SEQUENCE: 46

Ser His Thr Met Pro Lys Tyr Leu Leu Gly Ser Val Asn
 1               5                  10

<210> SEQ ID NO 47
<211> LENGTH: 70
<212> TYPE: PRT
<213> ORGANISM: Unknown
<220> FEATURE:
<223> OTHER INFORMATION: Lachesin sequence with a signal peptide
      cleavage site

<400> SEQUENCE: 47

Met Trp Arg Pro Ser Ile Ser Asn Cys Val Trp Ser Thr Leu Leu Leu
 1               5                  10                  15

Ala Ile Phe Val Gln Gln Thr Leu Ala Gln Arg Thr Pro Thr Ile Ser
            20                  25                  30

Tyr Ile Thr Gln Glu Gln Ile Lys Asp Ile Gly Gly Thr Val Glu Phe
        35                  40                  45

Asp Cys Ser Val Gln Tyr Ala Lys Glu Tyr Asn Val Leu Phe Leu Lys
    50                  55                  60

Thr Asp Ser Asp Pro Val
 65                  70

<210> SEQ ID NO 48
<211> LENGTH: 75
<212> TYPE: DNA
```

```
<213> ORGANISM: Unknown
<220> FEATURE:
<223> OTHER INFORMATION: restriction map and multiple cloning site of
      pIRES2-EGFP vector

<400> SEQUENCE: 48
gctagcgcta ccggactcag atctcgagct caagcttcga attctgcagt cgacggtacc    60
gcgggcccgg gatcc                                                    75

<210> SEQ ID NO 49
<211> LENGTH: 63
<212> TYPE: DNA
<213> ORGANISM: Unknown
<220> FEATURE:
<223> OTHER INFORMATION: nucleotide sequence of pGEX-4T-3 cloning vector

<400> SEQUENCE: 49
ctggttccgc gtggatcccc gaattcccgg gtcgactcga gcggccgcat cgtgactgac    60
tga                                                                 63

<210> SEQ ID NO 50
<211> LENGTH: 20
<212> TYPE: PRT
<213> ORGANISM: Unknown
<220> FEATURE:
<223> OTHER INFORMATION: amino acid sequence of pGEX-4T-3 cloning vector

<400> SEQUENCE: 50

Leu Val Pro Arg Gly Ser Pro Asn Ser Arg Val Asp Ser Ser Gly Arg
 1               5                  10                  15

Ile Val Thr Asp
            20

<210> SEQ ID NO 51
<211> LENGTH: 16
<212> TYPE: PRT
<213> ORGANISM: Unknown
<220> FEATURE:
<223> OTHER INFORMATION: portion of extracellular Betacam sequence which
      is not modeled and predicted to behave as a linker
      between D3 and the transmembrane domain

<400> SEQUENCE: 51

Thr Ser Val Gly Leu Glu Lys Leu Ala Gln Arg Gly Lys Ser Leu Ser
 1               5                  10                  15

<210> SEQ ID NO 52
<211> LENGTH: 12
<212> TYPE: PRT
<213> ORGANISM: Unknown
<220> FEATURE:
<223> OTHER INFORMATION: D1 loop of Betacam

<400> SEQUENCE: 52

Ser His Thr Met Pro Lys Tyr Leu Leu Gly Ser Val
 1               5                  10

<210> SEQ ID NO 53
<211> LENGTH: 13
<212> TYPE: PRT
<213> ORGANISM: Unknown
<220> FEATURE:
<223> OTHER INFORMATION: linker sequence in Lachesin

<400> SEQUENCE: 53
```

```
Thr Asp Ser Thr Pro Val Phe Leu Ser Thr Gly Ser Thr
 1              5                   10

<210> SEQ ID NO 54
<211> LENGTH: 32
<212> TYPE: DNA
<213> ORGANISM: Unknown
<220> FEATURE:
<223> OTHER INFORMATION: sense primer to amplify Betacam D1 domain

<400> SEQUENCE: 54
aattccatgg ctctgaaggt gaccgtgccg tc                                    32

<210> SEQ ID NO 55
<211> LENGTH: 30
<212> TYPE: DNA
<213> ORGANISM: Unknown
<220> FEATURE:
<223> OTHER INFORMATION: antisense primer to amplify Betacam D1 domain

<400> SEQUENCE: 55
caccagatct aggatcatcg acagtgactt                                       30

<210> SEQ ID NO 56
<211> LENGTH: 32
<212> TYPE: DNA
<213> ORGANISM: Unknown
<220> FEATURE:
<223> OTHER INFORMATION: sense primer to amplify Betacam D2 domain

<400> SEQUENCE: 56
aattccatgg ctcctgtcat gaagccaatg gt                                    32

<210> SEQ ID NO 57
<211> LENGTH: 30
<212> TYPE: DNA
<213> ORGANISM: Unknown
<220> FEATURE:
<223> OTHER INFORMATION: antisense primer to amplify Betacam D2 domain

<400> SEQUENCE: 57
caccagatct atatatggtg ggcataatga                                       30

<210> SEQ ID NO 58
<211> LENGTH: 31
<212> TYPE: DNA
<213> ORGANISM: Unknown
<220> FEATURE:
<223> OTHER INFORMATION: sense primer to amplify Betacam D3 domain

<400> SEQUENCE: 58
ggccgatatc ttatggacct tatggacttc a                                     31

<210> SEQ ID NO 59
<211> LENGTH: 31
<212> TYPE: DNA
<213> ORGANISM: Unknown
<220> FEATURE:
<223> OTHER INFORMATION: antisense primer to amplify Betacam D3 domain

<400> SEQUENCE: 59
gacgccatgg ctatgatgac tgtgaatcga g                                     31

<210> SEQ ID NO 60
<211> LENGTH: 32
<212> TYPE: DNA
```

```
<213> ORGANISM: Unknown
<220> FEATURE:
<223> OTHER INFORMATION: sense primer to amplify Betacam D1/D2 domain

<400> SEQUENCE: 60
aattccatgg ctctgaaggt gaccgtgccg tc                                32

<210> SEQ ID NO 61
<211> LENGTH: 30
<212> TYPE: DNA
<213> ORGANISM: Unknown
<220> FEATURE:
<223> OTHER INFORMATION: antisense primer to amplify Betacam D1/D2
      domain

<400> SEQUENCE: 61
caccagatct atatggtg ggcataatga                                     30

<210> SEQ ID NO 62
<211> LENGTH: 31
<212> TYPE: DNA
<213> ORGANISM: Unknown
<220> FEATURE:
<223> OTHER INFORMATION: sense primer to amplify Betacam D2/D3 domain

<400> SEQUENCE: 62
ggccaggcct tcctgtcatg aagccaatgg t                                 31

<210> SEQ ID NO 63
<211> LENGTH: 31
<212> TYPE: DNA
<213> ORGANISM: Unknown
<220> FEATURE:
<223> OTHER INFORMATION: antisense primer to amplify Betacam D2/D3
      domain

<400> SEQUENCE: 63
gacgccatgg ctatgatgac tgtgaatcga g                                 31
```